(12) United States Patent
Walder et al.

(10) Patent No.: US 10,838,939 B2
(45) Date of Patent: Nov. 17, 2020

(54) DNA DATA STORAGE USING REUSABLE NUCLEIC ACIDS

(71) Applicant: Integrated DNA Technologies, Inc., Coralville, IA (US)

(72) Inventors: Joseph Alan Walder, Chicago, IL (US); Jeffrey A. Manthey, North Liberty, IA (US); William E. Martin, III, Coralville, IA (US); Shawn Allen, Williamsburg, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 210 days.

(21) Appl. No.: 15/796,131

(22) Filed: Oct. 27, 2017

(65) Prior Publication Data

US 2018/0121478 A1 May 3, 2018

Related U.S. Application Data

(60) Provisional application No. 62/414,383, filed on Oct. 28, 2016.

(51) Int. Cl.
*G06F 16/22* (2019.01)
*G06N 3/12* (2006.01)
*G16B 30/00* (2019.01)

(52) U.S. Cl.
CPC ...... *G06F 16/2237* (2019.01); *G06F 16/2272* (2019.01); *G06N 3/123* (2013.01); *G16B 30/00* (2019.02)

(58) Field of Classification Search
CPC .......... G06F 16/2237; G06F 16/2272
USPC ........................................................ 707/745
See application file for complete search history.

(56) References Cited

U.S. PATENT DOCUMENTS

| 6,569,382 B1 * | 5/2003 | Edman ........... B01J 19/0046 422/68.1 |
| 6,652,808 B1 * | 11/2003 | Heller ............ B01J 19/0046 422/68.1 |
| 6,706,473 B1 * | 3/2004 | Edman ........... B01J 19/0046 435/6.12 |

(Continued)

FOREIGN PATENT DOCUMENTS

| EP | 3 067 809 | 9/2016 |
| WO | WO 2013178801 | 12/2013 |

OTHER PUBLICATIONS

Bornholt et al., "A DNA-based archival storage system," In Proceedings of the Twenty-First International Conference on Architectural Support for Programming Languages and Operating Systems, ACM, pp. 637-649 (2016).

(Continued)

*Primary Examiner* — Dung K Chau
(74) *Attorney, Agent, or Firm* — McDonnell Boehnen Hulbert & Berghoff LLP

(57) ABSTRACT

Disclosed herein are nucleic acid-based data storage systems and nucleic acid data storage constructs comprising reusable nucleic acid sequences, each representing information carried by a single bit (and, in some embodiments, one or more adjacent bits) within a bit string, and each furthermore representing the position of the single bit within the bit string. Also described are methods for storing data in the nucleic acid-based data storage systems and nucleic acid data storage constructs of the disclosure.

29 Claims, 25 Drawing Sheets

Specification includes a Sequence Listing.

(56) References Cited

U.S. PATENT DOCUMENTS

| | | | | |
|---|---|---|---|---|
| 2002/0087567 A1* | 7/2002 | Spiegler | ................ | G06F 16/284 |
| 2007/0138024 A1* | 6/2007 | Swanson | ................ | B82Y 15/00 |
| | | | | 205/656 |
| 2009/0313210 A1* | 12/2009 | Bestgen | .............. | G06F 16/2237 |
| 2012/0054196 A1* | 3/2012 | Marndi | ..................... | G06F 7/02 |
| | | | | 707/745 |
| 2016/0259886 A1* | 9/2016 | Li | .......................... | G16B 30/00 |
| 2016/0306923 A1* | 10/2016 | van Rooyen | .......... | G06N 3/002 |

OTHER PUBLICATIONS

Church et al., "Next-generation digital information storage in DNA," Science., 337(6102):1628 (2012).

Goldman et al., "Towards practical, high-capacity, low-maintenance information storage in synthesized DNA," Nature., 494(7435):77-80 (2013).

International Search Report of the International Searching Authority for International Application No. PCT/US2017/058766; dated Mar. 2, 2018, pp. 1-2.

Written Opinion of the International Searching Authority for International Application No. PCT/US2017/058766; dated Mar. 2, 2018, pp. 1-6.

International Preliminary Report on Patentability from then International Search Authority for International Application No. PCT/US2017/058766; dated Apr. 3, 2019, pp. 1-7.

* cited by examiner

|  | d1p1r | d1p2r | d1p3r | d1p4r | d1p5r | d1p6r |
|---|---|---|---|---|---|---|
| d1p1f | ■ | 1.49% | 1.68% | 1.45% | 1.52% | 1.40% |
| d1p2f | 1.60% | ■ | 1.53% | 1.53% | 1.52% | 1.46% |
| d1p3f | 1.88% | 1.62% | ■ | 1.65% | 1.68% | 1.54% |
| d1p4f | 1.55% | 1.52% | 1.58% | ■ | 1.57% | 1.48% |
| d1p5f | 1.74% | 1.60% | 1.75% | 1.69% | ■ | 1.59% |
| d1p6f | 1.38% | 1.33% | 1.37% | 1.36% | 1.37% | ■ |

FIGURE 9B

|      | d1p1r | d1p2r | d1p3r | d1p4r | d1p5r | d1p6r |
|------|-------|-------|-------|-------|-------|-------|
| d1p1f |      | 1.18% | 1.50% | 1.15% | 1.43% | 1.23% |
| d1p2f | 1.17% |      | 1.26% | 1.11% | 1.29% | 1.16% |
| d1p3f | 1.51% | 1.37% |      | 1.39% | 1.71% | 1.45% |
| d1p4f | 1.11% | 1.10% | 1.29% |      | 1.34% | 1.21% |
| d1p5f | 1.42% | 1.35% | 1.67% | 1.42% |      | 1.49% |
| d1p6f | 1.12% | 1.11% | 1.29% | 1.12% | 1.34% |      |

FIGURE 10B

|  | d1p1r | d1p2r | d1p3r | d1p4r | d1p5r | d1p6r |
|---|---|---|---|---|---|---|
| d1p1f |  | 1.41% | 1.43% | 1.30% | 1.32% | 1.21% |
| d1p2f | 1.43% |  | 1.27% | 1.36% | 1.30% | 1.23% |
| d1p3f | 1.59% | 1.44% |  | 1.39% | 1.40% | 1.26% |
| d1p4f | 1.33% | 1.37% | 1.27% |  | 1.31% | 1.23% |
| d1p5f | 1.45% | 1.40% | 1.36% | 1.38% |  | 1.27% |
| d1p6f | 1.21% | 1.24% | 1.12% | 1.19% | 1.17% |  |

FIGURE 11B

| | d1p1r | d1p2r | d1p3r | d1p4r | d1p5r | d1p6r |
|---|---|---|---|---|---|---|
| d1p1f | | 1.62% | 1.80% | 1.53% | 0.68% | 1.38% |
| d1p2f | 1.59% | | 1.45% | 1.44% | 0.62% | 1.27% |
| d1p3f | 2.03% | 1.68% | | 1.64% | 0.74% | 1.47% |
| d1p4f | 1.53% | 1.45% | 1.48% | | 0.63% | 1.31% |
| d1p5f | 0.74% | 0.66% | 0.71% | 0.66% | | 0.59% |
| d1p6f | 1.37% | 1.29% | 1.30% | 1.27% | 0.55% | |

FIGURE 12B

```
                          SEQUENCE LISTING

<160> NUMBER OF SEQ ID NOS: 1016

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
cagtagtccg gatgtaatgc caacttcaaa                                          30

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
cggccgattt catagttgcg cgttccagtc                                          30

<210> SEQ ID NO 3
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 3
tattaagtac tttagcgtca gtcgcaaagc                                          30

<210> SEQ ID NO 4
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 4
tgaaactcaa ggtgctttcg aaagccactt                                          30

<210> SEQ ID NO 5
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 5
ctaagatacc atcaccaaga tattgtagct                                          30

<210> SEQ ID NO 6
<211> LENGTH: 30
<212> TYPE: DNA
<213> ORGANISM: Artificial Sequence
```

```
<220> FEATURE:
<223> OTHER INFORMATION: Candidate 30mer Bit-Oligos

<400> SEQUENCE: 6
cacgtagaaa gaaagagaag tgtaccatca                                    30

<210> SEQ ID NO 7
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 7
aggactaagt cctcgctcct gtttcctttc                                    30

<210> SEQ ID NO 8
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 8
gaattcgtca actggaacca atactgaacc                                    30

<210> SEQ ID NO 9
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 9
gcttaatgaa cagttcttaa tcctgtcggc                                    30

<210> SEQ ID NO 10
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 10
agatctgtcc tcttcgtcca cgcctattta                                    30

<210> SEQ ID NO 11
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 11
ccaccaggta gttaacgtgc cggcatttac                                    30

<210> SEQ ID NO 12
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 12
gacgcactgg ttccacatct cgagttacac                                    30
```

```
<210> SEQ ID NO 13
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 13
cgctactcgc ataactttga gcattaatgc                                            30

<210> SEQ ID NO 14
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 14
ggattccggt ccttactcta ctgtacattg                                            30

<210> SEQ ID NO 15
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 15
accggaagaa gctagcgtag tttatctctc                                            30

<210> SEQ ID NO 16
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 16
tgttaatcga gttaccaatt ggctgaggaa                                            30

<210> SEQ ID NO 17
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 17
ccagtgtcgt tatggtgtga ttgagctctt                                            30

<210> SEQ ID NO 18
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 18
cttgcgccgg tgcgtataca atcagtccgt                                            30

<210> SEQ ID NO 19
<211> LENGTH: 30
<212> TYPE: DNA
<213> ORGANISM: Artificial Sequence
<220> FEATURE:
<223> OTHER INFORMATION: Candidate 30mer Bit-Oligos
```

```
<400> SEQUENCE: 19
cctggacctc tgcttctatt ctgctattca                                    30

<210> SEQ ID NO 20
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 20
tatacttgtc gcggcagagt gccgcctgaa                                    30

<210> SEQ ID NO 21
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 21
ctctgtgccg gatcaacaca tcatgattga                                    30

<210> SEQ ID NO 22
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 22
tctagtcctc tcggtttcat cgcgatgtta                                    30

<210> SEQ ID NO 23
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 23
ggcgaacaac aggttatact gtcttaagaa                                    30

<210> SEQ ID NO 24
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 24
atcgtttcga gctagcgcaa gccactctga                                    30

<210> SEQ ID NO 25
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 25
atcattctca tgatgccttc tttaagctcc                                    30

<210> SEQ ID NO 26
```

```
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 26
agtacatagt acacctttag tctggcgact                                          30

<210> SEQ ID NO 27
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 27
cttacgaatc cggtttgttc tagagactaa                                          30

<210> SEQ ID NO 28
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 28
taactcgatg ataatggctg cagacgtatc                                          30

<210> SEQ ID NO 29
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 29
aggaccttcg gcctcactcc agtcctaggt                                          30

<210> SEQ ID NO 30
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 30
cggtgactcg gaaagaaggt tatcatgacg                                          30

<210> SEQ ID NO 31
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 31
gcgcgctcgg acatgactcg tccaaggata                                          30

<210> SEQ ID NO 32
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 32
```

| | |
|---|---|
| atcgtgctgg ataccggtga aactatcata | 30 |

<210> SEQ ID NO 33
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 33

| | |
|---|---|
| ttcttccgtg gaatccacga cgcagtcttg | 30 |

<210> SEQ ID NO 34
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 34

| | |
|---|---|
| gcgtccactt ggcgaattcg cgaacaatag | 30 |

<210> SEQ ID NO 35
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 35

| | |
|---|---|
| tgccgttctt tcttggcgta ctccgccaac | 30 |

<210> SEQ ID NO 36
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 36

| | |
|---|---|
| aaccaatacc taataatcta gctgcagaac | 30 |

<210> SEQ ID NO 37
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 37

| | |
|---|---|
| cgctggccac ctggataact tggttcaaga | 30 |

<210> SEQ ID NO 38
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 38

| | |
|---|---|
| attgtgaatc ctataccgat gcatcgacca | 30 |

<210> SEQ ID NO 39
<211> LENGTH: 30
<212> TYPE: DNA

```
<213> ORGANISM: Artificial Sequence
<220> FEATURE:
<223> OTHER INFORMATION: Candidate 30mer Bit-Oligos

<400> SEQUENCE: 39
ccgcacgtta gccgtggtag tccacggact                                      30

<210> SEQ ID NO 40
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 40
caaggcgcct taccactatt tgaagcctcg                                      30

<210> SEQ ID NO 41
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 41
cgacgcctag cagtagccga tcggtgcaga                                      30

<210> SEQ ID NO 42
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 42
cgatccagct gcgttcttag acgaagaaac                                      30

<210> SEQ ID NO 43
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 43
cgtggctccg ctaccatttg tttcattaat                                      30

<210> SEQ ID NO 44
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 44
tggctttata tagcatgcgg catgactacg                                      30

<210> SEQ ID NO 45
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 45
aaggccgcca tgtggccatt ggcctgttgc                                      30
```

<210> SEQ ID NO 46
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 46
tcgtcgacat acgcttgtca ggaaagcagt                                       30

<210> SEQ ID NO 47
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 47
ttggatcacg ataccgcaat ccgcgcgtca                                       30

<210> SEQ ID NO 48
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 48
ggcttcaacc tttacgtgca cacgaccaaa                                       30

<210> SEQ ID NO 49
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 49
cttccgtacc tcattaatac ggttccgtag                                       30

<210> SEQ ID NO 50
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 50
ctttcatgaa gcgattgcac gcgacctctt                                       30

<210> SEQ ID NO 51
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 51
aagtcctaac cacggtcaac ggaggcgccg                                       30

<210> SEQ ID NO 52
<211> LENGTH: 30
<212> TYPE: DNA
<213> ORGANISM: Artificial Sequence
<220> FEATURE:

```
<223> OTHER INFORMATION: Candidate 30mer Bit-Oligos

<400> SEQUENCE: 52
ctatctggcg aaagaggcat aggacgaaag                                        30

<210> SEQ ID NO 53
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 53
atcataccat caatcctcag cattatggta                                        30

<210> SEQ ID NO 54
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 54
caacaaggcg agttgaattc tattatcttg                                        30

<210> SEQ ID NO 55
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 55
cgttcctgtg cactatggca aacaccactt                                        30

<210> SEQ ID NO 56
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 56
gaaactcctc tttgcacgga ctttagtact                                        30

<210> SEQ ID NO 57
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 57
gctttatctg tttccaggcc ttatttaggc                                        30

<210> SEQ ID NO 58
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 58
agtaccacgc atttagaaat cgattaacca                                        30
```

```
<210> SEQ ID NO 59
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 59
caatcacaaa tcttagacat cctcgtcgac                                          30

<210> SEQ ID NO 60
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 60
gtatccagtg tggaactaat atgctggatg                                          30

<210> SEQ ID NO 61
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 61
tgtacaggtg ccgattgcct aaacgacacc                                          30

<210> SEQ ID NO 62
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 62
ctaactgact gccacgcgtg gtgataactg                                          30

<210> SEQ ID NO 63
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 63
agttcagcaa ctcgagcctt tcagccagaa                                          30

<210> SEQ ID NO 64
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 64
tctcttcagc cgtaaagctt tataatcact                                          30

<210> SEQ ID NO 65
<211> LENGTH: 30
<212> TYPE: DNA
<213> ORGANISM: Artificial Sequence
<220> FEATURE:
<223> OTHER INFORMATION: Candidate 30mer Bit-Oligos
```

<400> SEQUENCE: 65
gcatcttgag cctcgcttca agaactattt                                          30

<210> SEQ ID NO 66
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 66
aggatacgcg tgtaactgtg gctctaccgg                                          30

<210> SEQ ID NO 67
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 67
cggaaaccaa ttccaatcga cgcattaatt                                          30

<210> SEQ ID NO 68
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 68
cctttggaca tgacaaagga tgtttccata                                          30

<210> SEQ ID NO 69
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 69
gctcttagtg tacatatgta ttccggtaga                                          30

<210> SEQ ID NO 70
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 70
acaaagttta ttgtcgcagc tggccaaacc                                          30

<210> SEQ ID NO 71
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 71
cgcacttatt atggtgctgt ctctggtgca                                          30

<210> SEQ ID NO 72
<211> LENGTH: 30

```
<212> TYPE: DNA
<213> ORGANISM: Artificial Sequence
<220> FEATURE:
<223> OTHER INFORMATION: Candidate 30mer Bit-Oligos

<400> SEQUENCE: 72
gtcacaggtc gcgaccatgg acatttaaga                                    30

<210> SEQ ID NO 73
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 73
aggcgcgcca atacacaaat aattaagtaa                                    30

<210> SEQ ID NO 74
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 74
gaaacgttgg ccacgtcttc tgtactcggt                                    30

<210> SEQ ID NO 75
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 75
atgttcctac gagcgtcgta gatagaatgc                                    30

<210> SEQ ID NO 76
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 76
cacctcctct ctatgttaac ttccactgct                                    30

<210> SEQ ID NO 77
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 77
gtttcgcttc gattgcttcc gtcgattgta                                    30

<210> SEQ ID NO 78
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 78
```

```
attattaacg gatagcgcgc tatttgctgt                                              30

<210> SEQ ID NO 79
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 79
gtgaaggaat cttaacggaa catgtgattc                                              30

<210> SEQ ID NO 80
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 80
cttgtcacca cgacgtcttt aagcctaaca                                              30

<210> SEQ ID NO 81
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 81
aagactacga caagcgatgc acgacaaaca                                              30

<210> SEQ ID NO 82
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 82
tattgcagaa gtatcaccgg ttagcaattt                                              30

<210> SEQ ID NO 83
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 83
attgcgctct aaatcgaacg ttgtcctgag                                              30

<210> SEQ ID NO 84
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 84
aaagaatgcg accaagctgt tcaagcttgc                                              30

<210> SEQ ID NO 85
<211> LENGTH: 30
<212> TYPE: DNA
<213> ORGANISM: Artificial Sequence
```

```
<220> FEATURE:
<223> OTHER INFORMATION: Candidate 30mer Bit-Oligos

<400> SEQUENCE: 85
tactaattcc agctgtacac tcttccatca                                              30

<210> SEQ ID NO 86
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 86
aagtcggtgc tcactgcaaa tttgcgttta                                              30

<210> SEQ ID NO 87
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 87
catcaagacc atccgttaca gagctcttaa                                              30

<210> SEQ ID NO 88
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 88
tgaatgtgta atcaggcctc ctcgttacca                                              30

<210> SEQ ID NO 89
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 89
ccaccaccaa tagtggatac aggcggtaag                                              30

<210> SEQ ID NO 90
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 90
agtgtagcgc ttcgacctca acgccatatt                                              30

<210> SEQ ID NO 91
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 91
acgcgcgtcc atcgtatcat ccacagttgg                                              30
```

<210> SEQ ID NO 92
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 92
atccggaccg cctagtgttg tccttatctt                              30

<210> SEQ ID NO 93
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 93
cgttaaagtg taacttcggt caggttaaat                              30

<210> SEQ ID NO 94
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 94
tgtccaaacg tgaagatctg gtaggcgagt                              30

<210> SEQ ID NO 95
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 95
acgtttcaat cgttggacgg ttaatcgttc                              30

<210> SEQ ID NO 96
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 96
tgtttgacta gcgcaaatca tactcgtacg                              30

<210> SEQ ID NO 97
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 97
tctcttcggt ttgctcgcca tctatagcga                              30

<210> SEQ ID NO 98
<211> LENGTH: 30
<212> TYPE: DNA
<213> ORGANISM: Artificial Sequence
<220> FEATURE:
<223> OTHER INFORMATION: Candidate 30mer Bit-Oligos

```
<400> SEQUENCE: 98
gaagttagca gtgactttca tctgtacagc                                    30

<210> SEQ ID NO 99
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 99
cgttgatcct taagttccat attggtaccg                                    30

<210> SEQ ID NO 100
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 100
aagacttcag ctcgaggctt tggtatcatt                                    30

<210> SEQ ID NO 101
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 101
cgttattata ataactcgca ttgagaccga                                    30

<210> SEQ ID NO 102
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 102
tagcctaaga gaaaggtgcc tatggccatc                                    30

<210> SEQ ID NO 103
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 103
aatgagtgcc aatatggcac tcactagaaa                                    30

<210> SEQ ID NO 104
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 104
cctcggtaga tcctaaatat attacactac                                    30

<210> SEQ ID NO 105
```

```
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 105
acttgtcata ctacagatgc ggcctgcggc                                          30

<210> SEQ ID NO 106
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 106
aaatagtggc ttctcagtcg cgaaacgtcc                                          30

<210> SEQ ID NO 107
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 107
gctgaaattg ttctgattaa tagccaccgg                                          30

<210> SEQ ID NO 108
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 108
gttgtttctt tacttcttct tgccacctcc                                          30

<210> SEQ ID NO 109
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 109
acaaccgctg atctctaccg cgtactgcag                                          30

<210> SEQ ID NO 110
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 110
tgctccttcc ttcacgtaca cgctgcattc                                          30

<210> SEQ ID NO 111
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 111
```
tgatcgcaag tgcgcgcgca aatctacgcg                                30

<210> SEQ ID NO 112
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 112
gttactatgt cctagctacc tcactttatg                                30

<210> SEQ ID NO 113
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 113
aaccgcctcg agatatacct actgaacaaa                                30

<210> SEQ ID NO 114
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 114
gctaccataa ccatagtcga agtggcatat                                30

<210> SEQ ID NO 115
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 115
tcctcgctaa ggcagacggc cggtacatag                                30

<210> SEQ ID NO 116
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 116
acgttctcac tagtatggcg gacctataac                                30

<210> SEQ ID NO 117
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 117
cttataagtc ataacgactg gaccacgata                                30

<210> SEQ ID NO 118
<211> LENGTH: 30
<212> TYPE: DNA

<213> ORGANISM: Artificial Sequence
<220> FEATURE:
<223> OTHER INFORMATION: Candidate 30mer Bit-Oligos

<400> SEQUENCE: 118
caccggtaag cagccttgtt acaatcctca            30

<210> SEQ ID NO 119
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 119
gccgccaacg tagatcaacg ctgttaacgt            30

<210> SEQ ID NO 120
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 120
caccgtctat aaatcgcacg atttaatgac            30

<210> SEQ ID NO 121
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 121
cgtcaccatc ggctagcggt cattctactc            30

<210> SEQ ID NO 122
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 122
aggcctcgaa catatcgtgc ctttagttcg            30

<210> SEQ ID NO 123
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 123
cttgattgac acttctaacg ttcatgttcc            30

<210> SEQ ID NO 124
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 124
gattgtcgag tatactgaat gacagtgata            30

<210> SEQ ID NO 125
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 125
catactggct gacggcatac tttcgcgaac                                    30

<210> SEQ ID NO 126
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 126
tataacaaca acgttacgcc gcgccgctga                                    30

<210> SEQ ID NO 127
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 127
cagactcaac actgattacg taggaaactg                                    30

<210> SEQ ID NO 128
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 128
ctatatctca atatatagac gagactgacg                                    30

<210> SEQ ID NO 129
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 129
ctcaactatt ctccgattgc aagtaatgtg                                    30

<210> SEQ ID NO 130
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 130
tcctgtatgc cggttaaagc ttcgcaaatg                                    30

<210> SEQ ID NO 131
<211> LENGTH: 30
<212> TYPE: DNA
<213> ORGANISM: Artificial Sequence
<220> FEATURE:

<223> OTHER INFORMATION: Candidate 30mer Bit-Oligos

<400> SEQUENCE: 131
cctgcgttat aagtgtaaga gaaatggcgt                                      30

<210> SEQ ID NO 132
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 132
ccaatagact aaacgtttca gcgcacctac                                      30

<210> SEQ ID NO 133
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 133
gcatcaactt caggagttcc ggagaaacca                                      30

<210> SEQ ID NO 134
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 134
ataacaagtt ctattggcag aagccaatgt                                      30

<210> SEQ ID NO 135
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 135
gatctaaatt tgcctgcgca attaagtacc                                      30

<210> SEQ ID NO 136
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 136
tcgactttcg taacttaatg atatccgcca                                      30

<210> SEQ ID NO 137
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 137
cggcttctat cgccgcctac gcgtccttaa                                      30

```
<210> SEQ ID NO 138
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 138
atatccacga gcgctaaaga tcgccagcag                                    30

<210> SEQ ID NO 139
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 139
agattaggtt tcgaccgacg tcttctaaac                                    30

<210> SEQ ID NO 140
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 140
ttgctgacag actaccagtt gatcatgaca                                    30

<210> SEQ ID NO 141
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 141
aggtcaagct tccgagacgg tagattatac                                    30

<210> SEQ ID NO 142
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 142
acaggcagcg agtccacgca tcatatatcg                                    30

<210> SEQ ID NO 143
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 143
aatagtcgcg agccacctga gtcgaatgtc                                    30

<210> SEQ ID NO 144
<211> LENGTH: 30
<212> TYPE: DNA
<213> ORGANISM: Artificial Sequence
<220> FEATURE:
<223> OTHER INFORMATION: Candidate 30mer Bit-Oligos
```

<400> SEQUENCE: 144
ccttcatgct cggaatgcgc ctctttaaat 30

<210> SEQ ID NO 145
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 145
taggttgcgc ttcagatact ttcagaagtc 30

<210> SEQ ID NO 146
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 146
aatcaacaca gtataccttg attcctaccg 30

<210> SEQ ID NO 147
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 147
gcattcctac acacctgtgg atatatcata 30

<210> SEQ ID NO 148
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 148
tcagcgcttc taaaccttaa cattcaatct 30

<210> SEQ ID NO 149
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 149
aattcgaaag cgctcgcata atatcatgca 30

<210> SEQ ID NO 150
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 150
gctcagaatc ctaaactaaa ccgatttctt 30

<210> SEQ ID NO 151
<211> LENGTH: 30

```
<212> TYPE: DNA
<213> ORGANISM: Artificial Sequence
<220> FEATURE:
<223> OTHER INFORMATION: Candidate 30mer Bit-Oligos

<400> SEQUENCE: 151
cctactagtc ggcctctcta aacgagcgaa                                30

<210> SEQ ID NO 152
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 152
aacgtccaag cgcgattcga actatggatt                                30

<210> SEQ ID NO 153
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 153
tatgcttcgt gacttcgcac ttgtttataa                                30

<210> SEQ ID NO 154
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 154
tacaaacctt tgatcattaa acaggcaagg                                30

<210> SEQ ID NO 155
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 155
ttgtccaact cagcgttagt tataagatga                                30

<210> SEQ ID NO 156
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 156
atcgcgagag actcgtgtca gcgcttgtat                                30

<210> SEQ ID NO 157
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 157
```

```
ccaatagcgt cctacaggtt tgctgctgct                                    30
```

<210> SEQ ID NO 158
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 158

```
ctcgtgtcct ggtgagctcc gatctatgtc                                    30
```

<210> SEQ ID NO 159
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 159

```
aatacaagtc caataccata catgctagcg                                    30
```

<210> SEQ ID NO 160
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 160

```
gctagaactc caccgtagtt cttatgcaac                                    30
```

<210> SEQ ID NO 161
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 161

```
atccagatcc taggcatgtc atttgtaagg                                    30
```

<210> SEQ ID NO 162
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 162

```
taggccaacc gatatctcct atttagcagc                                    30
```

<210> SEQ ID NO 163
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 163

```
gtgcacttca cttcatgact gaatctcacc                                    30
```

<210> SEQ ID NO 164
<211> LENGTH: 30
<212> TYPE: DNA
<213> ORGANISM: Artificial Sequence

```
<220> FEATURE:
<223> OTHER INFORMATION: Candidate 30mer Bit-Oligos

<400> SEQUENCE: 164
gtcaacacaa cttgatcact ctcgcagaca                                    30

<210> SEQ ID NO 165
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 165
atcagaacag cgtttcatgt tcttgttcat                                    30

<210> SEQ ID NO 166
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 166
actccttaat cataaacacc tttgcatgcc                                    30

<210> SEQ ID NO 167
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 167
aataacgagc tcaggataga acgataggtt                                    30

<210> SEQ ID NO 168
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 168
acgtggcgat tcctaaggca catatataac                                    30

<210> SEQ ID NO 169
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 169
acaaagaggc gaactgttcc acttaagttc                                    30

<210> SEQ ID NO 170
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 170
ttcacattac aagttaggat gctgcgtacg                                    30
```

```
<210> SEQ ID NO 171
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 171
tcatgatgag ccacaacgcc agatttcgat                                    30

<210> SEQ ID NO 172
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 172
gaagtcctat tacctccgta atgttaccta                                    30

<210> SEQ ID NO 173
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 173
agtagtagta gagcacgcgt tcgtacaaat                                    30

<210> SEQ ID NO 174
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 174
cttatgctat acctagacca ccattagcta                                    30

<210> SEQ ID NO 175
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 175
agccgaccga cgcgacctaa ctctgcagaa                                    30

<210> SEQ ID NO 176
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 176
agcgtctcta cttacagcta cttcagttgt                                    30

<210> SEQ ID NO 177
<211> LENGTH: 30
<212> TYPE: DNA
<213> ORGANISM: Artificial Sequence
<220> FEATURE:
<223> OTHER INFORMATION: Candidate 30mer Bit-Oligos
```

```
<400> SEQUENCE: 177
cacacaggtc cttaggatcc ttggagtcta                                              30

<210> SEQ ID NO 178
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 178
ctgagctcgg aattaccaag cagataatcc                                              30

<210> SEQ ID NO 179
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 179
aacgcaacct gctctgtata cttgaccata                                              30

<210> SEQ ID NO 180
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 180
gcactttcgt cgatacacca acaccggtcg                                              30

<210> SEQ ID NO 181
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 181
tgaagcacta catcttaaga ctaacattgc                                              30

<210> SEQ ID NO 182
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 182
gacgagccta ggctctaaag caccaccaaa                                              30

<210> SEQ ID NO 183
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 183
acgtattcag ttccaaggcc ggaactggcg                                              30

<210> SEQ ID NO 184
```

```
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 184
cgcttgcagt tcgtaatatt taggccaaat                                    30

<210> SEQ ID NO 185
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 185
ggcaagcgct gtttcgtgtc cgcgcaactt                                    30

<210> SEQ ID NO 186
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 186
gtggaattcg cttatactac agcaattgcc                                    30

<210> SEQ ID NO 187
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 187
aacaaagctt aagcgcatcc gttggcatga                                    30

<210> SEQ ID NO 188
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 188
ttcagaggct tctgttgttg ctccaacaat                                    30

<210> SEQ ID NO 189
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 189
tgagcatttg ccatcctgca aatatcaatc                                    30

<210> SEQ ID NO 190
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 190
```
gctaatgcac tcatttaagt cacgtgtaag                                              30

<210> SEQ ID NO 191
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 191
gtggccgcac cggtgttaga ttaggtagat                                              30

<210> SEQ ID NO 192
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 192
cattctctcc acagaatgcc ttctgacact                                              30

<210> SEQ ID NO 193
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 193
tctctctccg cttctaccgg caagtaatca                                              30

<210> SEQ ID NO 194
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 194
agacaacttt gcctggtatg cctggccttc                                              30

<210> SEQ ID NO 195
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 195
ccggatacag agccggcatg aacttgcgcc                                              30

<210> SEQ ID NO 196
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 196
ccaaacacgg atccatagtc aacatgacaa                                              30

<210> SEQ ID NO 197
<211> LENGTH: 30
<212> TYPE: DNA

```
<213> ORGANISM: Artificial Sequence
<220> FEATURE:
<223> OTHER INFORMATION: Candidate 30mer Bit-Oligos

<400> SEQUENCE: 197
aagcgctcgt catcgttcgg tactcagaaa                              30

<210> SEQ ID NO 198
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 198
atacttcggc cgtccgccac caaatacaat                              30

<210> SEQ ID NO 199
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 199
ccaaagcgtt tgtcgtataa acgctttgct                              30

<210> SEQ ID NO 200
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 200
gtcatccata cggcgttaca tatattaggc                              30

<210> SEQ ID NO 201
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 201
cattcagacg atgatgacat catgcttcca                              30

<210> SEQ ID NO 202
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 202
ttccttccac agttcggcgc gccgttatac                              30

<210> SEQ ID NO 203
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 203
cggtcgcagc gtgcacaacg ctatggaatt                              30
```

<210> SEQ ID NO 204
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 204
ctcctccttt ggctagctta agaaacatgt                                       30

<210> SEQ ID NO 205
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 205
gaatttacta ggtcctggcg tgctagtagt                                       30

<210> SEQ ID NO 206
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 206
atcaacaatc tctctcactc acactctaag                                       30

<210> SEQ ID NO 207
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 207
atgaaatctt tgtagttagg cggttaactc                                       30

<210> SEQ ID NO 208
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 208
agaactaatc aaccggcaat caacagcaac                                       30

<210> SEQ ID NO 209
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 209
attctacatc tgacaccgaa catgcatgtg                                       30

<210> SEQ ID NO 210
<211> LENGTH: 30
<212> TYPE: DNA
<213> ORGANISM: Artificial Sequence
<220> FEATURE:

<223> OTHER INFORMATION: Candidate 30mer Bit-Oligos

<400> SEQUENCE: 210
aacctctcac tgctagtgag tttcttctat              30

<210> SEQ ID NO 211
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 211
gtacgactcg tcactacagt gaccatctgt              30

<210> SEQ ID NO 212
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 212
cactaactat ttaacctagc taacgtccac              30

<210> SEQ ID NO 213
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 213
tgcaactcct cattcgcgag accactaaac              30

<210> SEQ ID NO 214
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 214
aaccaaagcc gtcgtacgat tagtgtagca              30

<210> SEQ ID NO 215
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 215
ctgtcgaaac aagtagatta tgcatttgcc              30

<210> SEQ ID NO 216
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 216
ggtctgaaca ccttggttta cggttcagcc              30

```
<210> SEQ ID NO 217
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 217
tacgccgtgt gtcagctggc aatagcctct                                   30

<210> SEQ ID NO 218
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 218
gtaggtattt atctaactcg ctcagcgagc                                   30

<210> SEQ ID NO 219
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 219
tgcgctcgat gtaaggcagt acgtagaaat                                   30

<210> SEQ ID NO 220
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 220
actcattggc tgtacaccac ctactttaga                                   30

<210> SEQ ID NO 221
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 221
ctaacgccta taggaagcaa cactctctat                                   30

<210> SEQ ID NO 222
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 222
aggtatgtcc ggcatacctc gtctatgcat                                   30

<210> SEQ ID NO 223
<211> LENGTH: 30
<212> TYPE: DNA
<213> ORGANISM: Artificial Sequence
<220> FEATURE:
<223> OTHER INFORMATION: Candidate 30mer Bit-Oligos
```

```
<400> SEQUENCE: 223
ttgcttagct acgacaaatc tccgcaattg                                      30

<210> SEQ ID NO 224
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 224
caataaccta cttcgacttc catatgaacc                                      30

<210> SEQ ID NO 225
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 225
acaaacgttc cgatttcgca gatccttgtg                                      30

<210> SEQ ID NO 226
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 226
catcatcagc cagttatcat ccgaagccta                                      30

<210> SEQ ID NO 227
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 227
ccaacattta gaacctagga acagtgtgca                                      30

<210> SEQ ID NO 228
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 228
agctcgccat ggactcctcg aaatactaat                                      30

<210> SEQ ID NO 229
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 229
tcttattcga aggcctctgt gcatctccat                                      30

<210> SEQ ID NO 230
<211> LENGTH: 30
```

-continued

<212> TYPE: DNA
<213> ORGANISM: Artificial Sequence
<220> FEATURE:
<223> OTHER INFORMATION: Candidate 30mer Bit-Oligos

<400> SEQUENCE: 230
gcctcaaggt ttgacgacag ccttgattta    30

<210> SEQ ID NO 231
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 231
ataacttcgc gcgcatgcca aacgcttagt    30

<210> SEQ ID NO 232
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 232
tcgacttcta gtagtagctc ttactctgaa    30

<210> SEQ ID NO 233
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 233
acattatctc atccatctat tagcgtacgt    30

<210> SEQ ID NO 234
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 234
ggcctacttt gcctcaaatt tcacgaaggc    30

<210> SEQ ID NO 235
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 235
ccagccgccg gcaagaacat ttaaatcctc    30

<210> SEQ ID NO 236
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 236
ttgcttgtaa cacttaacac aagtcgatga                                              30

<210> SEQ ID NO 237
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 237
cctccgacag agttcatagg tgtagctaat                                              30

<210> SEQ ID NO 238
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 238
gttaagttgc cgttagcagc aactactgca                                              30

<210> SEQ ID NO 239
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 239
ccggaccata cattagacca catatgctta                                              30

<210> SEQ ID NO 240
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 240
ctcgttgcgc attgatgctc aggacataac                                              30

<210> SEQ ID NO 241
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 241
cctttctcct actgatacct aaacagaaag                                              30

<210> SEQ ID NO 242
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 242
ccacatccga gagctcgcag cggagatcac                                              30

<210> SEQ ID NO 243
<211> LENGTH: 30
<212> TYPE: DNA
<213> ORGANISM: Artificial Sequence

```
<220> FEATURE:
<223> OTHER INFORMATION: Candidate 30mer Bit-Oligos

<400> SEQUENCE: 243
ctccttctat ggtcaatggc tgtcgaccta                                  30

<210> SEQ ID NO 244
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 244
taccactagt cgtgcgcgat ataggtggtc                                  30

<210> SEQ ID NO 245
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 245
tccttagaga tctaaatggc tgatgctgga                                  30

<210> SEQ ID NO 246
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 246
cactcaggaa caaatagaga actatcgatt                                  30

<210> SEQ ID NO 247
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 247
tcatgatcca atacgtgctt ataacctcgt                                  30

<210> SEQ ID NO 248
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 248
catttatcaa agctttcttt cgctccaatc                                  30

<210> SEQ ID NO 249
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 249
cttgaccgct atttataagg atgttactac                                  30
```

```
<210> SEQ ID NO 250
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 250
agatgacctc taggtgatag gacatgttgc                                           30

<210> SEQ ID NO 251
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 251
tttaatggat gtctcgagca acatctgcct                                           30

<210> SEQ ID NO 252
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 252
atgcgaaacc atggaacata agttcaccgt                                           30

<210> SEQ ID NO 253
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 253
gatatataag atcggcttgg tgatcttatc                                           30

<210> SEQ ID NO 254
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 254
aaacggtaac attcatatgt cacatcgcga                                           30

<210> SEQ ID NO 255
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 255
cacctaatac taattatatg gcacggaggt                                           30

<210> SEQ ID NO 256
<211> LENGTH: 30
<212> TYPE: DNA
<213> ORGANISM: Artificial Sequence
<220> FEATURE:
<223> OTHER INFORMATION: Candidate 30mer Bit-Oligos
```

-continued

<400> SEQUENCE: 256
cttgtaggcg tcatacacgt gtagagcgcc                                              30

<210> SEQ ID NO 257
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 257
gactcctgca acctcctcct aacaaccaca                                              30

<210> SEQ ID NO 258
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 258
gattataatc cgaacttgga tgaagcaaac                                              30

<210> SEQ ID NO 259
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 259
agtttctaca ttccggacca aagtcagttt                                              30

<210> SEQ ID NO 260
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 260
cgatccttaa atacaagcac cttaatcgga                                              30

<210> SEQ ID NO 261
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 261
tgaacactcc tctcgctcgc catatcgata                                              30

<210> SEQ ID NO 262
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 262
tcgctcaaag catgttctta gcatgttaaa                                              30

<210> SEQ ID NO 263

-continued

<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 263
gcgttcgcct agaccgtact gtggaatatt                30

<210> SEQ ID NO 264
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 264
caccattaat ttctccagtg cttcgagacc                30

<210> SEQ ID NO 265
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 265
gcttcagctg taccgcattc agaacttcag                30

<210> SEQ ID NO 266
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 266
aaactgttct aaatattgcg acggtcctac                30

<210> SEQ ID NO 267
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 267
ttcggagaca tgccgtgtca aatatataca                30

<210> SEQ ID NO 268
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 268
gtttggccga gcgcttctca gcttcttggt                30

<210> SEQ ID NO 269
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 269
gctctattct cgtcgtctct ataaaggaaa                                           30

<210> SEQ ID NO 270
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 270
tatctgatct ccaacgctcg gttgcaatat                                           30

<210> SEQ ID NO 271
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 271
cctttggctc ttcacttgtc tctcctctcc                                           30

<210> SEQ ID NO 272
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 272
gaggatgccg gcttgttcac cggcttagca                                           30

<210> SEQ ID NO 273
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 273
agagacaaat aaacgtccgc aatgtacatt                                           30

<210> SEQ ID NO 274
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 274
aaccactcta tcttagatac atagagtgcc                                           30

<210> SEQ ID NO 275
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 275
ggcatgtgat tgtacagatc atttcggttt                                           30

<210> SEQ ID NO 276
<211> LENGTH: 30
<212> TYPE: DNA

<213> ORGANISM: Artificial Sequence
<220> FEATURE:
<223> OTHER INFORMATION: Candidate 30mer Bit-Oligos

<400> SEQUENCE: 276
gcaaagcact aattaacgcg ctaagacgat                                    30

<210> SEQ ID NO 277
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 277
agcctaacaa tgtacaagta cacatcgtac                                    30

<210> SEQ ID NO 278
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 278
atatgagagc tcatccattt gtatcttccg                                    30

<210> SEQ ID NO 279
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 279
ggtatacaac catcgttcta caccaatgca                                    30

<210> SEQ ID NO 280
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 280
aacagccttt gattaatgac cttatagtgc                                    30

<210> SEQ ID NO 281
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 281
aagctgctac caatcttcaa cgtgcagctc                                    30

<210> SEQ ID NO 282
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 282
agctgtgaac ttggtccatc atcttaagtt                                    30

<210> SEQ ID NO 283
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 283
atgtatacca ctcaagcttg tatgtctcac                                           30

<210> SEQ ID NO 284
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 284
agtccacact gaatacaata tttcggacaa                                           30

<210> SEQ ID NO 285
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 285
ataaacaaag gaccgtacgg acttgtctca                                           30

<210> SEQ ID NO 286
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 286
gagtactagg agcatactaa catatgatca                                           30

<210> SEQ ID NO 287
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 287
caattgcatg cctctgatac ttagagtgac                                           30

<210> SEQ ID NO 288
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 288
ccagtttaga cactctcgat cgtggtagac                                           30

<210> SEQ ID NO 289
<211> LENGTH: 30
<212> TYPE: DNA
<213> ORGANISM: Artificial Sequence
<220> FEATURE:

<223> OTHER INFORMATION: Candidate 30mer Bit-Oligos

<400> SEQUENCE: 289
catcggtaac aaacagtagc tccttataat 30

<210> SEQ ID NO 290
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 290
aactagtgac ttgctcacct ggtggcatcg 30

<210> SEQ ID NO 291
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 291
ccaggtcgat cgacctcctc gctgtcgaca 30

<210> SEQ ID NO 292
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 292
gtgataaaga agtatcgatc gcctgacaga 30

<210> SEQ ID NO 293
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 293
gatatcttga ttacggaaga acacgaagta 30

<210> SEQ ID NO 294
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 294
ggtctcggca ttaatattat taacatccac 30

<210> SEQ ID NO 295
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 295
ggaccatctg gcgcacgcta tgcatacacc 30

```
<210> SEQ ID NO 296
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 296
gaacagatct aagttcgatt cctttgttcg                                30

<210> SEQ ID NO 297
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 297
atcggttccg tgcacttacc tctaaatacg                                30

<210> SEQ ID NO 298
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 298
tatgtccacc tagtcactat ccatgtccgc                                30

<210> SEQ ID NO 299
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 299
ccacactggt aatgctccaa ggaaccacac                                30

<210> SEQ ID NO 300
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 300
gacaatggag gttaactgaa tccatcaaat                                30

<210> SEQ ID NO 301
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 301
gagcgtcagc ttcattccaa caaagctgaa                                30

<210> SEQ ID NO 302
<211> LENGTH: 30
<212> TYPE: DNA
<213> ORGANISM: Artificial Sequence
<220> FEATURE:
<223> OTHER INFORMATION: Candidate 30mer Bit-Oligos
```

```
<400> SEQUENCE: 302
ggaaggaagg tcctctctta ggaggacctc                                30

<210> SEQ ID NO 303
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 303
aacgcgtaag ttcaacattt ggacctcgcc                                30

<210> SEQ ID NO 304
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 304
attatattcc atcaacaaac ctccggatgg                                30

<210> SEQ ID NO 305
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 305
ccagaaatgc atggctgttg tacaaccata                                30

<210> SEQ ID NO 306
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 306
tctcttactt gtcgttaacg ctttaacgtc                                30

<210> SEQ ID NO 307
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 307
tgtgaaagat ctaacgccaa tcgacaccga                                30

<210> SEQ ID NO 308
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 308
tgccgaccaa gtatagaatt agactatact                                30

<210> SEQ ID NO 309
<211> LENGTH: 30
```

-continued

```
<212> TYPE: DNA
<213> ORGANISM: Artificial Sequence
<220> FEATURE:
<223> OTHER INFORMATION: Candidate 30mer Bit-Oligos

<400> SEQUENCE: 309
catctataga catcgagtgt gagattggca                                30

<210> SEQ ID NO 310
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 310
ccatactact ataagcagcg cgcaggatca                                30

<210> SEQ ID NO 311
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 311
cactctgctt catagtatag tatcggtttc                                30

<210> SEQ ID NO 312
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 312
ttctacttgg cgtggttctt tggaagcttc                                30

<210> SEQ ID NO 313
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 313
ttcaatgtag ctatagtccg gctttaactt                                30

<210> SEQ ID NO 314
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 314
actaggtccg gcggatcggc ctttatatat                                30

<210> SEQ ID NO 315
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 315
```

```
caagtaggta ggtatctcta gagcctgtca                                              30

<210> SEQ ID NO 316
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 316
ggattgctaa tctagactag accgactagt                                              30

<210> SEQ ID NO 317
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 317
aaactacaag agagatcgtg atctcttatg                                              30

<210> SEQ ID NO 318
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 318
caacgcttca aacctacttt ctctataggc                                              30

<210> SEQ ID NO 319
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 319
ccgttcgatc tgaagatttg gtgcgcattt                                              30

<210> SEQ ID NO 320
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 320
cacctccaca tttaacacat gtaatacggt                                              30

<210> SEQ ID NO 321
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 321
accatacaac gccacacttt gatcaaccgt                                              30

<210> SEQ ID NO 322
<211> LENGTH: 30
<212> TYPE: DNA
<213> ORGANISM: Artificial Sequence
```

<220> FEATURE:
<223> OTHER INFORMATION: Candidate 30mer Bit-Oligos

<400> SEQUENCE: 322
tctaagcgtg caactataca agcatgcacc                              30

<210> SEQ ID NO 323
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 323
catattcacc acaaactaac ctcatatgct                              30

<210> SEQ ID NO 324
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 324
gactggtata ctgaccttga cctgtatata                              30

<210> SEQ ID NO 325
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 325
attatggatg ctcttctcgc agctatataa                              30

<210> SEQ ID NO 326
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 326
gatccgatgc gtcgcatgaa ctatagaata                              30

<210> SEQ ID NO 327
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 327
agtcttcttg gaatccatgg taataccttc                              30

<210> SEQ ID NO 328
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 328
ctagccgaaa ccgtaaccgt tacttccaac                              30

```
<210> SEQ ID NO 329
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 329
atagatacac tactgccttc cgtggcagtg                                    30

<210> SEQ ID NO 330
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 330
cgttatctgc agttgtcgcc tttagtagtc                                    30

<210> SEQ ID NO 331
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 331
tgtacactgc tttgtgtcct tctctcgtcg                                    30

<210> SEQ ID NO 332
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 332
gactggttaa attgcgacgc tagatcttgg                                    30

<210> SEQ ID NO 333
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 333
tgtctcctcc actagatata tcaccttgaa                                    30

<210> SEQ ID NO 334
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 334
ccattagaga agtccaggtg ttgaagagaa                                    30

<210> SEQ ID NO 335
<211> LENGTH: 30
<212> TYPE: DNA
<213> ORGANISM: Artificial Sequence
<220> FEATURE:
<223> OTHER INFORMATION: Candidate 30mer Bit-Oligos
```

<400> SEQUENCE: 335
atgatagacc tccatagtcc ttactagttt 30

<210> SEQ ID NO 336
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 336
tccgattaat ccgaaatcga tggtttacac 30

<210> SEQ ID NO 337
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 337
cgatatgcat ctaccttaag ttgaatagtg 30

<210> SEQ ID NO 338
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 338
gaatttacat aggctgatca caacctccat 30

<210> SEQ ID NO 339
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 339
accggctttg acgaaggcgg cttactcaat 30

<210> SEQ ID NO 340
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 340
aaaccggcga gaaatttaca tttgctgtta 30

<210> SEQ ID NO 341
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 341
ttcggatatc gaatctcgca atcgaatagg 30

<210> SEQ ID NO 342

```
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 342
aacaactcct ggagtaccgg tcaaatgaac                                    30

<210> SEQ ID NO 343
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 343
ttccaccgca tttgtgcgac aaatcatagt                                    30

<210> SEQ ID NO 344
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 344
accaattgta gctccgagac aacttctaga                                    30

<210> SEQ ID NO 345
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 345
gtagagcgca ttaggtatac tagattctat                                    30

<210> SEQ ID NO 346
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 346
gctataatgg ccttaaagtg tgcgcgccgc                                    30

<210> SEQ ID NO 347
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 347
gtccatcagc aacattagtc atgacaccgc                                    30

<210> SEQ ID NO 348
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 348
```
cagtctaggc ctttcttata tgatgtcctc                                      30

<210> SEQ ID NO 349
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 349
cacacacatc cagactgctc gccaacagca                                      30

<210> SEQ ID NO 350
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 350
cgcattccat tagacggagg cctaggcacc                                      30

<210> SEQ ID NO 351
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 351
caacatgcca actgaacgag tgcatgttct                                      30

<210> SEQ ID NO 352
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 352
cctagatgcc aatccgcact acaatccatg                                      30

<210> SEQ ID NO 353
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 353
acaaggccgc accatgctat taatacaacc                                      30

<210> SEQ ID NO 354
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 354
caggcatgta cgaacaaaca aaccatgtgg                                      30

<210> SEQ ID NO 355
<211> LENGTH: 30
<212> TYPE: DNA

-continued

<213> ORGANISM: Artificial Sequence
<220> FEATURE:
<223> OTHER INFORMATION: Candidate 30mer Bit-Oligos

<400> SEQUENCE: 355
gacgccgtat attggacaac tcaacaatat         30

<210> SEQ ID NO 356
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 356
tgtaggcgct acctgagctc cactaaagaa         30

<210> SEQ ID NO 357
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 357
aagctcgagt caagtgaata ggtttcacag         30

<210> SEQ ID NO 358
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 358
caagcacgca attccacctc cgatcgcgtt         30

<210> SEQ ID NO 359
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 359
tgactcgtaa gattctttaa acaaacgcca         30

<210> SEQ ID NO 360
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 360
ctgatcagtt ctcatactcc ttcgcaatgc         30

<210> SEQ ID NO 361
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 361
cggatacgta cctggtgcgt actggatgga         30

<210> SEQ ID NO 362
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 362
cttcgattgt tagcttcttg caatgcgaac                                   30

<210> SEQ ID NO 363
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 363
atgtcacacc gtggatgttc agaatctaga                                   30

<210> SEQ ID NO 364
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 364
acgctctatc cgttgtaacg ttcaagactg                                   30

<210> SEQ ID NO 365
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 365
tcactgtagc taggtaacta gtatatcgta                                   30

<210> SEQ ID NO 366
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 366
ttgttaatga gtaccacaat acaccatggc                                   30

<210> SEQ ID NO 367
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 367
gtctcagagg atagctaatc ataacatccg                                   30

<210> SEQ ID NO 368
<211> LENGTH: 30
<212> TYPE: DNA
<213> ORGANISM: Artificial Sequence
<220> FEATURE:

<223> OTHER INFORMATION: Candidate 30mer Bit-Oligos

<400> SEQUENCE: 368
ctgcgtccac tcacgtccag ctatcaacaa                                             30

<210> SEQ ID NO 369
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 369
cgcaatggta catgtttgac ataccacata                                             30

<210> SEQ ID NO 370
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 370
tcacactgaa gaaagcactg gttataacca                                             30

<210> SEQ ID NO 371
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 371
gccacaattc atcaggtagc taagtgctgt                                             30

<210> SEQ ID NO 372
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 372
tgcgattcca taggccggca gtgcgtcatt                                             30

<210> SEQ ID NO 373
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 373
aaccaagcgc tggtctttca cgttcataag                                             30

<210> SEQ ID NO 374
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 374
tgacggcgtt aactccattg attatttaca                                             30

```
<210> SEQ ID NO 375
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 375
tgttggcgcc gcttagaagg atggtcgtcg                                    30

<210> SEQ ID NO 376
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 376
tttagtagac catcctatcc tggtctaagc                                    30

<210> SEQ ID NO 377
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 377
agttcttcat acagacgcat taggatccaa                                    30

<210> SEQ ID NO 378
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 378
ccaagtcaca cattctatcg tctatctatc                                    30

<210> SEQ ID NO 379
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 379
gtcagcgaac ttgcgttgct gcatagctaa                                    30

<210> SEQ ID NO 380
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 380
atacgaggta ttagcacgat cgtcggtaac                                    30

<210> SEQ ID NO 381
<211> LENGTH: 30
<212> TYPE: DNA
<213> ORGANISM: Artificial Sequence
<220> FEATURE:
<223> OTHER INFORMATION: Candidate 30mer Bit-Oligos
```

```
<400> SEQUENCE: 381
agcctctaga tagttccagt ctcatttacc                                    30

<210> SEQ ID NO 382
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 382
cagcgacata tgacatactc ttgtttcatg                                    30

<210> SEQ ID NO 383
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 383
ctgtttaaag tcttcgaatc gagcaaacac                                    30

<210> SEQ ID NO 384
<211> LENGTH: 30
<212> TYPE: DNA
<213> ORGANISM: Artificial Sequence
<220> FEATURE:
<223> OTHER INFORMATION: Candidate 30mer Bit-Oligos

<400> SEQUENCE: 384
gtaacacgtt gtgaagctcc tcaattgttc                                    30

<210> SEQ ID NO 385
<211> LENGTH: 24
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 385
cgcagcctct atacgcgtct gacc                                          24

<210> SEQ ID NO 386
<211> LENGTH: 24
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 386
gcggaattcc atcctccgag gcag                                          24

<210> SEQ ID NO 387
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 387
acgaaaggta gaggtccgga gtg                                           23
```

```
<210> SEQ ID NO 388
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 388
agtccgaatc ggtcatccta ggt                                           23

<210> SEQ ID NO 389
<211> LENGTH: 24
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 389
ctgcctcgga ggatggaatt ccgc                                          24

<210> SEQ ID NO 390
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 390
acctaggatg accgattcgg act                                           23

<210> SEQ ID NO 391
<211> LENGTH: 21
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 391
tctggccatc actggaccta c                                             21

<210> SEQ ID NO 392
<211> LENGTH: 21
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 392
cgactccaca agctccacct t                                             21

<210> SEQ ID NO 393
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 393
cggtcgagaa actataggct cgg                                           23
```

<210> SEQ ID NO 394
<211> LENGTH: 23
<212> TYPE: DNA
<213> ORGANISM: Artificial Sequence
<220> FEATURE:
<223> OTHER INFORMATION: Candidate Primer Pair Sets (Well & Plate levels)

<400> SEQUENCE: 394
ggacaatggc aatactggac acc                                    23

<210> SEQ ID NO 395
<211> LENGTH: 21
<212> TYPE: DNA
<213> ORGANISM: Artificial Sequence
<220> FEATURE:
<223> OTHER INFORMATION: Candidate Primer Pair Sets (Well & Plate levels)

<400> SEQUENCE: 395
aaggtggagc ttgtggagtc g                                      21

<210> SEQ ID NO 396
<211> LENGTH: 23
<212> TYPE: DNA
<213> ORGANISM: Artificial Sequence
<220> FEATURE:
<223> OTHER INFORMATION: Candidate Primer Pair Sets (Well & Plate levels)

<400> SEQUENCE: 396
ggtgtccagt attgccattg tcc                                    23

<210> SEQ ID NO 397
<211> LENGTH: 20
<212> TYPE: DNA
<213> ORGANISM: Artificial Sequence
<220> FEATURE:
<223> OTHER INFORMATION: Candidate Primer Pair Sets (Well & Plate levels)

<400> SEQUENCE: 397
atggcctcgg acttgcctcc                                        20

<210> SEQ ID NO 398
<211> LENGTH: 20
<212> TYPE: DNA
<213> ORGANISM: Artificial Sequence
<220> FEATURE:
<223> OTHER INFORMATION: Candidate Primer Pair Sets (Well & Plate levels)

<400> SEQUENCE: 398
cggcagctca aaccaggcct                                        20

<210> SEQ ID NO 399
<211> LENGTH: 23
<212> TYPE: DNA
<213> ORGANISM: Artificial Sequence
<220> FEATURE:
<223> OTHER INFORMATION: Candidate Primer Pair Sets (Well & Plate levels)

<400> SEQUENCE: 399
ccggtcctct acgaccgcgg aac                                    23

<210> SEQ ID NO 400

```
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 400
gcctccatac gccactgtgc aca                                               23

<210> SEQ ID NO 401
<211> LENGTH: 20
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 401
aggcctggtt tgagctgccg                                                   20

<210> SEQ ID NO 402
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 402
tgtgcacagt ggcgtatgga ggc                                               23

<210> SEQ ID NO 403
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 403
aacctccgtc gtcgtaacag ctc                                               23

<210> SEQ ID NO 404
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 404
gtgtcttgca aagcagacgc agc                                               23

<210> SEQ ID NO 405
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 405
ggaaagttgg tgcacagtca acc                                               23

<210> SEQ ID NO 406
<211> LENGTH: 23
```

```
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 406
gcattcggca ctagcttacg tac                                             23

<210> SEQ ID NO 407
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 407
gctgcgtctg ctttgcaaga cac                                             23

<210> SEQ ID NO 408
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 408
gtacgtaagc tagtgccgaa tgc                                             23

<210> SEQ ID NO 409
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 409
acagaaatcc agaccggtga cac                                             23

<210> SEQ ID NO 410
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 410
ttgacgccgc aaataagatc tcc                                             23

<210> SEQ ID NO 411
<211> LENGTH: 22
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 411
acatcgccga cactttgcaa cg                                              22

<210> SEQ ID NO 412
<211> LENGTH: 22
<212> TYPE: DNA
```

```
<213> ORGANISM: Artificial Sequence
<220> FEATURE:
<223> OTHER INFORMATION: Candidate Primer Pair Sets (Well & Plate
      levels)

<400> SEQUENCE: 412
tccttgcaag ccttagcctt cc                                              22

<210> SEQ ID NO 413
<211> LENGTH: 23
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 413
ggagatctta tttgcggcgt caa                                             23

<210> SEQ ID NO 414
<211> LENGTH: 22
<212> TYPE: DNA
<213> ORGANISM: Artificial Sequence
<220> FEATURE:
<223> OTHER INFORMATION: Candidate Primer Pair Sets (Well & Plate
      levels)

<400> SEQUENCE: 414
ggaaggctaa ggcttgcaag ga                                              22

<210> SEQ ID NO 415
<211> LENGTH: 22
<212> TYPE: DNA
<213> ORGANISM: Artificial Sequence
<220> FEATURE:
<223> OTHER INFORMATION: Primer Pair Set 02

<400> SEQUENCE: 415
ctgcgactga gctcctgatt gg                                              22

<210> SEQ ID NO 416
<211> LENGTH: 22
<212> TYPE: DNA
<213> ORGANISM: Artificial Sequence
<220> FEATURE:
<223> OTHER INFORMATION: Primer Pair Set 02

<400> SEQUENCE: 416
cgtaggtgtt cgaattgcgc ct                                              22

<210> SEQ ID NO 417
<211> LENGTH: 23
<212> TYPE: DNA
<213> ORGANISM: Artificial Sequence
<220> FEATURE:
<223> OTHER INFORMATION: Primer Pair Set 02

<400> SEQUENCE: 417
attacgccta gacagtgcac gtc                                             23

<210> SEQ ID NO 418
<211> LENGTH: 23
<212> TYPE: DNA
<213> ORGANISM: Artificial Sequence
<220> FEATURE:
<223> OTHER INFORMATION: Primer Pair Set 02
```

```
<400> SEQUENCE: 418
gaccattgtg cacatacgcg acc                                           23

<210> SEQ ID NO 419
<211> LENGTH: 21
<212> TYPE: DNA
<213> ORGANISM: Artificial Sequence
<220> FEATURE:
<223> OTHER INFORMATION: Primer Pair Set 02

<400> SEQUENCE: 419
tccgccaccg caaactagtg c                                             21

<210> SEQ ID NO 420
<211> LENGTH: 21
<212> TYPE: DNA
<213> ORGANISM: Artificial Sequence
<220> FEATURE:
<223> OTHER INFORMATION: Primer Pair Set 02

<400> SEQUENCE: 420
gccaagcttc ctgaacggag c                                             21

<210> SEQ ID NO 421
<211> LENGTH: 23
<212> TYPE: DNA
<213> ORGANISM: Artificial Sequence
<220> FEATURE:
<223> OTHER INFORMATION: Primer Pair Set 02

<400> SEQUENCE: 421
aggtgatcaa ctccggcaga gtc                                           23

<210> SEQ ID NO 422
<211> LENGTH: 23
<212> TYPE: DNA
<213> ORGANISM: Artificial Sequence
<220> FEATURE:
<223> OTHER INFORMATION: Primer Pair Set 02

<400> SEQUENCE: 422
gtctgactag catgcaaggc acg                                           23

<210> SEQ ID NO 423
<211> LENGTH: 24
<212> TYPE: DNA
<213> ORGANISM: Artificial Sequence
<220> FEATURE:
<223> OTHER INFORMATION: Primer Pair Set 02

<400> SEQUENCE: 423
gctacgtagt caccggaact agcc                                          24

<210> SEQ ID NO 424
<211> LENGTH: 24
<212> TYPE: DNA
<213> ORGANISM: Artificial Sequence
<220> FEATURE:
<223> OTHER INFORMATION: Primer Pair Set 02

<400> SEQUENCE: 424
caatgattag gagcggtcga cgct                                          24

<210> SEQ ID NO 425
<211> LENGTH: 22
```

```
<212> TYPE: DNA
<213> ORGANISM: Artificial Sequence
<220> FEATURE:
<223> OTHER INFORMATION: Primer Pair Set 02

<400> SEQUENCE: 425
aggcgcaatt cgaacaccta cg                                          22

<210> SEQ ID NO 426
<211> LENGTH: 23
<212> TYPE: DNA
<213> ORGANISM: Artificial Sequence
<220> FEATURE:
<223> OTHER INFORMATION: Primer Pair Set 02

<400> SEQUENCE: 426
ggtcgcgtat gtgcacaatg gtc                                         23

<210> SEQ ID NO 427
<211> LENGTH: 21
<212> TYPE: DNA
<213> ORGANISM: Artificial Sequence
<220> FEATURE:
<223> OTHER INFORMATION: Primer Pair Set 02

<400> SEQUENCE: 427
gctccgttca ggaagcttgg c                                           21

<210> SEQ ID NO 428
<211> LENGTH: 23
<212> TYPE: DNA
<213> ORGANISM: Artificial Sequence
<220> FEATURE:
<223> OTHER INFORMATION: Primer Pair Set 02

<400> SEQUENCE: 428
cgtgccttgc atgctagtca gac                                         23

<210> SEQ ID NO 429
<211> LENGTH: 24
<212> TYPE: DNA
<213> ORGANISM: Artificial Sequence
<220> FEATURE:
<223> OTHER INFORMATION: Primer Pair Set 02

<400> SEQUENCE: 429
agcgtcgacc gctcctaatc attg                                        24

<210> SEQ ID NO 430
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 430 tggtat                                                             6

<210> SEQ ID NO 431
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 431
``` cctatc                                                                          6

<210> SEQ ID NO 432
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 432 gattgg                                                                          6

<210> SEQ ID NO 433
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 433 taggct                                                                          6

<210> SEQ ID NO 434
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 434 gctgct                                                                          6

<210> SEQ ID NO 435
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 435 gtctca                                                                          6

<210> SEQ ID NO 436
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 436 tgtatg                                                                          6

<210> SEQ ID NO 437
<211> LENGTH: 6
<212> TYPE: DNA
<213> ORGANISM: Artificial Sequence
<220> FEATURE:
<223> OTHER INFORMATION: ACAGAC

<400> SEQUENCE: 437 acagac                                                                          6

<210> SEQ ID NO 438
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 438 actagg                                                              6

<210> SEQ ID NO 439
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 439 accaat                                                              6

<210> SEQ ID NO 440
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 440 taactg                                                              6

<210> SEQ ID NO 441
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 441 gtgaaa                                                              6

<210> SEQ ID NO 442
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 442 tcaagc                                                              6

<210> SEQ ID NO 443
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 443 tacggc                                                              6

<210> SEQ ID NO 444
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 444 atagcg                                                              6

```
<210> SEQ ID NO 445
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 445 cagtcc                                                                    6

<210> SEQ ID NO 446
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 446 aacact                                                                    6

<210> SEQ ID NO 447
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 447 aagcag                                                                    6

<210> SEQ ID NO 448
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 448 ctactg                                                                    6

<210> SEQ ID NO 449
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 449 ggcgat                                                                    6

<210> SEQ ID NO 450
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 450 accttc                                                                    6

<210> SEQ ID NO 451
<211> LENGTH: 6
<212> TYPE: DNA
<213> ORGANISM: Artificial Sequence
<220> FEATURE:
<223> OTHER INFORMATION: Well Indexes for Primer Pair Design Set 02
```

```
<400> SEQUENCE: 451 tagagc                                                                     6

<210> SEQ ID NO 452
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 452 gcagca                                                                     6

<210> SEQ ID NO 453
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 453 tgtcag                                                                     6

<210> SEQ ID NO 454
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 454 acttag                                                                     6

<210> SEQ ID NO 455
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 455 ccaagt                                                                     6

<210> SEQ ID NO 456
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 456 cgcatc                                                                     6

<210> SEQ ID NO 457
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 457 ttgccg                                                                     6

<210> SEQ ID NO 458
```

-continued

<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 458 gaggtg                                                                  6

<210> SEQ ID NO 459
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 459 accgga                                                                  6

<210> SEQ ID NO 460
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 460 tttagc                                                                  6

<210> SEQ ID NO 461
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 461 ctggag                                                                  6

<210> SEQ ID NO 462
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 462 cctcct                                                                  6

<210> SEQ ID NO 463
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 463 gaaccg                                                                  6

<210> SEQ ID NO 464
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 464

```
cttgac                                                          6

<210> SEQ ID NO 465
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 465 agtggc                                                          6

<210> SEQ ID NO 466
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 466 gtcatg                                                          6

<210> SEQ ID NO 467
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 467 gttctc                                                          6

<210> SEQ ID NO 468
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 468 agcagg                                                          6

<210> SEQ ID NO 469
<211> LENGTH: 6
<212> TYPE: DNA
<213> ORGANISM: Artificial Sequence
<220> FEATURE:
<223> OTHER INFORMATION: Well Indexes for Primer Pair Design Set 02

<400> SEQUENCE: 469 ggtacg                                                          6

<210> SEQ ID NO 470
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 470 ctttccga                                                        8

<210> SEQ ID NO 471
<211> LENGTH: 8
```

```
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 471 agtagcta                                                              8

<210> SEQ ID NO 472
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 472 gttcagta                                                              8

<210> SEQ ID NO 473
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 473 tcctagtc                                                              8

<210> SEQ ID NO 474
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 474 ggtctgct                                                              8

<210> SEQ ID NO 475
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 475 caaaggta                                                              8

<210> SEQ ID NO 476
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 476 gatctcat                                                              8

<210> SEQ ID NO 477
<211> LENGTH: 8
<212> TYPE: DNA
```

```
<213> ORGANISM: Artificial Sequence
<220> FEATURE:
<223> OTHER INFORMATION: Document and Plate Indexes for Primer Pair
      Design Set 02

<400> SEQUENCE: 477 aaggagca                                                                  8

<210> SEQ ID NO 478
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 478 tcgaacac                                                                  8

<210> SEQ ID NO 479
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 479 gcgttctc                                                                  8

<210> SEQ ID NO 480
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 480 accgctga                                                                  8

<210> SEQ ID NO 481
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 481 tggtgcta                                                                  8

<210> SEQ ID NO 482
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 482 gtcgagct                                                                  8

<210> SEQ ID NO 483
<211> LENGTH: 8
<212> TYPE: DNA
<213> ORGANISM: Artificial Sequence
```

```
<220> FEATURE:
<223> OTHER INFORMATION: Document and Plate Indexes for Primer Pair
      Design Set 02

<400> SEQUENCE: 483 taccgaag                                                              8

<210> SEQ ID NO 484
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 484 cgacctca                                                              8

<210> SEQ ID NO 485
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 485 tctatcgg                                                              8

<210> SEQ ID NO 486
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 486 tcttctcg                                                              8

<210> SEQ ID NO 487
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 487 ttcacgct                                                              8

<210> SEQ ID NO 488
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 488 aggcttcg                                                              8

<210> SEQ ID NO 489
<211> LENGTH: 8
<212> TYPE: DNA
<213> ORGANISM: Artificial Sequence
<220> FEATURE:
```

```
<223> OTHER INFORMATION: Document and Plate Indexes for Primer Pair
      Design Set 02

<400> SEQUENCE: 489 aacatcca                                                                  8

<210> SEQ ID NO 490
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 490 agtccaaa                                                                  8

<210> SEQ ID NO 491
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 491 ccgatatg                                                                  8

<210> SEQ ID NO 492
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 492 tatgaggc                                                                  8

<210> SEQ ID NO 493
<211> LENGTH: 8
<212> TYPE: DNA
<213> ORGANISM: Artificial Sequence
<220> FEATURE:
<223> OTHER INFORMATION: Document and Plate Indexes for Primer Pair
      Design Set 02

<400> SEQUENCE: 493 ctccttta                                                                  8

<210> SEQ ID NO 494
<211> LENGTH: 24
<212> TYPE: DNA
<213> ORGANISM: Artificial Sequence
<220> FEATURE:
<223> OTHER INFORMATION: Primer Pair Set 01

<400> SEQUENCE: 494
atcctcaaca ggcgcatctc aacc                                               24

<210> SEQ ID NO 495
<211> LENGTH: 24
<212> TYPE: DNA
<213> ORGANISM: Artificial Sequence
<220> FEATURE:
<223> OTHER INFORMATION: Primer Pair Set 01
```

-continued

<400> SEQUENCE: 495
gttcaggcca ttgcgcagat gtta                                          24

<210> SEQ ID NO 496
<211> LENGTH: 23
<212> TYPE: DNA
<213> ORGANISM: Artificial Sequence
<220> FEATURE:
<223> OTHER INFORMATION: Primer Pair Set 01

<400> SEQUENCE: 496
tgcgaacgtc cattcgtcca tgc                                           23

<210> SEQ ID NO 497
<211> LENGTH: 23
<212> TYPE: DNA
<213> ORGANISM: Artificial Sequence
<220> FEATURE:
<223> OTHER INFORMATION: Primer Pair Set 01

<400> SEQUENCE: 497
cagctcctgg agctaggcca gaa                                           23

<210> SEQ ID NO 498
<211> LENGTH: 23
<212> TYPE: DNA
<213> ORGANISM: Artificial Sequence
<220> FEATURE:
<223> OTHER INFORMATION: Primer Pair Set 01

<400> SEQUENCE: 498
ctcaatggcc aacatgcgct gtg                                           23

<210> SEQ ID NO 499
<211> LENGTH: 23
<212> TYPE: DNA
<213> ORGANISM: Artificial Sequence
<220> FEATURE:
<223> OTHER INFORMATION: Primer Pair Set 01

<400> SEQUENCE: 499
gacctacgaa taaggagcgc tgg                                           23

<210> SEQ ID NO 500
<211> LENGTH: 24
<212> TYPE: DNA
<213> ORGANISM: Artificial Sequence
<220> FEATURE:
<223> OTHER INFORMATION: Primer Pair Set 01

<400> SEQUENCE: 500
gcacgtggta cttctagcaa tgcc                                          24

<210> SEQ ID NO 501
<211> LENGTH: 24
<212> TYPE: DNA
<213> ORGANISM: Artificial Sequence
<220> FEATURE:
<223> OTHER INFORMATION: Primer Pair Set 01

<400> SEQUENCE: 501
gctgtccgga gtgctgtaga tgtc                                          24

<210> SEQ ID NO 502
<211> LENGTH: 21

```
<212> TYPE: DNA
<213> ORGANISM: Artificial Sequence
<220> FEATURE:
<223> OTHER INFORMATION: Primer Pair Set 01

<400> SEQUENCE: 502
accagccttt cgacagccta c                                              21

<210> SEQ ID NO 503
<211> LENGTH: 21
<212> TYPE: DNA
<213> ORGANISM: Artificial Sequence
<220> FEATURE:
<223> OTHER INFORMATION: Primer Pair Set 01

<400> SEQUENCE: 503
cggtagcttg accattcgcg g                                              21

<210> SEQ ID NO 504
<211> LENGTH: 24
<212> TYPE: DNA
<213> ORGANISM: Artificial Sequence
<220> FEATURE:
<223> OTHER INFORMATION: Primer Pair Set 01

<400> SEQUENCE: 504
taacatctgc gcaatggcct gaac                                           24

<210> SEQ ID NO 505
<211> LENGTH: 23
<212> TYPE: DNA
<213> ORGANISM: Artificial Sequence
<220> FEATURE:
<223> OTHER INFORMATION: Primer Pair Set 01

<400> SEQUENCE: 505
ttctggccta gctccaggag ctg                                            23

<210> SEQ ID NO 506
<211> LENGTH: 23
<212> TYPE: DNA
<213> ORGANISM: Artificial Sequence
<220> FEATURE:
<223> OTHER INFORMATION: Primer Pair Set 01

<400> SEQUENCE: 506
ccagcgctcc ttattcgtag gtc                                            23

<210> SEQ ID NO 507
<211> LENGTH: 24
<212> TYPE: DNA
<213> ORGANISM: Artificial Sequence
<220> FEATURE:
<223> OTHER INFORMATION: Primer Pair Set 01

<400> SEQUENCE: 507
gacatctaca gcactccgga cagc                                           24

<210> SEQ ID NO 508
<211> LENGTH: 21
<212> TYPE: DNA
<213> ORGANISM: Artificial Sequence
<220> FEATURE:
<223> OTHER INFORMATION: Primer Pair Set 01

<400> SEQUENCE: 508
```

```
ccgcgaatgg tcaagctacc g                                            21
```

<210> SEQ ID NO 509
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 509

```
tcagta                                                              6
```

<210> SEQ ID NO 510
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 510

```
tactgt                                                              6
```

<210> SEQ ID NO 511
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 511

```
aaggat                                                              6
```

<210> SEQ ID NO 512
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 512

```
gatagt                                                              6
```

<210> SEQ ID NO 513
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 513

```
ccagtc                                                              6
```

<210> SEQ ID NO 514
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 514

```
taagcc                                                              6
```

<210> SEQ ID NO 515
<211> LENGTH: 6
<212> TYPE: DNA
<213> ORGANISM: Artificial Sequence

```
<220> FEATURE:
<223> OTHER INFORMATION: Indexes for Primer Pair Design Set 01

<400> SEQUENCE: 515 agaccg                                                                          6

<210> SEQ ID NO 516
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 516 ctagac                                                                          6

<210> SEQ ID NO 517
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 517 tggact                                                                          6

<210> SEQ ID NO 518
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 518 gtcgat                                                                          6

<210> SEQ ID NO 519
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 519 taacag                                                                          6

<210> SEQ ID NO 520
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 520 agtcag                                                                          6

<210> SEQ ID NO 521
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 521 ctatgg                                                                          6
```

<210> SEQ ID NO 522
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 522 aagcgg                                                                     6

<210> SEQ ID NO 523
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 523 aaacga                                                                     6

<210> SEQ ID NO 524
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 524 ctgaga                                                                     6

<210> SEQ ID NO 525
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 525 cctgtg                                                                     6

<210> SEQ ID NO 526
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 526 gcgatc                                                                     6

<210> SEQ ID NO 527
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 527 ggctga                                                                     6

<210> SEQ ID NO 528
<211> LENGTH: 6
<212> TYPE: DNA
<213> ORGANISM: Artificial Sequence
<220> FEATURE:
<223> OTHER INFORMATION: Indexes for Primer Pair Design Set 01

```
<400> SEQUENCE: 528 cgtttc                                                              6

<210> SEQ ID NO 529
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 529 ggaaga                                                              6

<210> SEQ ID NO 530
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 530 tacgta                                                              6

<210> SEQ ID NO 531
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 531 tgcctc                                                              6

<210> SEQ ID NO 532
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 532 ttgcag                                                              6

<210> SEQ ID NO 533
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 533 tctagc                                                              6

<210> SEQ ID NO 534
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 534 atccgc                                                              6

<210> SEQ ID NO 535
```

-continued

```
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 535 cgctac                                                                      6

<210> SEQ ID NO 536
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 536 ccacag                                                                      6

<210> SEQ ID NO 537
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 537 gtaact                                                                      6

<210> SEQ ID NO 538
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 538 ccaaga                                                                      6

<210> SEQ ID NO 539
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 539 ggttct                                                                      6

<210> SEQ ID NO 540
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 540 ccgaca                                                                      6

<210> SEQ ID NO 541
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 541
```

```
gccgaa                                                                     6

<210> SEQ ID NO 542
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 542 ccacct                                                                     6

<210> SEQ ID NO 543
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 543 acctgg                                                                     6

<210> SEQ ID NO 544
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 544 gctatg                                                                     6

<210> SEQ ID NO 545
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 545 tcgtca                                                                     6

<210> SEQ ID NO 546
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 546 cgaatt                                                                     6

<210> SEQ ID NO 547
<211> LENGTH: 6
<212> TYPE: DNA
<213> ORGANISM: Artificial Sequence
<220> FEATURE:
<223> OTHER INFORMATION: Indexes for Primer Pair Design Set 01

<400> SEQUENCE: 547 cgtcct                                                                     6

<210> SEQ ID NO 548
<211> LENGTH: 6
<212> TYPE: DNA
```

```
<213> ORGANISM: Artificial Sequence
<220> FEATURE:
<223> OTHER INFORMATION: Indexes for Primer Pair Design Set 01

<400> SEQUENCE: 548 gatgta                                                              6

<210> SEQ ID NO 549
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 549 tgtctgag                                                            8

<210> SEQ ID NO 550
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 550 gctatgga                                                            8

<210> SEQ ID NO 551
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 551 gatagcga                                                            8

<210> SEQ ID NO 552
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 552 ttcggcga                                                            8

<210> SEQ ID NO 553
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 553 cgtaattg                                                            8

<210> SEQ ID NO 554
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 554 agttcagg                                                            8
```

<210> SEQ ID NO 555
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 555 tggagtgt                                                                 8

<210> SEQ ID NO 556
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 556 gttctcgt                                                                 8

<210> SEQ ID NO 557
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 557 ctcggaac                                                                 8

<210> SEQ ID NO 558
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 558 ttgcttag                                                                 8

<210> SEQ ID NO 559
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 559 ccaagtgc                                                                 8

<210> SEQ ID NO 560
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 560 tctcgtta                                                                 8

<210> SEQ ID NO 561
<211> LENGTH: 8
<212> TYPE: DNA
<213> ORGANISM: Artificial Sequence
<220> FEATURE:

```
<223> OTHER INFORMATION: Indexes for Primer Pair Design Set 01

<400> SEQUENCE: 561 gtatcgag                                                                     8

<210> SEQ ID NO 562
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 562 tgaatagg                                                                     8

<210> SEQ ID NO 563
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 563 atccttct                                                                     8

<210> SEQ ID NO 564
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 564 tagtcgga                                                                     8

<210> SEQ ID NO 565
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 565 gagcctct                                                                     8

<210> SEQ ID NO 566
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 566 tagtatgc                                                                     8

<210> SEQ ID NO 567
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 567 ctcgattt                                                                     8
```

```
<210> SEQ ID NO 568
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 568 tcaacgtg                                                                    8

<210> SEQ ID NO 569
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 569 cctccaaa                                                                    8

<210> SEQ ID NO 570
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 570 cctggtct                                                                    8

<210> SEQ ID NO 571
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 571 ttgcgcca                                                                    8

<210> SEQ ID NO 572
<211> LENGTH: 8
<212> TYPE: DNA
<213> ORGANISM: Artificial Sequence
<220> FEATURE:
<223> OTHER INFORMATION: Indexes for Primer Pair Design Set 01

<400> SEQUENCE: 572 gtggaata                                                                    8

<210> SEQ ID NO 573
<211> LENGTH: 22
<212> TYPE: DNA
<213> ORGANISM: Artificial Sequence
<220> FEATURE:
<223> OTHER INFORMATION: Primer Pair Set 03

<400> SEQUENCE: 573
cggccgcacg attcatgtgc ag                                                   22

<210> SEQ ID NO 574
<211> LENGTH: 22
<212> TYPE: DNA
<213> ORGANISM: Artificial Sequence
<220> FEATURE:
<223> OTHER INFORMATION: Primer Pair Set 03
```

```
<400> SEQUENCE: 574
gtctgacgcg tagtcacgag ca                                           22

<210> SEQ ID NO 575
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 575
tctcgcactg tacatcgcac tcc                                          23

<210> SEQ ID NO 576
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 576
cggtatgctc gagctagtat gct                                          23

<210> SEQ ID NO 577
<211> LENGTH: 24
<212> TYPE: DNA
<213> ORGANISM: Artificial Sequence
<220> FEATURE:
<223> OTHER INFORMATION: Primer Pair Set 03

<400> SEQUENCE: 577
gaaactccgg tgtctatggc caag                                         24

<210> SEQ ID NO 578
<211> LENGTH: 24
<212> TYPE: DNA
<213> ORGANISM: Artificial Sequence
<220> FEATURE:
<223> OTHER INFORMATION: Primer Pair Set 03

<400> SEQUENCE: 578
ctgtgatgcg gtgatggaag gttc                                         24

<210> SEQ ID NO 579
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 579
ggatccaacc tgtgacacct tgc                                          23

<210> SEQ ID NO 580
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 580
ctcacaacgt taggagcttt gga                                          23

<210> SEQ ID NO 581
<211> LENGTH: 23
```

```
<212> TYPE: DNA
<213> ORGANISM: Artificial Sequence
<220> FEATURE:
<223> OTHER INFORMATION: primer pair set 03

<400> SEQUENCE: 581
gcgttcacct gccacgttca ctc                                              23

<210> SEQ ID NO 582
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 582
gtgaccgtga ttgtgcgcag ttt                                              23

<210> SEQ ID NO 583
<211> LENGTH: 22
<212> TYPE: DNA
<213> ORGANISM: Artificial Sequence
<220> FEATURE:
<223> OTHER INFORMATION: Primer Pair Set 03

<400> SEQUENCE: 583
tgctcgtgac tacgcgtcag ac                                               22

<210> SEQ ID NO 584
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 584
agcatactag ctcgagcata ccg                                              23

<210> SEQ ID NO 585
<211> LENGTH: 24
<212> TYPE: DNA
<213> ORGANISM: Artificial Sequence
<220> FEATURE:
<223> OTHER INFORMATION: Primer Pair Set 03

<400> SEQUENCE: 585
gaaccttcca tcaccgcatc acag                                             24

<210> SEQ ID NO 586
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 586
tccaaagctc ctaacgttgt gag                                              23

<210> SEQ ID NO 587
<211> LENGTH: 23
<212> TYPE: DNA
<213> ORGANISM: Artificial Sequence
<220> FEATURE:
<223> OTHER INFORMATION: Primer Pair Set 03

<400> SEQUENCE: 587
```

-continued

```
aaactgcgca caatcacggt cac                                              23

<210> SEQ ID NO 588
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 588 gcagac                                                                  6

<210> SEQ ID NO 589
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 589 tcgcaa                                                                  6

<210> SEQ ID NO 590
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 590 tgaggc                                                                  6

<210> SEQ ID NO 591
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 591 ctcgga                                                                  6

<210> SEQ ID NO 592
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 592 gtcgtg                                                                  6

<210> SEQ ID NO 593
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 593 aaactg                                                                  6

<210> SEQ ID NO 594
<211> LENGTH: 6
<212> TYPE: DNA
<213> ORGANISM: Artificial Sequence
```

```
<220> FEATURE:
<223> OTHER INFORMATION: Indexes for Primer Pair Design Set 03

<400> SEQUENCE: 594 gcacct                                                                      6

<210> SEQ ID NO 595
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 595 actgag                                                                      6

<210> SEQ ID NO 596
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 596 aacgtc                                                                      6

<210> SEQ ID NO 597
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 597 accggt                                                                      6

<210> SEQ ID NO 598
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 598 gttcct                                                                      6

<210> SEQ ID NO 599
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 599 ctaggc                                                                      6

<210> SEQ ID NO 600
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 600 cgccaa                                                                      6
```

```
<210> SEQ ID NO 601
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 601 tggatg                                                                     6

<210> SEQ ID NO 602
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 602 tccgaa                                                                     6

<210> SEQ ID NO 603
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 603 ccttta                                                                     6

<210> SEQ ID NO 604
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 604 gaccga                                                                     6

<210> SEQ ID NO 605
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 605 acagca                                                                     6

<210> SEQ ID NO 606
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 606 acgtag                                                                     6

<210> SEQ ID NO 607
<211> LENGTH: 6
<212> TYPE: DNA
<213> ORGANISM: Artificial Sequence
<220> FEATURE:
<223> OTHER INFORMATION: Indexes for Primer Pair Design Set 03
```

-continued

```
<400> SEQUENCE: 607 gcgatt                                                                    6

<210> SEQ ID NO 608
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 608 tgtcac                                                                    6

<210> SEQ ID NO 609
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 609 aacaac                                                                    6

<210> SEQ ID NO 610
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 610 gacgta                                                                    6

<210> SEQ ID NO 611
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 611 gcggaa                                                                    6

<210> SEQ ID NO 612
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 612 tcggag                                                                    6

<210> SEQ ID NO 613
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 613 cgcgtt                                                                    6

<210> SEQ ID NO 614
```

```
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 614 tcttgc                                                                     6

<210> SEQ ID NO 615
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 615 gcattt                                                                     6

<210> SEQ ID NO 616
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 616 aaagcg                                                                     6

<210> SEQ ID NO 617
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 617 agcatg                                                                     6

<210> SEQ ID NO 618
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 618 ctgtga                                                                     6

<210> SEQ ID NO 619
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 619 aggagg                                                                     6

<210> SEQ ID NO 620
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 620
``` tgagat                                                                          6

<210> SEQ ID NO 621
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 621 ctactg                                                                          6

<210> SEQ ID NO 622
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 622 atcgat                                                                          6

<210> SEQ ID NO 623
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 623 aacact                                                                          6

<210> SEQ ID NO 624
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 624 catagt                                                                          6

<210> SEQ ID NO 625
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 625 gcctag                                                                          6

<210> SEQ ID NO 626
<211> LENGTH: 6
<212> TYPE: DNA
<213> ORGANISM: Artificial Sequence
<220> FEATURE:
<223> OTHER INFORMATION: Indexes for Primer Pair Design Set 03

<400> SEQUENCE: 626 agaaga                                                                          6

<210> SEQ ID NO 627
<211> LENGTH: 6
<212> TYPE: DNA

```
<213> ORGANISM: Artificial Sequence
<220> FEATURE:
<223> OTHER INFORMATION: Indexes for Primer Pair Design Set 03

<400> SEQUENCE: 627 tcagtt                                                                    6

<210> SEQ ID NO 628
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 628 tacctaac                                                                  8

<210> SEQ ID NO 629
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 629 cttctatg                                                                  8

<210> SEQ ID NO 630
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 630 cgataccg                                                                  8

<210> SEQ ID NO 631
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 631 catcagct                                                                  8

<210> SEQ ID NO 632
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 632 gtcaaacg                                                                  8

<210> SEQ ID NO 633
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 633 gtctacgg                                                                  8
```

```
<210> SEQ ID NO 634
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 634 gtttagct                                                                 8

<210> SEQ ID NO 635
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 635 ttccagca                                                                 8

<210> SEQ ID NO 636
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 636 agctaaac                                                                 8

<210> SEQ ID NO 637
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 637 atctaggt                                                                 8

<210> SEQ ID NO 638
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 638 caccatgt                                                                 8

<210> SEQ ID NO 639
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 639 tgctgata                                                                 8

<210> SEQ ID NO 640
<211> LENGTH: 8
<212> TYPE: DNA
<213> ORGANISM: Artificial Sequence
<220> FEATURE:
```

<223> OTHER INFORMATION: Indexes for Primer Pair Design Set 03

<400> SEQUENCE: 640 tggtgcgt                                                                    8

<210> SEQ ID NO 641
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 641 actacaag                                                                    8

<210> SEQ ID NO 642
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 642 atcagcag                                                                    8

<210> SEQ ID NO 643
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 643 atccgtaa                                                                    8

<210> SEQ ID NO 644
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 644 aagagtag                                                                    8

<210> SEQ ID NO 645
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 645 ttatctgc                                                                    8

<210> SEQ ID NO 646
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 646 atcggagc                                                                    8

```
<210> SEQ ID NO 647
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 647 ggtggatc                                                                 8

<210> SEQ ID NO 648
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 648 ataccgct                                                                 8

<210> SEQ ID NO 649
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 649 accacgga                                                                 8

<210> SEQ ID NO 650
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 650 acacgctc                                                                 8

<210> SEQ ID NO 651
<211> LENGTH: 8
<212> TYPE: DNA
<213> ORGANISM: Artificial Sequence
<220> FEATURE:
<223> OTHER INFORMATION: Indexes for Primer Pair Design Set 03

<400> SEQUENCE: 651 caattcgc                                                                 8

<210> SEQ ID NO 652
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 652
gcaccgttcc actctaccgg ttc                                               23

<210> SEQ ID NO 653
<211> LENGTH: 23
<212> TYPE: DNA
<213> ORGANISM: Artificial Sequence
<220> FEATURE:
<223> OTHER INFORMATION: Primer Pair Set 04
```

```
<400> SEQUENCE: 653
ctaagctcgc ctaggtcgct tac                                        23

<210> SEQ ID NO 654
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 654
aatcgacaac cgcgttacct tgc                                        23

<210> SEQ ID NO 655
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 655
gaggatccaa gatcggcgtg ctt                                        23

<210> SEQ ID NO 656
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 656
gcacgcactg tatttgcgca ctc                                        23

<210> SEQ ID NO 657
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 657
gtctgatcag gcggaacgaa tgt                                        23

<210> SEQ ID NO 658
<211> LENGTH: 24
<212> TYPE: DNA
<213> ORGANISM: Artificial Sequence
<220> FEATURE:
<223> OTHER INFORMATION: Primer Pair Set 04

<400> SEQUENCE: 658
cggatccagc ttgagctttg catc                                       24

<210> SEQ ID NO 659
<211> LENGTH: 24
<212> TYPE: DNA
<213> ORGANISM: Artificial Sequence
<220> FEATURE:
<223> OTHER INFORMATION: Primer Pair Set 04

<400> SEQUENCE: 659
cagtaatcta cacgcagcgc tcat                                       24

<210> SEQ ID NO 660
<211> LENGTH: 23
```

-continued

```
<212> TYPE: DNA
<213> ORGANISM: Artificial Sequence
<220> FEATURE:
<223> OTHER INFORMATION: Primer Pair Set 04

<400> SEQUENCE: 660
cacctgtatg aggtaccgac cag                                              23

<210> SEQ ID NO 661
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 661
gcaagagtct atgttcggcg tgt                                              23

<210> SEQ ID NO 662
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 662
gtaagcgacc taggcgagct tag                                              23

<210> SEQ ID NO 663
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 663
aagcacgccg atcttggatc ctc                                              23

<210> SEQ ID NO 664
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 664
acattcgttc cgcctgatca gac                                              23

<210> SEQ ID NO 665
<211> LENGTH: 24
<212> TYPE: DNA
<213> ORGANISM: Artificial Sequence
<220> FEATURE:
<223> OTHER INFORMATION: Primer Pair Set 04

<400> SEQUENCE: 665
atgagcgctg cgtgtagatt actg                                             24

<210> SEQ ID NO 666
<211> LENGTH: 23
<212> TYPE: DNA
<213> ORGANISM: Artificial Sequence
<220> FEATURE:
<223> OTHER INFORMATION: Primer Pair Set 04

<400> SEQUENCE: 666
```

```
acacgccgaa catagactct tgc                                          23
```

<210> SEQ ID NO 667
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 667

```
tcagcg                                                              6
```

<210> SEQ ID NO 668
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 668

```
tgttca                                                              6
```

<210> SEQ ID NO 669
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 669

```
taatcc                                                              6
```

<210> SEQ ID NO 670
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 670

```
ttaggc                                                              6
```

<210> SEQ ID NO 671
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 671

```
caaggc                                                              6
```

<210> SEQ ID NO 672
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 672

```
caatac                                                              6
```

<210> SEQ ID NO 673
<211> LENGTH: 6
<212> TYPE: DNA
<213> ORGANISM: Artificial Sequence

```
<220> FEATURE:
<223> OTHER INFORMATION: Indexes for Primer Pair Design Set 04

<400> SEQUENCE: 673 ggcatc                                                                          6

<210> SEQ ID NO 674
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 674 accggt                                                                          6

<210> SEQ ID NO 675
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 675 ttgagc                                                                          6

<210> SEQ ID NO 676
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 676 tcatac                                                                          6

<210> SEQ ID NO 677
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 677 actgtt                                                                          6

<210> SEQ ID NO 678
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 678 tgccaa                                                                          6

<210> SEQ ID NO 679
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 679 ggacaa                                                                          6
```

```
<210> SEQ ID NO 680
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 680 gagata                                                                    6

<210> SEQ ID NO 681
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 681 caatca                                                                    6

<210> SEQ ID NO 682
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 682 acatca                                                                    6

<210> SEQ ID NO 683
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 683 tttcag                                                                    6

<210> SEQ ID NO 684
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 684 cgatga                                                                    6

<210> SEQ ID NO 685
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 685 tgtcct                                                                    6

<210> SEQ ID NO 686
<211> LENGTH: 6
<212> TYPE: DNA
<213> ORGANISM: Artificial Sequence
<220> FEATURE:
<223> OTHER INFORMATION: Indexes for Primer Pair Design Set 04
```

```
<400> SEQUENCE: 686 tagact                                                              6

<210> SEQ ID NO 687
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 687 catttc                                                              6

<210> SEQ ID NO 688
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 688 gacctg                                                              6

<210> SEQ ID NO 689
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 689 agcgga                                                              6

<210> SEQ ID NO 690
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 690 gttctg                                                              6

<210> SEQ ID NO 691
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 691 ctctgt                                                              6

<210> SEQ ID NO 692
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 692 cctaaa                                                              6

<210> SEQ ID NO 693
```

```
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 693 cgaagt                                                                    6

<210> SEQ ID NO 694
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 694 ttcgat                                                                    6

<210> SEQ ID NO 695
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 695 ctagtg                                                                    6

<210> SEQ ID NO 696
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 696 ggagga                                                                    6

<210> SEQ ID NO 697
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 697 tcggta                                                                    6

<210> SEQ ID NO 698
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 698 ccaggt                                                                    6

<210> SEQ ID NO 699
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 699
``` tatctg                                                                          6

<210> SEQ ID NO 700
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 700 cgttac                                                                          6

<210> SEQ ID NO 701
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 701 ccttta                                                                          6

<210> SEQ ID NO 702
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 702 aggatg                                                                          6

<210> SEQ ID NO 703
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 703 gtcata                                                                          6

<210> SEQ ID NO 704
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 704 atagag                                                                          6

<210> SEQ ID NO 705
<211> LENGTH: 6
<212> TYPE: DNA
<213> ORGANISM: Artificial Sequence
<220> FEATURE:
<223> OTHER INFORMATION: Indexes for Primer Pair Design Set 04

<400> SEQUENCE: 705 gctgtg                                                                          6

<210> SEQ ID NO 706
<211> LENGTH: 6
<212> TYPE: DNA

```
<213> ORGANISM: Artificial Sequence
<220> FEATURE:
<223> OTHER INFORMATION: Indexes for Primer Pair Design Set 04

<400> SEQUENCE: 706 gaagag                                                                    6

<210> SEQ ID NO 707
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 707 ccactatc                                                                  8

<210> SEQ ID NO 708
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 708 ccttggtg                                                                  8

<210> SEQ ID NO 709
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 709 actaccgc                                                                  8

<210> SEQ ID NO 710
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 710 ctttaacc                                                                  8

<210> SEQ ID NO 711
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 711 actaagtg                                                                  8

<210> SEQ ID NO 712
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 712 gcgtgtca                                                                  8
```

-continued

```
<210> SEQ ID NO 713
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 713 acatgtcg                                                                  8

<210> SEQ ID NO 714
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 714 tcgtattc                                                                  8

<210> SEQ ID NO 715
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 715 gctgctga                                                                  8

<210> SEQ ID NO 716
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 716 attcttcc                                                                  8

<210> SEQ ID NO 717
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 717 ggctagta                                                                  8

<210> SEQ ID NO 718
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 718 actagact                                                                  8

<210> SEQ ID NO 719
<211> LENGTH: 8
<212> TYPE: DNA
<213> ORGANISM: Artificial Sequence
<220> FEATURE:
```

-continued

<223> OTHER INFORMATION: Indexes for Primer Pair Design Set 04

<400> SEQUENCE: 719 aaggtcgt                                                                8

<210> SEQ ID NO 720
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 720 ttaagtgg                                                                8

<210> SEQ ID NO 721
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 721 ccgttacc                                                                8

<210> SEQ ID NO 722
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 722 ctatctcg                                                                8

<210> SEQ ID NO 723
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 723 agttagct                                                                8

<210> SEQ ID NO 724
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 724 catatcgt                                                                8

<210> SEQ ID NO 725
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 725 ttgacaga                                                                8

```
<210> SEQ ID NO 726
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 726 gagatctg                                                                   8

<210> SEQ ID NO 727
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 727 gccagtga                                                                   8

<210> SEQ ID NO 728
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 728 gtgaccaa                                                                   8

<210> SEQ ID NO 729
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 729 gtctcctg                                                                   8

<210> SEQ ID NO 730
<211> LENGTH: 8
<212> TYPE: DNA
<213> ORGANISM: Artificial Sequence
<220> FEATURE:
<223> OTHER INFORMATION: Indexes for Primer Pair Design Set 04

<400> SEQUENCE: 730 gatcggat                                                                   8

<210> SEQ ID NO 731
<211> LENGTH: 23
<212> TYPE: DNA
<213> ORGANISM: Artificial Sequence
<220> FEATURE:
<223> OTHER INFORMATION: Primer Pair Set 05

<400> SEQUENCE: 731
cctcggtttc gaaccatctg acg                                                 23

<210> SEQ ID NO 732
<211> LENGTH: 23
<212> TYPE: DNA
<213> ORGANISM: Artificial Sequence
<220> FEATURE:
<223> OTHER INFORMATION: Primer Pair Set 05
```

```
<400> SEQUENCE: 732
gtgcatatgc tgacgaagta gcg                                              23

<210> SEQ ID NO 733
<211> LENGTH: 22
<212> TYPE: DNA
<213> ORGANISM: Artificial Sequence
<220> FEATURE:
<223> OTHER INFORMATION: Primer Pair Set 05

<400> SEQUENCE: 733
gtgccactcc atacgtgaga cg                                               22

<210> SEQ ID NO 734
<211> LENGTH: 22
<212> TYPE: DNA
<213> ORGANISM: Artificial Sequence
<220> FEATURE:
<223> OTHER INFORMATION: Primer Pair Set 05

<400> SEQUENCE: 734
gatgctatga agactgccgc gg                                               22

<210> SEQ ID NO 735
<211> LENGTH: 24
<212> TYPE: DNA
<213> ORGANISM: Artificial Sequence
<220> FEATURE:
<223> OTHER INFORMATION: Primer Pair Set 05

<400> SEQUENCE: 735
catgtacact ccgctttctg gcta                                             24

<210> SEQ ID NO 736
<211> LENGTH: 24
<212> TYPE: DNA
<213> ORGANISM: Artificial Sequence
<220> FEATURE:
<223> OTHER INFORMATION: Primer Pair Set 05

<400> SEQUENCE: 736
ggaaaggagc tgcgtatgag ctgc                                             24

<210> SEQ ID NO 737
<211> LENGTH: 21
<212> TYPE: DNA
<213> ORGANISM: Artificial Sequence
<220> FEATURE:
<223> OTHER INFORMATION: Primer Pair Set 05

<400> SEQUENCE: 737
cagctggctt tcaccaatgc c                                                21

<210> SEQ ID NO 738
<211> LENGTH: 21
<212> TYPE: DNA
<213> ORGANISM: Artificial Sequence
<220> FEATURE:
<223> OTHER INFORMATION: Primer Pair Set 05

<400> SEQUENCE: 738
cgacacgact ttgccaagag c                                                21

<210> SEQ ID NO 739
<211> LENGTH: 21
```

```
<212> TYPE: DNA
<213> ORGANISM: Artificial Sequence
<220> FEATURE:
<223> OTHER INFORMATION: Primer Pair Set 05

<400> SEQUENCE: 739
tgtgcgctac tggacctcga t                                              21

<210> SEQ ID NO 740
<211> LENGTH: 21
<212> TYPE: DNA
<213> ORGANISM: Artificial Sequence
<220> FEATURE:
<223> OTHER INFORMATION: Primer Pair Set 05

<400> SEQUENCE: 740
ctggaggcgg tggcgtctag a                                              21

<210> SEQ ID NO 741
<211> LENGTH: 23
<212> TYPE: DNA
<213> ORGANISM: Artificial Sequence
<220> FEATURE:
<223> OTHER INFORMATION: Primer Pair Set 05

<400> SEQUENCE: 741
cgctacttcg tcagcatatg cac                                            23

<210> SEQ ID NO 742
<211> LENGTH: 22
<212> TYPE: DNA
<213> ORGANISM: Artificial Sequence
<220> FEATURE:
<223> OTHER INFORMATION: Primer Pair Set 05

<400> SEQUENCE: 742
ccgcggcagt cttcatagca tc                                             22

<210> SEQ ID NO 743
<211> LENGTH: 24
<212> TYPE: DNA
<213> ORGANISM: Artificial Sequence
<220> FEATURE:
<223> OTHER INFORMATION: Primer Pair Set 05

<400> SEQUENCE: 743
gcagctcata cgcagctcct ttcc                                           24

<210> SEQ ID NO 744
<211> LENGTH: 21
<212> TYPE: DNA
<213> ORGANISM: Artificial Sequence
<220> FEATURE:
<223> OTHER INFORMATION: Primer Pair Set 05

<400> SEQUENCE: 744
gctcttggca aagtcgtgtc g                                              21

<210> SEQ ID NO 745
<211> LENGTH: 21
<212> TYPE: DNA
<213> ORGANISM: Artificial Sequence
<220> FEATURE:
<223> OTHER INFORMATION: Primer Pair Set 05

<400> SEQUENCE: 745
```

```
tctagacgcc accgcctcca g                                              21
```

<210> SEQ ID NO 746
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 746

```
gagcct                                                                6
```

<210> SEQ ID NO 747
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 747

```
ccgact                                                                6
```

<210> SEQ ID NO 748
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 748

```
acggaa                                                                6
```

<210> SEQ ID NO 749
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 749

```
tttcag                                                                6
```

<210> SEQ ID NO 750
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 750

```
aagctt                                                                6
```

<210> SEQ ID NO 751
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 751

```
ccgtac                                                                6
```

<210> SEQ ID NO 752
<211> LENGTH: 6
<212> TYPE: DNA
<213> ORGANISM: Artificial Sequence

```
<220> FEATURE:
<223> OTHER INFORMATION: Indexes for Primer Pair Design Set 05

<400> SEQUENCE: 752 tatctg                                                                    6

<210> SEQ ID NO 753
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 753 ctattg                                                                    6

<210> SEQ ID NO 754
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 754 ggagaa                                                                    6

<210> SEQ ID NO 755
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 755 acctac                                                                    6

<210> SEQ ID NO 756
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 756 gtacac                                                                    6

<210> SEQ ID NO 757
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 757 gttatg                                                                    6

<210> SEQ ID NO 758
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 758 tggaca                                                                    6
```

```
<210> SEQ ID NO 759
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 759 cgtcat                                                                    6

<210> SEQ ID NO 760
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 760 acgatt                                                                    6

<210> SEQ ID NO 761
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 761 gtaaag                                                                    6

<210> SEQ ID NO 762
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 762 acagtc                                                                    6

<210> SEQ ID NO 763
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 763 cgagtt                                                                    6

<210> SEQ ID NO 764
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 764 atgtac                                                                    6

<210> SEQ ID NO 765
<211> LENGTH: 6
<212> TYPE: DNA
<213> ORGANISM: Artificial Sequence
<220> FEATURE:
<223> OTHER INFORMATION: Indexes for Primer Pair Design Set 05
```

-continued

<400> SEQUENCE: 765 taaagc                                                              6

<210> SEQ ID NO 766
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 766 acatag                                                              6

<210> SEQ ID NO 767
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 767 ggttgt                                                              6

<210> SEQ ID NO 768
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 768 caaaca                                                              6

<210> SEQ ID NO 769
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 769 cgtaaa                                                              6

<210> SEQ ID NO 770
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 770 acaccg                                                              6

<210> SEQ ID NO 771
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 771 cattag                                                              6

<210> SEQ ID NO 772

```
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 772 agcttg                                                                    6

<210> SEQ ID NO 773
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 773 tcgcgt                                                                    6

<210> SEQ ID NO 774
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 774 cagcat                                                                    6

<210> SEQ ID NO 775
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 775 taggcg                                                                    6

<210> SEQ ID NO 776
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 776 cgagga                                                                    6

<210> SEQ ID NO 777
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 777 cgtttc                                                                    6

<210> SEQ ID NO 778
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 778
``` aagcgc                                                              6

<210> SEQ ID NO 779
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 779 aaacgg                                                              6

<210> SEQ ID NO 780
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 780 tgcttc                                                              6

<210> SEQ ID NO 781
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 781 tagagt                                                              6

<210> SEQ ID NO 782
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 782 tgtcct                                                              6

<210> SEQ ID NO 783
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 783 ctgcga                                                              6

<210> SEQ ID NO 784
<211> LENGTH: 6
<212> TYPE: DNA
<213> ORGANISM: Artificial Sequence
<220> FEATURE:
<223> OTHER INFORMATION: Indexes for Primer Pair Design Set 05

<400> SEQUENCE: 784 agactg                                                              6

<210> SEQ ID NO 785
<211> LENGTH: 6
<212> TYPE: DNA

```
<213> ORGANISM: Artificial Sequence
<220> FEATURE:
<223> OTHER INFORMATION: Indexes for Primer Pair Design Set 05

<400> SEQUENCE: 785 gcgtga                                                              6

<210> SEQ ID NO 786
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 786 catgaaga                                                            8

<210> SEQ ID NO 787
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 787 cataacag                                                            8

<210> SEQ ID NO 788
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 788 ggttggac                                                            8

<210> SEQ ID NO 789
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 789 cctccaag                                                            8

<210> SEQ ID NO 790
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 790 tatcatcc                                                            8

<210> SEQ ID NO 791
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 791 tgcgctaa                                                            8
```

<210> SEQ ID NO 792
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 792 tattgtcg                                                              8

<210> SEQ ID NO 793
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 793 gaatggca                                                              8

<210> SEQ ID NO 794
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 794 tcgtgcta                                                              8

<210> SEQ ID NO 795
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 795 tcgcttcc                                                              8

<210> SEQ ID NO 796
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 796 tcaaaggc                                                              8

<210> SEQ ID NO 797
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 797 aattcgag                                                              8

<210> SEQ ID NO 798
<211> LENGTH: 8
<212> TYPE: DNA
<213> ORGANISM: Artificial Sequence
<220> FEATURE:

<223> OTHER INFORMATION: Indexes for Primer Pair Design Set 05

<400> SEQUENCE: 798 ctaccgtt                                                                    8

<210> SEQ ID NO 799
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 799 ccggtatg                                                                    8

<210> SEQ ID NO 800
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 800 tcaggtct                                                                    8

<210> SEQ ID NO 801
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 801 aagcaatc                                                                    8

<210> SEQ ID NO 802
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 802 ccttaatg                                                                    8

<210> SEQ ID NO 803
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 803 ggcacgtt                                                                    8

<210> SEQ ID NO 804
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 804 gttgtgca                                                                    8

```
<210> SEQ ID NO 805
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 805 cgttgacg                                                                 8

<210> SEQ ID NO 806
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 806 cgctttca                                                                 8

<210> SEQ ID NO 807
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 807 acagtcga                                                                 8

<210> SEQ ID NO 808
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 808 ttcagcgt                                                                 8

<210> SEQ ID NO 809
<211> LENGTH: 8
<212> TYPE: DNA
<213> ORGANISM: Artificial Sequence
<220> FEATURE:
<223> OTHER INFORMATION: Indexes for Primer Pair Design Set 05

<400> SEQUENCE: 809 accgctga                                                                 8

<210> SEQ ID NO 810
<211> LENGTH: 22
<212> TYPE: DNA
<213> ORGANISM: Artificial Sequence
<220> FEATURE:
<223> OTHER INFORMATION: Plate Level Design Construct 02

<400> SEQUENCE: 810
ctgcgactga gctcctgatt gg                                                22

<210> SEQ ID NO 811
<211> LENGTH: 22
<212> TYPE: DNA
<213> ORGANISM: Artificial Sequence
<220> FEATURE:
<223> OTHER INFORMATION: Plate Level Design Construct 02
```

<400> SEQUENCE: 811
cgtaggtgtt cgaattgcgc ct                                              22

<210> SEQ ID NO 812
<211> LENGTH: 23
<212> TYPE: DNA
<213> ORGANISM: Artificial Sequence
<220> FEATURE:
<223> OTHER INFORMATION: Plate Level Design Construct 02

<400> SEQUENCE: 812
attacgccta gacagtgcac gtc                                             23

<210> SEQ ID NO 813
<211> LENGTH: 23
<212> TYPE: DNA
<213> ORGANISM: Artificial Sequence
<220> FEATURE:
<223> OTHER INFORMATION: Plate Level Design Construct 02

<400> SEQUENCE: 813
gaccattgtg cacatacgcg acc                                             23

<210> SEQ ID NO 814
<211> LENGTH: 21
<212> TYPE: DNA
<213> ORGANISM: Artificial Sequence
<220> FEATURE:
<223> OTHER INFORMATION: Plate Level Design Construct 02

<400> SEQUENCE: 814
tccgccaccg caaactagtg c                                               21

<210> SEQ ID NO 815
<211> LENGTH: 21
<212> TYPE: DNA
<213> ORGANISM: Artificial Sequence
<220> FEATURE:
<223> OTHER INFORMATION: Plate Level Design Construct 02

<400> SEQUENCE: 815
gccaagcttc ctgaacggag c                                               21

<210> SEQ ID NO 816
<211> LENGTH: 23
<212> TYPE: DNA
<213> ORGANISM: Artificial Sequence
<220> FEATURE:
<223> OTHER INFORMATION: Plate Level Design Construct 02

<400> SEQUENCE: 816
aggtgatcaa ctccggcaga gtc                                             23

<210> SEQ ID NO 817
<211> LENGTH: 23
<212> TYPE: DNA
<213> ORGANISM: Artificial Sequence
<220> FEATURE:
<223> OTHER INFORMATION: Plate Level Design Construct 02

<400> SEQUENCE: 817
gtctgactag catgcaaggc acg                                             23

<210> SEQ ID NO 818
<211> LENGTH: 24

-continued

```
<212> TYPE: DNA
<213> ORGANISM: Artificial Sequence
<220> FEATURE:
<223> OTHER INFORMATION: Plate Level Design Construct 02

<400> SEQUENCE: 818
gctacgtagt caccggaact agcc                                              24

<210> SEQ ID NO 819
<211> LENGTH: 24
<212> TYPE: DNA
<213> ORGANISM: Artificial Sequence
<220> FEATURE:
<223> OTHER INFORMATION: Plate Level Design Construct 02

<400> SEQUENCE: 819
caatgattag gagcggtcga cgct                                              24

<210> SEQ ID NO 820
<211> LENGTH: 22
<212> TYPE: DNA
<213> ORGANISM: Artificial Sequence
<220> FEATURE:
<223> OTHER INFORMATION: Plate Level Design Construct 02

<400> SEQUENCE: 820
aggcgcaatt cgaacaccta cg                                                22

<210> SEQ ID NO 821
<211> LENGTH: 23
<212> TYPE: DNA
<213> ORGANISM: Artificial Sequence
<220> FEATURE:
<223> OTHER INFORMATION: Plate Level Design Construct 02

<400> SEQUENCE: 821
ggtcgcgtat gtgcacaatg gtc                                               23

<210> SEQ ID NO 822
<211> LENGTH: 21
<212> TYPE: DNA
<213> ORGANISM: Artificial Sequence
<220> FEATURE:
<223> OTHER INFORMATION: Plate Level Design Construct 02

<400> SEQUENCE: 822
gctccgttca ggaagcttgg c                                                 21

<210> SEQ ID NO 823
<211> LENGTH: 23
<212> TYPE: DNA
<213> ORGANISM: Artificial Sequence
<220> FEATURE:
<223> OTHER INFORMATION: Plate Level Design Construct 02

<400> SEQUENCE: 823
cgtgccttgc atgctagtca gac                                               23

<210> SEQ ID NO 824
<211> LENGTH: 24
<212> TYPE: DNA
<213> ORGANISM: Artificial Sequence
<220> FEATURE:
<223> OTHER INFORMATION: Plate Level Design Construct 02

<400> SEQUENCE: 824
```
agcgtcgacc gctcctaatc attg                                                   24

<210> SEQ ID NO 825
<211> LENGTH: 7
<212> TYPE: DNA
<213> ORGANISM: Artificial Sequence
<220> FEATURE:
<223> OTHER INFORMATION: Well 1

<400> SEQUENCE: 825 gtagatg                                                                       7

<210> SEQ ID NO 826
<211> LENGTH: 7
<212> TYPE: DNA
<213> ORGANISM: Artificial Sequence
<220> FEATURE:
<223> OTHER INFORMATION: Well 1

<400> SEQUENCE: 826 ggatagc                                                                       7

<210> SEQ ID NO 827
<211> LENGTH: 7
<212> TYPE: DNA
<213> ORGANISM: Artificial Sequence
<220> FEATURE:
<223> OTHER INFORMATION: Well 2

<400> SEQUENCE: 827 aggagtt                                                                       7

<210> SEQ ID NO 828
<211> LENGTH: 7
<212> TYPE: DNA
<213> ORGANISM: Artificial Sequence
<220> FEATURE:
<223> OTHER INFORMATION: Well 2

<400> SEQUENCE: 828 acgactg                                                                       7

<210> SEQ ID NO 829
<211> LENGTH: 7
<212> TYPE: DNA
<213> ORGANISM: Artificial Sequence
<220> FEATURE:
<223> OTHER INFORMATION: Well 3

<400> SEQUENCE: 829 gccttgt                                                                       7

<210> SEQ ID NO 830
<211> LENGTH: 7
<212> TYPE: DNA
<213> ORGANISM: Artificial Sequence
<220> FEATURE:
<223> OTHER INFORMATION: Well 3

<400> SEQUENCE: 830 acttctc                                                                       7

<210> SEQ ID NO 831
<211> LENGTH: 7
<212> TYPE: DNA
<213> ORGANISM: Artificial Sequence

```
<220> FEATURE:
<223> OTHER INFORMATION: Well 4

<400> SEQUENCE: 831 gactgag                                                                    7

<210> SEQ ID NO 832
<211> LENGTH: 7
<212> TYPE: DNA
<213> ORGANISM: Artificial Sequence
<220> FEATURE:
<223> OTHER INFORMATION: Well 4

<400> SEQUENCE: 832 ctcagat                                                                    7

<210> SEQ ID NO 833
<211> LENGTH: 7
<212> TYPE: DNA
<213> ORGANISM: Artificial Sequence
<220> FEATURE:
<223> OTHER INFORMATION: Well 5

<400> SEQUENCE: 833 tttcgca                                                                    7

<210> SEQ ID NO 834
<211> LENGTH: 7
<212> TYPE: DNA
<213> ORGANISM: Artificial Sequence
<220> FEATURE:
<223> OTHER INFORMATION: Well 5

<400> SEQUENCE: 834 gcttgat                                                                    7

<210> SEQ ID NO 835
<211> LENGTH: 7
<212> TYPE: DNA
<213> ORGANISM: Artificial Sequence
<220> FEATURE:
<223> OTHER INFORMATION: Well 6

<400> SEQUENCE: 835 agcgcta                                                                    7

<210> SEQ ID NO 836
<211> LENGTH: 7
<212> TYPE: DNA
<213> ORGANISM: Artificial Sequence
<220> FEATURE:
<223> OTHER INFORMATION: Well 6

<400> SEQUENCE: 836 cacaatc                                                                    7

<210> SEQ ID NO 837
<211> LENGTH: 7
<212> TYPE: DNA
<213> ORGANISM: Artificial Sequence
<220> FEATURE:
<223> OTHER INFORMATION: Well 7

<400> SEQUENCE: 837 ttggcgt                                                                    7
```

```
<210> SEQ ID NO 838
<211> LENGTH: 7
<212> TYPE: DNA
<213> ORGANISM: Artificial Sequence
<220> FEATURE:
<223> OTHER INFORMATION: Well 7

<400> SEQUENCE: 838 gaagcaa                                                                   7

<210> SEQ ID NO 839
<211> LENGTH: 7
<212> TYPE: DNA
<213> ORGANISM: Artificial Sequence
<220> FEATURE:
<223> OTHER INFORMATION: Well 8

<400> SEQUENCE: 839 tgagatc                                                                   7

<210> SEQ ID NO 840
<211> LENGTH: 7
<212> TYPE: DNA
<213> ORGANISM: Artificial Sequence
<220> FEATURE:
<223> OTHER INFORMATION: Well 8

<400> SEQUENCE: 840 cattcgt                                                                   7

<210> SEQ ID NO 841
<211> LENGTH: 7
<212> TYPE: DNA
<213> ORGANISM: Artificial Sequence
<220> FEATURE:
<223> OTHER INFORMATION: Well 9

<400> SEQUENCE: 841 gcgagaa                                                                   7

<210> SEQ ID NO 842
<211> LENGTH: 7
<212> TYPE: DNA
<213> ORGANISM: Artificial Sequence
<220> FEATURE:
<223> OTHER INFORMATION: Well 9

<400> SEQUENCE: 842 agcagag                                                                   7

<210> SEQ ID NO 843
<211> LENGTH: 7
<212> TYPE: DNA
<213> ORGANISM: Artificial Sequence
<220> FEATURE:
<223> OTHER INFORMATION: Well 10

<400> SEQUENCE: 843 caggttc                                                                   7

<210> SEQ ID NO 844
<211> LENGTH: 7
<212> TYPE: DNA
<213> ORGANISM: Artificial Sequence
<220> FEATURE:
<223> OTHER INFORMATION: Well 10
```

```
<400> SEQUENCE: 844 ctaagtg                                                              7

<210> SEQ ID NO 845
<211> LENGTH: 7
<212> TYPE: DNA
<213> ORGANISM: Artificial Sequence
<220> FEATURE:
<223> OTHER INFORMATION: Well 11

<400> SEQUENCE: 845 cctccat                                                              7

<210> SEQ ID NO 846
<211> LENGTH: 7
<212> TYPE: DNA
<213> ORGANISM: Artificial Sequence
<220> FEATURE:
<223> OTHER INFORMATION: Well 11

<400> SEQUENCE: 846 gttacgc                                                              7

<210> SEQ ID NO 847
<211> LENGTH: 7
<212> TYPE: DNA
<213> ORGANISM: Artificial Sequence
<220> FEATURE:
<223> OTHER INFORMATION: Well 12

<400> SEQUENCE: 847 catgtcc                                                              7

<210> SEQ ID NO 848
<211> LENGTH: 7
<212> TYPE: DNA
<213> ORGANISM: Artificial Sequence
<220> FEATURE:
<223> OTHER INFORMATION: Well 12

<400> SEQUENCE: 848 gacgtgt                                                              7

<210> SEQ ID NO 849
<211> LENGTH: 7
<212> TYPE: DNA
<213> ORGANISM: Artificial Sequence
<220> FEATURE:
<223> OTHER INFORMATION: Well 13

<400> SEQUENCE: 849 cgctgaa                                                              7

<210> SEQ ID NO 850
<211> LENGTH: 7
<212> TYPE: DNA
<213> ORGANISM: Artificial Sequence
<220> FEATURE:
<223> OTHER INFORMATION: Well 13

<400> SEQUENCE: 850 tgcgaat                                                              7

<210> SEQ ID NO 851
```

-continued

```
<211> LENGTH: 7
<212> TYPE: DNA
<213> ORGANISM: Artificial Sequence
<220> FEATURE:
<223> OTHER INFORMATION: Well 14

<400> SEQUENCE: 851 ttgtcct                                                                    7

<210> SEQ ID NO 852
<211> LENGTH: 7
<212> TYPE: DNA
<213> ORGANISM: Artificial Sequence
<220> FEATURE:
<223> OTHER INFORMATION: Well 14

<400> SEQUENCE: 852 atcgcat                                                                    7

<210> SEQ ID NO 853
<211> LENGTH: 7
<212> TYPE: DNA
<213> ORGANISM: Artificial Sequence
<220> FEATURE:
<223> OTHER INFORMATION: Well 15

<400> SEQUENCE: 853 aaagcac                                                                    7

<210> SEQ ID NO 854
<211> LENGTH: 7
<212> TYPE: DNA
<213> ORGANISM: Artificial Sequence
<220> FEATURE:
<223> OTHER INFORMATION: Well 15

<400> SEQUENCE: 854 cagatgg                                                                    7

<210> SEQ ID NO 855
<211> LENGTH: 7
<212> TYPE: DNA
<213> ORGANISM: Artificial Sequence
<220> FEATURE:
<223> OTHER INFORMATION: Well 16

<400> SEQUENCE: 855 catcagt                                                                    7

<210> SEQ ID NO 856
<211> LENGTH: 7
<212> TYPE: DNA
<213> ORGANISM: Artificial Sequence
<220> FEATURE:
<223> OTHER INFORMATION: Well 16

<400> SEQUENCE: 856 acgttcc                                                                    7

<210> SEQ ID NO 857
<211> LENGTH: 7
<212> TYPE: DNA
<213> ORGANISM: Artificial Sequence
<220> FEATURE:
<223> OTHER INFORMATION: Well 17

<400> SEQUENCE: 857
``` aatccga                                                              7

<210> SEQ ID NO 858
<211> LENGTH: 7
<212> TYPE: DNA
<213> ORGANISM: Artificial Sequence
<220> FEATURE:
<223> OTHER INFORMATION: Well 17

<400> SEQUENCE: 858 gtttcgt                                                              7

<210> SEQ ID NO 859
<211> LENGTH: 7
<212> TYPE: DNA
<213> ORGANISM: Artificial Sequence
<220> FEATURE:
<223> OTHER INFORMATION: Well 18

<400> SEQUENCE: 859 cctgttt                                                              7

<210> SEQ ID NO 860
<211> LENGTH: 7
<212> TYPE: DNA
<213> ORGANISM: Artificial Sequence
<220> FEATURE:
<223> OTHER INFORMATION: Well 18

<400> SEQUENCE: 860 aaccaga                                                              7

<210> SEQ ID NO 861
<211> LENGTH: 7
<212> TYPE: DNA
<213> ORGANISM: Artificial Sequence
<220> FEATURE:
<223> OTHER INFORMATION: Well 19

<400> SEQUENCE: 861 acttcgg                                                              7

<210> SEQ ID NO 862
<211> LENGTH: 7
<212> TYPE: DNA
<213> ORGANISM: Artificial Sequence
<220> FEATURE:
<223> OTHER INFORMATION: Well 19

<400> SEQUENCE: 862 tcctgat                                                              7

<210> SEQ ID NO 863
<211> LENGTH: 7
<212> TYPE: DNA
<213> ORGANISM: Artificial Sequence
<220> FEATURE:
<223> OTHER INFORMATION: Well 20

<400> SEQUENCE: 863 tttcggc                                                              7

<210> SEQ ID NO 864
<211> LENGTH: 7
<212> TYPE: DNA

```
<213> ORGANISM: Artificial Sequence
<220> FEATURE:
<223> OTHER INFORMATION: Well 20

<400> SEQUENCE: 864 ctagacg                                                                7

<210> SEQ ID NO 865
<211> LENGTH: 7
<212> TYPE: DNA
<213> ORGANISM: Artificial Sequence
<220> FEATURE:
<223> OTHER INFORMATION: Well 21

<400> SEQUENCE: 865 ttaggac                                                                7

<210> SEQ ID NO 866
<211> LENGTH: 7
<212> TYPE: DNA
<213> ORGANISM: Artificial Sequence
<220> FEATURE:
<223> OTHER INFORMATION: Well 21

<400> SEQUENCE: 866 gttaccg                                                                7

<210> SEQ ID NO 867
<211> LENGTH: 7
<212> TYPE: DNA
<213> ORGANISM: Artificial Sequence
<220> FEATURE:
<223> OTHER INFORMATION: Well 22

<400> SEQUENCE: 867 ctccgaa                                                                7

<210> SEQ ID NO 868
<211> LENGTH: 7
<212> TYPE: DNA
<213> ORGANISM: Artificial Sequence
<220> FEATURE:
<223> OTHER INFORMATION: Well 22

<400> SEQUENCE: 868 tcgtatc                                                                7

<210> SEQ ID NO 869
<211> LENGTH: 7
<212> TYPE: DNA
<213> ORGANISM: Artificial Sequence
<220> FEATURE:
<223> OTHER INFORMATION: Well 23

<400> SEQUENCE: 869 cctaagg                                                                7

<210> SEQ ID NO 870
<211> LENGTH: 7
<212> TYPE: DNA
<213> ORGANISM: Artificial Sequence
<220> FEATURE:
<223> OTHER INFORMATION: Well 23

<400> SEQUENCE: 870 atgtgag                                                                7
```

```
<210> SEQ ID NO 871
<211> LENGTH: 7
<212> TYPE: DNA
<213> ORGANISM: Artificial Sequence
<220> FEATURE:
<223> OTHER INFORMATION: Well 24

<400> SEQUENCE: 871 cagtcca                                                              7

<210> SEQ ID NO 872
<211> LENGTH: 7
<212> TYPE: DNA
<213> ORGANISM: Artificial Sequence
<220> FEATURE:
<223> OTHER INFORMATION: Well 24

<400> SEQUENCE: 872 tggacat                                                              7

<210> SEQ ID NO 873
<211> LENGTH: 7
<212> TYPE: DNA
<213> ORGANISM: Artificial Sequence
<220> FEATURE:
<223> OTHER INFORMATION: Well 25

<400> SEQUENCE: 873 atgacgt                                                              7

<210> SEQ ID NO 874
<211> LENGTH: 7
<212> TYPE: DNA
<213> ORGANISM: Artificial Sequence
<220> FEATURE:
<223> OTHER INFORMATION: Well 25

<400> SEQUENCE: 874 aggtcat                                                              7

<210> SEQ ID NO 875
<211> LENGTH: 7
<212> TYPE: DNA
<213> ORGANISM: Artificial Sequence
<220> FEATURE:
<223> OTHER INFORMATION: Well 26

<400> SEQUENCE: 875 aggacct                                                              7

<210> SEQ ID NO 876
<211> LENGTH: 7
<212> TYPE: DNA
<213> ORGANISM: Artificial Sequence
<220> FEATURE:
<223> OTHER INFORMATION: Well 26

<400> SEQUENCE: 876 tggtcca                                                              7

<210> SEQ ID NO 877
<211> LENGTH: 7
<212> TYPE: DNA
<213> ORGANISM: Artificial Sequence
<220> FEATURE:
```

<223> OTHER INFORMATION: Well 27

<400> SEQUENCE: 877 tgttcag                                                                 7

<210> SEQ ID NO 878
<211> LENGTH: 7
<212> TYPE: DNA
<213> ORGANISM: Artificial Sequence
<220> FEATURE:
<223> OTHER INFORMATION: Well 27

<400> SEQUENCE: 878 caaacgc                                                                 7

<210> SEQ ID NO 879
<211> LENGTH: 7
<212> TYPE: DNA
<213> ORGANISM: Artificial Sequence
<220> FEATURE:
<223> OTHER INFORMATION: Well 28

<400> SEQUENCE: 879 tgtccga                                                                 7

<210> SEQ ID NO 880
<211> LENGTH: 7
<212> TYPE: DNA
<213> ORGANISM: Artificial Sequence
<220> FEATURE:
<223> OTHER INFORMATION: Well 28

<400> SEQUENCE: 880 gcacaaa                                                                 7

<210> SEQ ID NO 881
<211> LENGTH: 7
<212> TYPE: DNA
<213> ORGANISM: Artificial Sequence
<220> FEATURE:
<223> OTHER INFORMATION: Well 29

<400> SEQUENCE: 881 ctcaaag                                                                 7

<210> SEQ ID NO 882
<211> LENGTH: 7
<212> TYPE: DNA
<213> ORGANISM: Artificial Sequence
<220> FEATURE:
<223> OTHER INFORMATION: Well 29

<400> SEQUENCE: 882 ttatggc                                                                 7

<210> SEQ ID NO 883
<211> LENGTH: 7
<212> TYPE: DNA
<213> ORGANISM: Artificial Sequence
<220> FEATURE:
<223> OTHER INFORMATION: Well 30

<400> SEQUENCE: 883 caaggtt                                                                 7

```
<210> SEQ ID NO 884
<211> LENGTH: 7
<212> TYPE: DNA
<213> ORGANISM: Artificial Sequence
<220> FEATURE:
<223> OTHER INFORMATION: Well 30

<400> SEQUENCE: 884 ccaagat                                                               7

<210> SEQ ID NO 885
<211> LENGTH: 7
<212> TYPE: DNA
<213> ORGANISM: Artificial Sequence
<220> FEATURE:
<223> OTHER INFORMATION: Well 31

<400> SEQUENCE: 885 ctagatc                                                               7

<210> SEQ ID NO 886
<211> LENGTH: 7
<212> TYPE: DNA
<213> ORGANISM: Artificial Sequence
<220> FEATURE:
<223> OTHER INFORMATION: Well 31

<400> SEQUENCE: 886 catcgat                                                               7

<210> SEQ ID NO 887
<211> LENGTH: 7
<212> TYPE: DNA
<213> ORGANISM: Artificial Sequence
<220> FEATURE:
<223> OTHER INFORMATION: Well 32

<400> SEQUENCE: 887 atgtcgc                                                               7

<210> SEQ ID NO 888
<211> LENGTH: 7
<212> TYPE: DNA
<213> ORGANISM: Artificial Sequence
<220> FEATURE:
<223> OTHER INFORMATION: Well 32

<400> SEQUENCE: 888 ccttaag                                                               7

<210> SEQ ID NO 889
<211> LENGTH: 7
<212> TYPE: DNA
<213> ORGANISM: Artificial Sequence
<220> FEATURE:
<223> OTHER INFORMATION: Well 33

<400> SEQUENCE: 889 aatgccg                                                               7

<210> SEQ ID NO 890
<211> LENGTH: 7
<212> TYPE: DNA
<213> ORGANISM: Artificial Sequence
<220> FEATURE:
<223> OTHER INFORMATION: Well 33
```

```
<400> SEQUENCE: 890 ggcaagt                                                                    7

<210> SEQ ID NO 891
<211> LENGTH: 7
<212> TYPE: DNA
<213> ORGANISM: Artificial Sequence
<220> FEATURE:
<223> OTHER INFORMATION: Well 34

<400> SEQUENCE: 891 tccgttg                                                                    7

<210> SEQ ID NO 892
<211> LENGTH: 7
<212> TYPE: DNA
<213> ORGANISM: Artificial Sequence
<220> FEATURE:
<223> OTHER INFORMATION: Well 34

<400> SEQUENCE: 892 ctactcg                                                                    7

<210> SEQ ID NO 893
<211> LENGTH: 7
<212> TYPE: DNA
<213> ORGANISM: Artificial Sequence
<220> FEATURE:
<223> OTHER INFORMATION: Well 35

<400> SEQUENCE: 893 gtcaaca                                                                    7

<210> SEQ ID NO 894
<211> LENGTH: 7
<212> TYPE: DNA
<213> ORGANISM: Artificial Sequence
<220> FEATURE:
<223> OTHER INFORMATION: Well 35

<400> SEQUENCE: 894 ctcctga                                                                    7

<210> SEQ ID NO 895
<211> LENGTH: 7
<212> TYPE: DNA
<213> ORGANISM: Artificial Sequence
<220> FEATURE:
<223> OTHER INFORMATION: Well 36

<400> SEQUENCE: 895 cgcaaac                                                                    7

<210> SEQ ID NO 896
<211> LENGTH: 7
<212> TYPE: DNA
<213> ORGANISM: Artificial Sequence
<220> FEATURE:
<223> OTHER INFORMATION: Well 36

<400> SEQUENCE: 896 ctggatg                                                                    7

<210> SEQ ID NO 897
<211> LENGTH: 7
```

```
<212> TYPE: DNA
<213> ORGANISM: Artificial Sequence
<220> FEATURE:
<223> OTHER INFORMATION: Well 37

<400> SEQUENCE: 897 tggcatc                                                                  7

<210> SEQ ID NO 898
<211> LENGTH: 7
<212> TYPE: DNA
<213> ORGANISM: Artificial Sequence
<220> FEATURE:
<223> OTHER INFORMATION: Well 37

<400> SEQUENCE: 898 taagccg                                                                  7

<210> SEQ ID NO 899
<211> LENGTH: 7
<212> TYPE: DNA
<213> ORGANISM: Artificial Sequence
<220> FEATURE:
<223> OTHER INFORMATION: Well 38

<400> SEQUENCE: 899 gtcagta                                                                  7

<210> SEQ ID NO 900
<211> LENGTH: 7
<212> TYPE: DNA
<213> ORGANISM: Artificial Sequence
<220> FEATURE:
<223> OTHER INFORMATION: Well 38

<400> SEQUENCE: 900 gctaaac                                                                  7

<210> SEQ ID NO 901
<211> LENGTH: 7
<212> TYPE: DNA
<213> ORGANISM: Artificial Sequence
<220> FEATURE:
<223> OTHER INFORMATION: Well 39

<400> SEQUENCE: 901 cttgcaa                                                                  7

<210> SEQ ID NO 902
<211> LENGTH: 7
<212> TYPE: DNA
<213> ORGANISM: Artificial Sequence
<220> FEATURE:
<223> OTHER INFORMATION: Well 39

<400> SEQUENCE: 902 ctccatc                                                                  7

<210> SEQ ID NO 903
<211> LENGTH: 7
<212> TYPE: DNA
<213> ORGANISM: Artificial Sequence
<220> FEATURE:
<223> OTHER INFORMATION: Well 40

<400> SEQUENCE: 903
```

-continued caagttg 7

<210> SEQ ID NO 904
<211> LENGTH: 7
<212> TYPE: DNA
<213> ORGANISM: Artificial Sequence
<220> FEATURE:
<223> OTHER INFORMATION: Well 40

<400> SEQUENCE: 904 cgtgaag 7

<210> SEQ ID NO 905
<211> LENGTH: 7
<212> TYPE: DNA
<213> ORGANISM: Artificial Sequence
<220> FEATURE:
<223> OTHER INFORMATION: Well 41

<400> SEQUENCE: 905 tgagacg 7

<210> SEQ ID NO 906
<211> LENGTH: 7
<212> TYPE: DNA
<213> ORGANISM: Artificial Sequence
<220> FEATURE:
<223> OTHER INFORMATION: Well 41

<400> SEQUENCE: 906 tacgtgg 7

<210> SEQ ID NO 907
<211> LENGTH: 7
<212> TYPE: DNA
<213> ORGANISM: Artificial Sequence
<220> FEATURE:
<223> OTHER INFORMATION: Well 42

<400> SEQUENCE: 907 gtagcat 7

<210> SEQ ID NO 908
<211> LENGTH: 7
<212> TYPE: DNA
<213> ORGANISM: Artificial Sequence
<220> FEATURE:
<223> OTHER INFORMATION: Well 42

<400> SEQUENCE: 908 aacctct 7

<210> SEQ ID NO 909
<211> LENGTH: 7
<212> TYPE: DNA
<213> ORGANISM: Artificial Sequence
<220> FEATURE:
<223> OTHER INFORMATION: Well 43

<400> SEQUENCE: 909 ctgatac 7

<210> SEQ ID NO 910
<211> LENGTH: 7
<212> TYPE: DNA
<213> ORGANISM: Artificial Sequence

```
<220> FEATURE:
<223> OTHER INFORMATION: Well 43

<400> SEQUENCE: 910 ggtgaaa                                                                      7

<210> SEQ ID NO 911
<211> LENGTH: 7
<212> TYPE: DNA
<213> ORGANISM: Artificial Sequence
<220> FEATURE:
<223> OTHER INFORMATION: Well 44

<400> SEQUENCE: 911 tccgaca                                                                      7

<210> SEQ ID NO 912
<211> LENGTH: 7
<212> TYPE: DNA
<213> ORGANISM: Artificial Sequence
<220> FEATURE:
<223> OTHER INFORMATION: Well 44

<400> SEQUENCE: 912 actcaag                                                                      7

<210> SEQ ID NO 913
<211> LENGTH: 7
<212> TYPE: DNA
<213> ORGANISM: Artificial Sequence
<220> FEATURE:
<223> OTHER INFORMATION: Well 45

<400> SEQUENCE: 913 gtcgttg                                                                      7

<210> SEQ ID NO 914
<211> LENGTH: 7
<212> TYPE: DNA
<213> ORGANISM: Artificial Sequence
<220> FEATURE:
<223> OTHER INFORMATION: Well 45

<400> SEQUENCE: 914 agtggat                                                                      7

<210> SEQ ID NO 915
<211> LENGTH: 7
<212> TYPE: DNA
<213> ORGANISM: Artificial Sequence
<220> FEATURE:
<223> OTHER INFORMATION: Well 46

<400> SEQUENCE: 915 gtcttcg                                                                      7

<210> SEQ ID NO 916
<211> LENGTH: 7
<212> TYPE: DNA
<213> ORGANISM: Artificial Sequence
<220> FEATURE:
<223> OTHER INFORMATION: Well 46

<400> SEQUENCE: 916 ccagcaa                                                                      7
```

```
<210> SEQ ID NO 917
<211> LENGTH: 7
<212> TYPE: DNA
<213> ORGANISM: Artificial Sequence
<220> FEATURE:
<223> OTHER INFORMATION: Well 47

<400> SEQUENCE: 917 agccaca                                                                  7

<210> SEQ ID NO 918
<211> LENGTH: 7
<212> TYPE: DNA
<213> ORGANISM: Artificial Sequence
<220> FEATURE:
<223> OTHER INFORMATION: Well 47

<400> SEQUENCE: 918 gcagttt                                                                  7

<210> SEQ ID NO 919
<211> LENGTH: 7
<212> TYPE: DNA
<213> ORGANISM: Artificial Sequence
<220> FEATURE:
<223> OTHER INFORMATION: Well 48

<400> SEQUENCE: 919 gttctac                                                                  7

<210> SEQ ID NO 920
<211> LENGTH: 7
<212> TYPE: DNA
<213> ORGANISM: Artificial Sequence
<220> FEATURE:
<223> OTHER INFORMATION: Well 48

<400> SEQUENCE: 920 agtctgc                                                                  7

<210> SEQ ID NO 921
<211> LENGTH: 7
<212> TYPE: DNA
<213> ORGANISM: Artificial Sequence
<220> FEATURE:
<223> OTHER INFORMATION: Well 49

<400> SEQUENCE: 921 gttcgct                                                                  7

<210> SEQ ID NO 922
<211> LENGTH: 7
<212> TYPE: DNA
<213> ORGANISM: Artificial Sequence
<220> FEATURE:
<223> OTHER INFORMATION: Well 49

<400> SEQUENCE: 922 ccaactg                                                                  7

<210> SEQ ID NO 923
<211> LENGTH: 7
<212> TYPE: DNA
<213> ORGANISM: Artificial Sequence
<220> FEATURE:
<223> OTHER INFORMATION: Well 50
```

```
<400> SEQUENCE: 923 attgagg                                                                  7

<210> SEQ ID NO 924
<211> LENGTH: 7
<212> TYPE: DNA
<213> ORGANISM: Artificial Sequence
<220> FEATURE:
<223> OTHER INFORMATION: Well 50

<400> SEQUENCE: 924 attagcg                                                                  7

<210> SEQ ID NO 925
<211> LENGTH: 7
<212> TYPE: DNA
<213> ORGANISM: Artificial Sequence
<220> FEATURE:
<223> OTHER INFORMATION: Well 51

<400> SEQUENCE: 925 cgagcat                                                                  7

<210> SEQ ID NO 926
<211> LENGTH: 7
<212> TYPE: DNA
<213> ORGANISM: Artificial Sequence
<220> FEATURE:
<223> OTHER INFORMATION: Well 51

<400> SEQUENCE: 926 ttaccag                                                                  7

<210> SEQ ID NO 927
<211> LENGTH: 7
<212> TYPE: DNA
<213> ORGANISM: Artificial Sequence
<220> FEATURE:
<223> OTHER INFORMATION: Well 52

<400> SEQUENCE: 927 ctcttag                                                                  7

<210> SEQ ID NO 928
<211> LENGTH: 7
<212> TYPE: DNA
<213> ORGANISM: Artificial Sequence
<220> FEATURE:
<223> OTHER INFORMATION: Well 52

<400> SEQUENCE: 928 tgtgcta                                                                  7

<210> SEQ ID NO 929
<211> LENGTH: 7
<212> TYPE: DNA
<213> ORGANISM: Artificial Sequence
<220> FEATURE:
<223> OTHER INFORMATION: Well 53

<400> SEQUENCE: 929 cttgctg                                                                  7

<210> SEQ ID NO 930
```

```
<211> LENGTH: 7
<212> TYPE: DNA
<213> ORGANISM: Artificial Sequence
<220> FEATURE:
<223> OTHER INFORMATION: Well 53

<400> SEQUENCE: 930 ctgtact                                                              7

<210> SEQ ID NO 931
<211> LENGTH: 7
<212> TYPE: DNA
<213> ORGANISM: Artificial Sequence
<220> FEATURE:
<223> OTHER INFORMATION: Well 54

<400> SEQUENCE: 931 gtcggat                                                              7

<210> SEQ ID NO 932
<211> LENGTH: 7
<212> TYPE: DNA
<213> ORGANISM: Artificial Sequence
<220> FEATURE:
<223> OTHER INFORMATION: Well 54

<400> SEQUENCE: 932 accgtta                                                              7

<210> SEQ ID NO 933
<211> LENGTH: 7
<212> TYPE: DNA
<213> ORGANISM: Artificial Sequence
<220> FEATURE:
<223> OTHER INFORMATION: Well 55

<400> SEQUENCE: 933 gtaaacg                                                              7

<210> SEQ ID NO 934
<211> LENGTH: 7
<212> TYPE: DNA
<213> ORGANISM: Artificial Sequence
<220> FEATURE:
<223> OTHER INFORMATION: Well 55

<400> SEQUENCE: 934 gtctact                                                              7

<210> SEQ ID NO 935
<211> LENGTH: 7
<212> TYPE: DNA
<213> ORGANISM: Artificial Sequence
<220> FEATURE:
<223> OTHER INFORMATION: Well 56

<400> SEQUENCE: 935 ggattgg                                                              7

<210> SEQ ID NO 936
<211> LENGTH: 7
<212> TYPE: DNA
<213> ORGANISM: Artificial Sequence
<220> FEATURE:
<223> OTHER INFORMATION: Well 56

<400> SEQUENCE: 936
``` gcatatg                                                              7

<210> SEQ ID NO 937
<211> LENGTH: 7
<212> TYPE: DNA
<213> ORGANISM: Artificial Sequence
<220> FEATURE:
<223> OTHER INFORMATION: Well 57

<400> SEQUENCE: 937 cctagga                                                              7

<210> SEQ ID NO 938
<211> LENGTH: 7
<212> TYPE: DNA
<213> ORGANISM: Artificial Sequence
<220> FEATURE:
<223> OTHER INFORMATION: Well 57

<400> SEQUENCE: 938 cgacttt                                                              7

<210> SEQ ID NO 939
<211> LENGTH: 7
<212> TYPE: DNA
<213> ORGANISM: Artificial Sequence
<220> FEATURE:
<223> OTHER INFORMATION: Well 58

<400> SEQUENCE: 939 aactctg                                                              7

<210> SEQ ID NO 940
<211> LENGTH: 7
<212> TYPE: DNA
<213> ORGANISM: Artificial Sequence
<220> FEATURE:
<223> OTHER INFORMATION: Well 58

<400> SEQUENCE: 940 ttaaccg                                                              7

<210> SEQ ID NO 941
<211> LENGTH: 7
<212> TYPE: DNA
<213> ORGANISM: Artificial Sequence
<220> FEATURE:
<223> OTHER INFORMATION: Well 59

<400> SEQUENCE: 941 caaacct                                                              7

<210> SEQ ID NO 942
<211> LENGTH: 7
<212> TYPE: DNA
<213> ORGANISM: Artificial Sequence
<220> FEATURE:
<223> OTHER INFORMATION: Well 59

<400> SEQUENCE: 942 gtgttca                                                              7

<210> SEQ ID NO 943
<211> LENGTH: 7
<212> TYPE: DNA

```
<213> ORGANISM: Artificial Sequence
<220> FEATURE:
<223> OTHER INFORMATION: Well 60

<400> SEQUENCE: 943 taactgg                                                              7

<210> SEQ ID NO 944
<211> LENGTH: 7
<212> TYPE: DNA
<213> ORGANISM: Artificial Sequence
<220> FEATURE:
<223> OTHER INFORMATION: Well 60

<400> SEQUENCE: 944 ctacagg                                                              7

<210> SEQ ID NO 945
<211> LENGTH: 7
<212> TYPE: DNA
<213> ORGANISM: Artificial Sequence
<220> FEATURE:
<223> OTHER INFORMATION: Well 61

<400> SEQUENCE: 945 acaagct                                                              7

<210> SEQ ID NO 946
<211> LENGTH: 7
<212> TYPE: DNA
<213> ORGANISM: Artificial Sequence
<220> FEATURE:
<223> OTHER INFORMATION: Well 61

<400> SEQUENCE: 946 tccagta                                                              7

<210> SEQ ID NO 947
<211> LENGTH: 7
<212> TYPE: DNA
<213> ORGANISM: Artificial Sequence
<220> FEATURE:
<223> OTHER INFORMATION: Well 62

<400> SEQUENCE: 947 tgatgtg                                                              7

<210> SEQ ID NO 948
<211> LENGTH: 7
<212> TYPE: DNA
<213> ORGANISM: Artificial Sequence
<220> FEATURE:
<223> OTHER INFORMATION: Well 62

<400> SEQUENCE: 948 ggaacaa                                                              7

<210> SEQ ID NO 949
<211> LENGTH: 7
<212> TYPE: DNA
<213> ORGANISM: Artificial Sequence
<220> FEATURE:
<223> OTHER INFORMATION: Well 63

<400> SEQUENCE: 949 aggcctt                                                              7
```

```
<210> SEQ ID NO 950
<211> LENGTH: 7
<212> TYPE: DNA
<213> ORGANISM: Artificial Sequence
<220> FEATURE:
<223> OTHER INFORMATION: Well 63

<400> SEQUENCE: 950 gaacaga                                                                 7

<210> SEQ ID NO 951
<211> LENGTH: 7
<212> TYPE: DNA
<213> ORGANISM: Artificial Sequence
<220> FEATURE:
<223> OTHER INFORMATION: Well 64

<400> SEQUENCE: 951 gcgttct                                                                 7

<210> SEQ ID NO 952
<211> LENGTH: 7
<212> TYPE: DNA
<213> ORGANISM: Artificial Sequence
<220> FEATURE:
<223> OTHER INFORMATION: Well 64

<400> SEQUENCE: 952 cagccat                                                                 7

<210> SEQ ID NO 953
<211> LENGTH: 7
<212> TYPE: DNA
<213> ORGANISM: Artificial Sequence
<220> FEATURE:
<223> OTHER INFORMATION: Well 65

<400> SEQUENCE: 953 tcactga                                                                 7

<210> SEQ ID NO 954
<211> LENGTH: 7
<212> TYPE: DNA
<213> ORGANISM: Artificial Sequence
<220> FEATURE:
<223> OTHER INFORMATION: Well 65

<400> SEQUENCE: 954 ttaggcg                                                                 7

<210> SEQ ID NO 955
<211> LENGTH: 7
<212> TYPE: DNA
<213> ORGANISM: Artificial Sequence
<220> FEATURE:
<223> OTHER INFORMATION: Well 66

<400> SEQUENCE: 955 actaacc                                                                 7

<210> SEQ ID NO 956
<211> LENGTH: 7
<212> TYPE: DNA
<213> ORGANISM: Artificial Sequence
<220> FEATURE:
```

<223> OTHER INFORMATION: Well 66

<400> SEQUENCE: 956 ctagcta                                                                          7

<210> SEQ ID NO 957
<211> LENGTH: 7
<212> TYPE: DNA
<213> ORGANISM: Artificial Sequence
<220> FEATURE:
<223> OTHER INFORMATION: Well 67

<400> SEQUENCE: 957 ggtcatc                                                                          7

<210> SEQ ID NO 958
<211> LENGTH: 7
<212> TYPE: DNA
<213> ORGANISM: Artificial Sequence
<220> FEATURE:
<223> OTHER INFORMATION: Well 67

<400> SEQUENCE: 958 ctccagt                                                                          7

<210> SEQ ID NO 959
<211> LENGTH: 7
<212> TYPE: DNA
<213> ORGANISM: Artificial Sequence
<220> FEATURE:
<223> OTHER INFORMATION: Well 68

<400> SEQUENCE: 959 ctcagtc                                                                          7

<210> SEQ ID NO 960
<211> LENGTH: 7
<212> TYPE: DNA
<213> ORGANISM: Artificial Sequence
<220> FEATURE:
<223> OTHER INFORMATION: Well 68

<400> SEQUENCE: 960 catctgg                                                                          7

<210> SEQ ID NO 961
<211> LENGTH: 7
<212> TYPE: DNA
<213> ORGANISM: Artificial Sequence
<220> FEATURE:
<223> OTHER INFORMATION: Well 69

<400> SEQUENCE: 961 tttgtgg                                                                          7

<210> SEQ ID NO 962
<211> LENGTH: 7
<212> TYPE: DNA
<213> ORGANISM: Artificial Sequence
<220> FEATURE:
<223> OTHER INFORMATION: Well 69

<400> SEQUENCE: 962 tgttggc                                                                          7

```
<210> SEQ ID NO 963
<211> LENGTH: 7
<212> TYPE: DNA
<213> ORGANISM: Artificial Sequence
<220> FEATURE:
<223> OTHER INFORMATION: Well 70

<400> SEQUENCE: 963 tgccata                                                              7

<210> SEQ ID NO 964
<211> LENGTH: 7
<212> TYPE: DNA
<213> ORGANISM: Artificial Sequence
<220> FEATURE:
<223> OTHER INFORMATION: Well 70

<400> SEQUENCE: 964 tactgcc                                                              7

<210> SEQ ID NO 965
<211> LENGTH: 7
<212> TYPE: DNA
<213> ORGANISM: Artificial Sequence
<220> FEATURE:
<223> OTHER INFORMATION: Well 71

<400> SEQUENCE: 965 tcgtagg                                                              7

<210> SEQ ID NO 966
<211> LENGTH: 7
<212> TYPE: DNA
<213> ORGANISM: Artificial Sequence
<220> FEATURE:
<223> OTHER INFORMATION: Well 71

<400> SEQUENCE: 966 cactagg                                                              7

<210> SEQ ID NO 967
<211> LENGTH: 7
<212> TYPE: DNA
<213> ORGANISM: Artificial Sequence
<220> FEATURE:
<223> OTHER INFORMATION: Well 72

<400> SEQUENCE: 967 atgaccg                                                              7

<210> SEQ ID NO 968
<211> LENGTH: 7
<212> TYPE: DNA
<213> ORGANISM: Artificial Sequence
<220> FEATURE:
<223> OTHER INFORMATION: Well 72

<400> SEQUENCE: 968 gtggaac                                                              7

<210> SEQ ID NO 969
<211> LENGTH: 7
<212> TYPE: DNA
<213> ORGANISM: Artificial Sequence
<220> FEATURE:
<223> OTHER INFORMATION: Well 73
```

```
<400> SEQUENCE: 969 aacttcc                                                                  7

<210> SEQ ID NO 970
<211> LENGTH: 7
<212> TYPE: DNA
<213> ORGANISM: Artificial Sequence
<220> FEATURE:
<223> OTHER INFORMATION: Well 73

<400> SEQUENCE: 970 agtatcc                                                                  7

<210> SEQ ID NO 971
<211> LENGTH: 7
<212> TYPE: DNA
<213> ORGANISM: Artificial Sequence
<220> FEATURE:
<223> OTHER INFORMATION: Well 74

<400> SEQUENCE: 971 taaccac                                                                  7

<210> SEQ ID NO 972
<211> LENGTH: 7
<212> TYPE: DNA
<213> ORGANISM: Artificial Sequence
<220> FEATURE:
<223> OTHER INFORMATION: Well 74

<400> SEQUENCE: 972 ccatttc                                                                  7

<210> SEQ ID NO 973
<211> LENGTH: 7
<212> TYPE: DNA
<213> ORGANISM: Artificial Sequence
<220> FEATURE:
<223> OTHER INFORMATION: Well 75

<400> SEQUENCE: 973 cagtgag                                                                  7

<210> SEQ ID NO 974
<211> LENGTH: 7
<212> TYPE: DNA
<213> ORGANISM: Artificial Sequence
<220> FEATURE:
<223> OTHER INFORMATION: Well 75

<400> SEQUENCE: 974 ttgcact                                                                  7

<210> SEQ ID NO 975
<211> LENGTH: 7
<212> TYPE: DNA
<213> ORGANISM: Artificial Sequence
<220> FEATURE:
<223> OTHER INFORMATION: Well 76

<400> SEQUENCE: 975 cgatttg                                                                  7

<210> SEQ ID NO 976
<211> LENGTH: 7
```

```
<212> TYPE: DNA
<213> ORGANISM: Artificial Sequence
<220> FEATURE:
<223> OTHER INFORMATION: Well 76

<400> SEQUENCE: 976 tctcctt                                                                7

<210> SEQ ID NO 977
<211> LENGTH: 7
<212> TYPE: DNA
<213> ORGANISM: Artificial Sequence
<220> FEATURE:
<223> OTHER INFORMATION: Well 77

<400> SEQUENCE: 977 aggtaac                                                                7

<210> SEQ ID NO 978
<211> LENGTH: 7
<212> TYPE: DNA
<213> ORGANISM: Artificial Sequence
<220> FEATURE:
<223> OTHER INFORMATION: Well 77

<400> SEQUENCE: 978 aacaggt                                                                7

<210> SEQ ID NO 979
<211> LENGTH: 7
<212> TYPE: DNA
<213> ORGANISM: Artificial Sequence
<220> FEATURE:
<223> OTHER INFORMATION: Well 78

<400> SEQUENCE: 979 gttagag                                                                7

<210> SEQ ID NO 980
<211> LENGTH: 7
<212> TYPE: DNA
<213> ORGANISM: Artificial Sequence
<220> FEATURE:
<223> OTHER INFORMATION: Well 78

<400> SEQUENCE: 980 ttagtgc                                                                7

<210> SEQ ID NO 981
<211> LENGTH: 7
<212> TYPE: DNA
<213> ORGANISM: Artificial Sequence
<220> FEATURE:
<223> OTHER INFORMATION: Well 79

<400> SEQUENCE: 981 ccaatgc                                                                7

<210> SEQ ID NO 982
<211> LENGTH: 7
<212> TYPE: DNA
<213> ORGANISM: Artificial Sequence
<220> FEATURE:
<223> OTHER INFORMATION: Well 79

<400> SEQUENCE: 982
```

-continued tccgagt 7

<210> SEQ ID NO 983
<211> LENGTH: 7
<212> TYPE: DNA
<213> ORGANISM: Artificial Sequence
<220> FEATURE:
<223> OTHER INFORMATION: Well 80

<400> SEQUENCE: 983 ggagcta 7

<210> SEQ ID NO 984
<211> LENGTH: 7
<212> TYPE: DNA
<213> ORGANISM: Artificial Sequence
<220> FEATURE:
<223> OTHER INFORMATION: Well 80

<400> SEQUENCE: 984 ggtacta 7

<210> SEQ ID NO 985
<211> LENGTH: 7
<212> TYPE: DNA
<213> ORGANISM: Artificial Sequence
<220> FEATURE:
<223> OTHER INFORMATION: Well 81

<400> SEQUENCE: 985 tctcatc 7

<210> SEQ ID NO 986
<211> LENGTH: 7
<212> TYPE: DNA
<213> ORGANISM: Artificial Sequence
<220> FEATURE:
<223> OTHER INFORMATION: Well 81

<400> SEQUENCE: 986 agatcac 7

<210> SEQ ID NO 987
<211> LENGTH: 7
<212> TYPE: DNA
<213> ORGANISM: Artificial Sequence
<220> FEATURE:
<223> OTHER INFORMATION: Well 82

<400> SEQUENCE: 987 tgccgtt 7

<210> SEQ ID NO 988
<211> LENGTH: 7
<212> TYPE: DNA
<213> ORGANISM: Artificial Sequence
<220> FEATURE:
<223> OTHER INFORMATION: Well 82

<400> SEQUENCE: 988 cgtactc 7

<210> SEQ ID NO 989
<211> LENGTH: 7
<212> TYPE: DNA
<213> ORGANISM: Artificial Sequence

```
<220> FEATURE:
<223> OTHER INFORMATION: Well 83

<400> SEQUENCE: 989 caggaaa                                                                 7

<210> SEQ ID NO 990
<211> LENGTH: 7
<212> TYPE: DNA
<213> ORGANISM: Artificial Sequence
<220> FEATURE:
<223> OTHER INFORMATION: Well 83

<400> SEQUENCE: 990 gccatat                                                                 7

<210> SEQ ID NO 991
<211> LENGTH: 7
<212> TYPE: DNA
<213> ORGANISM: Artificial Sequence
<220> FEATURE:
<223> OTHER INFORMATION: Well 84

<400> SEQUENCE: 991 acttgac                                                                 7

<210> SEQ ID NO 992
<211> LENGTH: 7
<212> TYPE: DNA
<213> ORGANISM: Artificial Sequence
<220> FEATURE:
<223> OTHER INFORMATION: Well 84

<400> SEQUENCE: 992 acgtgct                                                                 7

<210> SEQ ID NO 993
<211> LENGTH: 7
<212> TYPE: DNA
<213> ORGANISM: Artificial Sequence
<220> FEATURE:
<223> OTHER INFORMATION: Well 85

<400> SEQUENCE: 993 ctggttt                                                                 7

<210> SEQ ID NO 994
<211> LENGTH: 7
<212> TYPE: DNA
<213> ORGANISM: Artificial Sequence
<220> FEATURE:
<223> OTHER INFORMATION: Well 85

<400> SEQUENCE: 994 cgttagt                                                                 7

<210> SEQ ID NO 995
<211> LENGTH: 7
<212> TYPE: DNA
<213> ORGANISM: Artificial Sequence
<220> FEATURE:
<223> OTHER INFORMATION: Well 86

<400> SEQUENCE: 995 acctttc                                                                 7
```

<210> SEQ ID NO 996
<211> LENGTH: 7
<212> TYPE: DNA
<213> ORGANISM: Artificial Sequence
<220> FEATURE:
<223> OTHER INFORMATION: Well 86

<400> SEQUENCE: 996 gaacact                                                                  7

<210> SEQ ID NO 997
<211> LENGTH: 7
<212> TYPE: DNA
<213> ORGANISM: Artificial Sequence
<220> FEATURE:
<223> OTHER INFORMATION: Well 87

<400> SEQUENCE: 997 catgaac                                                                  7

<210> SEQ ID NO 998
<211> LENGTH: 7
<212> TYPE: DNA
<213> ORGANISM: Artificial Sequence
<220> FEATURE:
<223> OTHER INFORMATION: Well 87

<400> SEQUENCE: 998 aggagaa                                                                  7

<210> SEQ ID NO 999
<211> LENGTH: 7
<212> TYPE: DNA
<213> ORGANISM: Artificial Sequence
<220> FEATURE:
<223> OTHER INFORMATION: Well 88

<400> SEQUENCE: 999 tgcttag                                                                  7

<210> SEQ ID NO 1000
<211> LENGTH: 7
<212> TYPE: DNA
<213> ORGANISM: Artificial Sequence
<220> FEATURE:
<223> OTHER INFORMATION: Well 88

<400> SEQUENCE: 1000 cgcgaaa                                                                  7

<210> SEQ ID NO 1001
<211> LENGTH: 7
<212> TYPE: DNA
<213> ORGANISM: Artificial Sequence
<220> FEATURE:
<223> OTHER INFORMATION: Well 89

<400> SEQUENCE: 1001 ggtatgt                                                                  7

<210> SEQ ID NO 1002
<211> LENGTH: 7
<212> TYPE: DNA
<213> ORGANISM: Artificial Sequence
<220> FEATURE:
<223> OTHER INFORMATION: Well 89

-continued

<400> SEQUENCE: 1002 cgatcta                                                            7

<210> SEQ ID NO 1003
<211> LENGTH: 7
<212> TYPE: DNA
<213> ORGANISM: Artificial Sequence
<220> FEATURE:
<223> OTHER INFORMATION: Well 90

<400> SEQUENCE: 1003 acgtcca                                                            7

<210> SEQ ID NO 1004
<211> LENGTH: 7
<212> TYPE: DNA
<213> ORGANISM: Artificial Sequence
<220> FEATURE:
<223> OTHER INFORMATION: Well 90

<400> SEQUENCE: 1004 accaagt                                                            7

<210> SEQ ID NO 1005
<211> LENGTH: 7
<212> TYPE: DNA
<213> ORGANISM: Artificial Sequence
<220> FEATURE:
<223> OTHER INFORMATION: Well 91

<400> SEQUENCE: 1005 ctcacga                                                            7

<210> SEQ ID NO 1006
<211> LENGTH: 7
<212> TYPE: DNA
<213> ORGANISM: Artificial Sequence
<220> FEATURE:
<223> OTHER INFORMATION: Well 91

<400> SEQUENCE: 1006 ctacgct                                                            7

<210> SEQ ID NO 1007
<211> LENGTH: 7
<212> TYPE: DNA
<213> ORGANISM: Artificial Sequence
<220> FEATURE:
<223> OTHER INFORMATION: Well 92

<400> SEQUENCE: 1007 aacacgc                                                            7

<210> SEQ ID NO 1008
<211> LENGTH: 7
<212> TYPE: DNA
<213> ORGANISM: Artificial Sequence
<220> FEATURE:
<223> OTHER INFORMATION: Well 92

<400> SEQUENCE: 1008 cgacgaa                                                            7

<210> SEQ ID NO 1009

```
<211> LENGTH: 7
<212> TYPE: DNA
<213> ORGANISM: Artificial Sequence
<220> FEATURE:
<223> OTHER INFORMATION: Well 93

<400> SEQUENCE: 1009 cctgtga                                                                    7

<210> SEQ ID NO 1010
<211> LENGTH: 7
<212> TYPE: DNA
<213> ORGANISM: Artificial Sequence
<220> FEATURE:
<223> OTHER INFORMATION: Well 93

<400> SEQUENCE: 1010 agtacgc                                                                    7

<210> SEQ ID NO 1011
<211> LENGTH: 7
<212> TYPE: DNA
<213> ORGANISM: Artificial Sequence
<220> FEATURE:
<223> OTHER INFORMATION: Well 94

<400> SEQUENCE: 1011 gaagacg                                                                    7

<210> SEQ ID NO 1012
<211> LENGTH: 7
<212> TYPE: DNA
<213> ORGANISM: Artificial Sequence
<220> FEATURE:
<223> OTHER INFORMATION: Well 94

<400> SEQUENCE: 1012 ccttgca                                                                    7

<210> SEQ ID NO 1013
<211> LENGTH: 7
<212> TYPE: DNA
<213> ORGANISM: Artificial Sequence
<220> FEATURE:
<223> OTHER INFORMATION: Well 95

<400> SEQUENCE: 1013 cttaacg                                                                    7

<210> SEQ ID NO 1014
<211> LENGTH: 7
<212> TYPE: DNA
<213> ORGANISM: Artificial Sequence
<220> FEATURE:
<223> OTHER INFORMATION: Well 95

<400> SEQUENCE: 1014 acgagca                                                                    7

<210> SEQ ID NO 1015
<211> LENGTH: 7
<212> TYPE: DNA
<213> ORGANISM: Artificial Sequence
<220> FEATURE:
<223> OTHER INFORMATION: Well 96

<400> SEQUENCE: 1015
```

```
acatgtg                                                              7

<210> SEQ ID NO 1016
<211> LENGTH: 7
<212> TYPE: DNA
<213> ORGANISM: Artificial Sequence
<220> FEATURE:
<223> OTHER INFORMATION: Well 96

<400> SEQUENCE: 1016 aggaagc                                                              7
```

DNA DATA STORAGE USING REUSABLE NUCLEIC ACIDS

CROSS-REFERENCE TO RELATED APPLICATIONS

This application claims the benefit of U.S. Provisional Application No. 62/414,383, filed Oct. 28, 2016, the disclosure of which is hereby incorporated by reference in its entirety.

BACKGROUND

The ability to create data is outpacing the ability to store data. This is resulting in a storage gap, in that, significant portions of the data generated is being discarded. This is primarily due to the space required to store such data. For example, with the current media, which consists of magnetic tape and optical discs, storing a zettabyte of data would take many millions of units which would occupy an enormous amount of physical space. Durability is also another disadvantage as discs and tapes are usually rated for 3-5 years and 10-30 years, respectively.

DNA, however, has a storage density of 1 exabyte per cubic millimeter and is highly durable (half-life of over 500 years). The general method of using DNA for data storage involves converting data into a bit stream, which is converted into a DNA sequence, whereby each nucleotide within the nucleic acid sequence represents a bit. The sequence is then synthesized and stored.

In Church et al. (Science 337(6102):1628, 2012) DNA was encoded with digital information that included an HTML draft of a 53,400 word book written by the lead researcher, eleven JPG images and one JavaScript program. The researchers used a code where bits were mapped one-to-one with bases (A or C for zero, G or T for one). They also split the bit stream into addressed data blocks to eliminate the need for a long DNA construct. The order in which the data blocks are placed was encoded into each oligo in the form of a positional registry.

In Goldman et al. (Nature 494(7435):77-80, 2013), over five million bits of data, consisting of text files and audio files, were stored, retrieved and reproduced. They used an error-correcting encoding scheme to minimize data loss, and encoded the data in a series of overlapping short oligonucleotides identifiable through a sequence-based indexing scheme. Also, the sequences of the individual strands of DNA overlapped in such a way that each region of data was repeated four times to avoid errors.

Bornholt et al. (Bornholt J, Lopez R, Carmean D M, Ceze L, Seelig G, Strauss K. A DNA-based archival storage system. In Proceedings of the Twenty-First International Conference on Architectural Support for Programming Languages and Operating Systems, A C M, 2016, pp. 637-49) described a method for encoding, storing, retrieving, and decoding that enables random access of any one of the data sets. This method is more advantageous over the previous methods where all of the strands of synthetic DNA had to be sequenced in order to retrieve only one of several data sets. They accomplished this by flanking the oligos with primer binding sites that allow specific data sets to be amplified and read by their corresponding specific primers. This allows one to select which files to read when multiple files are present. To increase the density, they converted the bit stream from binary to base 3 via Huffman coding. Thus a base can be either 0, 1 or 2. To avoid homopolymers of a single base, which can result from long stretches of 0s, is or 2s, they used a rotating code by which the base corresponding to each value (0, 1 or 2) is dependent on the base preceding it. For example, a "1" will be represented by a G if the preceding base is A. If the preceding base is instead C, then the "1" will be represented by T. To make the reading of the data more reliable, they utilized an XOR function. For example, for oligos A and B, a third oligo will be prepared as A⊕B. If any one of the three oligos is lost, the other two can be used to recover data from that lost oligo.

In the above strategies, bits were encoded directly into the DNA molecule, thus requiring de novo synthesis of millions of DNA molecules with unique sequences. While array-based synthesizers can produce very small amounts and many in parallel, such technology is incapable of producing the oligonucleotides necessary to store even a single gigabyte of data. Furthermore, with today's next-generation sequencing (NGS) instruments, one can effectively read only ~150 bases of any one continuous strand of DNA. Thus, only a few bytes worth of information can be stored on, and read from, a given DNA molecule. Church et al. limited their molecules to contain only 12 bytes of information, or 12 characters because additional room was also needed to also store a positional registry. Given this strategy, storing one gigabyte would require 89,478,486 different molecules. This is not feasible with the most current DNA synthesis methods.

SUMMARY

The methods and compositions disclosed herein are not limited to specific advantages or functionality.

In one aspect, the disclosure provides nucleic acid-based data storage systems comprising a plurality of data storage nucleic acids, each data storage nucleic acid comprising one of N different bit-mer sequences, wherein each bit-mer sequence represents information carried by a single bit in a primary bit string n bits in length, wherein each bit-mer sequence represents the position of the single bit within the primary bit string, and wherein:

(i) N equals n where the primary bit string is a binary bit string, and where the presence of a data storage nucleic acid comprising a particular bit-mer sequence denotes a 1 and the absence of data storage nucleic acid comprising a particular a bit-mer sequence denotes a 0, or vice versa;

(ii) N equals 2·n where the primary bit string is a binary bit string, and where each of n bit-mer sequences denote a 1 at a particular position within the primary bit string and each of the other n bit-mer sequences denote a 0 at a particular position within the primary bit string; and (iii) N equals B·n where the primary bit string is a base-B bit string where B is greater than 2, and where each of B·n bit-mer sequences represents a particular base-B digit at a particular position within the primary bit string.

In some embodiments, each data storage nucleic acid further comprises one of x secondary positional indices, each secondary positional index comprising one or more secondary positional index nucleic acid sequences, wherein the data storage nucleic acids that represent bits from the same primary bit string all comprise the same secondary positional index, and wherein each secondary positional index represents the position of one of x primary bit strings relative to other primary bit strings within a secondary bit string x times n bits in length.

In some embodiments, each data storage nucleic acid further comprises one of y tertiary positional indices, each tertiary positional index comprising one or more tertiary positional index nucleic acid sequences, wherein the data storage nucleic acids that represent bits from the same secondary bit string all comprise the same tertiary positional index, and wherein each tertiary positional index represents the position of one of y secondary bit strings relative to other secondary bit strings within a tertiary bit string x times y times n bits in length.

In some embodiments, each data storage nucleic acid further comprises a document identification sequence and a document-specific primer binding sequence, wherein the data storage nucleic acids that represent bits from the same document all comprise the same document identification sequence and document-specific primer binding sequence.

In some embodiments, each data storage nucleic acid further comprises a page recognition sequence, wherein the data storage nucleic acids that represent bits from the same page within a document all comprise the same page recognition sequence, and wherein the page recognition sequence, together with the document identification sequence and document-specific primer binding sequence, forms a primer binding site allowing data storage nucleic acids sharing a single page recognition sequence to be selectively amplified from the system together.

In some embodiments, each data storage nucleic acid further comprises a folder identification sequence and a folder-specific primer binding sequence, wherein the data storage nucleic acids that represent bits from one or more documents in the same folder all comprise the same folder identification sequence and folder-specific primer binding sequence.

In another aspect, the disclosure provides methods for storing data in a nucleic acid-based data storage system, the methods comprising:
(a) converting the data into a base-B bit string;
(b) sub-dividing the base-B bit string into y secondary bit strings, and sub-dividing each secondary bit string into x primary bit strings n bits in length;
(c) for each of x primary bit strings:
   (i) performing one of:
      (A) where B equals 2, such that the base-B bit string is a binary bit string, from a library of n primary data storage nucleic acids, each comprising a single bit-mer sequence, each bit-mer sequence representing a specific position of a primary bit string n bits in length, selecting the primary data storage nucleic acid with the bit-mer sequence for each position of the primary bit string which is a 1, and selecting no primary data storage nucleic acid for each position of the primary bit string which is a 0;
      (B) where B equals 2, such that the base-B bit string is a binary bit string, from a library of 2·n primary data storage nucleic acids, each comprising a single bit-mer sequence, each of n bit-mer sequences representing a 1 at a specific position of a primary bit string n bits in length, and each of n other bit-mer sequences representing a 0 at a specific position of the primary bit string, selecting the primary data storage nucleic acid with the 1 bit-mer sequence for each position of the primary bit string which is a 1, and selecting the primary data storage nucleic acid with the 0 bit-mer sequence for each position of the primary bit string which is a 0; or
      (C) where B is greater than 2, from a library of B·n primary data storage nucleic acids, each comprising a single bit-mer sequence, each of B·n bit-mer sequences representing a particular base-B digit at a specific position of the primary bit string, selecting the primary data storage nucleic acid with the appropriate bit-mer sequence for each position of the primary bit string;
   wherein all primary data storage nucleic acids comprise the same 5' and 3' 1° primer binding sequences flanking the bit-mer sequence therein;
   (ii) pooling the selected data storage nucleic acids to form one of x pools of primary data storage nucleic acids storing the data of one of x primary bit strings;
   (iii) using a 1° primer pair that binds to the 5' and 3' 1° primer binding sequences to add to each primary data storage nucleic acid the same 5' and 3' secondary positional index sequences and, optionally, the same 5' and 3' 2° primer binding sequences to produce a pool of secondary data storage nucleic acids,
   wherein each of x pools of secondary data storage nucleic acids comprise different 5' and 3' secondary positional index sequences; and
(d) pooling the x pools of secondary data storage nucleic acids corresponding to the x primary bit strings within each of y secondary bit strings into a single pool, to form y pools of secondary data storage nucleic acids, each storing the data of one of y secondary bit strings.

In some embodiments, the base-B bit string is instead sub-divided into z tertiary bit strings, each tertiary bit string sub-divided into y secondary bit strings, and each secondary bit string sub-divided into x primary bit strings n bits in length, the method further comprising:
(e) for each of y pools of secondary data storage nucleic acids, using a 2° primer pair that binds to the 5' and 3' 2° primer binding sequences to add to each secondary data storage nucleic acid the same 5' and 3' tertiary positional index sequences; optionally, the same 5' and 3' tertiary recognition sequences; and, optionally, the same 5' and 3' document identification sequences and the same 5' and 3' document-specific primer binding sequences to produce tertiary data storage nucleic acids;
wherein each of y pools of tertiary data storage nucleic acids comprise different 5' and 3' tertiary positional index sequences; and
wherein tertiary data storage nucleic acids representing bits from the same document all comprise the same 5' and 3' document identification sequences and the same 5' and 3' document-specific primer binding sequences; and
(f) pooling they pools of tertiary data storage nucleic acids corresponding to they secondary bit strings within each of z tertiary bit strings into a single pool, to form z pools of tertiary data storage nucleic acids, each storing the data of one of z tertiary bit strings.

In some embodiments, the methods further comprise:
(g) using one or more 3° primers that bind to the 5' and 3' document-specific primer binding sequences to add to one or more of z pools of tertiary data storage nucleic acids the same 5' and 3' folder identification sequences and the same folder-specific primer binding sequences,
wherein tertiary data storage nucleic acids representing bits from one or more documents within the same folder all comprise the same 5' and 3' folder identification sequences and the same 5' and 3' folder-specific primer binding sequences.

In some embodiments of any of the methods, compositions, or systems of the disclosure, B is 256 such that the primary bit string is a base-256 bit string, and each bit-mer sequence represents a byte of information.

In another aspect, the disclosure provides data storage nucleic acids comprising:
(a) a bit-mer sequence, which represents information carried by a single bit in a primary bit string, and which further represents the position of the bit within the primary bit string.

In some embodiments, the data storage nucleic acids further comprise:
(b) a 5' secondary positional tag comprising
   (i) a 5' 1° primer binding sequence flanking the 5' end of the bit-mer sequence, and
   (ii) a 5' secondary positional index sequence flanking the 5' end of the 5' 1° primer binding sequence; and
(c) a 3' secondary positional tag comprising
   (i) a 3' 1° primer binding sequence flanking the 3' end of the bit-mer sequence, and
   (ii) a 3' secondary positional index sequence flanking the 3' end of the 3' 1° primer binding sequence;
wherein the 5' and 3' secondary positional index sequences represent the position of the primary bit string relative to one or more other primary bit strings within a secondary bit string.

In some embodiments, the 5' secondary positional index sequence is identical to the 3' secondary positional index sequence. In some embodiments, the 5' secondary positional index sequence is different from the 3' secondary positional index sequence.

In some embodiments, the data storage nucleic acids further comprise:
(d) a 5' tertiary positional tag comprising
   (i) a 5' 2° primer binding sequence flanking the 5' end of the 5' secondary positional index sequence,
   (ii) a 5' tertiary positional index sequence flanking the 5' end of the 5' 2° primer binding sequence, and
   (iii) optionally, a 5' tertiary recognition sequence flanking the 5' end of the 5' tertiary positional index sequence; and
(e) a 3' tertiary positional tag comprising
   (i) a 3' 2° primer binding sequence flanking the 3' end of the 3' secondary positional index sequence,
   (ii) a 3' tertiary positional index sequence flanking the 3' end of the 3' 2° primer binding sequence, and
   (iii) optionally, a 3' tertiary recognition sequence flanking the 3' end of the 3' tertiary positional index sequence;
wherein the 5' and 3' tertiary positional index sequences represent the position of the secondary bit string relative to one or more other secondary bit strings within a tertiary bit string.

In some embodiments, the 5' tertiary positional index sequence is identical to the 3' tertiary positional index sequence. In some embodiments, the 5' tertiary positional index sequence is different from the 3' tertiary positional index sequence.

In some embodiments, the data storage nucleic acids further comprise a 5' filing domain flanking the 5' end of the 5' tertiary positional index sequence, which comprises one or more of:
(f) a 5' document identification tag comprising
   (i) a 5' document identification sequence, and
   (ii) a 5' document-specific primer binding sequence flanking the 5' end of the 5' document identification sequence; or
(g) a 5' folder identification tag comprising
   (i) a 5' folder identification sequence, and
   (ii) a 5' folder-specific primer binding sequence flanking the 5' end of the 5' folder identification sequence.

In some embodiments, the data storage nucleic acids further comprise a 3' filing domain flanking the 3' end of the 3' tertiary positional index sequence, which comprises one or more of:
(f) a 3' document identification tag comprising
   (i) a 3' document identification sequence, and
   (ii) a 3' document-specific primer binding sequence flanking the 3' end of the 3' document identification sequence; or
(g) a 3' folder identification tag comprising
   (i) a 3' folder identification sequence, and
   (ii) a 3' folder-specific primer binding sequence flanking the 3' end of the 3' folder identification sequence.

In another aspect, the disclosure provides nucleic acid-based data storage systems comprising a plurality of data storage nucleic acids, each data storage nucleic acid comprising one of N different bit-mer sequences, wherein each bit-mer sequence represents:
(a) information carried by a bit in a primary bit string n bits in length and the position p of the bit within the primary bit string, and
(b) information carried by A adjacent bits in the primary bit string; and
wherein N equals $B^{(A+1)} \cdot n$ where the primary bit string is a base-B bit string, and where each of $B^{(A+1)} \cdot n$ bit-mer sequences represents a base-B digit at a particular position within the primary bit string along with the one or more base-B digits at the positions occupied by the A adjacent bits.

In another aspect, the disclosure provides methods for storing data in a nucleic acid-based data storage system, the methods comprising:
(a) converting the data into a base-B bit string;
(b) sub-dividing the base-B bit string into y secondary bit strings, and sub-dividing each secondary bit string into x primary bit strings n bits in length;
(c) for each of x primary bit strings:
   (i) from a library of $B^{(A+1)} \cdot n$ primary data storage nucleic acids, each comprising a single bit-mer sequence, each of $B^{(A+1)} \cdot n$ bit-mer sequences representing (1) a particular base-B digit at a specific position p of the primary bit string, in addition to (2) a base-B digit at each of A positions adjacent to position p, selecting the primary data storage nucleic acid with the appropriate bit-mer sequence for each position p of the primary bit string;
   wherein all primary data storage nucleic acids comprise the same 5' and 3' 1° primer binding sequences flanking the bit-mer sequence therein;
   (ii) pooling the selected data storage nucleic acids to form one of x pools of primary data storage nucleic acids storing the data of one of x primary bit strings;
   (iii) using a 1° primer pair that binds to the 5' and 3' 1° primer binding sequences to add to each primary data storage nucleic acid the same 5' and 3' secondary positional index sequences and, optionally, the same 5' and 3' 2° primer binding sequences to produce a pool of secondary data storage nucleic acids,
   wherein each of x pools of secondary data storage nucleic acids comprise different 5' and 3' secondary positional index sequences; and
(d) pooling the x pools of secondary data storage nucleic acids corresponding to the x primary bit strings within each of y secondary bit strings into a single pool, to form y pools of secondary data storage nucleic acids, each storing the data of one of y secondary bit strings.

BRIEF DESCRIPTION OF THE DRAWINGS

FIGS. 9A-9C show the depth of coverage for desired and undesired reads for Document 1, using Zero/One Bit Encoding and Discrete Primers taken from a pure source containing only Document 1 as described in Example 11. FIG. 9A shows the depth count distribution for desired (dark gray) and undesired (light gray) bits. FIG. 9B shows the occurrence of each mispairing of forward and reverse plate indices as a percentage of total reads. FIG. 9C shows the coverage of mispairings of forward and reverse well indices as a heat map where light gray indicates relatively low coverage and dark gray indicates relatively high coverage, with a low to high coverage range of around 80 to around 160. The black squares that make up the diagonal line represent the correct well barcode pairings.

FIGS. 10A-10C show the depth of coverage for desired and undesired reads for Document 2, using Zero/One Bit Encoding and Discrete Primers taken from a pure source containing only Document 2 as described in Example 11. FIG. 10A shows the depth count distribution for desired (dark gray) and undesired (light gray) bits. FIG. 10B shows the occurrence of each mispairing of forward and reverse plate indices as a percentage of total reads. FIG. 10C shows the coverage of mispairings of forward and reverse well indices as a heat map where light gray indicates relatively low coverage and dark gray indicates relatively high coverage, with a low to high coverage range of around 80 to around 160. The black squares that make up the diagonal line represent the correct well barcode pairings.

FIGS. 11A-11B show the depth of coverage for desired and undesired reads for Document 1, using Presence/Absence Bit Encoding and Shared Primers taken from a pure source containing only Document 1 as described in Example 11. FIG. 11A shows the depth count distribution for desired (dark gray) and undesired (light gray) bits. FIG. 11B shows the occurrence of each mispairing of forward and reverse plate indices as a percentage of total reads.

FIGS. 12A-12C show the depth of coverage for desired and undesired reads for Document 1, using Zero/One Bit Encoding and Discrete Primers, taken from a mixed source containing both Documents 1 and 2 as described in Example 11. FIG. 12A shows the depth count distribution for desired (dark gray) and undesired (light gray) bits. FIG. 12B shows the occurrence of each mispairing of forward and reverse plate indices as a percentage of total reads. FIG. 12C shows the coverage of mispairings of forward and reverse well indices as a heat map where light gray indicates relatively low coverage and dark gray indicates relatively high coverage, with a low to high coverage range of around 80 to around 160. The black squares that make up the diagonal line represent the correct well barcode pairings.

DETAILED DESCRIPTION

Figure 1A:
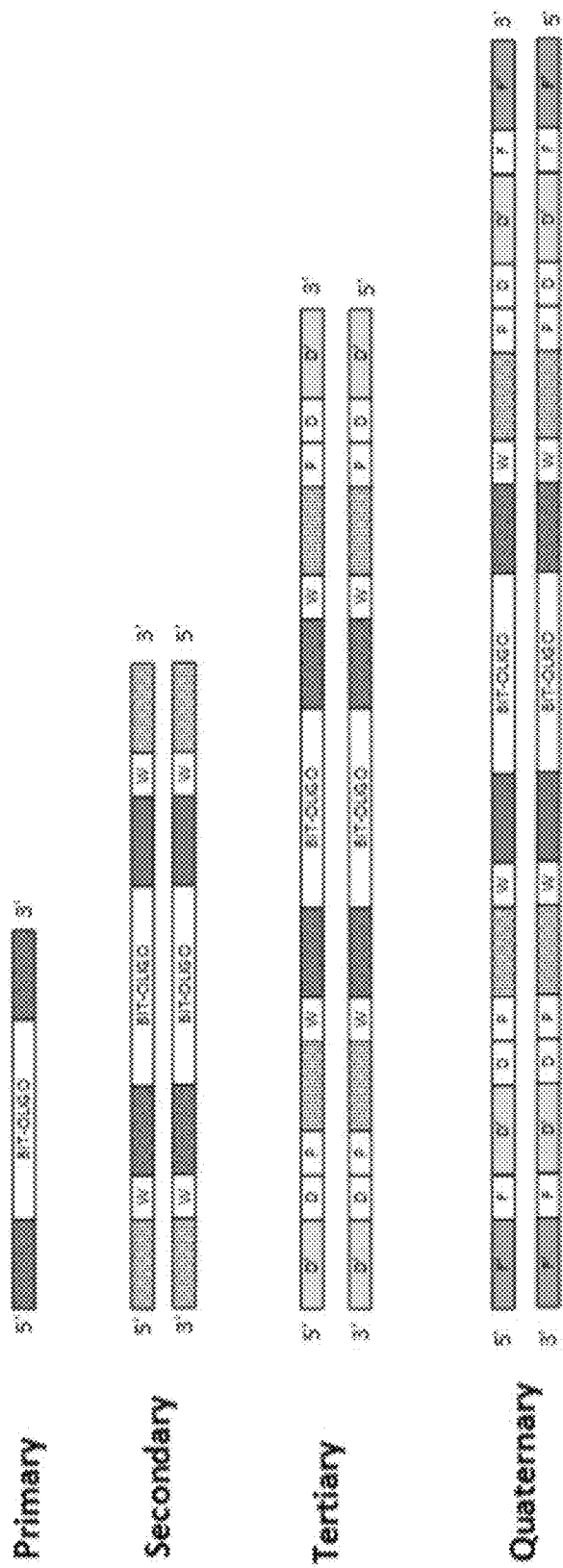
FIGS. 1A-1C show the hierarchical organization of data storage nucleic acid constructs of the disclosure and methods for reading them.

All publications, patents and patent applications cited herein are hereby expressly incorporated by reference for all purposes.

The present invention is directed to an oligonucleotide-based data storage system comprising a plurality of data storage oligonucleotides. In the present invention, the idea is not to store the bit directly in the DNA, as in systems where a single nucleotide represents a bit, or where a nucleic acid sequence represents a bit string, but rather to utilize different, reusable nucleic acid sequences, wherein each reusable nucleic acid sequence represents a single bit.

Before describing the disclosed methods and compositions in detail, a number of terms will be defined. As used herein, the singular forms "a", "an" and "the" include plural referents unless the context clearly dictates otherwise. For example, reference to "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "nucleic acid," "polynucleotide," "oligonucleotide," and "oligo" are interchangeable and refer to any biopolymer made from nucleotide monomers. Nucleic acids include DNA, RNA, derivatives thereof, or combinations thereof.

The term "polymerase chain reaction" or "PCR" as used herein refers to a technique used in molecular biology to amplify a single copy or a few copies of a piece of DNA across several orders of magnitude, generating thousands to millions of copies of a particular DNA sequence. The steps in PCR include 1) denaturing a target DNA; 2) annealing of the primers to the single-stranded DNA template; 3) extending using an enzyme, DNA polymerase, which synthesizes a new DNA strand complementary to the DNA template strand by adding dNTPs that are complementary to the template. In sum, denaturing involves heating a DNA sample to separate its two strands. Once separated, the two strands are used as templates to synthesize two new DNA strands. The synthesis is carried out using a DNA polymerase. Subsequently, the newly synthesized molecules are used as templates to generate two more copies of DNA. The two basic steps involved in PCR, denaturing and synthesis, are repeated multiple times using thermal cycling, consisting of repeated heating and cooling of the reaction for DNA melting and enzymatic replication of the DNA. Primers containing sequences complementary to the target region, along with the DNA polymerase, are key components to enable selective and repeated amplification. As PCR progresses, the DNA generated is itself used as a template for replication, setting in motion a chain reaction in which the DNA template is exponentially amplified. Each time the process of denaturing and synthesis occurs, the number of DNA molecules doubles. This makes it possible to generate one billion exact copies of an original target DNA.

As used herein, the term "amplify" refers to increasing the frequency of occurrence or concentration of a nucleic acid, as a result of replicating the nucleic acid by an in vivo or in vitro process, such as by gene duplication or polymerase chain reaction, respectively.

As used herein, the term "bit" refers to the smallest unit of data in a computing or data storage system. Although, in some embodiments, the term "bit" is synonymous and interchangeable with the term "binary digit," in other embodiments, the term "bit" as used herein may also refer to the smallest unit of data in higher-order numeral systems, such as base-3 (ternary), base-4 (quaternary), or base-N numeral systems, where N is any positive integer. Thus, in a base-3 system, the term "bit" as used herein is interchangeable with the terms "trinary digit" or "trit." In another example, in a base-256 system, a "bit" would represent the information of, and be interchangeable with, a "byte."

In some embodiments, the term "bit" refers to the smallest unit of data in a binary, or base-2, system. In such embodiments, a bit can have one of two values, which are most commonly represented as either a 0 or a 1. In embodiments, for example, in which the nucleic acid data storage constructs of the disclosure each represent a bit within a base-3 (ternary numeral) system, the bit is understood to be synonymous with a "trit" and can have one of three values, which are commonly represented as 0, 1, or 2. In some embodiments, the system is a base-256 system, such that the nucleic acid data storage constructs of the disclosure each represent a byte of information. In such embodiments, 256 bit-oligos are required at each position of the primary string to represent all 256 possible values.

Although computers usually provide instructions that can test and manipulate bits, they generally are designed to store data and execute instructions in bit multiples or "bytes." In most computer systems, there are eight bits in a byte. A single typed character measures one byte.

As used herein, the term "bit string" refers to a sequence of bits. Thus, an 8-bit byte can be represented as a bit string of eight bits. Similarly, a character string of three letters would consist of three bytes, each of eight bits, and thus could be represented as a bit string of 24 bits.

As used herein, the terms "bit-mer" and "bit-oligo" are interchangeable and refer to a nucleic acid sequence that, as a whole, represents a single bit within a bit string, including the position of the bit within the bit string. For example, a bit string that is four bits in length could be represented by four different bit-mer nucleic acid sequences, each 30 nucleotides (nt) in length, where each of the four 30-nt nucleic acid sequences represents not only the information carried by each bit, but also the position of each bit within the bit string.

The methods and products of the disclosure relate not to the storage of data within a DNA molecule where single nucleotides or even nucleotide codons within the DNA sequence represent bits such that a single oligonucleotide represents a bit string, but rather to the use of reusable nucleic acid data storage molecules wherein the molecules themselves each represent a single bit within a bit string, and wherein each molecule also represents the position of that single bit within the bit string. In some embodiments of the methods disclosed herein, in a pool comprising a plurality of data storage nucleic acid molecules, the presence of a particular data storage nucleic acid molecule represents a "1" within the bit string at that particular position, and the absence of a particular data storage nucleic acid molecule represents a "0" within the bit string at that particular position. In other embodiments, "0" at a particular position in a bit string can be represented by the presence of other specified nucleic acid data storage molecules, rather than by the absence of molecules that represent "1."

Thus, in one aspect, the disclosure provides nucleic acid-based data storage systems comprising a plurality of data storage nucleic acids, each data storage nucleic acid comprising one of N different bit-mer sequences, wherein each bit-mer sequence represents information carried by a single bit in a primary bit string n bits in length, wherein each bit-mer sequence represents the position of the single bit within the primary bit string, and wherein: (i) N equals n where the primary bit string is a binary bit string, and where the presence of a data storage nucleic acid comprising a particular bit-mer sequence denotes a 1 and the absence of data storage nucleic acid comprising a particular a bit-mer sequence denotes a 0, or vice versa; (ii) N equals 2·n where the primary bit string is a binary bit string, and where each of n bit-mer sequences denote a 1 at a particular position within the primary bit string and each of the other n bit-mer sequences denote a 0 at a particular position within the primary bit string; and (iii) N equals B·n where the primary bit string is a base-B bit string where B is greater than 2, and where each of B·n bit-mer sequences represents a particular base-B digit at a particular position within the primary bit string.

In some embodiments, each data storage nucleic acid further comprises one of x secondary positional indices, each secondary positional index comprising one or more secondary positional index nucleic acid sequences, wherein the data storage nucleic acids that represent bits from the same primary bit string all comprise the same secondary positional index, and wherein each secondary positional index represents the position of one of x primary bit strings relative to other primary bit strings within a secondary bit string x times n bits in length.

In some embodiments of any of the compositions or methods of the disclosure, secondary positional indices are referred to as well (W) indices, well-level indices, well barcodes, or well-level barcodes.

In some embodiments, each data storage nucleic acid further comprises one of y tertiary positional indices, each tertiary positional index comprising one or more tertiary positional index nucleic acid sequences, wherein the data storage nucleic acids that represent bits from the same secondary bit string all comprise the same tertiary positional index, and wherein each tertiary positional index represents the position of one of y secondary bit strings relative to other secondary bit strings within a tertiary bit string x times y times n bits in length.

In some embodiments of any of the compositions or methods of the disclosure, tertiary positional indices are referred to as plate (P) indices, plate-level indices, plate barcodes, or plate-level barcodes.

In some embodiments, each data storage nucleic acid further comprises a document identification sequence and a document-specific primer binding sequence, wherein the data storage nucleic acids that represent bits from the same document all comprise the same document identification sequence and document-specific primer binding sequence.

In some embodiments of any of the compositions or methods of the disclosure, document identification sequences are referred to as document (D) indices, document-level indices, document barcodes, or document-level barcodes.

In some embodiments, each data storage nucleic acid further comprises a page recognition sequence, wherein the data storage nucleic acids that represent bits from the same page within a document all comprise the same page recognition sequence, and wherein the page recognition sequence, together with the document identification sequence and document-specific primer binding sequence, forms a primer binding site allowing data storage nucleic acids sharing a single page recognition sequence to be selectively amplified from the system together.

In some embodiments of any of the compositions or methods of the disclosure, page recognition sequences are referred to as page (P*) identification sequences, page indices, page-level indices, page barcodes, page-level barcodes, page-level recognition sequences, or tertiary recognition sequences.

In some embodiments, each data storage nucleic acid further comprises a folder identification sequence and a folder-specific primer binding sequence, wherein the data storage nucleic acids that represent bits from one or more documents in the same folder all comprise the same folder identification sequence and folder-specific primer binding sequence.

In some embodiments of any of the compositions or methods of the disclosure, folder identification sequences are referred to as folder (F) indices, folder-level indices, folder barcodes, or folder-level barcodes.

In another aspect, the disclosure provides data storage nucleic acids comprising: (a) a bit-mer sequence, which represents information carried by a single bit in a primary bit string, and which further represents the position of the bit within the primary bit string.

In some embodiments, the data storage nucleic acids of the disclosure further comprise: (b) a 5' secondary positional tag comprising (i) a 5' 1° primer binding sequence flanking the 5' end of the bit-mer sequence, and (ii) a 5' secondary positional index sequence flanking the 5' end of the 5' 1° primer binding sequence; and/or (c) a 3' secondary positional tag comprising (i) a 3' 1° primer binding sequence flanking the 3' end of the bit-mer sequence, and (ii) a 3' secondary positional index sequence flanking the 3' end of the 3' 1° primer binding sequence; wherein the 5' and 3' secondary positional index sequences represent the position of the primary bit string relative to one or more other primary bit strings within a secondary bit string.

In some embodiments, the 5' secondary positional index sequence is identical to the 3' secondary positional index sequence. In some embodiments, the 5' secondary positional index sequence is different from the 3' secondary positional index sequence.

In some embodiments, the data storage nucleic acids of the disclosure further comprise: (d) a 5' tertiary positional tag comprising (i) a 5' 2° primer binding sequence flanking the 5' end of the 5' secondary positional index sequence, (ii) a 5' tertiary positional index sequence flanking the 5' end of the 5' 2° primer binding sequence, and (iii) optionally, a 5' tertiary recognition sequence flanking the 5' end of the 5' tertiary positional index sequence; and/or (e) a 3' tertiary positional tag comprising (i) a 3' 2° primer binding sequence flanking the 3' end of the 3' secondary positional index sequence, (ii) a 3' tertiary positional index sequence flanking the 3' end of the 3' 2° primer binding sequence, and (iii) optionally, a 3' tertiary recognition sequence flanking the 3' end of the 3' tertiary positional index sequence; wherein the 5' and 3' tertiary positional index sequences represent the position of the secondary bit string relative to one or more other secondary bit strings within a tertiary bit string. In some embodiments, the 5' tertiary positional index sequence is identical to the 3' tertiary positional index sequence. In some embodiments, the 5' tertiary positional index sequence is different from the 3' tertiary positional index sequence.

In some embodiments of any of the compositions or methods of the disclosure, tertiary recognition sequences are referred to as page recognition (P*) sequences or page-level recognition sequences.

In some embodiments, the data storage nucleic acids of the disclosure further comprise: a 5' filing domain flanking the 5' end of the 5' tertiary positional index sequence, which comprises one or more of: (f) a 5' document identification tag comprising (i) a 5' document identification sequence, and (ii) a 5' document-specific primer binding sequence flanking the 5' end of the 5' document identification sequence; and/or (g) a 5' folder identification tag comprising (i) a 5' folder identification sequence, and (ii) a 5' folder-specific primer binding sequence flanking the 5' end of the 5' folder identification sequence. In some embodiments, the data storage nucleic acids of the disclosure further comprise: a 3' filing domain flanking the 3' end of the 3' tertiary positional index sequence, which comprises one or more of: (f) a 3' document identification tag comprising (i) a 3' document identification sequence, and (ii) a 3' document-specific primer binding sequence flanking the 3' end of the 3' document identification sequence; and/or (g) a 3' folder identification tag comprising (i) a 3' folder identification sequence, and (ii) a 3' folder-specific primer binding sequence flanking the 3' end of the 3' folder identification sequence.

In some embodiments, the data storage nucleic acids of the disclosure are symmetrical in structure; that is, for every 5' tag (wherein a tag comprises a primer binding sequence and one or more index sequences) the nucleic acid construct also comprises a corresponding 3' tag. However, in some embodiments, the data storage nucleic acids of the disclosure are asymmetrical; that is, for one or more 5' tags, the construct does not comprise corresponding 3' tags, or alternatively for one or more 3' tags, the construct does not comprise corresponding 5' tags. A non-limiting example of an asymmetrical data storage nucleic acid is a construct comprising a bit-mer sequence, a 5' 1° primer binding sequence flanking the 5' end of the bit-mer sequence, a 5' secondary positional index sequence flanking the 5' end of the 5' 1° primer binding sequence, a 5' 2° primer binding sequence flanking the 5' end of the 5' secondary positional index sequence, a 5' tertiary positional index sequence flanking the 5' end of the 5' 2° primer binding sequence, a 5' document identification sequence, a 5' document-specific primer binding sequence flanking the 5' end of the 5' document identification sequence, a 5' folder identification sequence, and a 5' folder-specific primer binding sequence flanking the 5' end of the 5' folder identification sequence, but no corresponding 3' tags, sequences, or indices. Generally, however, the presence of two or more sequences for each level of hierarchical organization can help reduce encoding and/or reading errors. Furthermore, in embodiments in which the secondary positional indices comprise two sub-indices, such as where a well index is made up of (1) a row index and (2) a column index, the two sub-indices may be placed on either side of the bit-mer sequence (e.g., the row index on the 5' side and the column index on the 3' side, or vice versa); in such embodiments, the nucleic acid data storage construct will comprise both 5' and 3' indices for that organizational level.

FIG. 1A shows a schematic depicting different levels of organization for data storage nucleic acid molecules of the disclosure. The primary level of organization is a bit-mer itself, which comprises a nucleic acid that represents the information carried by a single bit, and which further represents the position of that single bit within a bit string. The primary bit-oligo is flanked by conserved (i.e. the same sequences are present on all bit-oligos within a given system) 1° primer binding domains, depicted in FIG. 1 as dark-shaded regions on either side of the central bit-oligo.

The secondary level of organization is the product of a 1° PCR step which adds the well indices. During the 1° PCR step, one or more 1° primers pair hybridize to and prime off of the conserved 1° primer binding domain(s) of the bit-mer (dark shaded), encode the well-specific indices (W), and terminate with the conserved binding domains for the 2° primers (light shaded regions flanking the "W" indices in FIG. 1).

In some embodiments, the tertiary level of organization is the product of a 2° PCR step which adds plate and document indices. In the 2° PCR step, one or more 2° primers hybridize and prime off of the conserved 2° primer binding domain(s) flanking the well indices (W), encode the plate and document specific indices (P and D, respectively), and terminate with the document-specific primer binding domains (D').

In some embodiments, the tertiary level of organization is the product of a 2° PCR step which adds page and document indices. In the 2° PCR step, one or more 2° primers hybridize and prime off of the conserved 2° primer binding domain(s) flanking the well indices (W), encode the plate and document specific indices (P and D, respectively), optionally with a Page recognition sequence (P*) in between the plate and document specific indices, and terminate with the document-specific primer binding domains (D').

The quaternary level of organization is the product of a 3° PCR step which adds one or more folder indices (F). The 3° primer set contains the document-specific primers that hybridize and prime off of document-specific primer binding sites (D'), encode folder indices (F), and terminate with folder-specific primer binding domains (denoted F' in FIG. 1). 3° PCR with the 3° primer set effectively assigns a document to a specified folder. Thus, if there is a folder with numerous documents and one desires to pull out a specific document, this can be achieved via PCR with primers that are both specific to that document's primer binding domain (D' regions in FIG. 1) and contain 5' tail regions containing NGS adapters such as P5 and P7 to be used with, for example, the Illumina-based NGS system.

In contrast to the 1° and 2° primer binding domains (dark and light gray shaded regions in FIG. 1), the Folder and Document level primer binding domains (F' and D') are specific and associated with their respective F and D indices.

In some embodiments, the Folder (F) and Document (D) indices are placed internally to their respective primer pair to create a dual-key system. Using a dual-key system provides greater protection from off-target effects. The first key is the primer pair used to amplify the Document. The second key is the document index D read during NGS to ensure that what was amplified is correct. A dual-key strategy may also be employed at the Folder level and any additional organizational levels encoded.

Thus, the Document (tertiary) level defines the smallest movable or sequenced unit and is not universally conserved. The Well and Plate levels are universally conserved.

In some embodiments, the Folder level is optional and is shown in FIG. 1 to demonstrate an additional level of hierarchical organization. The tertiary (3°) primer pair defines the addition of a document to a folder if no folder existed or with the intention of copying it to a new folder. In some embodiments, a folder is directly encoded into the 2° primer pair.

In some embodiments of the methods and products disclosed herein, the well indices ("W") represent the well of a receiving plate in which a pool of nucleic acid data storage constructs is assembled, where when completed, the pool contains the information in a bit string. However, as used herein, the term "well" represents any secondary level of organization and is not limited to the apparatus or particular manner in which a pool of nucleic acid data storage molecules is assembled or constructed. Thus, in some embodiments, data storage nucleic acid pools are assembled by liquid transfer of data storage nucleic acids from a master plate containing a plurality of N wells (each of which contains one of the N different bitmers) into a well of a receiving plate containing a plurality of (x) wells, such that the secondary level of organization corresponds to the well into which the primary data storage nucleic acids are initially pooled. However, in other embodiments, the secondary level of organization may correspond to a vial or tube or other container into which primary data storage nucleic acids are pooled. In this disclosure, any and all potential secondary levels of organization may be referred to herein as the "well" level of organization, regardless of whether a well in a plate is actually used in a given instance. As with the term "well," the terms "plate," "document," and "folder" are used herein to represent levels of organization and are not intended to limit the methods and products disclosed herein to the manner of assembly of a given nucleic acid-based data storage system. Thus, any and all potential tertiary levels of organization may be referred to herein as "plate" and/or "document" levels of organization, regardless of whether a plate is actually used in a given instance to assemble data storage nucleic acids, or whether the information encoded by the data storage nucleic acids is conceptualized as being associated with one or more documents.

As sequencing reads in NGS become longer, higher levels of organization are used as necessary or convenient. Thus, a given data storage system according to the disclosure may use quinary (5°), senary (6°), septenary (7°), octonary (8°), nonary (9°), and further levels of organization, including 5°, 6°, 7°, 8°, 9°, and further indices, primer binding sites, and PCR steps in order to organize, handle, read, analyze, or interpret the data encoded within a data storage nucleic acid system of the disclosure.

In some embodiments, the methods and products of the disclosure comprise an additional Page level of organization. In some embodiments, very large documents might exceed the capacity of a given NGS platform. In the encoding strategies of the disclosure, bit values are represented by a fully encoded construct. These constructs in turn typically require at least one entire NGS trace each to decode; therefore, the number of traces needed for decoding grows linearly with the number of bits to be encoded. For example, using the MiSeq platform with a trace size of 150 nt, two traces would be required to decode each 210 bp construct.

As used herein, the term "trace" refers to a single sequencing read of a single DNA library fragment (of which there may be, for example, millions). An NGS platform may be, for example, limited to traces that are 150 bases long. In such an example, if one is trying to sequence a library where the individual fragments are 300 bases long, two traces (one from each end), would be required to sequence a whole fragment.

As a non-limiting example, to effectively decode an exemplary document consisting of 109,568 bits, an average depth of, for example, 40 might be needed, where each depth increment is a consensus construct comprising of a forward and reverse trace (i.e., 2 traces). As a result the document would require an estimated 8.77 million viable traces to decode, assuming no traces are lost to contamination constructs. A typical MiSeq run generates ~35 million traces; thus, 14.4 NGS runs' worth of traces would be required to effectively decode the exemplary document. In another example, even a HiSeq 4000 instrument with a reported capacity of 10 billion traces per run could only decode 11.64% of 1 gigabyte worth of encoded data in a single run. Thus, it would take 8.6 HiSeq 4000 runs to decode 1 gigabyte of data assuming no construct contamination. Accordingly, in some embodiments, an additional "Page" extraction layer is present, which becomes the smallest decodable unit, whereas the document layer remains the smallest moveable unit.

In some embodiments, the "Page" is largely equivalent to the "Plate" level of organization described above. However, in some embodiments, liquid handling and/or dispensing mechanisms do not employ receiving plates or wells; thus, a Plate may instead be virtualized as the concept of a Page. In some embodiments, decoding of documents is achievable within a single NGS run on the scale of, for example, NextSeq or HiSeq platforms. In other embodiments, however, where the means to decode a document in a single NGS run is not available, the document may be separated into Pages.

Figure 13:
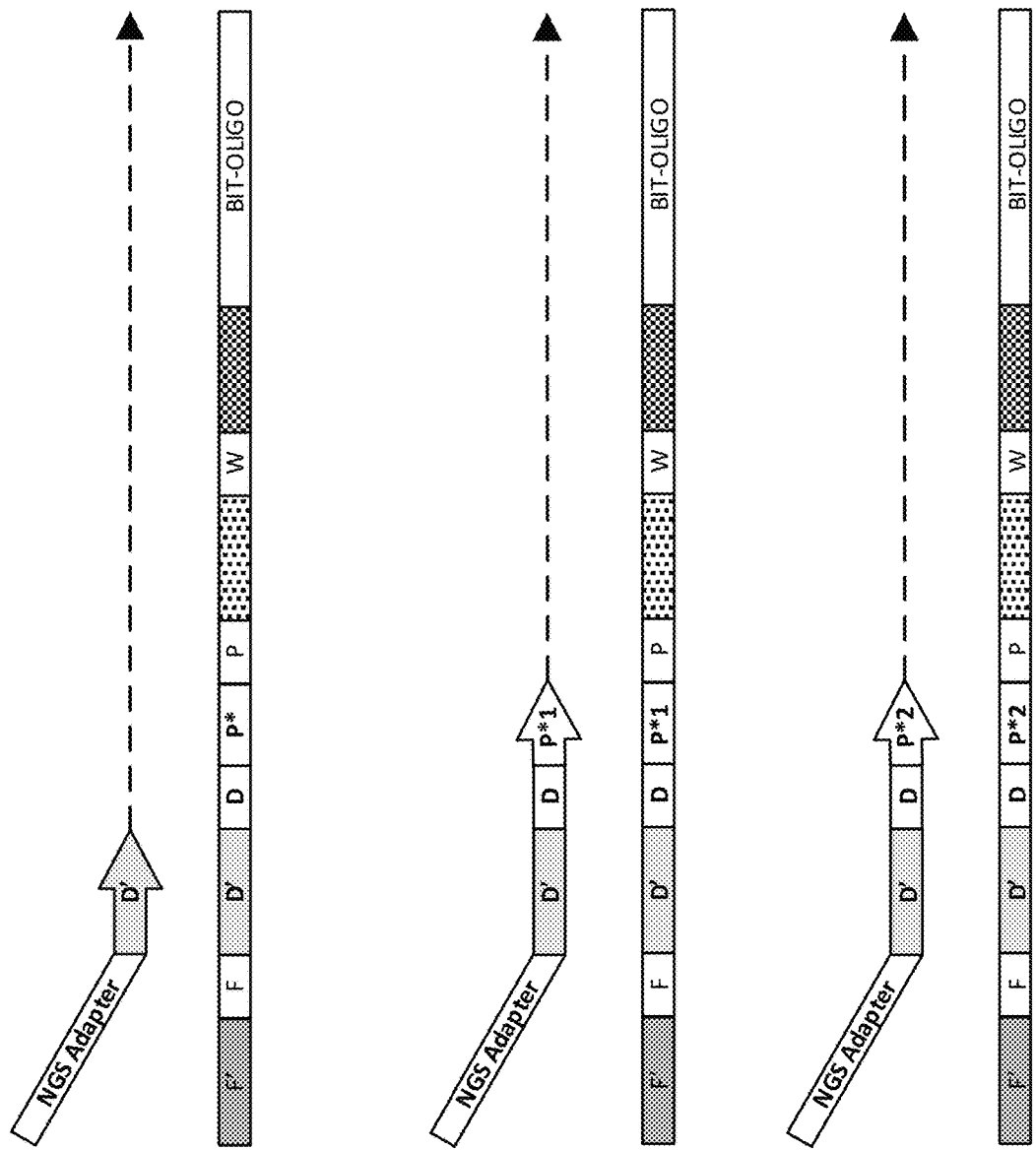
FIG. 13 is a schematic demonstrating how a large document, which requires multiple NGS runs to read, can be divided into Pages, where each page represents a separate NGS run, and ordered accordingly. The top panel represents a construct in a scenario in which the entirety of a document can be decoded within a single NGS run and, thus, only a single Page recognition sequence, P*, is used, and primers with only document-specific primer binding sites are sufficient for reading. The middle and bottom panels, on the other hand, represent the scenario where the document is too large to be decoded in a single NGS run and is thus divided into constructs comprising two page recognition sequences, P*1 and P*2. Here, the reading primers are designed to anneal to the page recognition sites, P*1 and P*2, in addition to the document-specific binding sites and the document index. In this way, the order can be determined for the different pages in the large document. In this scenario, while the document level is still the smallest moveable unit, the page would be the smallest readable unit.

FIG. 13 shows a schematic of construct organization that includes Pages. In such a construct, a Page-index (P*) (also referred to herein as a "page-level index", "page barcode", "page-level barcode", "page recognition domain," "page recognition sequence," or "tertiary recognition sequence") DNA segment is inserted between the Document (D) and Plate (P) barcodes. In general, the page index is large enough to provide primer binding specificity, but not sufficiently large to act as a standalone priming site. In some embodiments, the page index is 8-10 bp in size. FIG. 13 shows only the 5' side of the construct, where the D and P* barcodes are currently adjacent. Inserting a P* page index in between the D and P barcodes supplies the amplification specificity needed, but the P* page index is not large enough to stabilize binding of a primer on its own; rather, primer binding is dependent on the stability provided by the document-level D' priming and D barcode (identification) domains. In such embodiments, the construct is symmetrical with both 5' and 3' halves of the construct having a distinct P* index. Where the P barcode is reused across documents, so too is the P* site reused.

Extracting and tagging constructs with NGS adapters at either the Document level, in the case of one decoding NGS run, or at the Page level, for multiple decoding NGS runs, results in constructs that are nevertheless identical. Thus, independent of the extraction approach, the resulting amplicons allow for a unified means (analysis algorithm) for decoding the NGS data.

In the methods and nucleic acid data storage constructs of the disclosure, the bit-mers, hierarchical indices, and primer binding sequences can vary in length. For example, bit-mer sequences can be from about 5 to about 500, or from about 10 to 100, or about 10, or about 20, or about 30, or about 40, or about 50, or about 60, or about 70, or about 80, or about 90, or about 100, or about 120, or about 140, or about 150, or about 160, or about 180, or about 200 nucleotides in length. In some embodiments, the bit-mer sequences are 30 nucleotides in length. In general, the length of bit-mer sequences in systems that use a relatively small overall number of different bit-mer sequences, for example between 200 to 500 different bit-mer sequences, can be relatively small, such as about 30 nucleotides in length. This is because a 30 nt length is enough to maintain enough differences between one bit-mer sequence and another such that accidental transitions are relatively unlikely to occur. Systems in which there are greater numbers of different bit-mer sequences, however, tend to require that each bit-mer sequence be longer in order to provide greater differences between each sequence.

Regarding the nucleotide length of indices, as markers, they should be large enough to differentiate between all possible representatives present in the system. In some embodiments, the minimum length of index sequences is determined to be $\log_4 x$ where x is the total number of different indices in a completed construct. However, in general, sequences should be sufficiently different from each other (more than by just 1-2 bases) to be properly differentiated from each other in an NGS run. Thus, in some embodiments, bitmer and/or index sequence lengths are, at least in part, determined using Levenshtein distances (the number of edits needed to convert one sequence to another) with values of 12 for the bitmers, and values of 2 and 3 for the well and plate indices. Other factors that impact overall length are requirements such as percent G/C content and/or homopolymer content. For example, in some embodiments, bitmer and/or index sequences are designed with % GC content between 30-70%. In some embodiments, bitmer and/or index sequences are designed such that they do not comprise any homopolymers. These length and design considerations also apply to the design of primer binding sequences, with the addition of the need to maintain optimal Tm values and prevent primer dimers and cross-reactivity.

The upper limit for overall construct length is primarily determined by the maximum length of continuous sequence that can be read by the sequencing method used, such as next-generation sequencing (NGS). With current technology, the total length of the data storage nucleic acid typically does not exceed about 300 bases. In some embodiments, the overall lengths of final constructs do not exceed 200-210 nt. However, with continually improving sequencing technology, there is no foreseeable upper limit to the overall lengths of the data storage nucleic acid constructs. Additionally, the fact that oligos are assembled via PCR additions in the methods disclosed herein effectively circumvents current limitations in base-by-base oligo synthesis, which currently cannot produce oligos of more than 150-200 contiguous bases. The lower limit of overall construct length is influenced by how many bit strings will be encoded by a given system.

Regarding the overall number of different bit-mers to be used in a given system, typically as the number of bits to be encoded in a system increases, the number of initial different bit-mers used and/or number of indexing pairs at each hierarchical level of organization also increases.

In another aspect, the disclosure provides methods for storing data in a nucleic acid-based data storage system, the method comprising:
(a) converting the data into a base-B bit string;
(b) sub-dividing the base-B bit string into y secondary bit strings, and sub-dividing each secondary bit string into x primary bit strings n bits in length;
(c) for each of x primary bit strings:
  (i) performing one of: (A) where B equals 2, such that the base-B bit string is a binary bit string, from a library of n primary data storage nucleic acids, each comprising a single bit-mer sequence, each bit-mer sequence representing a specific position of a primary bit string n bits in length, selecting the primary data storage nucleic acid with the bit-mer sequence for each position of the primary bit string which is a 1, and selecting no primary data storage nucleic acid for each position of the primary bit string which is a 0; (B) where B equals 2, such that the base-B bit string is a binary bit string, from a library of 2·n primary data storage nucleic acids, each comprising a single bit-mer sequence, each of n bit-mer sequences representing a 1 at a specific position of a primary bit string n bits in length, and each of n other bit-mer sequences representing a 0 at a specific position of the primary bit string, selecting the primary data storage nucleic acid with the 1 bit-mer sequence for each position of the primary bit string which is a 1, and selecting the primary data storage nucleic acid with the 0 bit-mer sequence for each position of the primary bit string which is a 0; or (C) where B is greater than 2, from a library of B·n primary data storage nucleic acids, each comprising a single bit-mer sequence, each of B·n bit-mer sequences representing a particular base-B digit at a specific position of the primary bit string, selecting the primary data storage nucleic acid with the appropriate bit-mer sequence for each position of the primary bit string; wherein all primary data storage nucleic acids comprise the same 5' and 3' 1° primer binding sequences flanking the bit-mer sequence therein;
  (ii) pooling the selected data storage nucleic acids to form one of x pools of primary data storage nucleic acids storing the data of one of x primary bit strings;
  (iii) using a 1° primer pair that binds to the 5' and 3' 1° primer binding sequences to add to each primary data storage nucleic acid the same 5' and 3' secondary positional index sequences and, optionally, the same 5' and 3' 2° primer binding sequences to produce a pool of secondary data storage nucleic acids, wherein each of x pools of secondary data storage nucleic acids comprise different 5' and 3' secondary positional index sequences; and
(d) pooling the x pools of secondary data storage nucleic acids corresponding to the x primary bit strings within each of y secondary bit strings into a single pool, to form y pools of secondary data storage nucleic acids, each storing the data of one of y secondary bit strings.

For embodiments in which the data storage system contains only secondary bit strings, and no tertiary or higher-order bit strings, the encoded data may be read using primers that anneal to the 2° primer binding sites and contain tailed NGS primer binding sites (such as P5 and P7). In some embodiments, reading of secondary bit strings may be done as a validation step to ensure the plate-level (secondary) constructs were encoded correctly prior to forming tertiary constructs with a 2° PCR step. Pooling plates prior to appending plate indices with a 2° PCR step, however, would create a bit-mer pool with no way of distinguishing one plate from another (and thus the order of the corresponding secondary bit strings in the tertiary bit string). Furthermore, without the addition of document indices and document-specific primer binding sequences, there would be no way of retrieving specific documents from within a pool of documents. Nevertheless, systems comprising only lower-order data storage constructs, such as secondary constructs, are contemplated within the methods and constructs disclosed herein.

In some embodiments of the methods disclosed herein, the base-B bit string is instead sub-divided into z tertiary bit strings, each tertiary bit string sub-divided into y secondary bit strings, and each secondary bit string sub-divided into x primary bit strings n bits in length, the method further comprising:

(e) for each of y pools of secondary data storage nucleic acids, using a 2° primer pair that binds to the 5' and 3' 2° primer binding sequences to add to each secondary data storage nucleic acid the same 5' and 3' tertiary positional index sequences; optionally, the same 5' and 3' tertiary recognition sequences; and, optionally, the same 5' and 3' document identification sequences and the same 5' and 3' document-specific primer binding sequences to produce tertiary data storage nucleic acids; wherein each of y pools of tertiary data storage nucleic acids comprise different 5' and 3' tertiary positional index sequences; and wherein tertiary data storage nucleic acids representing bits from the same document all comprise the same 5' and 3' document identification sequences and the same 5' and 3' document-specific primer binding sequences; and (f) pooling they pools of tertiary data storage nucleic acids corresponding to the y secondary bit strings within each of z tertiary bit strings into a single pool, to form z pools of tertiary data storage nucleic acids, each storing the data of one of z tertiary bit strings.

In some embodiments, the methods disclosed herein further comprise (g) using one or more 3° primers that bind to the 5' and 3' document-specific primer binding sequences to add to one or more of z pools of tertiary data storage nucleic acids the same 5' and 3' folder identification sequences and the same folder-specific primer binding sequences, wherein tertiary data storage nucleic acids representing bits from one or more documents within the same folder all comprise the same 5' and 3' folder identification sequences and the same 5' and 3' folder-specific primer binding sequences.

In some embodiments of any of the disclosed aspects, B is 256 such that the primary bit string is a base-256 bit string, and each bit-mer sequence represents a byte of information.

In some embodiments of any of the disclosed aspects, the bit string is designed to provide redundancy at each position. For example, the data storage nucleic acid molecules used at each position within a bit string may represent more than a single bit. In such an example, for a binary system, the presence of a particular data storage nucleic acid molecule might represent "00," "01," "10," or "11" at a given position (i.e., effectively a quaternary system). Thus, the bit string "011010" might be encoded with the following 7 positions, each representing the bit at that position, as well as the preceding bit:

-0 01 11 10 01 10 0-

In such a system, if the data storage nucleic acid molecule at a given position is misread, mis-encoded, synthesized in error, or the information encoded by that data storage molecule is otherwise lost, then the information for that bit position would still be encoded by the adjacent data storage molecule to the right within the bit string, and the information would be preserved. A similar system is also contemplated by the disclosure in which each data storage molecule represents the bit at that position, as well as the following (rather than preceding) bit.

This concept may be extended indefinitely to produce additional redundancy within the system. For example, each data storage nucleic acid molecule might represent three bits of information: "000," "100," "010," "001," "011," "101," "011," and "111" (effectively a base-8 system). Following the same example as above, the bit string "011010" might be encoded with the following 8 positions, each representing the bit at that position, as well as both the preceding and following bit:

--0 -01 011 110 101 010 10- 0--

As before, in such a system, if the data storage nucleic acid molecule at a given position is misread, mis-encoded, synthesized in error, or the information encoded by that data storage molecule is otherwise lost, then the information for that bit position would still be encoded by the two adjacent data storage molecules both to the right and left of that position within the bit string, and the information would be preserved. In other examples where each data storage molecule represents the information carried by three bits, the data storage molecule at each position may represent the bit at that position, as well as the two adjacent bits preceding that position; or the bit at that position, as well as the adjacent two bits following that position.

Thus, in some embodiments of any of the disclosed aspects, each data storage nucleic acid molecule represents the information carried by a bit at a given position and one or more adjacent bits in a bit string. In some embodiments, a higher-order (e.g., a base-4 (quaternary), base-8, base-16, etc.) system is used to redundantly encode the information of a lower-order (e.g., binary) system.

As used herein, the term "adjacent" in relation to a given position p refers to one or two groups of contiguous positions, wherein for each group of contiguous positions, one of the contiguous positions adjoins or is next to the given position p. Adjacent bit positions may be upstream, downstream, or a combination of upstream and downstream of a given position p. For example, given a bit position p within a bit string, and further given, as an example, four adjacent bit positions $p_A$, there are a number of ways the exemplary four adjacent bit positions could be arranged as contemplated by the disclosure. All four adjacent bit positions could be positioned upstream of position p, at positions p−4, p−3, p−2, and p−1:

... $p_A$ $p_A$ $p_A$ $p_A$ p ... ;

all four adjacent bit positions could be positioned downstream of position p, at positions p+1, p+2, p+3, and p+4:

... p $p_A$ $p_A$ $p_A$ $p_A$ ... ;

or the four adjacent positions could be split into two groups of (1) one or more upstream adjacent bit positions and (2) one or more downstream adjacent bit positions:

... $p_A$ p $p_A$ $p_A$ $p_A$ ... ,

... $p_A$ $p_A$ p $p_A$ $p_A$ ... , or

... $p_A$ $p_A$ $p_A$ p $p_A$ ... .

Thus, in another aspect, the disclosure provides nucleic acid-based data storage systems and methods of storing data by using the nucleic-acid based data storage systems, the nucleic acid-based data storage systems comprising a plurality of data storage nucleic acids, each data storage nucleic acid comprising one of N different bit-mer sequences, wherein each bit-mer sequence represents: (a) information carried by a bit in a primary bit string n bits in length and the position p of the bit within the primary bit string, and (b) information carried by A adjacent bits in the primary bit string; and wherein N equals $B^{(A+1)} \cdot n$ where the primary bit string is a base-B bit string, and where each of $B^{(A+1)} \cdot n$ bit-mer sequences represents a base-B digit at a particular position within the primary bit string along with the one or more base-B digits at the positions occupied by the A adjacent bits. In some embodiments, A is 1, or 2, or 3, or 4, or 5, or 6, or 7, or 8, or 9, or 10. In some embodiments, A is from 1 to 4. In some embodiments, A is 1. In some embodiments, A is 2. In some embodiments, A is 3. In some embodiments, A is 4.

In some embodiments, each data storage nucleic acid further comprises one of x secondary positional indices, each secondary positional index comprising one or more secondary positional index nucleic acid sequences, wherein the data storage nucleic acids that represent bits from the same primary bit string all comprise the same secondary positional index, and wherein each secondary positional index represents the position of one of x primary bit strings relative to other primary bit strings within a secondary bit string x times n bits in length. In some embodiments, each data storage nucleic acid further comprises one of y tertiary positional indices, each tertiary positional index comprising one or more tertiary positional index nucleic acid sequences, wherein the data storage nucleic acids that represent bits from the same secondary bit string all comprise the same tertiary positional index, and wherein each tertiary positional index represents the position of one of y secondary bit strings relative to other secondary bit strings within a tertiary bit string x times y times n bits in length. In some embodiments, each data storage nucleic acid further comprises a document identification sequence and a document-specific primer binding sequence, wherein the data storage nucleic acids that represent bits from the same document all comprise the same document identification sequence and document-specific primer binding sequence. In some embodiments, each data storage nucleic acid further comprising a page recognition sequence, wherein the data storage nucleic acids that represent bits from the same page within a document all comprise the same page recognition sequence, and wherein the page recognition sequence, together with the document identification sequence and document-specific primer binding sequence, forms a primer binding site allowing data storage nucleic acids sharing a single page recognition sequence to be selectively amplified from the system together. In some embodiments, each data storage nucleic acid further comprises a folder identification sequence and a folder-specific primer binding sequence, wherein the data storage nucleic acids that represent bits from one or more documents in the same folder all comprise the same folder identification sequence and folder-specific primer binding sequence. In some embodiments, B is 256 such that the primary bit string is a base-256 bit string.

In another aspect, the disclosure provides methods for storing data in a nucleic acid-based data storage system, the methods comprising: (a) converting the data into a base-B bit string; (b) sub-dividing the base-B bit string into y secondary bit strings, and sub-dividing each secondary bit string into x primary bit strings n bits in length; (c) for each of x primary bit strings: (i) from a library of $B^{(A+1)}$ n primary data storage nucleic acids, each comprising a single bit-mer sequence, each of $B^{(A+1)}$ n bit-mer sequences representing (1) a particular base-B digit at a specific position p of the primary bit string, in addition to (2) a base-B digit at each of A positions adjacent to position p, selecting the primary data storage nucleic acid with the appropriate bit-mer sequence for each position p of the primary bit string; wherein all primary data storage nucleic acids comprise the same 5' and 3' 1° primer binding sequences flanking the bit-mer sequence therein; (ii) pooling the selected data storage nucleic acids to form one of x pools of primary data storage nucleic acids storing the data of one of x primary bit strings; (iii) using a 1° primer pair that binds to the 5' and 3' 1° primer binding sequences to add to each primary data storage nucleic acid the same 5' and 3' secondary positional index sequences and, optionally, the same 5' and 3' 2° primer binding sequences to produce a pool of secondary data storage nucleic acids, wherein each of x pools of secondary data storage nucleic acids comprise different 5' and 3' secondary positional index sequences; and (d) pooling the x pools of secondary data storage nucleic acids corresponding to the x primary bit strings within each of y secondary bit strings into a single pool, to form y pools of secondary data storage nucleic acids, each storing the data of one of y secondary bit strings.

In some embodiments, the base-B bit string is instead sub-divided into z tertiary bit strings, each tertiary bit string sub-divided into y secondary bit strings, and each secondary bit string sub-divided into x primary bit strings n bits in length, the method further comprising: (e) for each of y pools of secondary data storage nucleic acids, using a 2° primer pair that binds to the 5' and 3' 2° primer binding sequences to add to each secondary data storage nucleic acid the same 5' and 3' tertiary positional index sequences; optionally, the same 5' and 3' tertiary recognition sequences; and, optionally, the same 5' and 3' document identification sequences and the same 5' and 3' document-specific primer binding sequences to produce tertiary data storage nucleic acids; wherein each of y pools of tertiary data storage nucleic acids comprise different 5' and 3' tertiary positional index sequences; and wherein tertiary data storage nucleic acids representing bits from the same document all comprise the same 5' and 3' document identification sequences and the same 5' and 3' document-specific primer binding sequences; and (f) pooling they pools of tertiary data storage nucleic acids corresponding to they secondary bit strings within each of z tertiary bit strings into a single pool, to form z pools of tertiary data storage nucleic acids, each storing the data of one of z tertiary bit strings.

In some embodiments, the methods further comprise (g) using one or more 3° primers that bind to the 5' and 3' document-specific primer binding sequences to add to one or more of z pools of tertiary data storage nucleic acids the same 5' and 3' folder identification sequences and the same folder-specific primer binding sequences, wherein tertiary data storage nucleic acids representing bits from one or more documents within the same folder all comprise the same 5' and 3' folder identification sequences and the same 5' and 3' folder-specific primer binding sequences. In some embodiments, B is 256 such that the primary bit string is a base-256 bit string and each bit-mer sequence represents (1) a byte of information at a specific position p of the primary bit string, in addition to (2) a byte of information at each of A positions adjacent to position p.

The methods of the disclosure can, for example, be practiced by starting with an initial known master bit-mer (bit-oligo) plate where each well in the plate contains a bit-mer of a different sequence. The bit-mers of the master plate are then transferred to a receiving plate such that a different combination of the master plate bit-mers will be pooled into each well of the receiving plate. The master plate bit-mer sequences define the bits that are pooled in a given well as well as the order of those bits laid out in the well. If the master plate contains 1536 different bit-mers, for example, each well of the receiving plate can store 192 bytes of information.

To uniquely identify each well position a bit came from, PCR is performed on all the molecules in each well with well-specific index-containing primer pairs. This encodes which well a bit came from. Hence one 1536-well plate's worth of 192-byte wells is 294,912 bytes (~295 kilobytes) of information. Plate-specific binding domains are also added during this initial PCR step. This enables the ability to encode plate and document level indices, which together define a registry of how the bits are laid out.

To store 1 gigabyte of information in this particular example would require 1740 total different oligonucleotide sequences (1536 bit-mers+80 plate indices (32×48)+124 document indices (76×48)). This is with utilizing paired indexing where one index is used to mark a whole row in the plate, and where a second index is used to mark a whole column in the plate. It is the intersection of the two indices that maps the specific positional location and thus provides the order for the bits by well and by plate. In other words, paired indexing leads to a 51K fold reduction in the number of unique oligonucleotide sequences needed and drastically reduces the chemical synthesis required to store the 1 GB of data. In addition to the synthesis savings and the ability to reuse bit-mer oligos independent of the data to be encoded, to encode another 1 gigabytes of information by way of current methods would require another 89.5 million oligos where as it would take only another 124 new oligos to encode that information with the instant method by way of PCR encoding and mixing.

The reusable nature of the bit-mer nucleic acids used in conjunction with the methods and nucleic acid data storage constructs disclosed herein make it possible to design many of the nucleic acid sequences used in a data storage system only once. Because of this, optimized sequences can be designed and used repeatedly without having to design, synthesize, and use sub-optimal sequences, as would be inevitable in systems requiring new sequences to be designed for every project. As an example of sequence optimization enabled by the reusability of the bit-mers disclosed herein, reusable bit-mers can be carefully designed and tested to minimize homopolymers and secondary structure formation.

Furthermore, since many of the nucleic acid sequences used in the disclosed methods and products are reusable, they can be prepared in bulk. As a result, in using the methods and nucleic acid data storage constructs disclosed herein, little to no synthesis is required during the step of encoding data. For example, all bit-oligos and 1° primers can be synthesized beforehand in bulk. For the 2° primers, the region that anneals to the primer binding site of the well primer (light gray block flanking the W indices in FIG. 1) is conserved and the plate and document indices need only be different for different plates and documents, respectively. The document-level primer binding site (D') need only be different for different documents.

As another example, to store $10^7$ gigabytes of information, using a 1536 megabyte master plate and 1536 well receiving plates, 185,000 secondary primers are needed. By using the methods and nucleic acid data storage constructs disclosed herein, this can be accomplished using fewer than one million nucleic acid sequences. In contrast, using the scheme described by Bornholt et al. (Bornholt J, Lopez R, Carmean D M, Ceze L, Seelig G, Strauss K. A DNA-based archival storage system. In Proceedings of the Twenty-First International Conference on Architectural Support for Programming Languages and Operating Systems, A C M, 2016, pp. 637-49), in which each nucleotide represents a base-3 bit (or "trit"), only 80 bits (10 bytes) of information can be stored per oligo, which results in $10^8$ oligonucleotides per gigabyte. Thus, storage of $10^7$ gigabytes under the Bornholt method would require $10^{15}$ oligos.

Figure 1B:
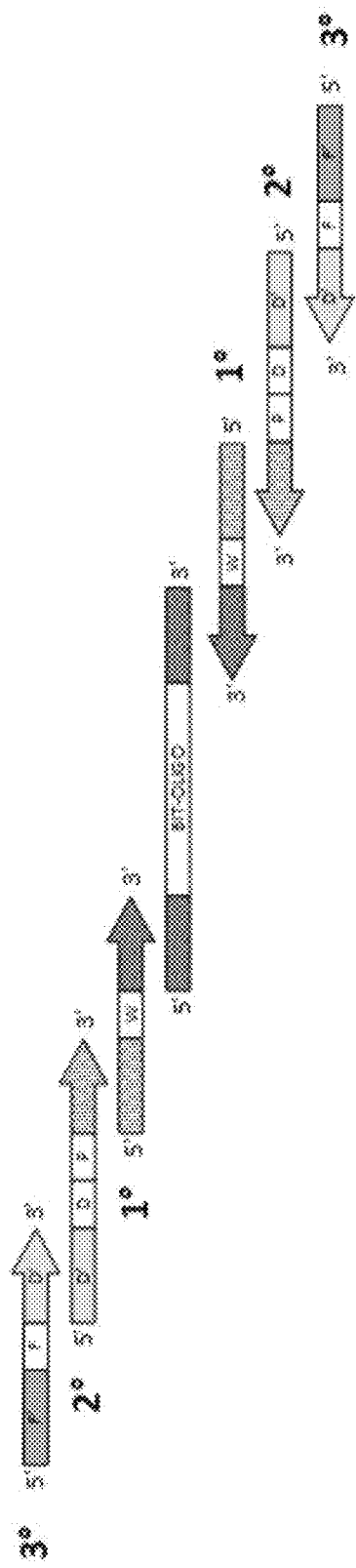

FIG. 1B is a schematic showing how the indices and primer binding regions are added to a bit-mer for each level of organization via PCR primers according to the methods of the disclosure. The bit-mers (center block), with their conserved flanking primer binding regions (dark shaded block) are each present in the wells of a master plate, with many copies of one bit-mer sequence per well. The sequences of the bit-mers indicate their order in the bit string. For example, in a 1536 well plate, each well will contain a bit-mer with a specific sequence. The sequence of each bit-mer will indicate whether the bit is in position 1, 2, 3 . . . or 1536. The flanking primer binding sequences are conserved among all bit-mers.

When encoding a bit string, the bit-mers from the master plate are transferred to one well of a receiving plate via a liquid transfer method (by acoustic droplet ejection, for example). In embodiments where the bit string is base-2, depending on the binary sequence of the bit string, some bit-mers will be transferred (indicating a 1) and some not (indicating a 0). For example, for the code 10010, bit-mers 1 and 4 will be transferred to the receiving well while bit-mers 2, 3, and 5 will not be transferred. Each well of the receiving plate would, in this example, contain a bit string of 1536 bits where the presence or absence of each bit-mer represents a 1 or 0 respectively. If the receiving plate has 1536 wells and each well has 1536 bits of information, then the plate, as a whole, will have $1536^2$, or 2,259,296 bits of information total.

The order in which the 1536 bit-containing wells are placed in the bit string is encoded using well-level indices which are specific to each well of the receiving plate. These well indices are added to the bit-mer via a 1° PCR reaction using 1° primers (see FIG. 1B) which are present in each well prior to the addition of the bit-mers. In FIG. 1B, the primers on the right-hand side anneal to and prime off of the 3' regions of the strands shown. The primers on the 5' left-hand side anneal to and prime off of the 3' regions of the extension products generating with the right-hand primers. Each 1° primer has a conserved priming region (dark shaded arrow) that hybridizes with the conserved flanking region of the bit-mer and a well index (W) that designates which well the bit-mers are in and thus their order in the bit string, as well as a conserved primer-binding region (light shaded block) that is later used for PCR with the 2° primers.

Following the 1° PCR step, the wells of the receiving plate are pooled into a single tube. For large documents, multiple receiving plates must be used and placed in order as well. To determine which receiving plate a bit-mer originated from, plate indices are used and are added via the 2° primers. In FIG. 1B, the 2° primers on the right-hand side anneal to and prime off of the original bit-mers while the primers on the left anneal and prime off of the opposite strands of original bit-mers that were made by the priming and extension of the right-hand side primers. Each 2° primer contains a conserved priming region (light shaded arrow) that hybridizes with the conserved flanking region of the 1° primer, a plate index (P) to designate the plate of origin, a document index (D) to designate the document the bits are part of, and a document-specific primer binding site (D', block) with a sequence that is specific to each document. For example, a large document containing multiple plates will have multiple plate indices but a single document index and document-specific primer binding site. The document-specific primer binding site will be used to access specific documents via PCR using document-specific primers. This enables one to read certain documents and not others when multiple documents are present in a single tube.

Optionally, one can place multiple documents into a folder. This can be accomplished via PCR with 3° primers which contain multiple primer regions (D', arrow) that hybridize with the document-specific primer binding domains of the 2° primers, one sequence for each different document, a folder index (F) that designates the folder and a folder-specific primer binding region (F', block) to be used for amplifying and reading specific folders if multiple folders are present in a single tube. Alternatively, if one knows the folder a particular document will be placed in as the document is being created, the folder index and folder-specific primer binding domains could be incorporated in the 2° primer with no need for the 3° primer set. As sequencing reads in NGS become longer, these constructs can be made longer and more complex as well through the use of 4° and higher primer pairs.

Figure 1C:
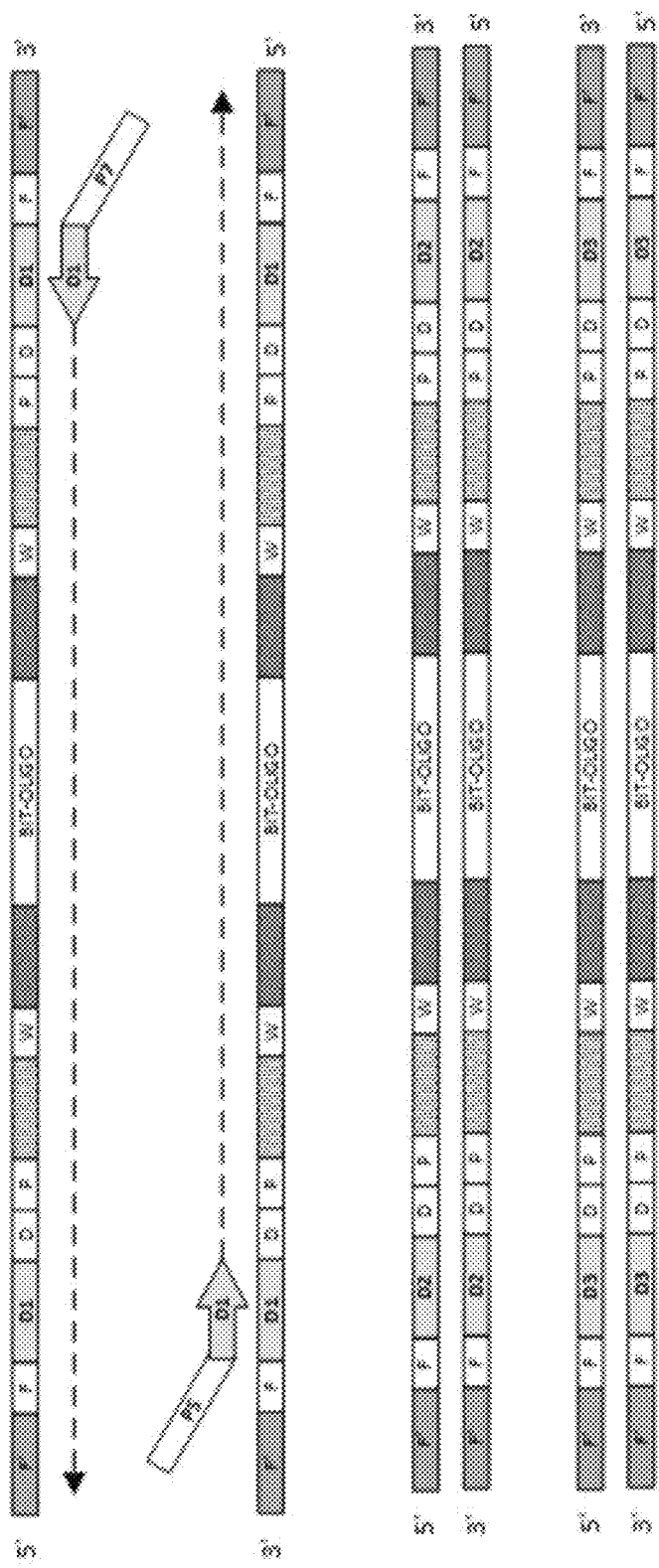

FIG. 1C is a schematic demonstrating how files can be selectively read when multiple files are present. For example, constructs representing data for document one (D1) are amplified with the D1 specific primers. Constructs representing documents 2 and 3 (D2 and D3) are not amplified. In this example, the document-specific primers are tailed with adapters (P5 and P7 in this case) that will be used for sequencing. Although the bit constructs shown above are quaternary structures, this reading step could be performed on tertiary structures as well since they comprise document indices and document-specific primer-binding domains. However, this step cannot be performed on primary or secondary level bit constructs.

Assembly of data storage nucleic acid constructs

Any known method for assembling, joining, conjugating, and/or ligating nucleic acid molecules is contemplated for assembly of the data storage nucleic acid constructs of the disclosure. As disclosed in the Examples herein, polymerase chain reaction (PCR) may be used to, for example, append any additional sequences, such as positional index sequences, document identification sequences, folder identification sequences, primer binding sequences, etc. to each data storage nucleic acid molecule.

In some embodiments, additional sequences, such as index sequences, identification sequences, primer binding sequences, etc. are appended to data storage nucleic acid molecules by ligation with one or more ligases.

In some embodiments, additional sequences, such as index sequences, identification sequences, primer binding sequences, etc. are conjugated to data storage nucleic acid molecules by chemical means. Any chemical conjugation method may be used to append additional sequences as long as the product of the conjugation can still be read by a polymerase. For example, click chemistry methods may be used to append additional sequences to data storage nucleic acid molecules of the disclosure. Click chemistry methods typically include chemical reactions that share some or all of the following characteristics: reactions that are modular, reactions that are wide in scope, reactions that give very high chemical yields, reactions that generate only inoffensive byproducts, reactions that are stereospecific, reactions that are physiologically stable, reactions that exhibit a large thermodynamic driving force (>84 kJ/mol) to favor a reaction with a single reaction product (a distinct exothermic reaction makes a reactant "spring-loaded"), and reactions that have high atom economy. Click chemistry reactions preferably: have simple reaction conditions, use readily available starting materials and reagents, use no solvent or use a solvent that is benign or easily removed (preferably water), and/or provide simple product isolation by non-chromatographic methods (crystallisation or distillation). Many of the click chemistry criteria are subjective, and even if measurable and objective criteria could be agreed upon, it is unlikely that any reaction will be perfect for every situation and application. However, several reactions have been identified that qualify as click chemistry reactions, for example: [3+2] cycloadditions, such as the Huisgen 1,3-dipolar cycloaddition, in particular the Cu(I)-catalyzed stepwise variant; thiol-ene reaction; Diels-Alder reaction and inverse electron demand Diels-Alder reaction; [4+1] cycloadditions between isonitriles (isocyanides) and tetrazines; nucleophilic substitution especially to small strained rings like epoxy and aziridine compounds; carbonyl-chemistry-like formation of ureas but not reactions of the aldol type due to low thermodynamic driving force; and addition reactions to carbon-carbon double bonds like dihydroxylation or the alkynes in the thiol-yne reaction. Specific examples of click chemistry reactions include: copper(I)-catalyzed azide-alkyne cycloaddition (CuAAC); strain-promoted azide-alkyne cycloaddition (SPAAC); strain-promoted alkyne-nitrone cycloaddition (SPANC); alkene and azide [3+2] cycloaddition; alkene and tetrazine inverse-demand Diels-Alder; and alkene and tetrazole photoclick reaction.

EXAMPLES

The Examples that follow are illustrative of specific embodiments of the invention, and various uses thereof. They are set forth for explanatory purposes only, and are not to be taken as limiting the invention.

Example 1: Design of Bit-Oligos

A proof-of-concept (POC) system was designed, the first phase of which was to generate 384 distinct nucleic acid bit-mer sequences that would make up the bit library, with one bit-mer per well (central "bit-oligo" sequence in FIG. 1). Terms used to describe this sequence include "bit-oligo" and "bit-mer." The sequence length can vary to ensure uniqueness but does not need to be excessive as there must be sufficient room to include the Well, Plate, and Document level priming domains and indices. To include Folder level priming domains and indices would require extra care in keeping the size of the different domains down but still maintaining uniqueness. Increased NGS read capabilities would allow for more room to design. For this POC, bit-mers 30 bp in length were used, leading to an overall length of the document-level (tertiary) constructs between 200 to 210 base pairs once all primers and indices were added.

The design strategy implemented used the Levenshtein distance to compute edit distance between all bit-oligo sequences. This metric derives how many steps it would take to change one sequence into another accounting not only for substitutions, but also insertions and deletions. The minimum allowed edit distance was 12, and the average allowed edit distance for the designed candidate set was 17.4. In addition to edit distance, GC content was included in the filtering mechanism by limiting the allowed range of GC content to between 35% to 65%, with a targeted GC content value of 45%; the actual average GC content of the designed candidate set was 45.8%.

The final piece in designing the set of 30 bp sequences was to avoid certain sequence motifs (AAAA, CCC, GGG, and TTTT) and to minimize motifs within sequences (no duplicate motifs of size 6) and between sequences (no duplicate motifs of size 10). The resulting sequences are shown in Table 1.

TABLE 1

Candidate 30 mer bit-oligo sequences

| | |
|---|---|
| SEQ ID NO: 1 | CAGTAGTCCGGATGTAATGCCAACTTCAAA |
| SEQ ID NO: 2 | CGGCCGATTTCATAGTTGCGCGTTCCAGTC |
| SEQ ID NO: 3 | TATTAAGTACTTTAGCGTCAGTCGCAAAGC |
| SEQ ID NO: 4 | TGAAACTCAAGGTGCTTTCGAAAGCCACTT |
| SEQ ID NO: 5 | CTAAGATACCATCACCAAGATATTGTAGCT |
| SEQ ID NO: 6 | CACGTAGAAAGAAAGAGAAGTGTACCATCA |
| SEQ ID NO: 7 | AGGACTAAGTCCTCGCTCCTGTTTCCTTTC |
| SEQ ID NO: 8 | GAATTCGTCAACTGGAACCAATACTGAACC |
| SEQ ID NO: 9 | GCTTAATGAACAGTTCTTAATCCTGTCGGC |
| SEQ ID NO: 10 | AGATCTGTCCTCTTCGTCCACGCCTATTTA |
| SEQ ID NO: 11 | CCACCAGGTAGTTAACGTGCCGGCATTTAC |
| SEQ ID NO: 12 | GACGCACTGGTTCCACATCTCGAGTTACAC |
| SEQ ID NO: 13 | CGCTACTCGCATAACTTTGAGCATTAATGC |
| SEQ ID NO: 14 | GGATTCCGGTCCTTACTCTACTGTACATTG |
| SEQ ID NO: 15 | ACCGGAAGAAGCTAGCGTAGTTTATCTCTC |
| SEQ ID NO: 16 | TGTTAATCGAGTTACCAATTGGCTGAGGAA |
| SEQ ID NO: 17 | CCAGTGTCGTTATGGTGTGATTGAGCTCTT |
| SEQ ID NO: 18 | CTTGCGCCGGTGCGTATACAATCAGTCCGT |
| SEQ ID NO: 19 | CCTGGACCTCTGCTTCTATTCTGCTATTCA |
| SEQ ID NO: 20 | TATACTTGTCGCGGCAGAGTGCCGCCTGAA |
| SEQ ID NO: 21 | CTCTGTGCCGGATCAACACATCATGATTGA |
| SEQ ID NO: 22 | TCTAGTCCTCTCGGTTTCATCGCGATGTTA |
| SEQ ID NO: 23 | GGCGAACAACAGGTTATACTGTCTTAAGAA |
| SEQ ID NO: 24 | ATCGTTTCGAGCTAGCGCAAGCCACTCTGA |
| SEQ ID NO: 25 | ATCATTCTCATGATGCCTTCTTTAAGCTCC |
| SEQ ID NO: 26 | AGTACATAGTACACCTTTAGTCTGGCGACT |
| SEQ ID NO: 27 | CTTACGAATCCGGTTTGTTCTAGAGACTAA |
| SEQ ID NO: 28 | TAACTCGATGATAATGGCTGCAGACGTATC |
| SEQ ID NO: 29 | AGGACCTTCGGCCTCACTCCAGTCCTAGGT |
| SEQ ID NO: 30 | CGGTGACTCGGAAAGAAGGTTATCATGACG |
| SEQ ID NO: 31 | GCGCGCTCGGACATGACTCGTCCAAGGATA |
| SEQ ID NO: 32 | ATCGTGCTGGATACCGGTGAAACTATCATA |
| SEQ ID NO: 33 | TTCTTCCGTGGAATCCACGACGCAGTCTTG |
| SEQ ID NO: 34 | GCGTCCACTTGGCGAATTCGCGAACAATAG |
| SEQ ID NO: 35 | TGCCGTTCTTCTTGGCGTACTCCGCCAAC |
| SEQ ID NO: 36 | AACCAATACCTAATAATCTAGCTGCAGAAC |
| SEQ ID NO: 37 | CGCTGGCCACCTGGATAACTTGGTTCAAGA |
| SEQ ID NO: 38 | ATTGTGAATCCTATACCGATGCATCGACCA |
| SEQ ID NO: 39 | CCGCACGTTAGCCGTGGTAGTCCACGGACT |
| SEQ ID NO: 40 | CAAGGCGCCTTACCACTATTTGAAGCCTCG |
| SEQ ID NO: 41 | CGACGCCTAGCAGTAGCCGATCGGTGCAGA |
| SEQ ID NO: 42 | CGATCCAGCTGCGTTCTTAGACGAAGAAAC |
| SEQ ID NO: 43 | CGTGGCTCCGCTACCATTTGTTTCATTAAT |
| SEQ ID NO: 44 | TGGCTTTATATAGCATGCGGCATGACTACG |
| SEQ ID NO: 45 | AAGGCCGCCATGTGGCCATTGGCCTGTTGC |
| SEQ ID NO: 46 | TCGTCGACATACGCTTGTCAGGAAAGCAGT |
| SEQ ID NO: 47 | TTGGATCACGATACCGCAATCCGCGCGTCA |
| SEQ ID NO: 48 | GGCTTCAACCTTTACGTGCACACGACCAAA |
| SEQ ID NO: 49 | CTTCCGTACCTCATTAATACGGTTCCGTAG |
| SEQ ID NO: 50 | CTTTCATGAAGCGATTGCACGCGACCTCTT |
| SEQ ID NO: 51 | AAGTCCTAACCACGGTCAACGGAGGCGCCG |
| SEQ ID NO: 52 | CTATCTGGCGAAAGAGGCATAGGACGAAAG |
| SEQ ID NO: 53 | ATCATACCATCAATCCTCAGCATTATGGTA |
| SEQ ID NO: 54 | CAACAAGGCGAGTTGAATTCTATTATCTTG |
| SEQ ID NO: 55 | CGTTCCTGTGCACTATGGCAAACACCACTT |
| SEQ ID NO: 56 | GAAACTCCTCTTTGCACGGACTTTAGTACT |
| SEQ ID NO: 57 | GCTTTATCTGTTTCCAGGCCTTATTTAGGC |
| SEQ ID NO: 58 | AGTACCACGCATTTAGAAATCGATTAACCA |
| SEQ ID NO: 59 | CAATCACAAATCTTAGACATCCTCGTCGAC |
| SEQ ID NO: 60 | GTATCCAGTGTGGAACTAATATGCTGGATG |
| SEQ ID NO: 61 | TGTACAGGTGCCGATTGCCTAAACGACACC |
| SEQ ID NO: 62 | CTAACTGACTGCCACGCGTGGTGATAACTG |
| SEQ ID NO: 63 | AGTTCAGCAACTCGAGCCTTTCAGCCAGAA |
| SEQ ID NO: 64 | TCTCTTCAGCCGTAAAGCTTTATAATCACT |
| SEQ ID NO: 65 | GCATCTTGAGCCTCGCTTCAAGAACTATTT |
| SEQ ID NO: 66 | AGGATACGCGTGTAACTGTGGCTCTACCGG |
| SEQ ID NO: 67 | CGGAAACCAATTCCAATCGACGCATTAATT |
| SEQ ID NO: 68 | CCTTTGGACATGACAAAGGATGTTTCCATA |
| SEQ ID NO: 69 | GCTCTTAGTGTACATATGTATTCCGGTAGA |
| SEQ ID NO: 70 | ACAAAGTTTATTGTCGCAGCTGGCCAAACC |
| SEQ ID NO: 71 | CGCACTTATTATGGTGCTGTCTCTGGTGCA |
| SEQ ID NO: 72 | GTCACAGGTCGCGACCATGGACATTTAAGA |
| SEQ ID NO: 73 | AGGCGCGCCAATACACAAATAATTAAGTAA |
| SEQ ID NO: 74 | GAAACGTTGGCCACGTCTTCTGTACTCGGT |
| SEQ ID NO: 75 | ATGTTCCTACGAGCGTCGTAGATAGAATGC |
| SEQ ID NO: 76 | CACCTCCTCTCTATGTTAACTTCCACTGCT |
| SEQ ID NO: 77 | GTTTCGCTTCGATTGCTTCCGTCGATTGTA |
| SEQ ID NO: 78 | ATTATTAACGGATAGCGCGCTATTTGCTGT |

TABLE 1 -continued

Candidate 30 mer bit-oligo sequences

| | |
|---|---|
| SEQ ID NO: 79 | GTGAAGGAATCTTAACGGAACATGTGATTC |
| SEQ ID NO: 80 | CTTGTCACCACGACGTCTTTAAGCCTAACA |
| SEQ ID NO: 81 | AAGACTACGACAAGCGATGCACGACAAACA |
| SEQ ID NO: 82 | TATTGCAGAAGTATCACCGGTTAGCAATTT |
| SEQ ID NO: 83 | ATTGCGCTCTAAATCGAACGTTGTCCTGAG |
| SEQ ID NO: 84 | AAAGAATGCGACCAAGCTGTTCAAGCTTGC |
| SEQ ID NO: 85 | TACTAATTCCAGCTGTACACTCTTCCATCA |
| SEQ ID NO: 86 | AAGTCGGTGCTCACTGCAAATTTGCGTTTA |
| SEQ ID NO: 87 | CATCAAGACCATCCGTTACAGAGCTCTTAA |
| SEQ ID NO: 88 | TGAATGTGTAATCAGGCCTCCTCGTTACCA |
| SEQ ID NO: 89 | CCACCACCAATAGTGGATACAGGCGGTAAG |
| SEQ ID NO: 90 | AGTGTAGCGCTTCGACCTCAACGCCATATT |
| SEQ ID NO: 91 | ACGCGCGTCCATCGTATCATCCACAGTTGG |
| SEQ ID NO: 92 | ATCCGGACCGCCTAGTGTTGTCCTTATCTT |
| SEQ ID NO: 93 | CGTTAAAGTGTAACTTCGGTCAGGTTAAAT |
| SEQ ID NO: 94 | TGTCCAAACGTGAAGATCTGGTAGGCGAGT |
| SEQ ID NO: 95 | ACGTTTCAATCGTTGGACGGTTAATCGTTC |
| SEQ ID NO: 96 | TGTTTGACTAGCGCAAATCATACTCGTACG |
| SEQ ID NO: 97 | TCTCTTCGGTTTGCTCGCCATCTATAGCGA |
| SEQ ID NO: 98 | GAAGTTAGCAGTGACTTTCATCTGTACAGC |
| SEQ ID NO: 99 | CGTTGATCCTTAAGTTCCATATTGGTACCG |
| SEQ ID NO: 100 | AAGACTTCAGCTCGAGGCTTTGGTATCATT |
| SEQ ID NO: 101 | CGTTATTATAATAACTCGCATTGAGACCGA |
| SEQ ID NO: 102 | TAGCCTAAGAGAAAGGTGCCTATGGCCATC |
| SEQ ID NO: 103 | AATGAGTGCCAATATGGCACTCACTAGAAA |
| SEQ ID NO: 104 | CCTCGGTAGATCCTAAATATATTACACTAC |
| SEQ ID NO: 105 | ACTTGTCATACTACAGATGCGGCCTGCGGC |
| SEQ ID NO: 106 | AAATAGTGGCTTCTCAGTCGCGAAACGTCC |
| SEQ ID NO: 107 | GCTGAAATTGTTCTGATTAATAGCCACCGG |
| SEQ ID NO: 108 | GTTGTTTCTTTACTTCTTCTTGCCACCTCC |
| SEQ ID NO: 109 | ACAACCGCTGATCTCTACCGCGTACTGCAG |
| SEQ ID NO: 110 | TGCTCCTTCCTTCACGTACACGCTGCATTC |
| SEQ ID NO: 111 | TGATCGCAAGTGCGCGCGCAAATCTACGCG |
| SEQ ID NO: 112 | GTTACTATGTCCTAGCTACCTCACTTTATG |
| SEQ ID NO: 113 | AACCGCCTCGAGATATACCTACTGAACAAA |
| SEQ ID NO: 114 | GCTACCATAACCATAGTCGAAGTGGCATAT |
| SEQ ID NO: 115 | TCCTCGCTAAGGCAGACGGCCGGTACATAG |
| SEQ ID NO: 116 | ACGTTCTCACTAGTATGGCGGACCTATAAC |
| SEQ ID NO: 117 | CTTATAAGTCATAACGACTGGACCACGATA |
| SEQ ID NO: 118 | CACCGGTAAGCAGCCTTGTTACAATCCTCA |
| SEQ ID NO: 119 | GCCGCCAACGTAGATCAACGCTGTTAACGT |
| SEQ ID NO: 120 | CACCGTCTATAAATCGCACGATTTAATGAC |
| SEQ ID NO: 121 | CGTCACCATCGGCTAGCGGTCATTCTACTC |
| SEQ ID NO: 122 | AGGCCTCGAACATATCGTGCCTTTAGTTCG |
| SEQ ID NO: 123 | CTTGATTGACACTTCTAACGTTCATGTTCC |
| SEQ ID NO: 124 | GATTGTCGAGTATACTGAATGACAGTGATA |
| SEQ ID NO: 125 | CATACTGGCTGACGGCATACTTTCGCGAAC |
| SEQ ID NO: 126 | TATAACAACAACGTTACGCCGCGCCGCTGA |
| SEQ ID NO: 127 | CAGACTCAACACTGATTACGTAGGAAACTG |
| SEQ ID NO: 128 | CTATATCTCAATATATAGACGAGACTGACG |
| SEQ ID NO: 129 | CTCAACTATTCTCCGATTGCAAGTAATGTG |
| SEQ ID NO: 130 | TCCTGTATGCCGGTTAAAGCTTCGCAAATG |
| SEQ ID NO: 131 | CCTGCGTTATAAGTGTAAGAGAAATGGCGT |
| SEQ ID NO: 132 | CCAATAGACTAAACGTTTCAGCGCACCTAC |
| SEQ ID NO: 133 | GCATCAACTTCAGGAGTTCCGGAGAAACCA |
| SEQ ID NO: 134 | ATAACAAGTTCTATTGGCAGAAGCCAATGT |
| SEQ ID NO: 135 | GATCTAAATTTGCCTGCGCAATTAAGTACC |
| SEQ ID NO: 136 | TCGACTTTCGTAACTTAATGATATCCGCCA |
| SEQ ID NO: 137 | CGGCTTCTATCGCCGCCTACGCGTCCTTAA |
| SEQ ID NO: 138 | ATATCCACGAGCGCTAAAGATCGCCAGCAG |
| SEQ ID NO: 139 | AGATTAGGTTTCGACCGACGTCTTCTAAAC |
| SEQ ID NO: 140 | TTGCTGACAGACTACCAGTTGATCATGACA |
| SEQ ID NO: 141 | AGGTCAAGCTTCCGAGACGGTAGATTATAC |
| SEQ ID NO: 142 | ACAGGCAGCGAGTCCACGCATCATATATCG |
| SEQ ID NO: 143 | AATAGTCGCGAGCCACCTGAGTCGAATGTC |
| SEQ ID NO: 144 | CCTTCATGCTCGGAATGCGCCTCTTTAAAT |
| SEQ ID NO: 145 | TAGGTTGCGCTTCAGATACTTTCAGAAGTC |
| SEQ ID NO: 146 | AATCAACACAGTATACCTTGATTCCTACCG |
| SEQ ID NO: 147 | GCATTCCTACACACCTGTGGATATATCATA |
| SEQ ID NO: 148 | TCAGCGCTTCTAAACCTTAACATTCAATCT |
| SEQ ID NO: 149 | AATTCGAAAGCGCTCGCATAATATCATGCA |
| SEQ ID NO: 150 | GCTCAGAATCCTAAACTAAACCGATTTCTT |
| SEQ ID NO: 151 | CCTACTAGTCGGCCTCTCTAAACGAGCGAA |
| SEQ ID NO: 152 | AACGTCCAAGCGCGATTCGAACTATGGATT |
| SEQ ID NO: 153 | TATGCTTCGTGACTTCGCACTTGTTTATAA |
| SEQ ID NO: 154 | TACAAACCTTTGATCATTAAACAGGCAAGG |
| SEQ ID NO: 155 | TTGTCCAACTCAGCGTTAGTTATAAGATGA |
| SEQ ID NO: 156 | ATCGCGAGAGACTCGTGTCAGCGCTTGTAT |

TABLE 1 -continued

Candidate 30 mer bit-oligo sequences

| SEQ ID NO: 157 | CCAATAGCGTCCTACAGGTTTGCTGCTGCT |
| --- | --- |
| SEQ ID NO: 158 | CTCGTGTCCTGGTGAGCTCCGATCTATGTC |
| SEQ ID NO: 159 | AATACAAGTCCAATACCATACATGCTAGCG |
| SEQ ID NO: 160 | GCTAGAACTCCACCGTAGTTCTTATGCAAC |
| SEQ ID NO: 161 | ATCCAGATCCTAGGCATGTCATTTGTAAGG |
| SEQ ID NO: 162 | TAGGCCAACCGATATCTCCTATTTAGCAGC |
| SEQ ID NO: 163 | GTGCACTTCACTTCATGACTGAATCTCACC |
| SEQ ID NO: 164 | GTCAACACAACTTGATCACTCTCGCAGACA |
| SEQ ID NO: 165 | ATCAGAACAGCGTTTCATGTTCTTGTTCAT |
| SEQ ID NO: 166 | ACTCCTTAATCATAAACACCTTTGCATGCC |
| SEQ ID NO: 167 | AATAACGAGCTCAGGATAGAACGATAGGTT |
| SEQ ID NO: 168 | ACGTGGCGATTCCTAAGGCACATATATAAC |
| SEQ ID NO: 169 | ACAAAGAGGCGAACTGTTCCACTTAAGTTC |
| SEQ ID NO: 170 | TTCACATTACAAGTTAGGATGCTGCGTACG |
| SEQ ID NO: 171 | TCATGATGAGCCACAACGCCAGATTTCGAT |
| SEQ ID NO: 172 | GAAGTCCTATTACCTCCGTAATGTTACCTA |
| SEQ ID NO: 173 | AGTAGTAGTAGAGCACGCGTTCGTACAAAT |
| SEQ ID NO: 174 | CTTATGCTATACCTAGACCACCATTAGCTA |
| SEQ ID NO: 175 | AGCCGACCGACGCGACCTAACTCTGCAGAA |
| SEQ ID NO: 176 | AGCGTCTCTACTTACAGCTACTTCAGTTGT |
| SEQ ID NO: 177 | CACACAGGTCCTTAGGATCCTTGGAGTCTA |
| SEQ ID NO: 178 | CTGAGCTCGGAATTACCAAGCAGATAATCC |
| SEQ ID NO: 179 | AACGCAACCTGCTCTGTATACTTGACCATA |
| SEQ ID NO: 180 | GCACTTTCGTCGATACACCAACACCGGTCG |
| SEQ ID NO: 181 | TGAAGCACTACATCTTAAGACTAACATTGC |
| SEQ ID NO: 182 | GACGAGCCTAGGCTCTAAAGCACCACCAAA |
| SEQ ID NO: 183 | ACGTATTCAGTTCCAAGGCCGGAACTGGCG |
| SEQ ID NO: 184 | CGCTTGCAGTTCGTAATATTTAGGCCAAAT |
| SEQ ID NO: 185 | GGCAAGCGCTGTTTCGTGTCCGCGCAACTT |
| SEQ ID NO: 186 | GTGGAATTCGCTTATACTACAGCAATTGCC |
| SEQ ID NO: 187 | AACAAAGCTTAAGCGCATCCGTTGGCATGA |
| SEQ ID NO: 188 | TTCAGAGGCTTCTGTTGTTGCTCAACAAT |
| SEQ ID NO: 189 | TGAGCATTTGCCATCCTGCAAATATCAATC |
| SEQ ID NO: 190 | GCTAATGCACTCATTTAAGTCACGTGTAAG |
| SEQ ID NO: 191 | GTGGCCGCACCGGTGTTAGATTAGGTAGAT |
| SEQ ID NO: 192 | CATTCTCTCCACAGAATGCCTTCTGACACT |
| SEQ ID NO: 193 | TCTCTCTCCGCTTCTACCGGCAAGTAATCA |
| SEQ ID NO: 194 | AGACAACTTTGCCTGGTATGCCTGGCCTTC |
| SEQ ID NO: 195 | CCGGATACAGAGCCGGCATGAACTTGCGCC |
| SEQ ID NO: 196 | CCAAACACGGATCCATAGTCAACATGACAA |
| SEQ ID NO: 197 | AAGCGCTCGTCATCGTTCGGTACTCAGAAA |
| SEQ ID NO: 198 | ATACTTCGGCCGTCCGCCACCAAATACAAT |
| SEQ ID NO: 199 | CCAAAGCGTTTGTCGTATAAACGCTTTGCT |
| SEQ ID NO: 200 | GTCATCCATACGGCGTTACATATATTAGGC |
| SEQ ID NO: 201 | CATTCAGACGATGATGACATCATGCTTCCA |
| SEQ ID NO: 202 | TTCCTTCCACAGTTCGGCGCGCCGTTATAC |
| SEQ ID NO: 203 | CGGTCGCAGCGTGCACAACGCTATGGAATT |
| SEQ ID NO: 204 | CTCCTCCTTTGGCTAGCTTAAGAAACATGT |
| SEQ ID NO: 205 | GAATTTACTAGGTCCTGGCGTGCTAGTAGT |
| SEQ ID NO: 206 | ATCAACAATCTCTCTCACTCACACTCTAAG |
| SEQ ID NO: 207 | ATGAAATCTTTGTAGTTAGGCGGTTAACTC |
| SEQ ID NO: 208 | AGAACTAATCAACCGGCAATCAACAGCAAC |
| SEQ ID NO: 209 | ATTCTACATCTGACACCGAACATGCATGTG |
| SEQ ID NO: 210 | AACCTCTCACTGCTAGTGAGTTTCTTCTAT |
| SEQ ID NO: 211 | GTACGACTCGTCACTACAGTGACCATCTGT |
| SEQ ID NO: 212 | CACTAACTATTTAACCTAGCTAACGTCCAC |
| SEQ ID NO: 213 | TGCAACTCCTCATTCGCGAGACCACTAAAC |
| SEQ ID NO: 214 | AACCAAAGCCGTCGTACGATTAGTGTAGCA |
| SEQ ID NO: 215 | CTGTCGAAACAAGTAGATTATGCATTTGCC |
| SEQ ID NO: 216 | GGTCTGAACACCTTGGTTTACGGTTCAGCC |
| SEQ ID NO: 217 | TACGCCGTGTGTCAGCTGGCAATAGCCTCT |
| SEQ ID NO: 218 | GTAGGTATTTATCTAACTCGCTCAGCGAGC |
| SEQ ID NO: 219 | TGCGCTCGATGTAAGGCAGTACGTAGAAAT |
| SEQ ID NO: 220 | ACTCATTGGCTGTACACCACCTACTTTAGA |
| SEQ ID NO: 221 | CTAACGCCTATAGGAAGCAACACTCTCTAT |
| SEQ ID NO: 222 | AGGTATGTCCGGCATACCTCGTCTATGCAT |
| SEQ ID NO: 223 | TTGCTTAGCTACGACAAATCCCGCAATTG |
| SEQ ID NO: 224 | CAATAACCTACTTCGACTTCCATATGAACC |
| SEQ ID NO: 225 | ACAAACGTTCCGATTTCGCAGATCCTTGTG |
| SEQ ID NO: 226 | CATCATCAGCCAGTTATCATCCGAAGCCTA |
| SEQ ID NO: 227 | CCAACATTTAGAACCTAGGAACAGTGTGCA |
| SEQ ID NO: 228 | AGCTCGCCATGGACTCCTCGAAATACTAAT |
| SEQ ID NO: 229 | TCTTATTCGAAGGCCTCTGTGCATCTCCAT |
| SEQ ID NO: 230 | GCCTCAAGGTTTGACGACAGCCTTGATTTA |
| SEQ ID NO: 231 | ATAACTTCGCGCGCATGCCAAACGCTTAGT |
| SEQ ID NO: 232 | TCGACTTCTAGTAGTAGCTCTTACTCTGAA |
| SEQ ID NO: 233 | ACATTATCTCATCCATCTATTAGCGTACGT |
| SEQ ID NO: 234 | GGCCTACTTTGCCTCAAATTTCACGAAGGC |

TABLE 1-continued

Candidate 30 mer bit-oligo sequences

| SEQ ID NO: 235 | CCAGCCGCCGGCAAGAACATTTAAATCCTC |
|---|---|
| SEQ ID NO: 236 | TTGCTTGTAACACTTAACACAAGTCGATGA |
| SEQ ID NO: 237 | CCTCCGACAGAGTTCATAGGTGTAGCTAAT |
| SEQ ID NO: 238 | GTTAAGTTGCCGTTAGCAGCAACTACTGCA |
| SEQ ID NO: 239 | CCGGACCATACATTAGACCACATATGCTTA |
| SEQ ID NO: 240 | CTCGTTGCGCATTGATGCTCAGGACATAAC |
| SEQ ID NO: 241 | CCTTTCTCCTACTGATACCTAAACAGAAAG |
| SEQ ID NO: 242 | CCACATCCGAGAGCTCGCAGCGGAGATCAC |
| SEQ ID NO: 243 | CTCCTTCTATGGTCAATGGCTGTCGACCTA |
| SEQ ID NO: 244 | TACCACTAGTCGTGCGCGATATAGGTGGTC |
| SEQ ID NO: 245 | TCCTTAGAGATCTAAATGGCTGATGCTGGA |
| SEQ ID NO: 246 | CACTCAGGAACAAATAGAGAACTATCGATT |
| SEQ ID NO: 247 | TCATGATCCAATACGTGCTTATAACCTCGT |
| SEQ ID NO: 248 | CATTTATCAAAGCTTTCTTTCGCTCCAATC |
| SEQ ID NO: 249 | CTTGACCGCTATTTATAAGGATGTTACTAC |
| SEQ ID NO: 250 | AGATGACCTCTAGGTGATAGGACATGTTGC |
| SEQ ID NO: 251 | TTTAATGGATGTCTCGAGCAACATCTGCCT |
| SEQ ID NO: 252 | ATGCGAAACCATGGAACATAAGTTCACCGT |
| SEQ ID NO: 253 | GATATATAAGATCGGCTTGGTGATCTTATC |
| SEQ ID NO: 254 | AAACGGTAACATTCATATGTCACATCGCGA |
| SEQ ID NO: 255 | CACCTAATACTAATTATATGGCACGGAGGT |
| SEQ ID NO: 256 | CTTGTAGGCGTCATACACGTGTAGAGCGCC |
| SEQ ID NO: 257 | GACTCCTGCAACCTCCTCCTAACAACCACA |
| SEQ ID NO: 258 | GATTATAATCCGAACTTGGATGAAGCAAAC |
| SEQ ID NO: 259 | AGTTTCTACATTCCGGACCAAAGTCAGTTT |
| SEQ ID NO: 260 | CGATCCTTAAATACAAGCACCTTAATCGGA |
| SEQ ID NO: 261 | TGAACACTCCTCTCGCTCGCCATATCGATA |
| SEQ ID NO: 262 | TCGCTCAAAGCATGTTCTTAGCATGTTAAA |
| SEQ ID NO: 263 | GCGTTCGCCTAGACCGTACTGTGGAATATT |
| SEQ ID NO: 264 | CACCATTAATTTCTCCAGTGCTTCGAGACC |
| SEQ ID NO: 265 | GCTTCAGCTGTACCGCATTCAGAACTTCAG |
| SEQ ID NO: 266 | AAACTGTTCTAAATATTGCGACGGTCCTAC |
| SEQ ID NO: 267 | TTCGGAGACATGCCGTGTCAAATATATACA |
| SEQ ID NO: 268 | GTTTGGCCGAGCGCTTCTCAGCTTCTTGGT |
| SEQ ID NO: 269 | GCTCTATTCTCGTCGTCTCTATAAAGGAAA |
| SEQ ID NO: 270 | TATCTGATCTCCAACGCTCGGTTGCAATAT |
| SEQ ID NO: 271 | CCTTTGGCTCTTCACTTGTCTCTCCTCTCC |
| SEQ ID NO: 272 | GAGGATGCCGGCTTGTTCACCGGCTTAGCA |
| SEQ ID NO: 273 | AGAGACAAATAAACGTCCGCAATGTACATT |
| SEQ ID NO: 274 | AACCACTCTATCTTAGATACATAGAGTGCC |
| SEQ ID NO: 275 | GGCATGTGATTGTACAGATCATTTCGGTTT |
| SEQ ID NO: 276 | GCAAAGCACTAATTAACGCGCTAAGACGAT |
| SEQ ID NO: 277 | AGCCTAACAATGTACAAGTACACATCGTAC |
| SEQ ID NO: 278 | ATATGAGAGCTCATCCATTTGTATCTTCCG |
| SEQ ID NO: 279 | GGTATACAACCATCGTTCTACACCAATGCA |
| SEQ ID NO: 280 | AACAGCCTTTGATTAATGACCTTATAGTGC |
| SEQ ID NO: 281 | AAGCTGCTACCAATCTTCAACGTGCAGCTC |
| SEQ ID NO: 282 | AGCTGTGAACTTGGTCCATCATCTTAAGTT |
| SEQ ID NO: 283 | ATGTATACCACTCAAGCTTGTATGTCTCAC |
| SEQ ID NO: 284 | AGTCCACACTGAATACAATATTTCGGACAA |
| SEQ ID NO: 285 | ATAAACAAAGGACCGTACGGACTTGTCTCA |
| SEQ ID NO: 286 | GAGTACTAGGAGCATACTAACATATGATCA |
| SEQ ID NO: 287 | CAATTGCATGCCTCTGATACTTAGAGTGAC |
| SEQ ID NO: 288 | CCAGTTTAGACACTCTCGATCGTGGTAGAC |
| SEQ ID NO: 289 | CATCGGTAACAAACAGTAGCTCCTTATAAT |
| SEQ ID NO: 290 | AACTAGTGACTTGCTCACCTGGTGGCATCG |
| SEQ ID NO: 291 | CCAGGTCGATCGACCTCCTCGCTGTCGACA |
| SEQ ID NO: 292 | GTGATAAAGAAGTATCGATCGCCTGACAGA |
| SEQ ID NO: 293 | GATATCTTGATTACGGAAGAACACGAAGTA |
| SEQ ID NO: 294 | GGTCTCGGCATTAATATTATTAACATCCAC |
| SEQ ID NO: 295 | GGACCATCTGGCGCACGCTATGCATACACC |
| SEQ ID NO: 296 | GAACAGATCTAAGTTCGATTCCTTTGTTCG |
| SEQ ID NO: 297 | ATCGGTTCCGTGCACTTACCTCTAAATACG |
| SEQ ID NO: 298 | TATGTCCACCTAGTCACTATCCATGTCCGC |
| SEQ ID NO: 299 | CCACACTGGTAATGCTCCAAGGAACCACAC |
| SEQ ID NO: 300 | GACAATGGAGGTTAACTGAATCCATCAAAT |
| SEQ ID NO: 301 | GAGCGTCAGCTTCATTCCAACAAAGCTGAA |
| SEQ ID NO: 302 | GGAAGGAAGGTCCTCTCTTAGGAGGACCTC |
| SEQ ID NO: 303 | AACGCGTAAGTTCAACATTTGGACCTCGCC |
| SEQ ID NO: 304 | ATTATATTCCATCAACAAACCTCCGGATGG |
| SEQ ID NO: 305 | CCAGAAATGCATGGCTGTTGTACAACCATA |
| SEQ ID NO: 306 | TCTCTTACTTGTCGTTAACGCTTTAACGTC |
| SEQ ID NO: 307 | TGTGAAAGATCTAACGCCAATCGACACCGA |
| SEQ ID NO: 308 | TGCCGACCAAGTATAGAATTAGACTATACT |
| SEQ ID NO: 309 | CATCTATAGACATCGAGTGTGAGATTGGCA |
| SEQ ID NO: 310 | CCATACTACTATAAGCAGCGCGCAGGATCA |
| SEQ ID NO: 311 | CACTCTGCTTCATAGTATAGTATCGGTTTC |
| SEQ ID NO: 312 | TTCTACTTGGCGTGGTTCTTTGGAAGCTTC |

TABLE 1 -continued

Candidate 30 mer bit-oligo sequences

| | |
|---|---|
| SEQ ID NO: 313 | TTCAATGTAGCTATAGTCCGGCTTTAACTT |
| SEQ ID NO: 314 | ACTAGGTCCGGCGGATCGGCCTTTATATAT |
| SEQ ID NO: 315 | CAAGTAGGTAGGTATCTCTAGAGCCTGTCA |
| SEQ ID NO: 316 | GGATTGCTAATCTAGACTAGACCGACTAGT |
| SEQ ID NO: 317 | AAACTACAAGAGAGATCGTGATCTCTTATG |
| SEQ ID NO: 318 | CAACGCTTCAAACCTACTTTCTCTATAGGC |
| SEQ ID NO: 319 | CCGTTCGATCTGAAGATTTGGTGCGCATTT |
| SEQ ID NO: 320 | CACCTCCACATTTAACACATGTAATACGGT |
| SEQ ID NO: 321 | ACCATACAACGCCACACTTTGATCAACCGT |
| SEQ ID NO: 322 | TCTAAGCGTGCAACTATACAAGCATGCACC |
| SEQ ID NO: 323 | CATATTCACCACAAACTAACCTCATATGCT |
| SEQ ID NO: 324 | GACTGGTATACTGACCTTGACCTGTATATA |
| SEQ ID NO: 325 | ATTATGGATGCTCTTCTCGCAGCTATATAA |
| SEQ ID NO: 326 | GATCCGATGCGTCGCATGAACTATAGAATA |
| SEQ ID NO: 327 | AGTCTTCTTGGAATCCATGGTAATACCTTC |
| SEQ ID NO: 328 | CTAGCCGAAACCGTAACCGTTACTTCCAAC |
| SEQ ID NO: 329 | ATAGATACACTACTGCCTTCCGTGGCAGTG |
| SEQ ID NO: 330 | CGTTATCTGCAGTTGTCGCCTTTAGTAGTC |
| SEQ ID NO: 331 | TGTACACTGCTTTGTGTCCTTCTCTCGTCG |
| SEQ ID NO: 332 | GACTGGTTAAATTGCGACGCTAGATCTTGG |
| SEQ ID NO: 333 | TGTCTCCTCCACTAGATATATCACCTTGAA |
| SEQ ID NO: 334 | CCATTAGAGAAGTCCAGGTGTTGAAGAGAA |
| SEQ ID NO: 335 | ATGATAGACCTCCATAGTCCTTACTAGTTT |
| SEQ ID NO: 336 | TCCGATTAATCCGAAATCGATGGTTTACAC |
| SEQ ID NO: 337 | CGATATGCATCTACCTTAAGTTGAATAGTG |
| SEQ ID NO: 338 | GAATTTACATAGGCTGATCACAACCTCCAT |
| SEQ ID NO: 339 | ACCGGCTTTGACGAAGGCGGCTTACTCAAT |
| SEQ ID NO: 340 | AAACCGGCGAGAAATTTACATTTGCTGTTA |
| SEQ ID NO: 341 | TTCGGATATCGAATCTCGCAATCGAATAGG |
| SEQ ID NO: 342 | AACAACTCCTGGAGTACCGGTCAAATGAAC |
| SEQ ID NO: 343 | TTCCACCGCATTTGTGCGACAAATCATAGT |
| SEQ ID NO: 344 | ACCAATTGTAGCTCCGAGACAACTTCTAGA |
| SEQ ID NO: 345 | GTAGAGCGCATTAGGTATACTAGATTCTAT |
| SEQ ID NO: 346 | GCTATAATGGCCTTAAAGTGTGCGCGCCGC |
| SEQ ID NO: 347 | GTCCATCAGCAACATTAGTCATGACACCGC |
| SEQ ID NO: 348 | CAGTCTAGGCCTTTCTTATATGATGTCCTC |
| SEQ ID NO: 349 | CACACACATCCAGACTGCTCGCCAACAGCA |
| SEQ ID NO: 350 | CGCATTCCATTAGACGGAGGCCTAGGCACC |
| SEQ ID NO: 351 | CAACATGCCAACTGAACGAGTGCATGTTCT |
| SEQ ID NO: 352 | CCTAGATGCCAATCCGCACTACAATCCATG |
| SEQ ID NO: 353 | ACAAGGCCGCACCATGCTATTAATACAACC |
| SEQ ID NO: 354 | CAGGCATGTACGAACAAACAAACCATGTGG |
| SEQ ID NO: 355 | GACGCCGTATATTGGACAACTCAACAATAT |
| SEQ ID NO: 356 | TGTAGGCGCTACCTGAGCTCCACTAAAGAA |
| SEQ ID NO: 357 | AAGCTCGAGTCAAGTGAATAGGTTTCACAG |
| SEQ ID NO: 358 | CAAGCACGCAATTCCACCTCCGATCGCGTT |
| SEQ ID NO: 359 | TGACTCGTAAGATTCTTTAAACAAACGCCA |
| SEQ ID NO: 360 | CTGATCAGTTCTCATACTCCTTCGCAATGC |
| SEQ ID NO: 361 | CGGATACGTACCTGGTGCGTACTGGATGGA |
| SEQ ID NO: 362 | CTTCGATTGTTAGCTTCTTGCAATGCGAAC |
| SEQ ID NO: 363 | ATGTCACACCGTGGATGTTCAGAATCTAGA |
| SEQ ID NO: 364 | ACGCTCTATCCGTTGTAACGTTCAAGACTG |
| SEQ ID NO: 365 | TCACTGTAGCTAGGTAACTAGTATATCGTA |
| SEQ ID NO: 366 | TTGTTAATGAGTACCACAATACACCATGGC |
| SEQ ID NO: 367 | GTCTCAGAGGATAGCTAATCATAACATCCG |
| SEQ ID NO: 368 | CTGCGTCCACTCACGTCCAGCTATCAACAA |
| SEQ ID NO: 369 | CGCAATGGTACATGTTTGACATACCACATA |
| SEQ ID NO: 370 | TCACACTGAAGAAAGCACTGGTTATAACCA |
| SEQ ID NO: 371 | GCCACAATTCATCAGGTAGCTAAGTGCTGT |
| SEQ ID NO: 372 | TGCGATTCCATAGGCCGGCAGTGCGTCATT |
| SEQ ID NO: 373 | AACCAAGCGCTGGTCTTTCACGTTCATAAG |
| SEQ ID NO: 374 | TGACGGCGTTAACTCCATTGATTATTTACA |
| SEQ ID NO: 375 | TGTTGGCGCCGCTTAGAAGGATGGTCGTCG |
| SEQ ID NO: 376 | TTTAGTAGACCATCCTATCCTGGTCTAAGC |
| SEQ ID NO: 377 | AGTTCTTCATACAGACGCATTAGGATCCAA |
| SEQ ID NO: 378 | CCAAGTCACACATTCTATCGTCTATCTATC |
| SEQ ID NO: 379 | GTCAGCGAACTTGCGTTGCTGCATAGCTAA |
| SEQ ID NO: 380 | ATACGAGGTATTAGCACGATCGTCGGTAAC |
| SEQ ID NO: 381 | AGCCTCTAGATAGTTCCAGTCTCATTTACC |
| SEQ ID NO: 382 | CAGCGACATATGACATACTCTTGTTTCATG |
| SEQ ID NO: 383 | CTGTTTAAAGTCTTCGAATCGAGCAAACAC |
| SEQ ID NO: 384 | GTAACACGTTGTGAAGCTCCTCAATTGTTC |

Well- and Plate-Level Primer Pair Design

The second phase in designing the POC system was to generate conserved Well and Plate level primer binding domain sequences (regions shown flanking the "bit-oligo" sequences and "W" index sequence, respectively, in FIG. 1) that are used in the primary (1°) round of PCR to encode the Well index and prepare the samples to be encoded by the Plate and Document indices. The targeted length for these primer binding domains was 20-25 nt. Since these were to be used in PCR, a targeted $T_M$ of 65° C. was used, a length of ~22 nt, and a GC content of ~55%-60%. The PCR conditions that were used are as follows; [Oligo]=200 nM, [Na⁺]=22 mM, [Mg⁺⁺]=1.5 mM, [dNTP]=0.8 mM.

The design strategy implemented was to generate a candidate pool of 26 primers with a starting size of 25 nt for length. As with the bit-oligo design strategy, the Levenshtein distance was then used to compute edit distance between candidate primer sequences with a minimum allowed edit distance of 12. Next, the GC content was limited to 45% to 65% to eliminate candidates with extreme GC values. The final step in the initial filtering was to avoid certain sequence motifs (AAAA, CCC, GGG, TTTT, ATATA, CGCGC, TATAT, GCGCG, CACAC, ACACA, GTGTG, TGTGT, AGAGA, GAGAG, CTCTC, and TCTCT) and to minimize motifs within sequences (no duplicate motifs of size 6) and between sequences (no duplicate motifs of size 12). Sequences that failed the initial filters were replaced with new candidates and the process was repeated until all 26 candidate sequences passed.

Unlike the bit-oligos the design strategy continues with primer pair designs at the Well and Plate levels. For the primer design phase, the length was set to 22 nt (±2 nt) with a maximum allowed length of 24 nt, $T_M$ was set to 65° C. (±3° C.), GC content was set to 55% (45%-70%), internal repeat size set to 9, 3' repeat size set to 7, and the primer pair $T_M$ difference set to 2° C. The design engine assumed a target input sequence to design the primer pairs from hence a 30 nt poly N segment is used as a place holder for the bit-oligo domain for the initial Well level primer pair design.

Within a primer pair design iteration every combination of sequences was attempted, excluding sets where the same sequence was on both ends. For solutions with no design warnings (clean), the primer pair was then scored against all bit-oligos previously designed to ensure the primer pair was clean with the real targets. From all the clean designs within the iteration the best scoring design was returned. When a primer pair was not clean they were recorded and the worst offenders were removed from the candidate list. If no clean primer pairs were found, hence no candidates remained, a new set of candidate sequences was generated, filtered, and designed until a single clean primer pair was found. Even when a clean primer pair was found the worst offenders were removed from the candidate list and the list was repopulated back up to the desired count in preparation for designing primer pairs at the Plate level.

The same primer pair process was used for the Plate level primer pair except that the target sequence included the 30 nt poly N segment and also the Well level primer pair flanked by 8 nt poly N as a place holder for the Well indices. Once the Well level primer pair was found, it was locked in and all remaining design iterations were to find a compatible Plate level primer pair. From this round of designing 5 primer pair sets were generated.

Candidate Primer Pair Sets (Well and Plate Levels) (SEQ ID NOs Appear in Square Brackets Following Each Sequence)

Plate Level Design Construct 01
CGCAGCCTCTATACGCGTCTGACC[385]<WellIndex5>
<WellIndex3>GCGGAATTCCATCCTCCGAGGCAG[380]
ACGAAAGGTAGAGGTCCGGAGTG[387]
<Payload>AGTCCGAATCGGTCATCCTAGGT[388]

|  | %GC | Tm |
|---|---|---|
| Plate Primer Pairs (Length: 24) | | |
| Forward: CGCAGCCTCTATACGCGTCTGACC[385] | 62.5 | 66.6 |
| Reverse: CTGCCTCGGAGGATGGAATTCCGC[389] | 62.5 | 67.3 |
| Well Primer Pairs (Length: 23) | | |
| Forward: ACGAAAGGTAGAGGTCCGGAGTG[387] | 56.5 | 63.9 |
| Reverse: ACCTAGGATGACCGATTCGGACT[390] | 52.2 | 63.3 |

Plate Level Design Construct 02
TCTGGCCATCACTGGACCTAC[391]<WellIndex5>
<WellIndex3>CGACTCCACAAGCTCCACCTT[392]
CGGTCGAGAAACTATAGGCTCGG[393]
<Payload>GGACAATGGCAATACTGGACACC[394]

|  | %GC | Tm |
|---|---|---|
| Plate Primer Pairs (Length: 21) | | |
| Forward: TCTGGCCATCACTGGACCTAC[391] | 57.1 | 62.1 |
| Reverse: AAGGTGGAGCTTGTGGAGTCG[395] | 57.1 | 62.9 |
| Well Primer Pairs (Length: 23) | | |
| Forward: CGGTCGAGAAACTATAGGCTCGG[393] | 56.5 | 62.5 |
| Reverse: GGTGTCCAGTATTGCCATTGTCC[396] | 52.2 | 62.3 |

Plate Level Design Construct 03
ATGGCCTCGGACTTGCCTCC[397]<WellIndex5>
<WellIndex3>CGGCAGCTCAAACCAGGCCT[398]
CCGGTCCTCTACGACCGCGGAAC[399]
<Payload>GCCTCCATACGCCACTGTGCACA[400]

|  | %GC | Tm |
|---|---|---|
| Plate Primer Pairs (Length: 20) | | |
| Forward: ATGGCCTCGGACTTGCCTCC[397] | 65.0 | 65.0 |
| Reverse: AGGCCTGGTTTGAGCTGCCG[401] | 65.0 | 65.9 |
| Well Primer Pairs (Length: 23) | | |
| Forward: CCGGTCCTCTACGACCGCGGAAC[399] | 69.6 | 68.3 |
| Reverse: TGTGCACAGTGGCGTATGGAGGC[402] | 60.9 | 67.5 |

Plate Level Design Construct 04
AACCTCCGTCGTCGTAACAGCTC[403]<WellIndex5>
<Well Index3>GTGTCTTGCAAAGCAGACGCAGC[404]
GGAAAGTTGGTGCACAGTCAACC[405]
<Payload>GCATTCGGCACTAGCTTACGTAC [406]

|  | %GC | Tm |
|---|---|---|
| Plate Primer Pairs (Length: 23) | | |
| Forward: AACCTCCGTCGTCGTAACAGCTC[403] | 56.5 | 64.6 |
| Reverse: GCTGCGTCTGCTTTGCAAGACAC[407] | 56.5 | 65.3 |
| Well Primer Pairs (Length: 23) | | |
| Forward: GGAAAGTTGGTGCACAGTCAACC[405] | 52.2 | 62.9 |
| Reverse: GTACGTAAGCTAGTGCCGAATGC[408] | 52.2 | 62.0 |

Plate Level Design Construct OS
ACAGAAATCCAGACCGGTGACAC <WellIndex3>
TTGACGCCGCAAATAAGATCTCC[410]
ACATCGCCGACACTTTGCAACG [412]

|  | %GC | Tm |
|---|---|---|
| Plate Primer Pairs (Length: 23) | | |
| Forward: ACAGAAATCCAGACCGGTGACAC[409] | 52.2 | 63.2 |
| Reverse: GGGAGATCTTATTTGCGGCGTCAA[413] | 47.8 | 62.0 |

```
Well Primer Pairs (Length: 22)

Forward: ACATCGCCGACACTTTGCAACG[411]    54.5  64.7
Reverse: GGAAGGCTAAGGCTTGCAAGGA[414]    54.5  63.5
```

Example 2: Primer Pair and Index Design for 2° Document Level Primers

Five full primer pair and index sets were designed assuming typical Synth Bio PCR conditions and a desired Tm of 65° C. A PCR design engine was used to design the primers. Primer pair design was executed from the bit-oligo out (Well, Plate, then Document) with the appropriate sequence content minus the indices. In other words, the Plate level primer pairs were designed against the Well level primers and all 384 bit-oligos. Indices were then designed and examined in the context of various PCR primer pairs.

For the Document level primer)(2° (sequences flanking the document level indices "D" in FIG. 1), three distinct primer pairs were generated. Each of the three document primer pairs is specific to one of three potential documents.

In this particular case, the minimum allowed edit distance were reduced to 10 and the $T_M$ difference was relaxed to ±3° C. Five primer pair sets were generated where each primer pair was designed a few times each (Well/Plate=5, Document=3) then the best scoring pair was taken.

Forty Well-level indices were designed for each Primer Pair Set, assuming 384 well plate matrix (16 rows, 24 columns), with a size of 6 bp, a minimum allowed edit distance of 2, and a GC content range of 30%-70% while avoiding the same motifs as the primers. Each candidate group of 40 was examined against all the bit-oligo constructs possible and for PCR reactions with the Plate and Document level primer pairs. Internal repeats to avoid was set to 10. While only 6 indices were needed at the Document and Plate level, a set of 24 were designed to allow for more plates per document. These were designed under the same context as the Well level indices, but at a size of 8 bp and a minimum allowed edit distance of 3.

After completing the design of all components in the POC system, a final in silico validation was executed to confirm that all primer pairs were compatible for all constructs possible (147,456) resulting in 1.77 million design checks across all 5 primer pairs and 5 Primer Pair Sets. Some parameters were relaxed since all full constructs were available; internal repeat size to avoid was set to 12, and 3' repeat size to avoid was set to 8, although 3' pentamer repeats were disabled and terminal repeats were enabled for Plate and Document level primer pair examinations. All five Primer Pair Sets were clean upon validation and the $2^{nd}$ Primer Pair Set was chosen as the design solution for this proof of concept. All resulting oligos were then synthesized.

Figure 2:
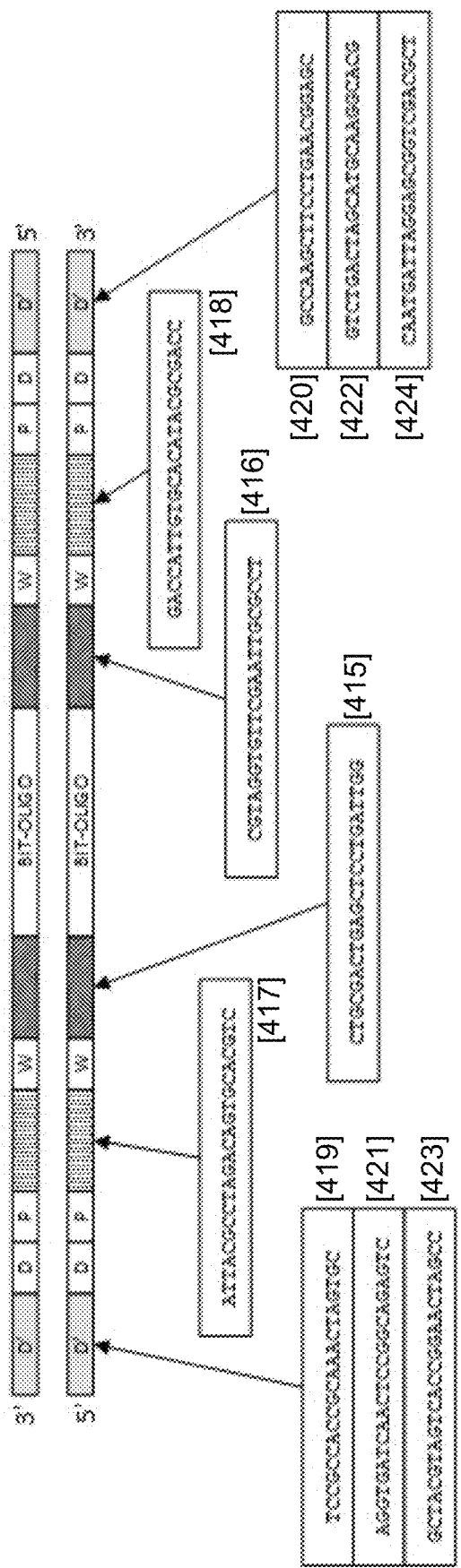
FIG. 2 shows a tertiary nucleic acid bit construct with sequences used in Example 2. This schematic shows the conserved sequences of the primary (dark shaded) and secondary (light shaded) levels of organization as well as the non-conserved sequences of the tertiary level of organization (D'). This construct was used to create three documents, each with its own document-specific sequences on the 5' and 3' ends.

A tertiary nucleic acid POC bit construct, with the sequences from Primer Pair Set 02 included, is illustrated in FIG. 2. This shows the initial design to encode up to 3 separate documents with 18.4 kilobytes of data.

Primer Pair Set 02 (SEQ ID NOs Appear in Square Brackets Following Each Sequence)

```
Well Construct
CTGCGACTGAGCTCCTGATTGG[415]<Payload>
CGTAGGTGTTCGAATTGCGCCT[416]

Plate Construct
ATTACGCCTAGACAGTGCACGTC[417]<WellIndex5>
<WellConstruct>
<WellIndex3>GACCATTGTGCACATACGCGACC[418]

Document 1 Construct
TCCGCCACCGCAAACTAGTGC[419]<DocPlateIndex5>
<PlateConstruct>
<DocPlateIndex3>GCCAAGCTTCCTGAACGGAGC[420]

Document 2 Construct
AGGTGATCAACTCCGGCAGAGTC[421]<DocPlateIndex5>
<PlateConstruct>
<DocPlateIndex3>GTCTGACTAGCATGCAAGGCACG[422]

Document 3 Construct
GCTACGTAGTCACCGGAACTAGCC[423]<DocPlateIndex5>
<PlateConstruct>
<DocPlateIndex3>CAATGATTAGGAGCGGTCGACGCT[424]

%GC    Tm

Well Primer Pair (Length: 22)

Forward: CTGCGACTGAGCTCCTGATTGG[415]         59.1   63.4
Reverse: AGGCGCAATTCGAACACCTACG[425]         54.5   63.9

Plate Primer Pair (Length: 23)

Forward: ATTACGCCTAGACAGTGCACGTC[417]        52.2   63.1
Reverse: GGTCGCGTATGTGCACAATGGTC[426]        56.5   64.5

Document 1 Primer Pair (Length: 21)

Forward: TCCGCCACCGCAAACTAGTGC[419]          61.9   65.9
Reverse: GCTCCGTTCAGGAAGCTTGGC[427]          61.9   64.3

Document 2 Primer Pair (Length: 23)

Forward: AGGTGATCAACTCCGGCAGAGTC[421]        56.5   64.5
Reverse: CGTGCCTTGCATGCTAGTCAGAC[428]        56.5   64.1

Document 3 Primer Pair (Length: 24)

Forward: GCTACGTAGTCACCGGAACTAGCC[423]       58.3   64.5
Reverse: AGCGTCGACCGCTCCTAATCATTG[429]       54.2   65.1

Well Indices for Primer Pair Design Set 02
TGGTAT[430], CCTATC[431], GATTGG[432],
TAGGCT[433], GCTGCT[434], GTCTCA[435],
TGTATG[436], ACAGAC[437], ACTAGG[438],
ACCAAT[439], TAACTG[440], GTGAAA[441],
TCAAGC[442], TACGGC[443], ATAGCG[444],
CAGTCC[445], AACACT[446], AAGCAG[447],
CTACTG[448], GGCGAT[449], ACCTTC[450],
TAGAGC[451], GCAGCA[452], TGTCAG[453],
ACTTAG[454], CCAAGT[455], CGCATC[456],
TTGCCG[457], GAGGTG[458], ACCGGA[459],
TTTAGC[460], CTGGAG[461], CCTCCT[462],
GAACCG[463], CTTGAC[464], AGTGGC[465],
GTCATG[466], GTTCTC[467], AGCAGG[468],
GGTACG[469]

Document and Plate Indices for Primer Pair
Design Set 02
CTTTCCGA[470], AGTAGCTA[471], GTTCAGTA[472],
TCCTAGTC[473], GGTCTGCT[474], CAAAGGTA[475],
GATCTCAT[476], AAGGAGCA[477], TCGAACAC[478],
GCGTTCTC[479], ACCGCTGA[480], TGGTGCTA[481],
GTCGAGCT[482], TACCGAAG[483], CGACCTCA[484],
TCTATCGG[485], TCTTCTCG[486], TTCACGCT[487],
AGGCTTCG[488], AACATCCA[489], AGTCCAAA[490],
CCGATATG[491], TATGAGGC[492], CTCCTTTA[493]
```

Design Solutions for the Other Four Primer Pair Sets

Primer Pair Set 01 (SEQ ID NOs Appear in Square Brackets Following Each Sequence)

```
Well Construct
ATCCTCAACAGGCGCATCTCAACC[494]<Payload>
GTTCAGGCCATTGCGCAGATGTTA[495]

Plate Construct
TGCGAACGTCCATTCGTCCATGC[496]<WellIndex5>
<WellConstruct><WellIndex3>
CAGCTCCTGGAGCTAGGCCAGAA[497]

Document 1 Construct
CTCAATGGCCAACATGCGCTGTG[498]<DocPlateIndex5>
<PlateConstruct><DocPlateIndex3>
GACCTACGAATAAGGAGCGCTGG[499]

Document 2 Construct
GCACGTGGTACTTCTAGCAATGCC[500]<DocPlateIndex5>
<PlateConstruct><DocPlateIndex3>
GCTGTCCGGAGTGCTGTAGATGTC[501]

Document 3 Construct
ACCAGCCTTTCGACAGCCTAC[502]<DocPlateIndex5>
<PlateConstruct><DocPlateIndex3>
CGGTAGCTTGACCATTCGCGG[503]

%GC    Tm
Well Primer Pair (Length: 24)

Forward: ATCCTCAACAGGCGCATCTCAACC[494]   54.2   65.6
Reverse: TAACATCTGCGCAATGGCCTGAAC[504]   50.0   64.5

Plate Primer Pair (Length: 23)

Forward: TGCGAACGTCCATTCGTCCATGC[496]    56.5   66.1
Reverse: TTCTGGCCTAGCTCCAGGAGCTG[505]    60.9   66.2

Document 1 Primer Pair (Length: 23)

Forward: CTCAATGGCCAACATGCGCTGTG[498]    56.5   65.4
Reverse: CCAGCGCTCCTTATTCGTAGGTC[506]    56.5   63.1

Document 2 Primer Pair (Length: 24)

Forward: GCACGTGGTACTTCTAGCAATGCC[500]   54.2   64.3
Reverse: GACATCTACAGCACTCCGGACAGC[507]   58.3   65.0

Document 3 Primer Pair (Length: 21)

Forward: ACCAGCCTTTCGACAGCCTAC[502]      57.1   62.9
Reverse: CCGCGAATGGTCAAGCTACCG[508]      61.9   63.9

Indices for Primer Pair Design Set 01
TCAGTA[509], TACTGT[510], AAGGAT[511],
GATAGT[512], CCAGTC[513], TAAGCC[514],
AGACCG[515], CTAGAC[516], TGGACT[517],
GTCGAT[518], TAACAG[519], AGTCAG[520],
CTATGG[521], AAGCGG[522], AAACGA[523],
CTGAGA[524], CCTGTG[525], GCGATC[526],
GGCTGA[527], CGTTTC[528], GGAAGA[529],
TACGTA[530], TGCCTC[531], TTGCAG[532],
TCTAGC[533], ATCCGC[534], CGCTAC[535],
CCACAG[536], GTAACT[537], CCAAGA[538],
GGTTCT[539], CCGACA[540], GCCGAA[541],
CCACCT[542], ACCTGG[543], GCTATG[544],
TCGTCA[545], CGAATT[546], CGTCCT[547],
GATGTA[548]

Indices for Primer Pair Design Set 01
TGTCTGAG[549], GCTATGGA[550], GATAGCGA[551],
TTCGGCGA[552], CGTAATTG[553], AGTTCAGG[554],
TGGAGTGT[555], GTTCTCGT[556], CTCGGAAC[557],
TTGCTTAG[558], CCAAGTGC[559], TCTCGTTA[560],
GTATCGAG[561], TGAATAGG[562], ATCCTTCT[563],
TAGTCGGA[564], GAGCCTCT[565], TAGTATGC[566],
CTCGATTT[567], TCAACGTG[568], CCTCCAAA[569],
CCTGGTCT[570], TTGCGCCA[571], GTGGAATA[572]
```

Primer Pair Set 03 (SEQ ID NOs Appear in Square Brackets Following Each Sequence)

```
Well Construct
CGGCCGCACGATTCATGTGCAG[573]<Payload>
GTCTGACGCGTAGTCACGAGCA[574]

Plate Construct
TCTCGCACTGTACATCGCACTCC[575]<WellIndex5>
<WellConstruct><WellIndex3>
CGGTATGCTCGAGCTAGTATGCT[576]

Document 1 Construct
GAAACTCCGGTGTCTATGGCCAAG[577]<DocPlateIndex5>
<PlateConstruct><DocPlateIndex3>
CTGTGATGCGGTGATGGAAGGTTC[578]

Document 2 Construct
GGATCCAACCTGTGACACCTTGC[579]<DocPlateIndex5>
<PlateConstruct><DocPlateIndex3>
CTCACAACGTTAGGAGCTTTGGA[580]

Document 3 Construct
GCGTTCACCTGCCACGTTCACTC[581]<DocPlateIndex5>
<PlateConstruct><DocPlateIndex3>
GTGACCGTGATTGTGCGCAGTTT[582]

Well Primer Pair (Length: 22)              %GC    Tm
Forward: CGGCCGCACGATTCATGTGCAG[573]      63.6   66.8
Reverse: TGCTCGTGACTACGCGTCAGAC[583]      59.1   64.6
Plate Primer Pair (Length: 23)
Forward: TCTCGCACTGTACATCGCACTCC[575]     56.5   64.7
Reverse: AGCATACTAGCTCGAGCATACCG[584]     52.2   62.3
Document 1 Primer Pair (Length: 24)
Forward: GAAACTCCGGTGTCTATGGCCAAG[577]    54.2   63.7
Reverse: GAACCTTCCATCACCGCATCACAG[585]    54.2   64.1
Document 2 Primer Pair (Length: 23)
Forward: GGATCCAACCTGTGACACCTTGC[579]     56.5   64.1
Reverse: TCCAAAGCTCCTAACGTTGTGAG[586]     47.8   61.4
Document 3 Primer Pair (Length: 23)
Forward: GCGTTCACCTGCCACGTTCACTC[581]     60.9   66.2
Reverse: AAACTGCGCACAATCACGGTCAC[587]     52.2   64.8

Indices for Primer Pair Design Set 03
GCAGAC[588], TCGCAA[589], TGAGGC[590],
CTCGGA[591], GTCGTG[592], AAACTG[593],
GCACCT[594], ACTGAG[595], AACGTC[596],
ACCGGT[597], GTTCCT[598], CTAGGC[599],
CGCCAA[600], TGGATG[601], TCCGAA[602],
CCTTTA[603], GACCGA[604], ACAGCA[605],
ACGTAG[606], GCGATT[607], TGTCAC[608],
AACAAC[609], GACGTA[610], GCGGAA[611],
TCGGAG[612], CGCGTT[613], TCTTGC[614],
GCATTT[615], AAAGCG[616], AGCATG[617],
CTGTGA[618], AGGAGG[619], TGAGAT[620],
CTACTG[621], ATCGAT[622], AACACT[623],
CATAGT[624], GCCTAG[625], AGAAGA[626],
TCAGTT[627]

Indices for Primer Pair Design Set 03
TACCTAAC[628], CTTCTATG[629], CGATACCG[630],
CATCAGCT[631], GTCAAACG[632], GTCTACGG[633],
GTTTAGCT[634], TTCCAGCA[635], AGCTAAAC[636],
ATCTAGGT[637], CACCATGT[638], TGCTGATA[639],
TGGTGCGT[640], ACTACAAG[641], ATCAGCAG[642],
ATCCGTAA[643], AAGAGTAG[644], TTATCTGC[645],
ATCGGAGC[646], GGTGGATC[647], ATACCGCT[648],
ACCACGGA[649], ACACGCTC[650], CAATTCGC[651]
```

Primer Pair Set 04 (SEQ ID NOs Appear in Square Brackets Following Each Sequence)

```
Well Construct
GCACCGTTCCACTCTACCGGTTC[652]<Payload>
CTAAGCTCGCCTAGGTCGCTTAC[653]

Plate Construct
AATCGACAACCGCGTTACCTTGC[654]<WellIndex5>
<WellConstruct><WellIndex3>
GAGGATCCAAGATCGGCGTGCTT[655]
```

Document 1 Construct
GCACGCACTGTATTTGCGCACTC[656]<DocPlateIndex5>
<PlateConstruct><DocPlateIndex3>G
TCTGATCAGGCGGAACGAATGT[657]

Document 2 Construct
CGGATCCAGCTTGAGCTTTGCATC[658]<DocPlateIndex5>
<PlateConstruct><DocPlateIndex3>
CAGTAATCTACACGCAGCGCTCAT[659]

Document 3 Construct
CACCTGTATGAGGTACCGACCAG[660]<DocPlateIndex5>
<PlateConstruct><DocPlateIndex3>
GCAAGAGTCTATGTTCGGCGTGT[661]

|  | %GC | Tm |
| --- | --- | --- |
| Well Primer Pair (Length: 23) | | |
| Forward: GCACCGTTCCACTCTACCGGTTC[652] | 60.9 | 65.3 |
| Reverse: GTAAGCGACCTAGGCGAGCTTAG[662] | 56.5 | 62.8 |
| Plate Primer Pair (Length: 23) | | |
| Forward: AATCGACAACCGCGTTACCTTGC[654] | 52.2 | 64.4 |
| Reverse: AAGCACGCCGATCTTGGATCCTC[663] | 56.5 | 65.2 |
| Document 1 Primer Pair (Length: 23) | | |
| Forward: GCACGCACTGTATTTGCGCACTC[656] | 56.5 | 65.3 |
| Reverse: ACATTCGTTCCGCCTGATCAGAC[664] | 52.2 | 63.4 |
| Document 2 Primer Pair (Length: 24) | | |
| Forward: CGGATCCAGCTTGAGCTTTGCATC[658] | 54.2 | 64.6 |
| Reverse: ATGAGCGCTGCGTGTAGATTACTG[665] | 50.0 | 63.5 |
| Document 3 Primer Pair (Length: 23) | | |
| Forward: CACCTGTATGAGGTACCGACCAG[660] | 56.5 | 62.4 |
| Reverse: ACACGCCGAACATAGACTCTTGC[666] | 52.2 | 63.5 |

Indices for Primer Pair Design Set 04
TCAGCG[667], TGTTCA[668], TAATCC[669],
TTAGGC[670], CAAGGC[671], CAATAC[672],
GGCATC[673], ACCGGT[674], TTGAGC[675],
TCATAC[676], ACTGTT[677], TGCCAA[678],
GGACAA[679], GAGATA[680], CAATCA[681],
ACATCA[682], TTTCAG[683], CGATGA[684],
TGTCCT[685], TAGACT[686], CATTTC[687],
GACCTG[688], AGCGGA[689], GTTCTG[690],
CTCTGT[691], CCTAAA[692], CGAAGT[693],
TTCGAT[694], CTAGTG[695], GGAGGA[696],
TCGGTA[697], CCAGGT[698], TATCTG[699],
CGTTAC[700], CCTTTA[701], AGGATG[702],
GTCATA[703], ATAGAG[704], GCTGTG[705],
GAAGAG[706]

Indices for Primer Pair Design Set 04
CCACTATC[707], CCTTGGTG[708], ACTACCGC[709],
CTTTAACC[710], ACTAAGTG[711], GCGTGTCA[712],
ACATGTCG[713], TCGTATTC[714], GCTGCTGA[715],
ATTCTTCC[716], GGCTAGTA[717], ACTAGACT[718],
AAGGTCGT[719], TTAAGTGG[720], CCGTTACC[721],
CTATCTCG[722], AGTAGCT[723], CATATCGT[724],
TTGACAGA[725], GAGATCTG[726], GCCAGTGA[727],
GTGACCAA[728], GTCTCCTG[729], GATCGGAT[730]

Primer Pair Set 05 (SEQ ID NOs Appear in Square Brackets Following Each Sequence)

Well Construct
CCTCGGTTTCGAACCATCTGACG[731]<Payload>
GTGCATATGCTGACGAAGTAGCG[732]

Plate Construct
GTGCCACTCCATACGTGAGACG[733]<WellIndex5>
<WellConstruct><WellIndex3>
GATGCTATGAAGACTGCCGCGG[734]

Document 1 Construct
CATGTACACTCCGCTTTCTGGCTA[735]<DocPlateIndex5>
<PlateConstruct><DocPlateIndex3>
GGAAAGGAGCTGCGTATGAGCTGC[736]

Document 2 Construct
CAGCTGGCTTTCACCAATGCC[737]<DocPlateIndex5>
<PlateConstruct><DocPlateIndex3>
CGACACGACTTTGCCAAGAGC[738]

Document 3 Construct
TGTGCGCTACTGGACCTCGAT[739]<DocPlateIndex5>
<PlateConstruct><DocPlateIndex3>
CTGGAGGCGGTGGCGTCTAGA[740]

|  | %GC | Tm |
| --- | --- | --- |
| Well Primer Pair (Length: 23) | | |
| Forward: CCTCGGTTTCGAACCATCTGACG[731] | 56.5 | 63.6 |
| Reverse: CGCTACTTCGTCAGCATATGCAC[741] | 52.2 | 62.2 |
| Plate Primer Pair (Length: 22) | | |
| Forward: GTGCCACTCCATACGTGAGACG[733] | 59.1 | 63.2 |
| Reverse: CCGCGGCAGTCTTCATAGCATC[742] | 59.1 | 63.9 |
| Document 1 Primer Pair (Length: 24) | | |
| Forward: CATGTACACTCCGCTTTCTGGCTA[735] | 50.0 | 63.2 |
| Reverse: GCAGCTCATACGCAGCTCCTTTCC[743] | 58.3 | 65.9 |
| Document 2 Primer Pair (Length: 21) | | |
| Forward: CAGCTGGCTTTCACCAATGCC[737] | 57.1 | 63.1 |
| Reverse: GCTCTTGGCAAAGTCGTGTCG[744] | 57.1 | 62.4 |
| Document 3 Primer Pair (Length: 21) | | |
| Forward: TGTGCGCTACTGGACCTCGAT[739] | 57.1 | 64.1 |
| Reverse: TCTAGACGCCACCGCCTCCAG[745] | 66.7 | 66.2 |

Indices for Primer Pair Design Set 05
GAGCCT[746], CCGACT[747], ACGGAA[748],
TTTCAG[749], AAGCTT[750], CCGTAC[751],
TATCTG[752], CTATTG[753], GGAGAA[754],
ACCTAC[755], GTACAC[756], GTTATG[757],
TGGACA[758], CGTCAT[759], ACGATT[760],
GTAAAG[761], ACAGTC[762], CGAGTT[763],
ATGTAC[764], TAAAGC[765], ACATAG[766],
GGTTGT[767], CAAACA[768], CGTAAA[769],
ACACCG[770], CATTAG[771], AGCTTG[772],
TCGCGT[773], CAGCAT[774], TAGGCG[775],
CGAGGA[776], CGTTTC[777], AAGCGC[778],
AAACGG[779], TGCTTC[780], TAGAGT[781],
TGTCCT[782], CTGCGA[783], AGACTG[784],
GCGTGA[785]

Indices for Primer Pair Design Set 05
CATGAAGA[786], CATAACAG[787], GGTTGGAC[788],
CCTCCAAG[789], TATCATCC[790], TGCGCTAA[791],
TATTGTCG[792], GAATGGCA[793], TCGTGCTA[794],
TCGCTTCC[795], TCAAAGGC[796], AATTCGAG[797],
CTACCGTT[798], CCGGTATG[799], TCAGGTCT[800],
AAGCAATC[801], CCTTAATG[802], GGCACGTT[803],
GTTGTGCA[804], CGTTGACG[805], CGCTTTCA[806],
ACAGTCGA[807], TTCAGCGT[808], ACCGCTGA[809]

Example 3: Document Encoding

After completing the design of the 384 bit-oligos [SEQ ID NO. 1-384], Well, Plate, and Document primer binding domains, 40 Well Indices (16 left, 24 right) and multiple Plate and Document Indices, the next phase in the POC was to encode data into 1s and 0s, and then translate this information into which bit-oligos must be present (signifying a 1) or absent (signifying a 0) in the wells to encode the defined data.

Two documents were encoded for this POC, 1) a 2011 RNase H-dependent PCR (rhPCR) publication and 2) an IDT logo. The article is 58,088 bytes in size, just over 3 plates worth of information. Additional Plate level indices were designed in order to eventually encode the full publication into a single Document versus just the Abstract, Background, and Method sections. However, for the initial POC experiment, only the abstract, background, and methods were included to fit within the 18.4 kb size specification. Also encoded was a version of the Integrated DNA Technologies, Inc. logo (14,571 bytes in size, ~80% of a plate) which was encoded as a second Document.

Sequences Use in POC (SEQ ID NOs Appear in Square Brackets Following Each Sequence)

```
Plate Level Design Construct 02
Well Construct
CTGCGACTGAGCTCCTGATTGG[810]<Payload>
CGTAGGTGTTCGAATTGCGCCT[811]

Plate Construct
ATTACGCCTAGACAGTGCACGTC[812]<WellIndex5>
<WellConstruct><WellIndex3>GACCATTGTGCACATAC
GCGACC[813]

Document 1 Construct
TCCGCCACCGCAAACTAGTGC[814]<DocPlateIndex5>
<PlateConstruct><DocPlateIndex3>GCCAAGCTTC
CTGAACGGAGC[815]

Document 2 Construct
AGGTGATCAACTCCGGCAGAGTC[816]<DocPlateIndex5>
<PlateConstruct><DocPlateIndex3>GTCTGACT
AGCATGCAAGGCACG[817]

Document 3 Construct
GCTACGTAGTCACCGGAACTAGCC[818]<DocPlateIndex5>
<PlateConstruct><DocPlateIndex3>CAATGAT
TAGGAGCGGTCGACGCT[819]
```

|  | %GC | Tm |
|---|---|---|
| Well Primer Pair (Length: 22) | | |
| Forward: CTGCGACTGAGCTCCTGATTGG[810] | 59.1 | 63.4 |
| Reverse: AGGCGCAATTCGAACACCTACG[820] | 54.5 | 63.9 |
| Plate Primer Pair (Length: 23) | | |
| Forward: ATTACGCCTAGACAGTGCACGTC[812] | 52.2 | 63.1 |
| Reverse: GGTCGCGTATGTGCACAATGGTC[821] | 56.5 | 64.5 |
| Document 1 Primer Pair (Length: 21) | | |
| Forward: TCCGCCACCGCAAACTAGTGC[814] | 61.9 | 65.9 |
| Reverse: GCTCCGTTCAGGAAGCTTGGC[822] | 61.9 | 64.3 |
| Document 2 Primer Pair (Length: 23) | | |
| Forward: AGGTGATCAACTCCGGCAGAGTC[816] | 56.5 | 64.5 |
| Reverse: CGTGCCTTGCATGCTAGTCAGAC[823] | 56.5 | 64.1 |
| Document 3 Primer Pair (Length: 24) | | |
| Forward: GCTACGTAGTCACCGGAACTAGCC[818] | 58.3 | 64.5 |
| Reverse: AGCGTCGACCGCTCCTAATCATTG[824] | 54.2 | 65.1 |

Text encoding was managed by directly encoding to the extended ASCII format. Since the work was performed using C#.Net the original ASCII format is in 7 bit (0-127), but 8 bit was needed, especially since some special characters/symbols (®,™, °, ±, µ) were present in the portion of the publication to be encoded and are included only in the extended ASCII format. To accommodate this, the Windows-1252 format was specified defining the full 8-bit encoding to generate the byte array. Image file encoding was managed by reading the file into a byte array using C#.Net's File.ReadAllBytes function. Each respective byte array was then converted into their bit array, and the bit array form of "<eof>" was appended as a tag to denote when the end of the data stream had been reached. Inclusion of the end tag was needed, as it is highly unlikely that a document would be divisible by the number of wells in a plate and then divisible by the number of bits maximally stored in a well. In some embodiments, the document could be initiated with a 'bof' or with a header containing information about the document or file. Although this strategy was not employed in this initial POC system, it could be beneficial for use in other systems.

Once the bit array was generated, it was divided into smaller bit arrays with a size of 384. The publication text with the end tag fully completed a 384 well plate with 384 bits per well. For the image file, only 304 wells were defined with only 256 bits in the last well. Given the storage strategy employed for this POC experiment, the bit-oligos associated with the 1-valued bits were deposited into the well, whereas bit-oligos associated with 0-valued bits were excluded from the well.

Figure 3:
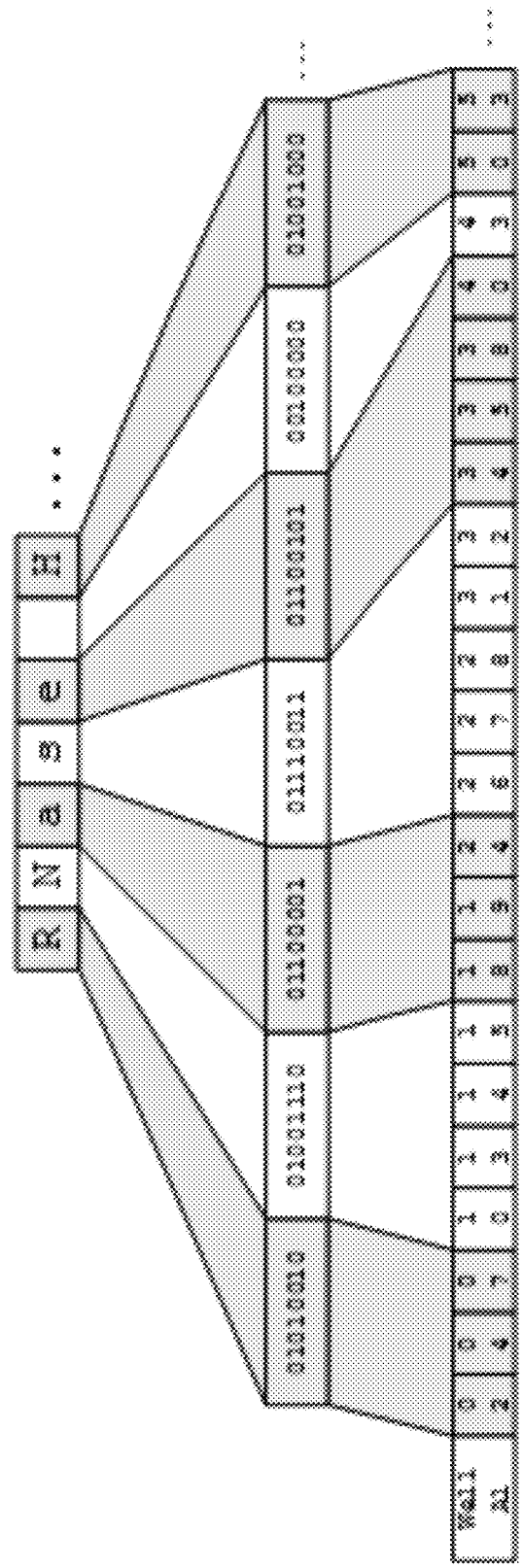
FIG. 3 depicts encoding of the term "RNase H" according to methods of the disclosure. The term was first converted into bits (0 or 1) where each letter (and space) corresponds to a byte (8 bits). Then each bit was converted to bit-oligos where the presence or absence of the corresponding bit-oligo represents a 1 or 0, respectively.

In the "RNase H" text example shown in FIG. 3, each character is translated into its bit array. Then, bits 1-384 (SEQ ID NOs: 1-384) are sequentially ordered, where bits 1-8 (SEQ ID NOs: 1-8) define the first byte, bits 9-16 (SEQ ID NOs: 9-16) define the second byte, continuing to bits 377-384 (SEQ ID NOs: 377-384), which define the 48th byte. For the encoding method employed in the POC experiment, and as shown in FIG. 3, only the bit-oligos representing the "1" values were deposited into a well; bit-oligos 2, 4, and 7 for the $1^{st}$ byte representing 'R,' to bit-oligos 50 and 53 for the $7^{th}$ byte representing 'H'.

Hence the encoded data is a series of bit-oligo designations for every well containing bit data, which is used to program the liquid transfer handler into moving the necessary bit-oligos from their Master Plate locations to the Receiving Plate destination. Another map may be generated which correlates which wells each bit-oligo is to be deposited into; this too may be useful to a liquid handling system if it is able to multi-dispense several wells worth of the same bit-oligo into different destination wells. Finally, the raw bit array is reported for each well for troubleshooting needs.

For the "RNase H" example in FIG. 3, the presence of the sequences of bit-oligos 2, 4, 7, 10 and the absence of bit-oligos 1, 3, 5, 6 will later be detected via the NGS run. For the word "RNase H", all the bit-oligos are from the same well (A1) of the receiving plate and have the same well index (the combination of the well indices from the 5' and 3' 1° primers). This goes up to bit-oligo 384 since, in this particular embodiment, 384 bit-oligos were used from a 384 well master plate and a combination of these 384 bit-oligos, where some are absent and some are present, are transferred to each of the 384 wells of the receiving plate. Bit-oligo 385 would have the same central bit-oligo sequence as bit-oligo 1 since they are derived from the same well of the master plate, yet it would have a different well index from oligos 1-384 that were derived from well A1. Bits 385-768 are derived from well A2, which is indicated by their associated well index, which is sequenced during the NGS run. With this strategy, 147,456 bits could be derived from one receiving plate. These 147,456 bits derived from the same receiving plate will have the same plate index (P) which is added via PCR with the 2° primers.

In a case using more than one plate, bit 147,457 would be derived from the first well of a second receiving plate. It would have the same well index as bits 1-384, but would have a different, plate-specific index that indicates that it is from the second plate that would be read by NGS and would designate that bit-oligo as bit 147,457 and not bit 1. This method is not limited to 384-well master and receiving plates. Plates with a higher number of wells could be used as well (1536-well plates, for example).

Once the bit-oligos are pooled and tagged, they are read by NGS and the output data recorded in fastq files. For this POC experiment, this process was carried out in silico and used to generated mock fastq files. These mock fastq files were then placed in order using the well and plate indices and converted to a binary string using the methodology described below.

Example 4: NGS Analysis and Document Decoding

An NGS analysis pipeline was developed and tailored specifically for decoding fastq files generated after NGS sequencing of the pooled bit-oligos, which identifies the bit-oligos and outputs the resultant bit stream.

Using this method, the mock fastq files from Example 3 were processed into arrays of bits, which were then translated back into either the text file representing the portion of the encoded scientific article or the JPEG logo file.

BLAST was used to identify the various components within the encoded bit-oligos. A BitLibrary.fasta file was used as the BLAST library to compare against the traces within the fastq files. The library contained all of the designed elements used in encoding the two documents—all Document/Plate/Well level primer and index sequences as well as the bit-oligo segments. In the BLAST command below, the culling limit was used to prevent BLAST from generating very large result files by restricting the results to return only the best hit for a given region. Without the culling limit, for each trace, every single element in the BitLibrary file would be similar enough to pass the eValue threshold.

Blast Command:
blastn.exe -task blastn -word_size 11 -evalue 0.1 -dust no -culling_limit 1 -outfmt 5 -db {1}-query {0}.fasta -out {0}.xml -num_threads 3

Upon identifying the elements present within the traces for a given cluster a consensus was made of which elements were present for each cluster. The names of the elements defined row and column coordinate information for the Well level index elements, and with the bit-oligo iterator, the ordering of bits was determined.

For this proof of concept experiment, the size of the bit stream to be decoded was known and fixed (384*384) and thus was initialized as 147,456 "0"s. Due to the encoding strategy only the bits with a value of 1 were present as oligos in the fastq file. Thus, based on the coordinate information provided by the Well level indices and bit-oligos, the resultant positional indices in the bit stream were changed to 1. Finally, since both documents (scientific article and JPEG file) were terminated with an encoded "<eof>" tag, the last bit stream matching "001111000110010101101111011001100011110" was assumed to be the end of each data stream, such that all remaining "0"s were trimmed off to generate the final bit stream product, which was used to generate a report.

In the report, a summary was provided for which Document/Plate- and Well-level indices, and bit-oligos were identified and their counts. This was then followed by the actual bit stream as determined by the above analysis, and finally the observed bits present and their respective counts. For the mock fastq files generated for each document, the distribution of bit-oligos as determined by the mock fastq files and NGS analysis was within 0.01% of expected. The mock fastq files were generated to produce on average a depth of coverage of 45 (range of 18-76) for each document.

From the reports, the bit streams were then extracted, decoded into bytes and then either written into a file in the case of the logo or converted into characters to generate the text and saved to a text file. The image file was compared to the original using the Beyond Compare 4 program and was identified as being equal. When the same was done for the text a single character difference was identified. Near the end of the text was the word "ΔCq" and it turns out "Δ" is not part of the extended ASCII table. All other symbols present in the text; μ. (181), ° (176),™ (153), and ® (174) were covered and were previously identified, but not Δ. Accordingly, the text was modified to "dCq" and re-encoded in preparation for the actual oligo mixing and PCR amplification steps.

Example 5: NGS Mock Analysis with Mutated Traces

The next fastq file mockings to be analyzed introduced sequencing errors at a few different rates to ensure the analysis pipeline can overcome these scenarios. The initial mock fastq files and analysis related to perfect traces representing the different bits present. This was to establish that the mapping files generated to direct which bit-oligos were to be deposited into which wells were correct. The analysis pipeline used in Example 4 thus assumed a perfect present/absence of bit-oligos and thus no accidental contamination of other bit-oligos not meant to be present was accounted for and ignored. However, real encoded bit-oligos (including primer domains and indices) are likely to incorporate deletions and substitutions. Deletions will primarily originate from the oligos themselves and then substitutions will come about from the rounds of PCR needed for the encoding process.

BLAST is quite robust in dealing with near perfect matches and with how the primer domains, indices, and bit-oligos were designed between the two the probability of miss-identifying an encoded bit should be at a minimum. The other error to contend with is accidental contamination of other bit-oligos into wells that should be devoid of them. For this a bit mechanism to ignore or include needs to be incorporated to identify the difference between intentional and unintentional bit information.

Working with the original clean fastq files for both documents, a script was developed to purposely introduce deletions and substitutions and then save them out to different files. Using a random number generator choosing between 1 and 10,000, if the value was greater or equal to 20 for deletion, then a deletion would be inserted somewhere randomly within the trace. A new random number between 1 and 10,000 was chosen and if greater or equal to 10 for substitutions, then a substitution was introduced. Any time a trace was selected to be mutated, either by deletion or substitution, it was then eligible to be mutated further allowing for some more severe mutations to occur.

From this work and analysis, several bits of information were then accidentally converted to other encoded bits.

While many were converted to the intended bits, a few were converted to encoded bits that were meant to be present at a count of 1. Thus, the general depth of coverage for all the encoded bits was important towards determining which were true bits versus false bits. The strategy developed was to identify the average depth across all the bits present then, with the use of the Poisson distribution equation, create a depth cutoff where the distribution probability was less than $1E^{-8}$. However, in some cases a normal/Poisson distribution may not accurately reflect how well the bits were equally deposited, mixed, then PCR'd during the encoding process. The probability function may thus need to be adjusted, possibly by the incorporation of a skewness coefficient, to fit the data.

Example 6: NGS Analysis with Encoded, Synthesized Oligonucleotides

Following the mock fastq investigations of Examples 4 and 5, actual bit-oligos were synthesized and pooled as in Example 3 to encode the above-described scientific article and image files.

To read the encoded documents, the extraction primers used were in the 90-100 nt range and each primer was replicated 10 times with the difference being a spread of 1-10 Ns to help in phasing on the MiSeq NGS sequencing instrument. Each set of 10 extraction primers were pooled in equal amounts and then added to the respective PCR reaction. These primers made the resulting amplicons compatible with the Nextera kit, as well as distinctly indexed. The amount of phiX was increased from the normal 1.5% to about 10% and the primers used to extract the sample were designed to phase shift the sample, all of which helped minimize phasing issues on the instrument.

A template titration for the extraction PCR was performed since it was not known how much template would be needed or which amount would generate enough material. Samples were run on a fragment analyzer to gauge how much material was present and overall quality.

The documents were amplified with the corresponding primers which were tailed with P5 and P7 adaptors so as to be read on the MiSeq. Prior to reading, AMPure bead clean-up was performed as well as KAPA quantitation for normalizing the sample.

A bit by bit comparison was done between a control bit stream, generated by simulation, and the bit stream generated from the actual NGS data. Since the last 4 rows of data were missing due to problems with the transfer, only 12 rows worth of data were assessed-110,592 of the 147,456 bits describing the text document. With this first attempt of encoding the document, 3,142 bits (2.84%) differed from the control, 1.56% were 0-to-1 transitions and 1.29% were 1-to-0 transitions. This in turn resulted in 2,706 bytes/characters to be different out of the first 13,824 bytes/characters (19.6%). With the number of bits differing from the control, the range of affected bytes is 2.8% (all bits clustered into 393 bytes) to 22.7% (all bits scattered).

Shown below is an example of text (title and authors) showing some output from the NGS-deciphered data. The encoded text includes returns and new lines, which causes text to drop to a new line, and which is encoded by 2 bytes. If either or both of these bits are mis-read, a new line is not created. The characters 'Mj' between the word "primers" and "Joseph Dobosy" in the below NGS text is where the new line should have been. Also, because the manner in which lower case and upper case characters are laid out in the ASCII code, the third bit in a byte is the difference between upper (0) and lower (1) for a letter and is why most of the names were read to be lower case.

Figure 4:
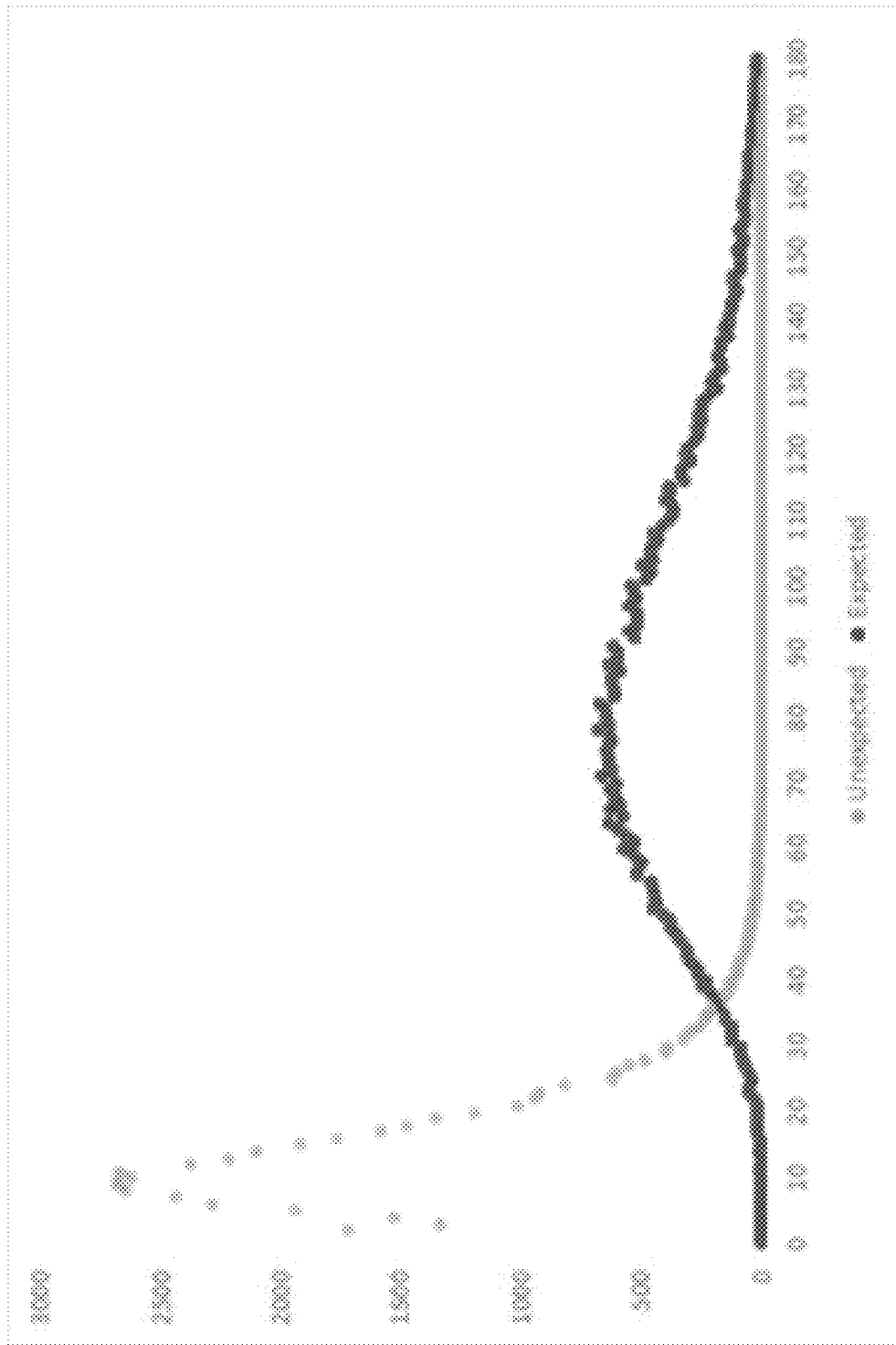
FIG. 4 depicts a graph showing the distribution of depth counts of the expected (dark gray) and unexpected (light gray) bits in Example 6. The initial strategy for deciding an appropriate depth count cutoff was based on the mean depth. This required assuming a single distribution population and was grossly skewed low. The cutoff was manually set to 35, the approximate intersect of the expected and unexpected plots. The light gray dots represent all of the unexpected bits identified, whereas the dark gray dots highlight the depth distribution for only the bits expected for encoding the document. The last 4 rows (96 wells) were omitted from this graph as they were largely absent from the NGS run.

Control Text (2 Lines):

RNase H-dependent PCR (rhPCR) improved specificity and single nucleotide polymorphism detection using blocked cleavable primers Joseph R Dobosy, Scott D Rose, Kristin R Beltz, Susan M Rupp, Kristy M Powers, Mark A Behlke and Joseph A Walder NGS Deciphered (1 Line):

sncseblmdepundent'per hrhper):'improved specificity'and'siogleanecleotide'pol}morphism deteatimf'using'blocked cleavable primersMjjosep' R dobmsy,'scott'd'rose, kristin r Beltz,'susan M bupp, Kristy m Powers, m'rk a Behlke ald joseph a walder The distribution depth counts of the expected (dark gray) and unexpected (light gray) bits is shown in FIG. 4. The initial strategy for deciding an appropriate depth count cutoff was based on the mean depth. This required assuming a single distribution population and was grossly skewed low. The cutoff was manually set to 35, the approximate intersect of the expected and unexpected plots. The light gray dots represent all of the unexpected bits identified, whereas the dark gray dots highlight the depth distribution for only the bits expected for encoding the document. The last 4 rows (96 wells) were omitted from this graph as they were largely absent from the NGS run.

Example 7: Mini Text Encoding Experiments

Additional experiments were designed and conducted to address sample contamination. Minimizing transfer contamination and evolving the design strategy to tolerate contamination were the focal points of these investigations. Starting with fresh stock of primers and bit-oligos, two control experiments and six mini text encoding iterations were designed and 8 new primer pairs were synthesized to tag each of the experiments to be pooled for the upcoming NGS run.

One area of potential contamination is in the transfer of the well index primers into the pooled bit-oligos. Forward primers were common within each row and reverse primers were common within each column in the original design layout (Primer Pair Matrix). However, it appears that the liquid transfer handler creates splash-back of the contents in a given destination well back into source wells and ultimately caused every reverse primer to be present in every forward primer and vice versa. While the previous experiments reused the source plates used in the original encoding attempt, for this experiment fresh primer stocks were used. This acted as a control where a discrete bit was transferred into each well. 16 wells were encoded and thus 16 bits and 4 forwards and 4 reverses were used.

For the second control experiment the same 16 bits were discretely transferred but then distinct forwards and reverses were used for each well (Discrete Primer Pairs), as shown in Table 2. Hence 16 forward primers and 16 reverse primers created the 16 primer pairs where no primer was used more than once. This simplified transferring and pooling of the primers and kept working primers pairs clean of transfer contamination.

TABLE 2

Pair matrix vs. Discrete format for 1° primers

| Primer Pair Matrix | | | Discrete Primer Pairs | | |
|---|---|---|---|---|---|
| Forward | Reverse | Bit | Forward | Reverse | Bit |
| 1 | 1 | 1 | 1 | 1 | 1 |
| 1 | 2 | 2 | 2 | 2 | 2 |
| 1 | 3 | 3 | 3 | 3 | 3 |
| 1 | 4 | 4 | 4 | 4 | 4 |
| 2 | 1 | 5 | 5 | 5 | 5 |
| 2 | 2 | 6 | 6 | 6 | 6 |
| 2 | 3 | 7 | 7 | 7 | 7 |
| 2 | 4 | 8 | 8 | 8 | 8 |
| 3 | 1 | 9 | 9 | 9 | 9 |
| 3 | 2 | 10 | 10 | 10 | 10 |
| 3 | 3 | 11 | 11 | 11 | 11 |
| 3 | 4 | 12 | 12 | 12 | 12 |
| 4 | 1 | 13 | 13 | 13 | 13 |
| 4 | 2 | 14 | 14 | 14 | 14 |
| 4 | 3 | 15 | 15 | 15 | 15 |
| 4 | 4 | 16 | 16 | 16 | 16 |

The second half of the experiment was to encode a smaller text utilizing the above primer pair strategies. The Primer Pair Matrix was performed twice: (1) following the original order, transferring forward primers, reverse primers, then bits; and (2) changing the order, transferring bits, then forward primers, and finally reverse primers. In addition to these two iterations a third encoding experiment was performed using the Discrete Primer Pair strategy. These iterations examined the contamination being introduced by the primer transfers.

Another set of the three primer pair strategies was included but where the 0 bits were represented by a bit-oligo.

The original encoding strategy had only the 1 bits represented by a bit-oligo and thus any 0 bits were represented by the absence of the bit-oligo at a given bit position. However, due to contamination levels and the fact that the absence of oligos was meaningful information the encoding may be more tolerant to contamination where the 0 bit is specifically represented by a bit-oligo. Upon making this change, the dynamics for decoding change from a presence level threshold to a competition between two possible bit-oligos for each bit position. Thus, bit-oligos 1-192 serve as the "1" bit representative and bit-oligos 193-384 serve as the "0" bit representative resulting in a bit depth of 192 bits per well. With only 16 wells, 3,072 bits (384 bytes/characters) is all that can be encoded.

The following text 383 characters in length was encoded as a single line. The 384$^{th}$ byte is a null character (all zeros) which served as an internal control as did the first bit in each of the bytes encoded. All characters in this text resided within the first 128 characters of the ASCII table, meaning that the first 1 bit was not present. In other words, every 8$^{th}$ bit position was a 0 starting with bit position 1 (1, 9, 17, 25 . . . , 177) and bit positions 185-192 were also 0's.

RNase H-dependent PCR (rhPCR): improved specificity and single nucleotide polymorphism detection using blocked cleavable primers; Joseph R Dobosy, Scott D Rose, Kristin R Beltz, Susan M Rupp, Kristy M Powers, Mark A Behlke and Joseph A Walder; rhPCR eliminates the formation of primer dimers and markedly improves the specificity of PCR with respect to off-target amplification.

In all, 8 separate experiments were set up for encoding, 8 new primer pairs were designed and synthesized, representing plates 2-9 for document 1. Using the plate index to isolate the experiments allowed for all experiments to be pooled together and extracted together with a single document primer pair tagged with a single index pair for the next NGS run. The downstream analysis decoded the bits as normal then segregated by plate index prior to decoding each respective plate index's worth of constructs.

Example 8: Comparison of Shared Primer and Discrete Primer Strategies

Control experiments were performed using 16 bit indices and either Shared primers or Discrete primers. Shared primers is where 4 forward primers and 4 reverse primers were used to generate the 16 pairwise index pairs and each primer was used in 4 reactions. Discrete primers is where 16 forward primers and 16 reverse primers were used to generate the 16 pairwise index pairs but each primer was only used once. The advantage of using discrete primer pairs is with the ability to tolerate low levels of primer contamination. Any combination of index pairs not intended can simply be filtered out whereas when the primers are shared across multiple reactions all combinations are therefore valid index pairs and combinations due to contamination cannot be differentiated from the true index pairs.

Example 9: Comparison of the Presence/Absence Bit Encoding Strategy with the Zero/One Bit Encoding Strategy Experiments were conducted encoding a small text using different strategies.

The first three experiments utilized the Presence/Absence Bit Encoding strategy which was the original strategy attempted, in which a "1" is denoted by the presence of a bit-oligo at that position, and a "0" is denoted by the absence of a bit-oligo at that position. Within these three experiments, the first two used the Shared index pair strategy where the bits were dispensed first then the primers, versus a strategy where the primers were dispensed first then the bits. The third experiment used the Discrete index pair strategy described in Example 8.

Experiments 4-6 had the same arrangement of index pair strategies, but utilized the Zero/One Bit Encoding strategy where not only were the "1" bit values represented by bit constructs but also were the "0" bit values. This strategy relies on a presence competition between the "1" bit value and the "0" bit value at each bit position. Ideally, this equates to seeking out which construct representative is at a higher frequency over the other at a given bit position to distinguish between "0" and "1."

Figure 6A:
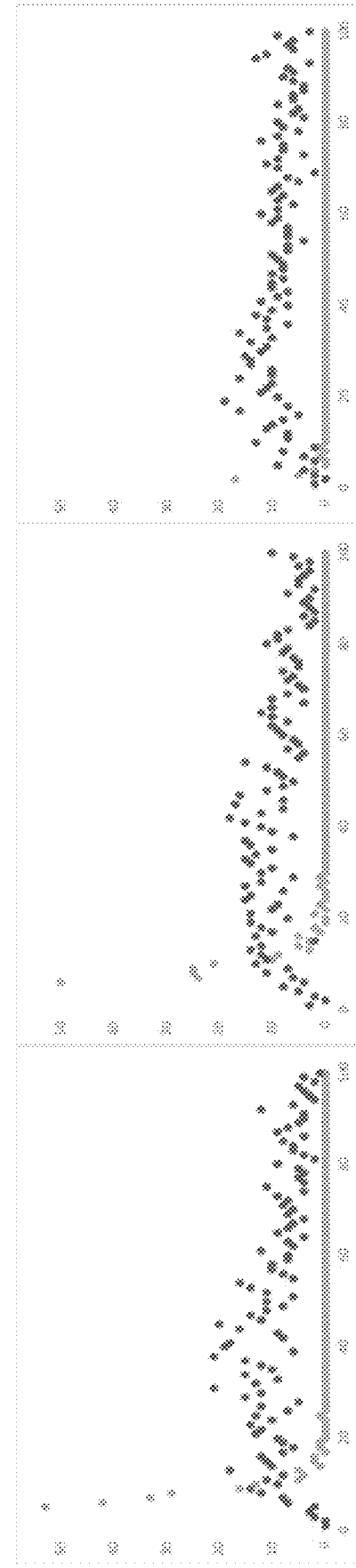
FIGS. 6A-6B shows the depth count distribution for desired (dark gray) and undesired (light gray) bits for the Presence/Absence Bit Encoding strategy (FIG. 6A) as compared to the Zero/One Bit Encoding strategy (FIG. 6B) as described in Example 9.
Figure 6B:
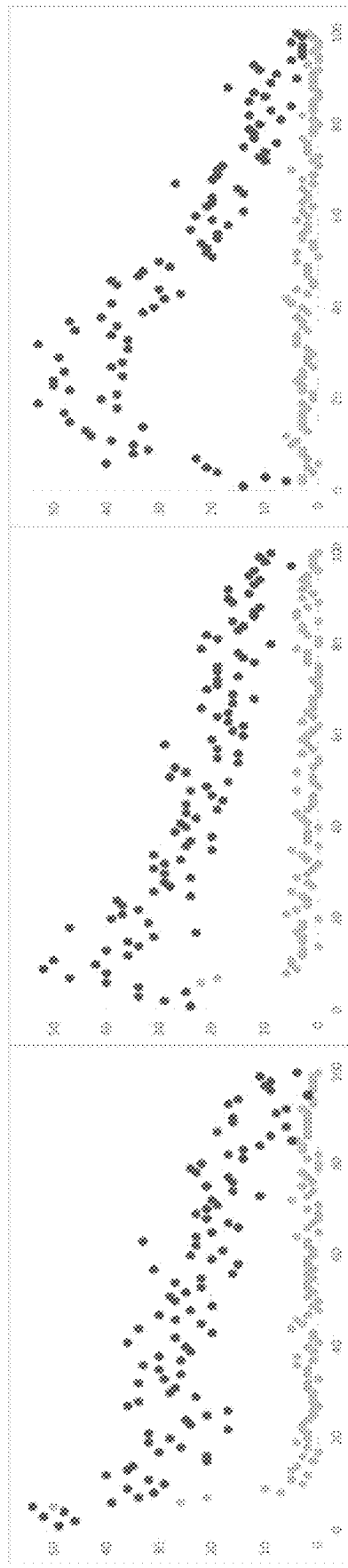

When examining Shared versus Discrete index pairs the first observation related to the low depth of coverage frequencies (FIGS. 6A-6B). For Shared index pairs, the contaminating signal showed a very high frequency of 1-10 depth where the low depth of coverage was 1400-1600 dropping into the few hundreds then few dozen before dropping below 5. This was present regardless of the bit encoding strategy. For Discrete index pairs, the ability to remove the vast majority of index pairs resulted in the contaminating signal being much lower. Independent of the bit encoding strategy, the single depth of coverage was in the 100-200 range but quickly dropping down to low counts. Neither strategy completely eliminated all undesired constructs because not only was there contamination across primers, but also across bit-oligos. Due to the Discrete index pair strategy the threshold used to distinguish and decode true versus false information was 3 versus 11 for the Shared index pair strategy.

When examining Presence/Absence versus Zero/One Bit Encoding, more bit constructs were used for the Zero/One and thus led to a stronger presence of desired bits versus the Presence/Absence encoding strategy. However, the number of undesired constructs was near zero after about a depth of 20 for the Presence/Absence strategy whereas a low level of constructs existed beyond depths of 100 and greater for the Zero/One strategy. Fortunately, Zero/One Bit Encoding does not rely on a low level threshold cutoff, but rather a simple competition which defines true and false information.

The final examination related to how the different strategies performed with the encoding/decoding of the test document. The test document with the end of file tag '<eof>' was 383 bytes (3064 bits) in size and fit within the encoding structure of 192 bits per well and 16 wells giving a total potential 3072 bits of data. The text chosen was the title, authors, and the conclusion within the abstract of a scientific article. All characters were in the original ASCII table (0 . . . 127) and needed only 7 bits leaving the first bit in each byte as a "0" value. In addition to those constant "0" positions the last byte following the end of file tag was all "0" values; therefore, any constructs present representing the "1" value within the last byte were erroneous and were used to gauge contamination levels.

Encoded Test Text

RNase H-dependent PCR (rhPCR): improved specificity and single nucleotide polymorphism detection using blocked cleavable primers; Joseph R Dobosy, Scott D Rose, Kristin R Beltz, Susan M Rupp, Kristy M Powers, Mark A Behlke and Joseph A Walder; rhPCR eliminates the formation of primer dimers and markedly improves the specificity of PCR with respect to off-target amplification.

The Presence/Absence Bit Encoding strategy, regardless of the Shared versus Discrete index pairs, had a bit-encoding correctness of ~97% ranging in a character encoding correctness of 82%-92% with the 92% coming from the Discrete index pair strategy. For the Zero/One Bit Encoding strategy, the encoding had some issues where the logic for the bit pooling appeared to be problematic. The first 24 bits in each well had the "1" bit representative present with an average depth of 56 versus the "0" bit representative present well below 1 for depth. Similarly, essentially no bit-oligos (other than contaminants) were dispensed for bits 49-71 in each well. This was most likely due to an error in the oligo transfer step. ~24% of the bits were affected by these two procedure issues. Upon ignoring these problematic bit positions and assessing the bit quality of the remaining bit positions, the Zero/One Bit Encoding strategy was found to result in 100% accuracy, regardless of the index pair strategy that was used.

Example 10: Multiple Plate Text Encoding Experiment

From the previous encoding experiments, a contamination-tolerant strategy was selected whereby discrete well-indexed primers were used, along with specifically encoding the zero bit value with its own bit-oligo. This strategy was used to encode an abbreviated text. The document was based on the same scientific article as above, using the title, authors, and the first two paragraphs of the Results section. The text size with returns was 2,297 characters/bytes, which, with the inclusion of the end of file tag, "<eof>", the total bit size was 18,416. Utilizing the additional plate indexed primers for document 1 the encoding was able to reuse the 16 well and 192 bit positions per well layout used in the previous mini encoding experiments. The encoding effort resulted in using six plate indexed primer pairs (indices 2-7), 16 discrete well indexed primers pairs, and 192 bit positions (6×16×192) generating a usable bit footprint of 18,432. The last 16 bits were not used. The experiment resulted in 99.25% bit accuracy and 96.9% character/byte accuracy.

The NGS run for this experiment resulted in 3.7 million identified constructs within the traces. 28% of the constructs had mixed plate indices and were removed. Another 2% went to plate index 1 which was not part of the experiment but thought to be contamination through the well-indexed primers as they were all made on the same plate. Plate indices 8 and 9 were seen but not part of full encoded constructs. Finally, 6% of the constructs were due to mixed well indexed primer pairs and/or inadvertent bit-oligos. Overall, 2.4 million constructs were associated with expected constructs. Representation across the 6 plate indices was a fairly uniform 15-18% with an anticipated depth of coverage of ~120-140 per construct. Representation at the well index level fluctuated more where as previously seen well 4 was about 45% of the average even with the 50% increase in primer concentration in the reactions. Well 10 also showed a lower level of ~57% of the average while wells 1, 2, and 12 were 40-45% higher than the average.

Figure 7A:
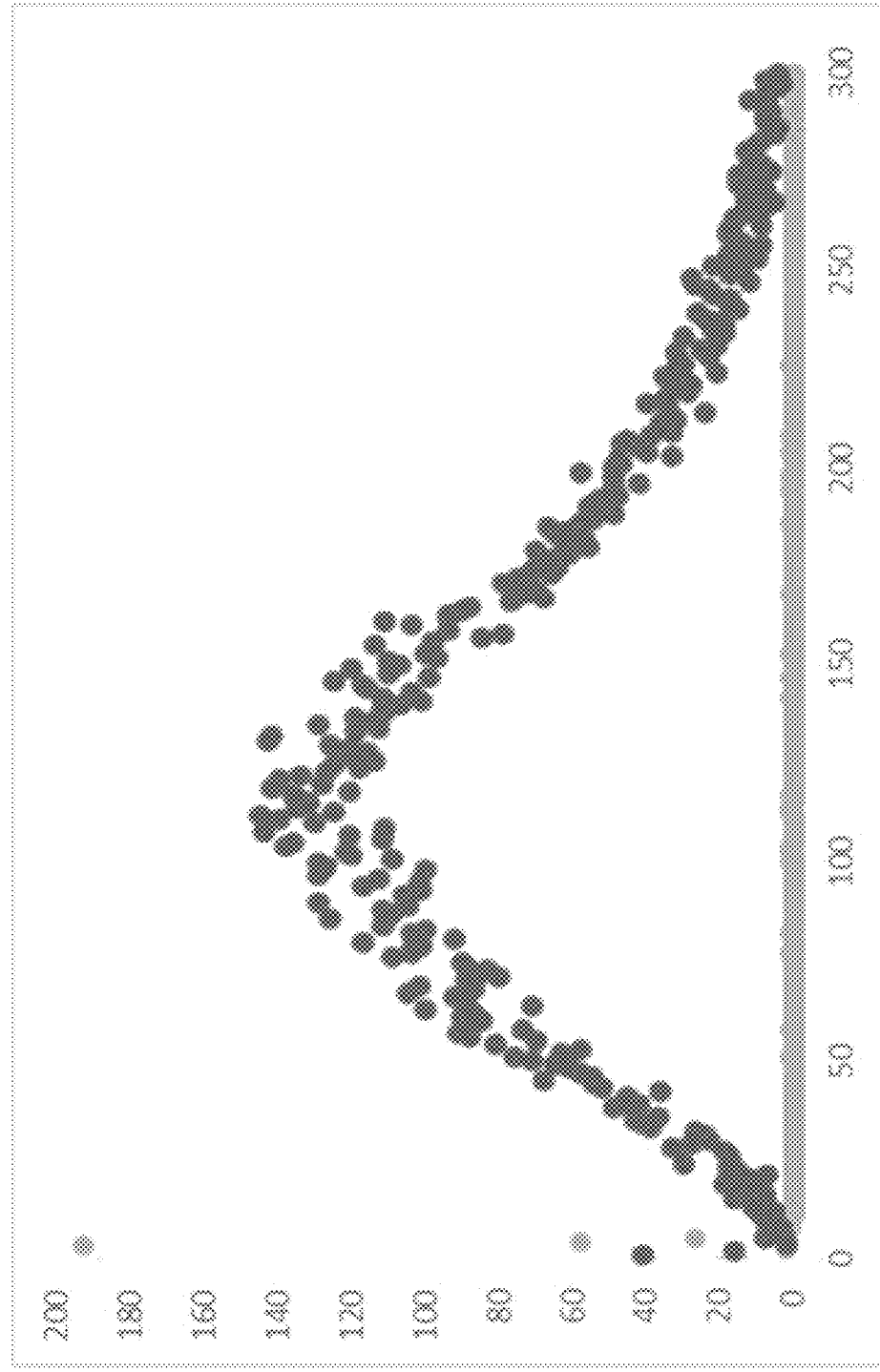
FIG. 7A shows a depth of coverage distribution of expected versus unexpected bits as described in Example 10.
Figure 7B:
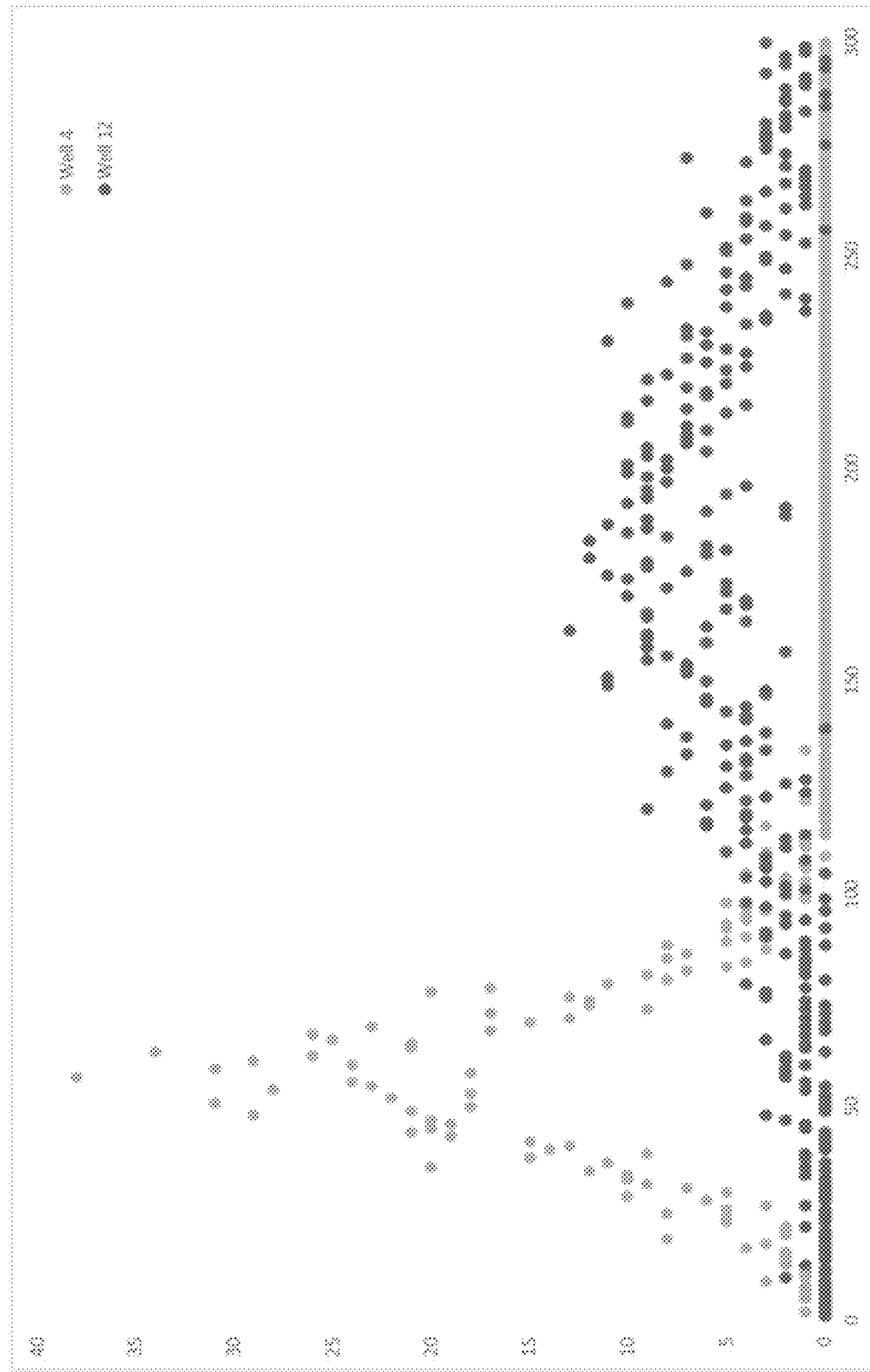
FIG. 7B shows the distribution difference between wells 4 and 12 in Example 10.
Figure 7C:
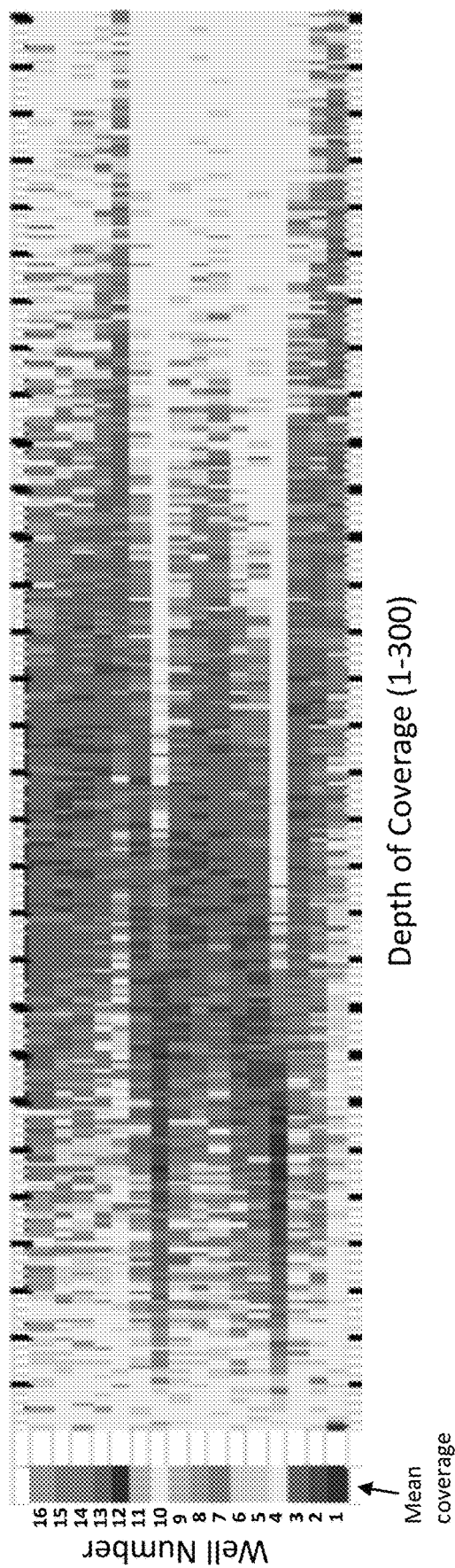
FIG. 7C shows a depth of coverage distribution heat map for all 16 wells as described in Example 10, where light gray indicates relatively low coverage and dark gray indicates relatively high coverage.

The depth of coverage distribution of expected versus unexpected bits (FIG. 7A) demonstrated a continual improvement for separating out the two populations. Unfortunately, even with the higher median depth of coverage, 115, the distribution of expected bits still included bits with depth values in the single digits, and there were still some unexpected bits with depths upwards of 250. Interestingly, examining the distribution difference between wells on different ends of the spectrum shows that while well 4 had a lower average depth, it also exhibited a tighter distribution, whereas well 12, having a higher average depth, had a broad distribution and still had some depths in the single digits (FIG. 7B). Changing the depth of coverage distribution of wells into a heat map (FIG. 7C, well 1 at the bottom, well 16 at the top) shows that the lower-averaged wells demonstrated tighter distributions versus their higher average depth counterparts. The variability of well depth of coverage behavior did not negatively impact the decoding outcome.

Decoding the bit construct from the NGS run data resulted in 99.25% (139 errors) correctness at the bit level and 96.9% (71 errors) correctness at the character/byte level. The errors were accounted for by only three occurrences. The entire well of plate 7, well 1 failed to transfer during the plate pooling step. While 50% of the bit positions had errors, none of the bit positions, 192 bits and 24 characters/bytes, failed to have any depth outside of low level contamination. This well accounted for $\frac{2}{3}^{rd}$ of the bit errors, but only $\frac{1}{3}^{rd}$ of the character/byte errors. The other two occurrences accounting for the errors were bit drop outs; bit 18 (one bit value) and bit 299 (zero bit value) failed to be present when they were called for across all well and plate positions. Due to the sporadic nature of the bit drop outs, every instance affected a distinct character/byte and thus was the cause for $\frac{2}{3}^{rd}$ the character/byte errors.

Figure 8:
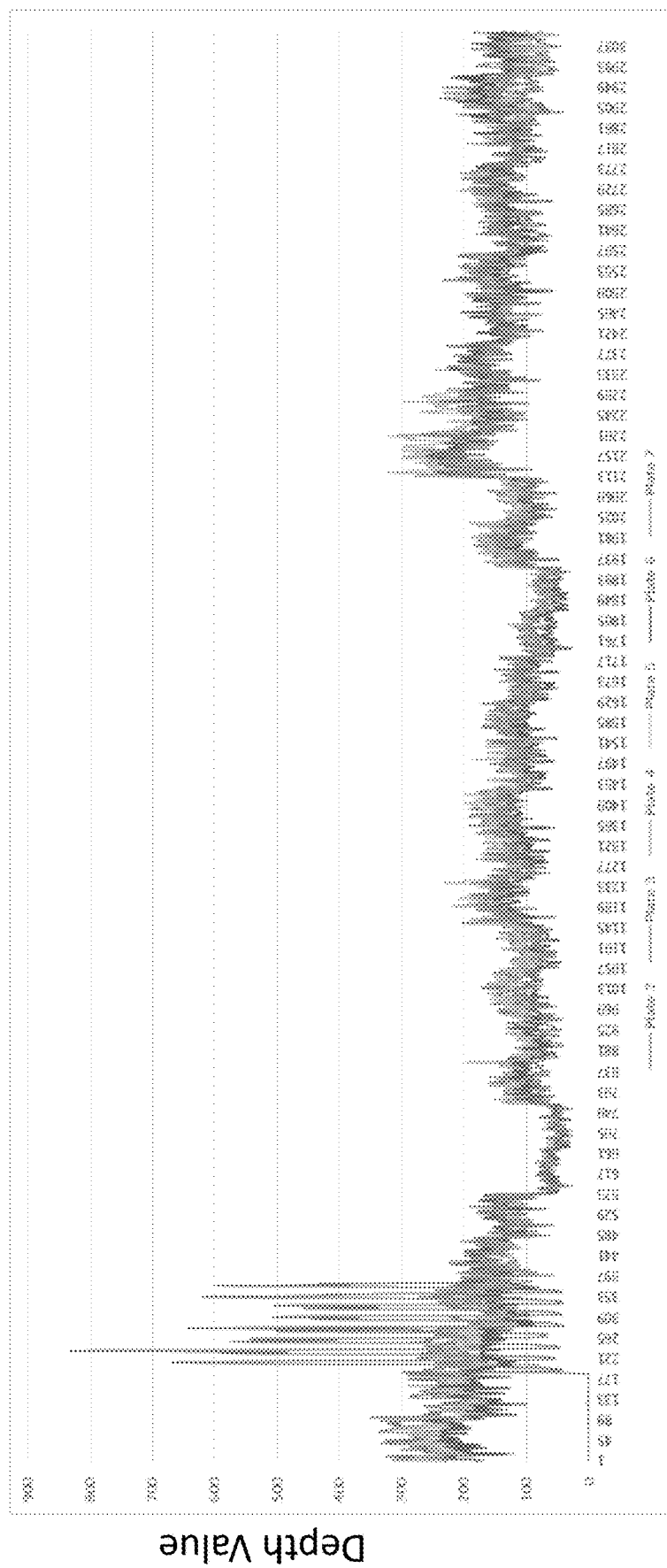
FIG. 8 shows a plot of the signal delta across every bit position of every plate, as described in Example 10.

Examining the zero/one bit-encoding strategy on a larger scale, the signal delta across every bit position of every plate was plotted, with each plate being its own series (FIG. 8). In the resulting plot, bits incorporating wells 4, 10, and 12 are readily identifiable due to their low and high average depth of coverage values. The fact that the delta largely corresponds to the depth of the expected bit construct indicates that the opposing bit construct for each bit position was consistently nearly absent. Plate 3, well 2 showed an unusual pattern of very high delta values but fortunately this did not negatively impact the outcome. The complete drop out of Plate 7, well 1 is also apparent, but in general, the well index primer pairs performed uniformly between plates.

Resultant Encoded Text Document with Errors Highlighted

The decoded text is shown below with errors in underlined and bold typeface.

RNase H-dependent PCR (rhPCR): improved specificity and single nucleotide 0olymorphism detection u3ing blocked cleavable primers Joseph R Dobosy, Scott D Rose, Kristin R Beltz, Susan M Rupp, Kristy M Powers, Mark A Behlke and Joseph A Walder Results Recombinant RNase H2 from Pyrococcu3 *abyssi*

The rnhb gene #oding for the Type II R ase H from *Pyrococcus a"yssi* has been identified previously. We produced and purified recombina.t *Pyrococcus abyssi* RNa3e H2 from *E. coli* as outlined in the additional methods (Additional fil% 2). As expected, the e.zyme was found to cleav% heteroduplex substrates having a single ribonu#leotide comprising any /f the four RNA bases. M!ss spectrometry analysi3 confirmed that cleavag% occurred on the 5'-sid% of the RNA residue, yielding one fragment with a free 3'-oH group and ! second with a 5'-ribon5cleotide phosphate (see Figure S1, Additional f)le 3). Importantly, sin'le-stranded RNAcontaini.g oligonucleotides were not cleaved or otherwis% degraded, demonstratin' the absence of any con4aminating nuclease acti6ity in the enzyme preparation.

Magnesium req5irements were optimized for P.a. rNase H2 by examining the dependence of the cleavage rates on Mg2+ concentration for 4he single rC containing 30mer heteroduplex substrate S-rC 14-1-15 at 70° C. Maximum activity was achieved around 4 mM Mg2+ and high levels of act)vity were seen in the r!nge of 1 mM to 10 mM Mg2+, similar to other RNase H2 enzymes characterize$. The enzyme maintained over 90% activity at 2m_ Mg2+, and only dropped to 61% of optimal activity in 1 mM mg2+ (see Figure S2, Additional file 4). No cleavage was observed in the absence of divalent cations. As with other Type II RNase H e.zymes, P.a. RNase H2 al3o has the ability to ut)lize Mn2+ and Co2+ in p,ace of Mg2+(data not s(own).

The 5'-reaction 0roduct formed upon clea6age with RNase H2 has t(e structure of a normal primer used to initia @ @',.^4L@ ꞵ quence is entirely DNA and ends in a 3'-hydroxyl group. Reaction conditions for P.a. rNase H2 are compatible with the buffers commonly employed in PCR (Mg2+ concentration3, pH, etc.). If the enz9me has sufficient therm!l stability and a high %nough turnover rate, thin it should be possible to perform primer cleav!ge/activation in real time during PCR.

The character accuracy was 96.9% for this encoding/decoding experiment, which was significantly higher than previous efforts. Overall, the lowest signal delta at a given bit position was ~45-50, but the majority of the time was 80-200. In contrast to previous experiments where only 16*192 characters were encoded, this experiment kept the same 16*192 plate footprint, but encoded across 6 plates equating to a 18,432 character capacity.

Example 11: Multiple Plate Text Encoding Experiment with Larger File Size

This Example demonstrates how the strategies described above can be used to encode and decode larger files. It further demonstrates the effectiveness of the method in reading a single document from a mixed pool of oligonucleotides that encode multiple documents. Unlike in Example 10, where the encoding footprint was 6×16×192 (six 16-well plates with 192 bits per well), the encoding footprint for the current example is 6×96×192, with six 96-well plates, and a bit density of 192 per well, resulting in 110,592 bits or 13,824 bytes/characters. New barcodes were designed to expand to 96 discrete well barcode pairs and 6 plate barcode pairs. All primers and bit-oligos synthesized using the IDT TruGrade® Processing Service.

Two text documents, Document 1 and Document 2, were encoded into DNA, with either the Presence/Absence Bit Encoding with a Shared Primer Pair Matrix Method or the Zero/One Bit Encoding with Discrete Primer Pairs Method. Document 1 contains snippets from the RNase H-dependent PCR paper discussed above; which contains a total of 13,691 characters. The full bit encoding size for this document, including the <eof> tag, is 109,568 bits. Document 2 is the full 1953 Double Helix paper by Watson and Crick and the full Nobel Prize presentation speech, which together contains a total of 12,883 characters and a full bit encoding size, including the <eof> tag, of 103,104 bits.

The Document Indices used for Document 1 were SEQ ID NOs: 472 and 473. The Document Indices used for Document 2 were SEQ ID NOs: 474 and 475. The six pairs of plate indices used for both documents were SEQ ID NOs: 470, 471, and 478-487. The 96 pairs of well indices used for both documents were SEQ ID NOs: 825-1016, as shown in Table 3.

TABLE 3

Well indices used for encoding Documents 1 and 2 in Example 11.

| Well 1 | GTAGATG [825] | GGATAGC [826] |
| Well 2 | AGGAGTT [827] | ACGACTG [828] |
| Well 3 | GCCTTGT [829] | ACTTCTC [830] |
| Well 4 | GACTGAG [831] | CTCAGAT [832] |
| Well 5 | TTTCGCA [833] | GCTTGAT [834] |
| Well 6 | AGCGCTA [835] | CACAATC [836] |
| Well 7 | TTGGCGT [837] | GAAGCAA [838] |
| Well 8 | TGAGATC [839] | CATTCGT [840] |
| Well 9 | GCGAGAA [841] | AGCAGAG [842] |
| Well 10 | CAGGTTC [843] | CTAAGTG [844] |
| Well 11 | CCTCCAT [845] | GTTACGC [846] |
| Well 12 | CATGTCC [847] | GACGTGT [848] |
| Well 13 | CGCTGAA [849] | TGCGAAT [850] |
| Well 14 | TTGTCCT [851] | ATCGCAT [852] |
| Well 15 | AAAGCAC [853] | CAGATGG [854] |
| Well 16 | CATCAGT [855] | ACGTTCC [856] |
| Well 17 | AATCCGA [857] | GTTTCGT [858] |
| Well 18 | CCTGTTT [859] | AACCAGA [860] |
| Well 19 | ACTTCGG [861] | TCCTGAT [862] |

TABLE 3 -continued

Well indices used for encoding Documents 1 and 2 in Example 11.

| Well | | |
|---|---|---|
| Well 20 | TTTCGGC [863] | CTAGACG [864] |
| Well 21 | TTAGGAC [865] | GTTACCG [866] |
| Well 22 | CTCCGAA [867] | TCGTATC [868] |
| Well 23 | CCTAAGG [869] | ATGTGAG [870] |
| Well 24 | CAGTCCA [871] | TGGACAT [872] |
| Well 25 | ATGACGT [873] | AGGTCAT [874] |
| Well 26 | AGGACCT [875] | TGGTCCA [876] |
| Well 27 | TGTTCAG [877] | CAAACGC [878] |
| Well 28 | TGTCCGA [879] | GCACAAA [880] |
| Well 29 | CTCAAAG [881] | TTATGGC [882] |
| Well 30 | CAAGGTT [883] | CCAAGAT [884] |
| Well 31 | CTAGATC [885] | CATCGAT [886] |
| Well 32 | ATGTCGC [887] | CCTTAAG [888] |
| Well 33 | AATGCCG [889] | GGCAAGT [890] |
| Well 34 | TCCGTTG [891] | CTACTCG [892] |
| Well 35 | GTCAACA [893] | CTCCTGA [894] |
| Well 36 | CGCAAAC [895] | CTGGATG [896] |
| Well 37 | TGGCATC [897] | TAAGCCG [898] |
| Well 38 | GTCAGTA [899] | GCTAAAC [900] |
| Well 39 | CTTGCAA [901] | CTCCATC [902] |
| Well 40 | CAAGTTG [903] | CGTGAAG [904] |
| Well 41 | TGAGACG [905] | TACGTGG [906] |
| Well 42 | GTAGCAT [907] | AACCTCT [908] |
| Well 43 | CTGATAC [909] | GGTGAAA [910] |
| Well 44 | TCCGACA [911] | ACTCAAG [912] |
| Well 45 | GTCGTTG [913] | AGTGGAT [914] |
| Well 46 | GTCTTCG [915] | CCAGCAA [916] |
| Well 47 | AGCCACA [917] | GCAGTTT [918] |
| Well 48 | GTTCTAC [919] | AGTCTGC [920] |
| Well 49 | GTTCGCT [921] | CCAACTG [922] |
| Well 50 | ATTGAGG [923] | ATTAGCG [924] |
| Well 51 | CGAGCAT [925] | TTACCAG [926] |
| Well 52 | CTCTTAG [927] | TGTGCTA [928] |
| Well 53 | CTTGCTG [929] | CTGTACT [930] |
| Well 54 | GTCGGAT [931] | ACCGTTA [932] |
| Well 55 | GTAAACG [933] | GTCTACT [934] |
| Well 56 | GGATTGG [935] | GCATATG [936] |
| Well 57 | CCTAGGA [937] | CGACTTT [938] |
| Well 58 | AACTCTG [939] | TTAACCG [940] |
| Well 59 | CAAACCT [941] | GTGTTCA [942] |
| Well 60 | TAACTGG [943] | CTACAGG [944] |
| Well 61 | ACAAGCT [945] | TCCAGTA [946] |
| Well 62 | TGATGTG [947] | GGAACAA [948] |
| Well 63 | AGGCCTT [949] | GAACAGA [950] |
| Well 64 | GCGTTCT [951] | CAGCCAT [952] |
| Well 65 | TCACTGA [953] | TTAGGCG [954] |
| Well 66 | ACTAACC [955] | CTAGCTA [956] |
| Well 67 | GGTCATC [957] | CTCCAGT [958] |
| Well 68 | CTCAGTC [959] | CATCTGG [960] |
| Well 69 | TTTGTGG [961] | TGTTGGC [962] |
| Well 70 | TGCCATA [963] | TACTGCC [964] |
| Well 71 | TCGTAGG [965] | CACTAGG [966] |
| Well 72 | ATGACCG [967] | GTGGAAC [968] |
| Well 73 | AACTTCC [969] | AGTATCC [970] |
| Well 74 | TAACCAC [971] | CCATTTC [972] |
| Well 75 | CAGTGAG [973] | TTGCACT [974] |
| Well 76 | CGATTTG [975] | TCTCCTT [976] |
| Well 77 | AGGTAAC [977] | AACAGGT [978] |
| Well 78 | GTTAGAG [979] | TTAGTGC [980] |
| Well 79 | CCAATGC [981] | TCCGAGT [982] |
| Well 80 | GGAGCTA [983] | GGTACTA [984] |
| Well 81 | TCTCATC [985] | AGATCAC [986] |
| Well 82 | TGCCGTT [987] | CGTACTC [988] |
| Well 83 | CAGGAAA [989] | GCCATAT [990] |
| Well 84 | ACTTGAC [991] | ACGTGCT [992] |
| Well 85 | CTGGTTT [993] | CGTTAGT [994] |
| Well 86 | ACCTTTC [995] | GAACACT [996] |
| Well 87 | CATGAAC [997] | AGGAGAA [998] |
| Well 88 | TGCTTAG [999] | CGCGAAA [1000] |
| Well 89 | GGTATGT [1001] | CGATCTA [1002] |
| Well 90 | ACGTCCA [1003] | ACCAAGT [1004] |
| Well 91 | CTCACGA [1005] | CTACGCT [1006] |
| Well 92 | AACACGC [1007] | CGACGAA [1008] |
| Well 93 | CCTGTGA [1009] | AGTACGC [1010] |
| Well 94 | GAAGACG [1011] | CCTTGCA [1012] |

TABLE 3 -continued

Well indices used for encoding Documents 1 and 2 in Example 11.

| Well 95 | CTTAACG [1013] | ACGAGCA [1014] |
|---|---|---|
| Well 96 | ACATGTG [1015] | AGGAAGC [1016] |

SEQ ID NOs are shown in square brackets.

After encoding into oligos both documents were decoded via NGS as described above. Overall, four decodings were performed:
(1) Document 1, encoded via the Zero/One Bit Encoding with Discrete Primer Pairs Method, was decoded from a pure pool of oligonucleotides (pure source) that only contained those oligonucleotides encoding Document 1;
(2) Document 2, encoded via the Zero/One Bit Encoding with Discrete Primer Pairs Method, was decoded from a pure pool of oligonucleotides that only contained those oligonucleotides encoding Document 2;
(3) Document 1, encoded via the Presence/Absence Bit Encoding with a Shared Primer Pair Matrix Method, was decoded from a pure pool of oligonucleotides that only contained those oligonucleotides encoding Document 1; and
(4) Document 1, encoded via the Zero/One Bit Encoding with Discrete Primer Pairs Method, was decoded from a mixed pool of oligonucleotides that contained both oligonucleotides encoding Document 1 and oligonucleotides encoding Document 2.

Figure 9A:
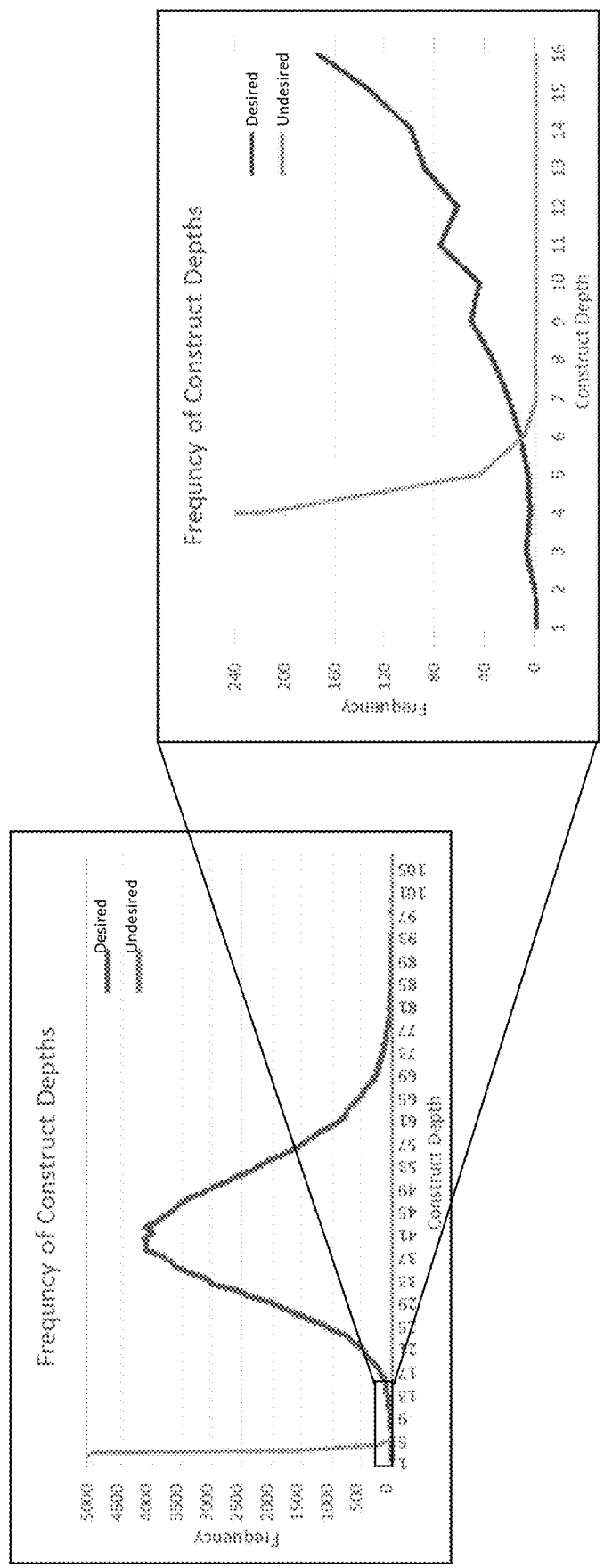

For Document 1 encoded via the Zero/One Bit Encoding with Discrete Primer Pairs Method and decoded from a pure source (encoding experiment (1), above), the encoding accuracy was 99.999087% (1 incorrect bit in 109,568 bits). Plate 1, well 29, bit position 140 had a depth of coverage of 2 for both the 1-bit and 0-bit construct, resulting in a 'R' to 'B' conversion (see output below). In general, bits 140 and 209 showed marked reduction in their representation across all of the 0-bit encoding strategies compared to the rest of the bits. These led to the extended lower distribution tail. The cause of the erroneous bit call was not due to any liquid handling miscue. The low end of the normal distribution of desired construct depths crossed paths with the distribution of undesired constructs. This path crossover is shown in FIG. 9A. The graph on the left shows the depth count distribution (The relationship describing how many constructs had a specified depth of coverage) for desired (dark gray) and undesired (light gray) bit constructs. The graph on the right shows an expanded part of the graph on the left, showing the overlap of desired and undesired bit constructs. The law of averages determined that 0.294 bits could be called incorrectly out of the 109,568 bits encoded. 21 other bit positions were at risk for being mis-called with depths ranging from 1 to 4. In other words, if this document sample was run on NGS 100 times, 74.5% would be perfect, 21.9% would have a single bit error, and 3.6% would have greater than a single bit error.

For this decoding, 10.5 million viable clusters, forward and reverse traces, were analyzed from the NGS instrument, of which 2.86 million were unique constructs. Of the 10.5 million viable clusters, 4.5 million had the desired document/plate- and well-level barcode pairings.

Undesired document/plate barcode pairings accounted for 46.4% of the 10.5 million viable clusters, equating to an average of 1.55% for each of the 30 undesired pairs. FIG. 9B shows the percent contribution of each of the 30 undesired document/plate barcode pairings. One possible explanation for this amount of mispairings is that the document/plate barcoded primers were not exhausted, leading to a relatively large population of document/plate barcode primers persisting in the pooled product and participated in the final extraction PCR reaction and being erroneously incorporated. The PCR conditions were equivalent with the document/plate barcoded primer amount being 5 fold greater than the well barcoded primers. PCR conditions were as such to ensure product bands were viewable for each step. This may thus be the reason for the degree of undesired pairings at the document/plate barcode level being about 5-fold greater than at the well barcode level.

Figure 9C:
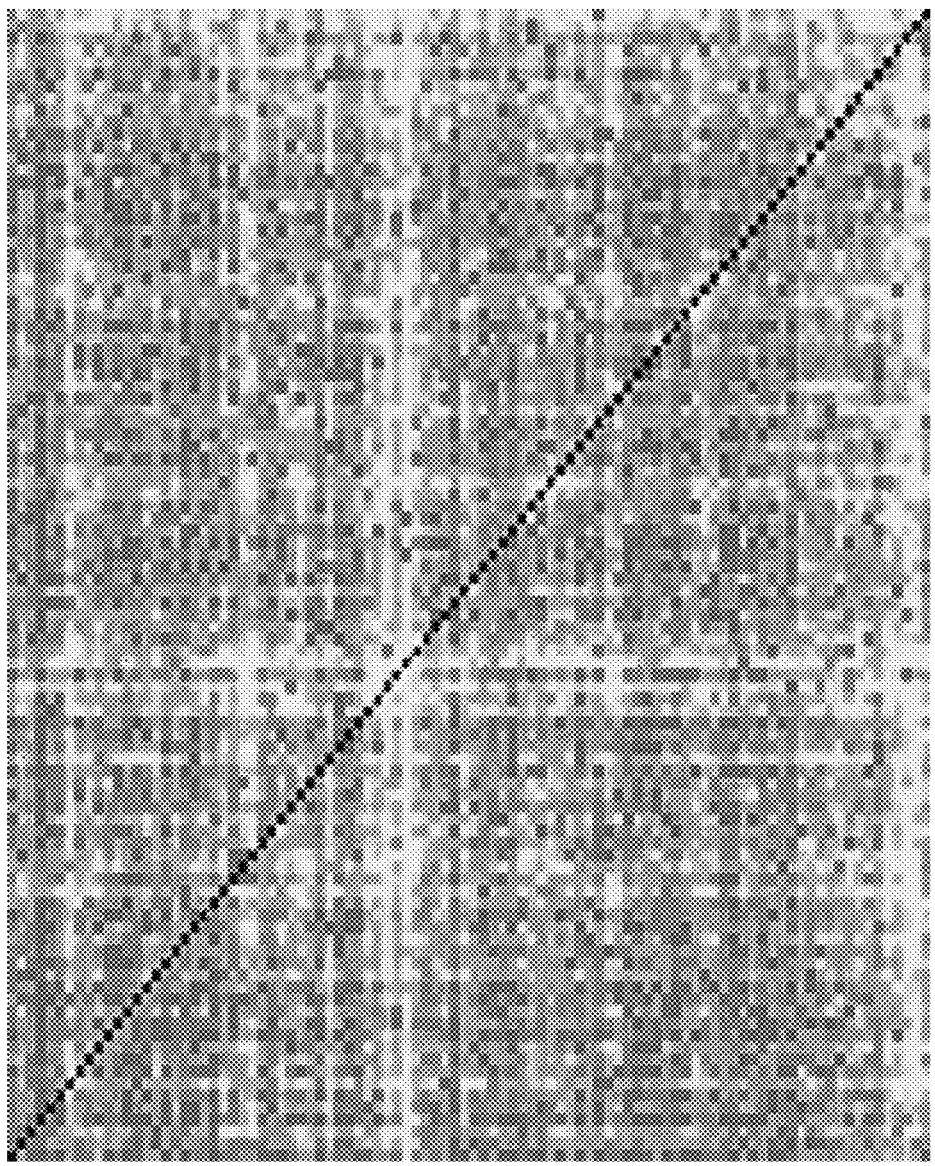

Undesired well barcode pairings accounted for 10.3% of the 10.5 million viable clusters, equating to an average of 0.0021% for each of the 9,120 undesired pairs. FIG. 9C shows the coverage of mispairings of forward and reverse well indices as a heat map where light gray indicates relatively low coverage and dark gray indicates relatively high coverage, with a low to high coverage range of around 80 to around 160. The black squares that make up the diagonal line represent the correct well barcode pairings.

Undesired constructs with desired document/plate and well barcode pairings, but with other issues, accounted for 0.17% of the 10.5 million viable clusters.

The data also suggests that document/plate barcoded primers have a 12.4% contamination level. The well barcoded primers have a 0.46% contamination level. Document 2 document/plate barcodes were identified in some document/plate barcode pairs but at very low levels. The presence of Document 2 barcodes indicate potential contamination during synthesis or due to incorrect identification from NGS data. Base calling quality (Q-score) is generally poorer near the ends of traces.

For Document 2, encoded via the Zero/One Bit Encoding with Discrete Primer Pairs Method and decoded from a pure source (encoding experiment (2), above), the encoding accuracy was 100%. The distributions across document/plate-barcoded and well-barcoded primers and desired and undesired bit constructs were very similar to the metrics for the first document encoding.

Figure 10A:
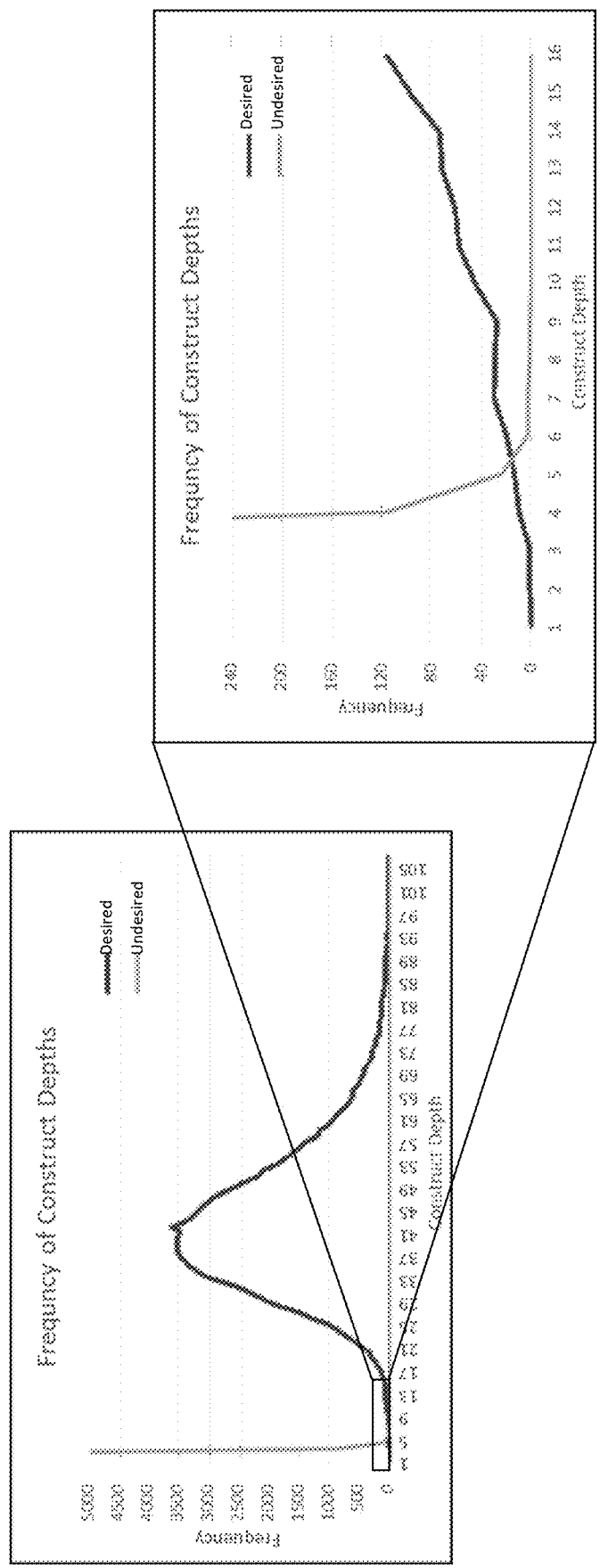

The low end of the normal distribution of desired construct depths crossed paths with the distribution of undesired constructs (FIG. 10A). Law of averages determined that 0.128 bits could be called incorrectly out of the 103,040 bits encoded. 26 bit positions were at risk for being miss called with depths ranging from 1 to 4. In other words, if this document sample was run on NGS 100 times, 88% would be perfect, 11.3% would have a single bit error, and 0.7% would have greater than a single bit error.

For this decoding, 8.6 million viable clusters, forward and reverse traces, were analyzed from the NGS instrument, of which 2.18 million were unique constructs. Of the 8.6 million viable clusters, 5.2 million had the desired document/plate- and well-level barcode pairings.

Undesired document/plate barcode pairings accounted for 39.3% of the 8.6 million viable clusters, equating to an average of 1.31% for each of the 30 undesired pairs. FIG. 10B shows the percent contribution of each of the 30 undesired document/plate barcode pairings.

Figure 10C:
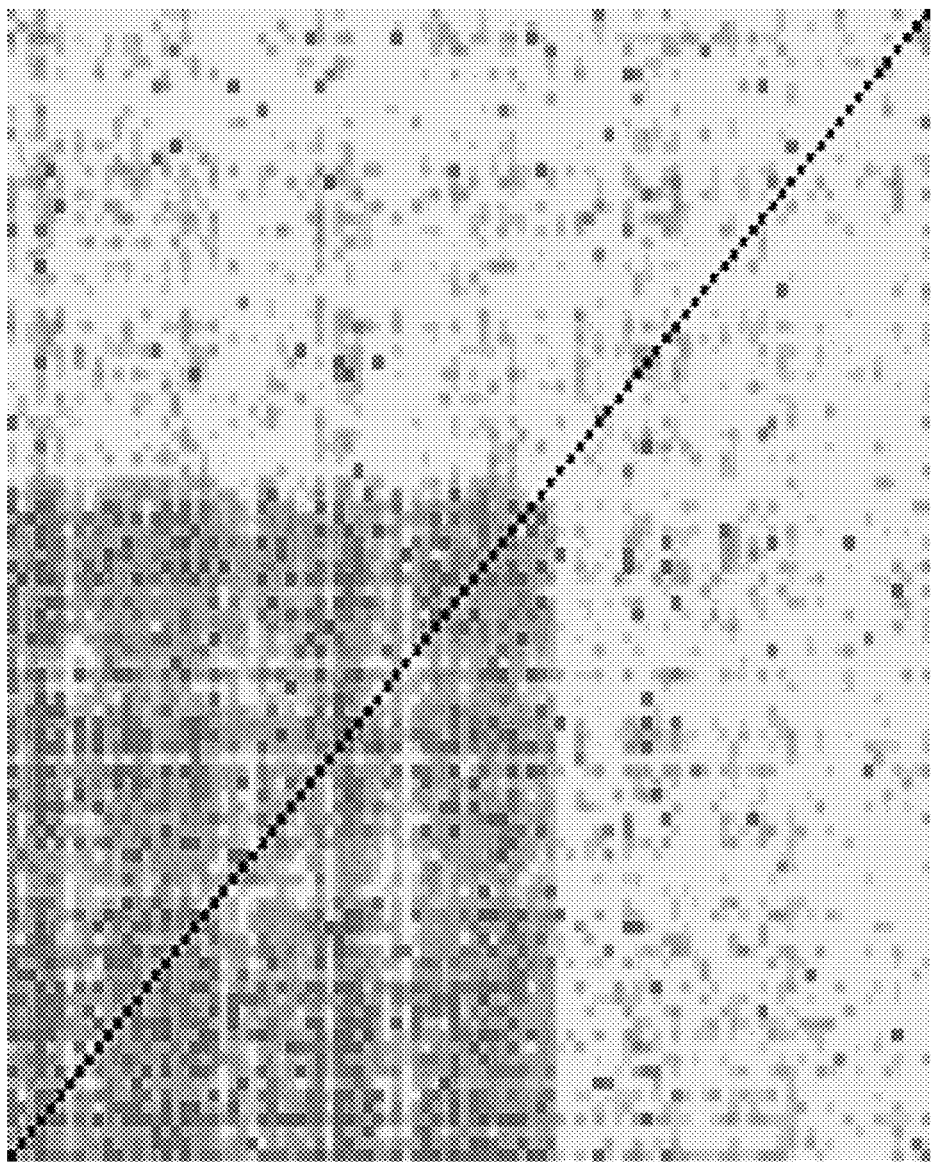

Undesired well barcode pairings accounted for 9.8% of the 8.6 million viable clusters, equating to an average of 0.0018% for each of the 9,120 undesired pairs. FIG. 10C shows the coverage of mispairings of forward and reverse well indices as a heat map where light gray indicates relatively low coverage and dark gray indicates relatively high coverage, with a low to high coverage range of around 80 to around 160. The black squares that make up the diagonal line represent the correct well barcode pairings.

Undesired constructs with desired document/plate and well barcode pairings, but with other issues, accounted for 0.14% of the 8.6 million viable clusters.

The data also suggests that document/plate-barcoded primers have a 11.4% contamination level. The well-barcoded primers have a 0.42% contamination level. Document 1 document/plate barcodes were identified in some document/plate barcode pairs but at very low levels.

For Document 1, encoded via the Presence/Absence Bit Encoding with a Shared Primer Pair Matrix Method and decoded from a pure source (encoding experiment (3), above), the encoding accuracy was 99.84393% (171 incorrect bits in 109,568 bits). 154 bits were incorrectly decoded as a 0-bit while 17 bits were incorrectly decoded as a 1-bit.

With the presence/absence encoding strategy, decoding the data requires a depth threshold to identify the incorrect information in order to ignore it.

Figure 11A:
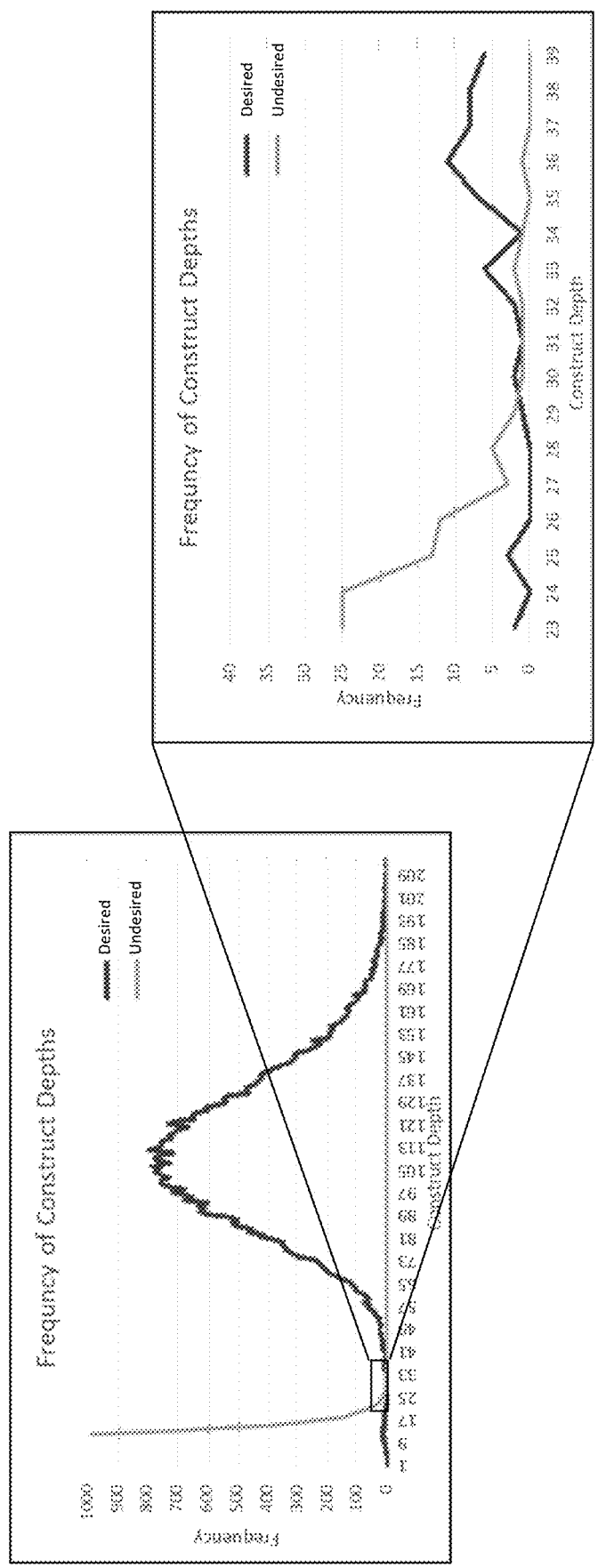

In this case, the threshold was determined to be a depth of 27 or higher. Manual inspection concluded that adjusting the value either lower or higher did not improve the decoding accuracy. The cause of the erroneous bits call was not due to any liquid handling miscue. The low end of the normal distribution of desired construct depths crossed paths with the distribution of undesired constructs (FIG. 11A).

Further analysis identified a small sub group of desired bit constructs with depths within the depths of the undesired bit constructs. However, enough of a distribution overlap existed such that a perfect decoding could be achieved.

For this decoding, 9.8 million viable clusters, forward and reverse traces, were analyzed from the NGS instrument, of which 145,100 were unique constructs. Of the 9.8 million viable clusters, 5.6 million had the desired document/plate- and well-level barcode pairings.

Undesired document/plate barcode pairings accounted for 39.6% of the 9.8 million viable clusters, equating to an average of 1.32% for each of the 30 undesired pairs. FIG. 11B shows the percent contribution of each of the 30 undesired document/plate barcode pairings.

Document 2 document/plate barcodes were identified in some document/plate barcode pairs but at very low levels.

For Document 1, encoded via the Zero/One Bit Encoding with Discrete Primer Pairs Method and decoded from a mixed source (encoding experiment (4), above), the encoding accuracy was 100%.

Figure 12A:
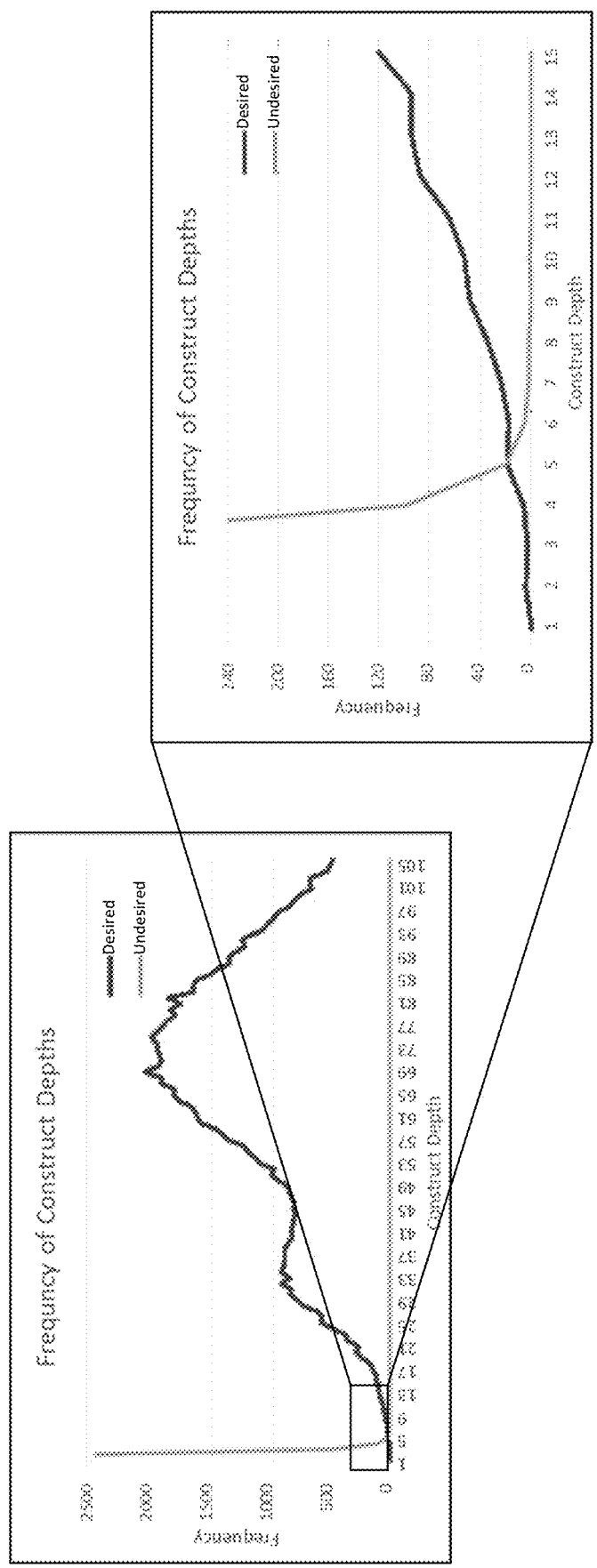

The sample was ran on a different MiSeq flow cell (2×300) than normal (2×150). This generated more traces (~37% increase) and longer traces. Thus, the full 210 bp construct was present on each trace. The median depth of coverage increased from ~40 from previous runs to 73. The distributions across document/plate barcodes showed a larger spread than previous runs where plate 5 was 45% of the plate 1 to 4 average and plate 6 was 82%. This led to a bimodal distribution of the desired constructs and a distinct second distribution largely made up of plate 5 constructs with a median depth of 33 (FIG. 12A). The low end of the second distribution of desired construct depths crossed paths with the distribution of undesired constructs. The law of averages determined that 0.168 bits could be called incorrectly out of the 109,568 bits encoded. 32 bit positions were at risk for being miss called with depths of 2 to 5. In other words, if this document sample was run on NGS 100 times, 85% would be perfect, 14% would have a single bit error, and 1% would have greater than a single bit error.

For this decoding, 14.3 million viable clusters, forward and reverse traces, were analyzed from the NGS instrument, of which 3.15 million were unique constructs. Of the 14.3 million viable clusters, 7.6 million had the desired document/plate and well level barcode pairings.

Undesired document/plate barcode pairings accounted for 36.4% of the 14.3 million viable clusters, equating to an average of 1.22% for each of the 30 undesired pairs. FIG. 12B shows the percent contribution of each of the 30 undesired document/plate barcode pairings.

Figure 12C:
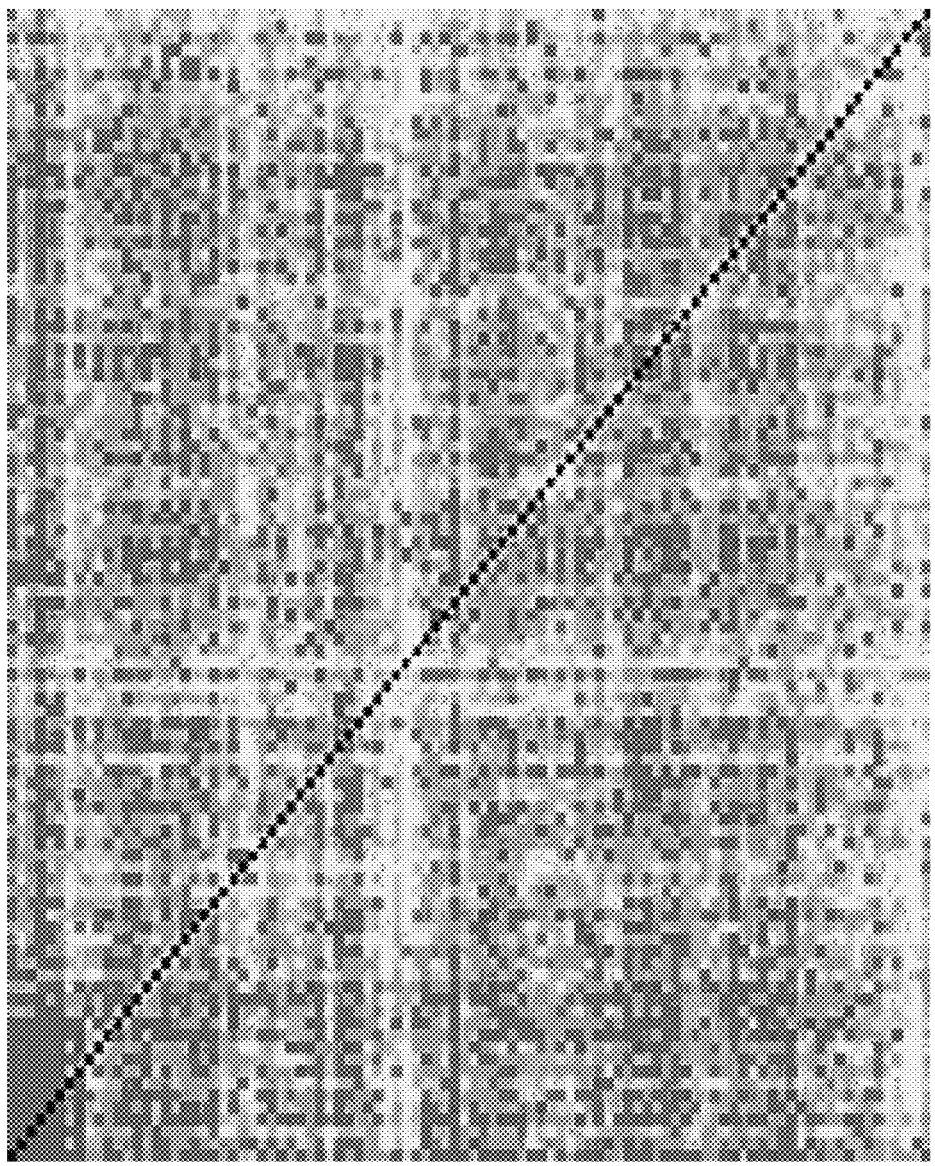

Undesired well barcode pairings accounted for 16% of the 14.3 million viable clusters, equating to an average of 0.0018% for each of the 9,120 undesired pairs. FIG. 12C shows the coverage of mispairings of forward and reverse well indices as a heat map where light gray indicates relatively low coverage and dark gray indicates relatively high coverage, with a low to high coverage range of around 110 to around 225. The black squares that make up the diagonal line represent the correct well barcode pairings.

Undesired constructs with desired document/plate and well barcode pairings, but with other issues, accounted for 0.17% of the 14.3 million viable clusters.

The data also suggests that document/plate-barcoded primers have a 11.0% contamination level. The well-barcoded primers have a 0.42% contamination level. Document 2 document/plate barcodes were identified in some document/plate barcode pairs but at very low levels.

The resultant encoded text for Document 1, encoded via the Zero/One Bit Encoding with Discrete Primer Pairs Method and decoded from a pure source, with the single R to B conversion underlined in bold typeface, is as follows:

RNase H-dependent PCR (rhPCR): improved specificity and single nucleotide polymorphism detection using blocked cleavable primers Joseph R Dobosy, Scott D Rose, Kristin R Beltz, Susan M Rupp, Kristy M Powers, Mark A Behlke and Joseph A Walder Abstract Background: The polymerase chain reaction (PCR) is commonly used to detect the presence of nucleic acid sequences both in research and diagnostic settings. While high specificity is often achieved, biological requirements sometimes necessitate that primers are placed in suboptimal locations which lead to problems with the formation of primer dimers and/or misamplification of homologous sequences. Results: *Pyrococcus abyssi* (P.a.) BNase H2 was used to enable PCR to be performed using blocked primers containing a single ribonucleotide residue which are activated via cleavage by the enzyme (rhPCR). Cleavage occurs 5'- to the RNA base following primer hybridization to the target DNA. The requirement of the primer to first hybridize with the target sequence to gain activity eliminates the formation of primer-dimers and greatly reduces misamplification of closely related sequences. Mismatches near the scissile linkage decrease the efficiency of cleavage by RNase H2, further increasing the specificity of the assay. When applied to the detection of single nucleotide polymorphisms (SNPs), rhPCR was found to be far more sensitive than standard allele-specific PCR. In general, the best discrimination occurs when the mismatch is placed at the RNA:DNA base pair. Conclusion: rhPCR eliminates the formation of primer dimers and markedly improves the specificity of PCR with respect to off-target amplification. These advantages of the assay should find utility in challenging qPCR applications such as genotyping, high level multiplex assays and rare allele detection.

Background; Quantitative PCR (qPCR) is usually performed in realtime mode using fluorescence detection methods. In one commonly used format (the 5'-nuclease assay), qPCR involves three oligonucleotides wherein the forward and reverse primers direct DNA amplification spanning the hybridization site for a third fluorescently labeled oligonucleotide probe. The probe typically contains a fluorescence reporter dye and a quencher. Separation of the reporter and quencher due to cleavage of the probe by the 5'-nuclease activity of the DNA polymerase leads to an increase of fluorescence and a detectable signal. Quantitative PCR can also use nucleic acid binding dyes such as SYBR® Green or Eva Green® that increase fluorescence in the presence of double-stranded DNA (dsDNA). Nucleic acid binding dye systems use only two oligonucleotides, the forward and reverse primers, which direct amplification of the target. Once amplification has occurred, the dye binds to the double stranded DNA and generates a fluorescent signal without the need for a third dye-labeled oligonucleotide probe. Dye binding assays are less expensive and are very convenient; however, they are inherently less specific than three-oligonucleotide systems since signal is generated from any amplification event.

Formation of primer-dimers and off-target amplification are common problems in PCR. These competing side reactions are a particular problem with low copy number targets due to the high number of cycles required for amplification and in multiplex assays where many different primers must function well together. While "primer-dimers" are often thought to arise from self-amplification of primers due to overlapping 3'-ends, these species can also be generated when there is little apparent complementarity between the primers. More complex oligomeric products of greater length than primer-dimers are also observed in some cases. The formation of primer-dimers can give rise to a false positive signal in dye-binding qPCR assays, and can lead to false negative results by consumption of primers and other reaction components. Several methods can be used to reduce these undesired side reactions, or mitigate their effects. Physical barrier methods can be used to separate reaction components until an elevated temperature is reached. Use of a chemically or antibody inactivated "hot-start" polymerase can alleviate mis-priming at low temperature, but at significant additional cost. "Nesting" of primers can detect the desired product among the previously amplified PCR products, but this technique is not applicable to qPCR. Melt-curve analysis done as an additional end-point step in dye-binding qPCR assays can help demonstrate assay specificity by revealing the existence of multiple amplicons, but cannot prevent or limit their formation. Often several assays must be designed and empirically tested before one is found that does not result in multiple melt peaks.

A wide variety of approaches have been employed to confer single-base specificity to PCR assays with the goal of detecting single nucleotide polymorphisms (SNPs). Assays have been based on either of two methods: differential amplification of the variant alleles (allele-specific PCR, or ASPCR) or discrimination between the alleles following or concurrent with unbiased amplification of the target sequence. The most common format for detection concurrent with unbiased amplification is the 5'-nuclease assay. In that case, a fluorescence-quenched probe, which is degraded by the 5'-nuclease activity of the DNA polymerase, is designed to bind preferentially to the match sequence relative to a mismatch sequence. In order to distinguish effectively between hybridization of an exact match and a single base pair mismatch, relatively short probes, 12-16 bases in length, are needed. To achieve binding of the probe under conditions of the extension reaction with temperatures typically between 55° C. and 70° C., modified bases such as locked nucleic acids (LNAs) or pendant groups such as a minor groove binder (MGB) are incorporated into the oligonucleotide to increase the Tm.

In ASPCR, the SNP is positioned at or near the 3'-end of the primer such that a mismatch with the template inhibits initiation of DNA synthesis. Even with careful optimization of reaction conditions, the success rate is highly variable. Assays can be improved by incorporating modified bases or by introducing a secondary mismatch within the primer. The most serious shortcoming of this assay format is that once extension has occurred off of a mismatched target, the primer becomes incorporated in the amplicon. After the newly synthesized strand is copied, the primer forms a perfect match with the template and no further discrimination can be achieved. Even if the efficiency of replication of the template is reduced 100-fold due to the mismatch, there would only be a differential amplification of 6-7 cycles between alleles.

Here we describe the properties of a thermophilic archaeal RNase H2 enzyme from *Pyrococcus abyssi*, and methods to use this enzyme in a coupled reaction for PCR based assays (RNase H2-dependant PCR or rhPCR) shown schematically in FIG. 1. Primers containing a single RNA residue are modified at or near the 3'-end of the oligonucleotide to prevent extension by DNA polymerase. Deblocking and activation of the primers occur upon hybridization to the target DNA sequence and subsequent cleavage by RNase H2. The *Pyrococcus abyssi* (P.a.) RNase H2 enzyme has sufficient thermal stability and a high enough turnover rate to perform this function in real time during thermocycling. Cleavage occurs at the 5'-side of the RNA base leaving a DNA oligonucleotide with a 3'-hydroxyl that is competent to function as a primer. P.a. RNase H2 has minimal activity at room temperature so that use of this enzyme in rhPCR with blocked primers enables a universal hot start reaction with any thermostable DNA polymerase. Little to no modification in reaction temperatures, cycling times, or analysis procedures is required for inclusion of the RNase H2 enzyme into current end-point PCR and qPCR methods. The requirement for hybridization of the primers to the target sequence for activation prevents template independent reactions such as the formation of primer-dimers. Mismatches at or near the RNA:DNA base pair significantly decrease the efficiency of cleavage by RNase H2, minimizing misamplification of partially homologous sequences. When utilized for the detection of single nucleotide polymorphisms (SNPs), rhPCR was found to be far more sensitive than standard allele-specific PCR. Discrimination between variant alleles is generally greatest when the mismatch is positioned at the RNA:DNA base pair.

DISCUSSION

Primer Cleavage Dependent PCR

Several coupled reaction schemes have been proposed for PCR in which a hybridization dependent primer activation step is linked to primer extension. In the pyrophosphorolysis-activated polymerization (PAP) assay, a blocked 3'-terminal nucleotide is cleaved by attack of pyrophosphate (reverse of the polymerization reaction). For this to occur efficiently, high concentrations of pyrophosphate are required which may inhibit some polymerases. The range of blocking groups that can be accommodated at the 3'-terminus is very limited. A 3'-terminal dideoxynucleotide has been utilized in most studies. Of the four bases, only dideoxy-C can be readily incorporated using standard methods of oligonucleotide synthesis, limiting widespread use of this technique.

A coupled PCR assay has been proposed in which a blocked primer is cleaved after hybridization to the target sequence by a nicking restriction endonuclease. A restriction enzyme that has an asymmetric recognition sequence or that cuts only one strand at a hemimethylated site would be required to avoid cleavage of the template. To our knowledge, this reaction scheme has never been demonstrated experimentally. In any event, the requirement that the restriction enzyme recognition sequence be located near the 3'-end of the primer would severely limit the use of this method.

Use of both RNase H1 and RNase H2 to effect primer cleavage in a coupled PCR assay has been reported previously in the patent literature but minimally characterized. Unlike the Type II RNase H enzymes, Type I enzymes will not cleave a substrate having a single RNA residue. At least 3 consecutive RNA residues are required, and 4 for a high level of catalytic activity. Thus, use of a Type I RNase H in rhPCR would require that the primer have at least four consecutive RNA residues. This adds substantially to the cost and complexity of the synthesis of the primer and increases its susceptibility to degradation. The cleaved primer would terminate in two or more RNA residues which can inhibit primer extension and these RNA residues would be incorporated into the amplicon. Sagawa et al. suggested that the specificity of Type II RNases H would be similar to that of a restriction enzyme and that cleavage, and hence amplification, would be completely prevented if there was a mismatch at the RNA:DNA base pair within the duplex formed between the primer and the template. Although this is not true, as seen in the present study, coupling RNase H2 cleavage to primer extension can be used to greatly boost the specificity of PCR.

Recognition of Substrates Having Base-Pair Mismatches by Type II RNase H Enzymes RNase H2 plays an important role in the removal of RNA residues misincorporated into DNA due either to incomplete removal of RNA primers used to initiate DNA synthesis or polymerase errors. Consistent with its role in DNA repair, Type II RNase H enzymes are also able to cleave substrates where there is an RNA:DNA base pair mismatch, but at a rate reduced compared to the corresponding perfect duplex. For P.a. RNase H2, the rate of the reaction is decreased by about 10-fold (FIG. 3). A decrease in rate of similar magnitude is seen with a mismatch on the 5'-side of the cleavage site (position "−1"). Mismatches at the "−3", "−2", and "+1" positions gave rise to smaller reductions in the cleavage rate. Outside of this region, effects of a base pair mismatch were negligible. In all cases, the only products observed by mass spectrometry, and by electrophoresis using radiolabeled substrates, reflected cleavage on the 5'-side of the RNA residue. More detailed kinetic studies of the effects of mismatches on cleavage rates are in progress.

Enhanced Specificity of rhPCR

Figure 5:
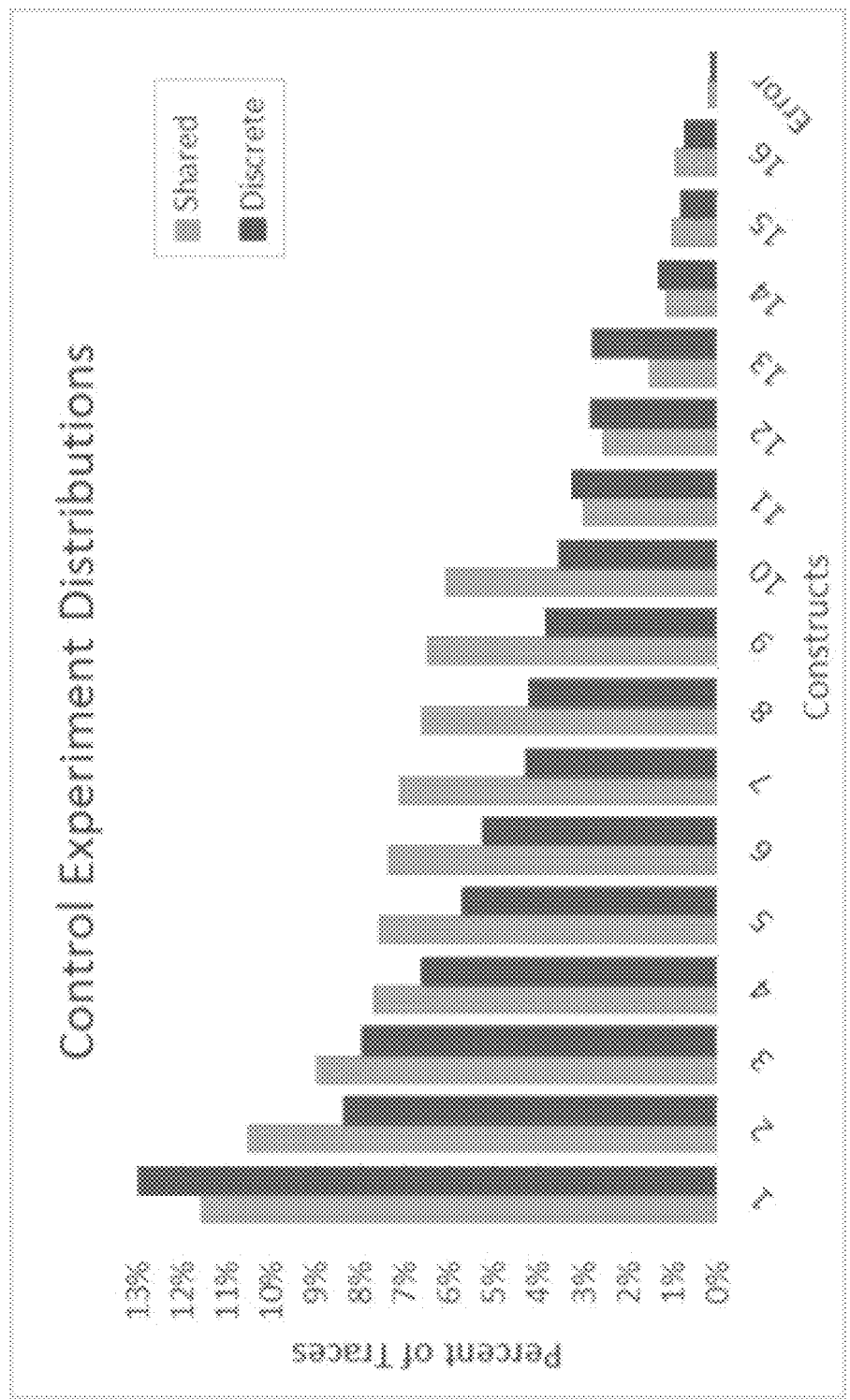
FIG. 5 shows a distribution table comparing the Shared (light gray) with the Discrete (dark gray) primer strategy with respect to the percent of total trace reading (Y axis) for oligo constructs 1-16 (X axis). Both strategies show a broad distribution of intended bit constructs, labeled 1-16, versus the largest unintended bit constructs, labeled Error, being 4.5-5.0 fold lower than the lowest intended bit construct. The bit constructs were ordered highest to lowest in their Percent of Traces. The highest percent for the Discrete strategy was 27.5%, however, this value was removed from the graph to provide better resolution at the 10% and lower range. Both strategies indicate that 90% of the constructs were the desired constructs respectively, 90% of the undesired constructs had one of the 16 intended bit indices encoded but with different well index pairs. With the Discrete index pairs these constructs would be ignored whereas the Shared index pairs would be kept.

Coupling cleavage by RNase H2 to primer extension in rhPCR leads to greater specificity both with respect to template independent mispriming events (e.g., primerdimer formation) and unwanted amplification of related sequences. The formation of primer-dimers is prevented even in assays that are very prone to this side reaction (FIG. 5). This feature of rhPCR should be particularly beneficial in multiplex assays. The specificity of the assay with respect to misamplification of homologous sequences is far greater than can be achieved by PCR using unmodified primers. When there are mismatches over or neighboring the RNase H2 cleavage sites of both primers, the ?Cq values observed are extremely large. For the HRAS gene, the ?Cq between the rat and human sequences was greater than 50 cycles. This high degree of specificity should be very useful for the detection of low levels of heterologous DNA in xenogeneic transplant models (e.g., human tumors grown in a mouse host) and in other instances where there are related targets having closely spaced variations in sequence. In SNP detection, where it is necessary to exploit the effect of a single base pair mismatch on cleavage by RNase H2, the assay also shows far greater discrimination than can be achieved with standard allelespecific PCR.

Example 12: Moving Documents

In the POC methods described above, the lowest movable unit is the document. In these preceding examples, all documents were placed in the same folder; that is, the documents were associated with different D indices, but the same F index. In some embodiments, different documents may be transferred between different folders. This is done by diluting the tube contents (i.e., pooled bit-oligos) and amplifying to desired documents with a new 3° primer with document specific primer regions (regions marked D' in FIG. 1), but with a new folder index (F) and folder specific primer binding site (regions marked F' in FIG. 1). This effectively transfers the chosen documents from their original folder to the new folder. The transferred documents can then be amplified and read simultaneously using primers that hybridize with the new folder-specific primer binding site.

Alternatively, biotin containing primers with document- or folder-specific priming regions are used to capture certain documents or folders and physically remove them from one tube and then transferred to another tube.

Example 13: Alternative Use of Document Index (D)

The POC experiments above used a dual-key method where the document-specific primer binding site (regions marked D' in FIG. 1) is used to specifically amplify a certain document. During the NGS run, the document-specific index (D) is read to make sure that it is, in fact, reading that document. Another strategy is to have the document primer binding site be conserved, use it to extract all documents, but use a primer with a 3' anti-D region as well to extract a specific document.

This could also be done with the folder index, where the folder primer binding site is conserved and a primer against this conserved region with a 3' anti-F region is used to pull out a specific folder. This strategy is associated with high selectivity since it uses the 3' side of the primer. Note that in the examples disclosed herein, the document indices, D, are 8 bases in length, which provide significant primer selectivity.

Alternatively, RNase H2 primers are used to make the PCR more specific to the D and/or F indices. This also prevents the primers from interacting with each other.

Example 14: Different Options for Reading Data

There are different options for reading data. Every document in a folder can be read by amplifying with the P5/P7 fused to the folder-specific primer. Alternatively, certain documents can be read, either within the folder or from multiple folders, by performing a multiplex reaction with the P5/P7 fused to the different document specific primers. If the document-specific primer binding sequences are known, those documents can be amplified and read, even without knowing what folder each one is in.

Alternatively, instead of adding folder indices with 3° primers, the folder indices and folder-specific primer binding sites can be incorporated in the 2° primers.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A collection of data storage nucleic acids comprising:
a plurality of data storage nucleic acids, each data storage nucleic acid comprising one of N different bit-mer sequences,
wherein each bit-mer sequence represents information carried by a single bit in a primary bit string n bits in length,
wherein each bit-mer sequence represents a position of the single bit within the primary bit string, and
wherein:
(i) N equals n where the primary bit string is a binary bit string, wherein each data storage nucleic acid comprising one of N different bit-mer sequences can be present or absent in the collection of data storage nucleic acids, and wherein the presence of a data storage nucleic acid comprising a particular bit-mer sequence denotes a 1 and the absence of data storage nucleic acid comprising a particular a bit-mer sequence denotes a 0 at a particular position within the primary bit string, or vice versa;
(ii) N equals 2·n where the primary bit string is a binary bit string, and where each of n bit-mer sequences denote a 1 at a particular position within the primary bit string and each of the other n bit-mer sequences denote a 0 at a particular position within the primary bit string; and
(iii) N equals B·n where the primary bit string is a base-B bit string where B is greater than 2, and where each of B·n bit-mer sequences represents a particular base-B digit at a particular position within the primary bit string.

2. The collection of data storage nucleic acids of claim 1, each data storage nucleic acid further comprising one of x secondary positional indices, each secondary positional index comprising one or more secondary positional index nucleic acid sequences,
wherein the data storage nucleic acids that represent bits from the same primary bit string all comprise the same secondary positional index, and
wherein each secondary positional index represents the position of one of x primary bit strings relative to other primary bit strings within a secondary bit string x times n bits in length.

3. The collection of data storage nucleic acids of claim 2, each data storage nucleic acid further comprising one of y tertiary positional indices, each tertiary positional index comprising one or more tertiary positional index nucleic acid sequences,
wherein the data storage nucleic acids that represent bits from the same secondary bit string all comprise the same tertiary positional index, and
wherein each tertiary positional index represents the position of one of y secondary bit strings relative to other secondary bit strings within a tertiary bit string x times y times n bits in length.

4. The collection of data storage nucleic acids of claim 1, each data storage nucleic acid further comprising a document identification sequence and a document-specific primer binding sequence,
wherein the data storage nucleic acids that represent bits from the same document all comprise the same document identification sequence and document-specific primer binding sequence.

5. The collection of data storage nucleic acids of claim 4, each data storage nucleic acid further comprising a folder identification sequence and a folder-specific primer binding sequence,
wherein the data storage nucleic acids that represent bits from one or more documents in the same folder all comprise the same folder identification sequence and folder-specific primer binding sequence.

6. The collection of data storage nucleic acids of claim 4, each data storage nucleic acid further comprising a page recognition sequence,
wherein the data storage nucleic acids that represent bits from the same page within a document all comprise the same page recognition sequence, and
wherein the page recognition sequence, together with the document identification sequence and document-specific primer binding sequence, forms a primer binding site allowing data storage nucleic acids sharing a single page recognition sequence to be selectively amplified from the collection together.

7. The collection of data storage nucleic acids of claim 1, wherein B is 256 such that the primary bit string is a base-256 bit string and each bit-mer sequence represents a byte of information.

8. A method for storing data in a collection of data storage nucleic acids, the method comprising:
(a) converting the data into a base-B bit string;
(b) sub-dividing the base-B bit string into y secondary bit strings, and sub-dividing each secondary bit string into x primary bit strings n bits in length;
(c) for each of x primary bit strings:
(i) performing one of:
(A) where B equals 2, such that the base-B bit string is a binary bit string, from a library of n primary data storage nucleic acids, each comprising a single bit-mer sequence, each bit-mer sequence representing a specific position of a primary bit string n bits in length, selecting the primary data storage nucleic acid with the bit-mer sequence for each position of the primary bit string which is a 1, and selecting no primary data storage nucleic acid for each position of the primary bit string which is a 0;

(B) where B equals 2, such that the base-B bit string is a binary bit string, from a library of 2·n primary data storage nucleic acids, each comprising a single bit-mer sequence, each of n bit-mer sequences representing a 1 at a specific position of a primary bit string n bits in length, and each of n other bit-mer sequences representing a 0 at a specific position of the primary bit string, selecting the primary data storage nucleic acid with the 1 bit-mer sequence for each position of the primary bit string which is a 1, and selecting the primary data storage nucleic acid with the 0 bit-mer sequence for each position of the primary bit string which is a 0; or (C) where B is greater than 2, from a library of B·n primary data storage nucleic acids, each comprising a single bit-mer sequence, each of B·n bit-mer sequences representing a particular base-B digit at a specific position of the primary bit string, selecting the primary data storage nucleic acid with the appropriate bit-mer sequence for each position of the primary bit string;

wherein all primary data storage nucleic acids comprise the same 5' and 3' 1° primer binding sequences flanking the bit-mer sequence therein;

(ii) pooling the selected data storage nucleic acids to form one of x pools of primary data storage nucleic acids storing the data of one of x primary bit strings;

(iii) using a 1° primer pair that binds to the 5' and 3' 1° primer binding sequences to add to each primary data storage nucleic acid the same 5' and 3' secondary positional index sequences and, optionally, the same 5' and 3' 2° primer binding sequences to produce a pool of secondary data storage nucleic acids, wherein each of x pools of secondary data storage nucleic acids comprise different 5' and 3' secondary positional index sequences; and (d) pooling the x pools of secondary data storage nucleic acids corresponding to the x primary bit strings within each of y secondary bit strings into a single pool, to form y pools of secondary data storage nucleic acids, each storing the data of one of y secondary bit strings.

9. The method of claim 8, wherein the base-B bit string is instead sub-divided into z tertiary bit strings, each tertiary bit string sub-divided into y secondary bit strings, and each secondary bit string sub-divided into x primary bit strings n bits in length, the method further comprising:

(e) for each of y pools of secondary data storage nucleic acids, using a 2° primer pair that binds to the 5' and 3' 2° primer binding sequences to add to each secondary data storage nucleic acid the same 5' and 3' tertiary positional index sequences;

optionally, the same 5' and 3' tertiary recognition sequences; and, optionally, the same 5' and 3' document identification sequences and the same 5' and 3' document-specific primer binding sequences to produce tertiary data storage nucleic acids;

wherein each of y pools of tertiary data storage nucleic acids comprise different 5' and 3' tertiary positional index sequences; and wherein tertiary data storage nucleic acids representing bits from the same document all comprise the same 5' and 3' document identification sequences and the same 5' and 3' document-specific primer binding sequences; and pooling they pools of tertiary data storage nucleic acids corresponding to the y secondary bit strings within each of z tertiary bit strings into a single pool, to form z pools of tertiary data storage nucleic acids, each storing the data of one of z tertiary bit strings.

10. The method of claim 9, further comprising:

(g) using one or more 3° primers that bind to the 5' and 3' document-specific primer binding sequences to add to one or more of z pools of tertiary data storage nucleic acids the same 5' and 3' folder identification sequences and the same folder-specific primer binding sequences, wherein tertiary data storage nucleic acids representing bits from one or more documents within the same folder all comprise the same 5' and 3' folder identification sequences and the same 5' and 3' folder-specific primer binding sequences.

11. The method of claim 8, wherein B is 256 such that the primary bit string is a base-256 bit string and each bit-mer sequence represents a byte of information.

12. A data storage nucleic acid comprising:

(a) a bit-mer sequence, which represents information carried by a single bit in a primary bit string, and which further represents a position of the bit within the primary bit string;

(b) a 5' secondary positional tag comprising
  (i) a 5' 1° primer binding sequence flanking the 5' end of the bit-mer sequence, and
  (ii) a 5' secondary positional index sequence flanking the 5' end of the 5' 1° primer binding sequence; and (c) a 3' secondary positional tag comprising
  (i) a 3' 1° primer binding sequence flanking the 3' end of the bit-mer sequence, and
  (ii) a 3' secondary positional index sequence flanking the 3' end of the 3' 1° primer binding sequence;

wherein the 5' and 3' secondary positional index sequences represent the position of the primary bit string relative to one or more other primary bit strings within a secondary bit string.

13. The data storage nucleic acid of claim 12, wherein the 5' secondary positional index sequence is identical to the 3' secondary positional index sequence.

14. The data storage nucleic acid of claim 12, wherein the 5' secondary positional index sequence is different from the 3' secondary positional index sequence.

15. The data storage nucleic acid of claim 12, further comprising:

(d) a 5' tertiary positional tag comprising
  (i) a 5' 2° primer binding sequence flanking the 5' end of the 5' secondary positional index sequence,
  (ii) a 5' tertiary positional index sequence flanking the 5' end of the 5' 2° primer binding sequence, and
  (iii) optionally, a 5' tertiary recognition sequence flanking the 5' end of the 5' tertiary positional index sequence; and (e) a 3' tertiary positional tag comprising
  (i) a 3' 2° primer binding sequence flanking the 3' end of the 3' secondary positional index sequence,
  (ii) a 3' tertiary positional index sequence flanking the 3' end of the 3' 2° primer binding sequence, and (iii) optionally, a 3' tertiary recognition sequence flanking the 3' end of the 3' tertiary positional index sequence;

wherein the 5' and 3' tertiary positional index sequences represent the position of the secondary bit string relative to one or more other secondary bit strings within a tertiary bit string.

16. The data storage nucleic acid of claim 15, wherein the 5' tertiary positional index sequence is identical to the 3' tertiary positional index sequence.

17. The data storage nucleic acid of claim 15, further comprising a 5' filing domain flanking the 5' end of the 5' tertiary positional index sequence, which comprises one or more of:
(f) a 5' document identification tag comprising
(i) a 5' document identification sequence, and
(ii) a 5' document-specific primer binding sequence flanking the 5' end of the 5' document identification sequence; or
(g) a 5' folder identification tag comprising
(i) a 5' folder identification sequence, and
(ii) a 5' folder-specific primer binding sequence flanking the 5' end of the 5' folder identification sequence.

18. The data storage nucleic acid of claim 15, further comprising a 3' filing domain flanking the 3' end of the 3' tertiary positional index sequence, which comprises one or more of:
(f) a 3' document identification tag comprising
(i) a 3' document identification sequence, and
(ii) a 3' document-specific primer binding sequence flanking the 3' end of the 3' document identification sequence; or
(g) a 3' folder identification tag comprising
(i) a 3' folder identification sequence, and
(ii) a 3' folder-specific primer binding sequence flanking the 3' end of the 3' folder identification sequence.

19. A collection of data storage nucleic acids comprising:
a plurality of data storage nucleic acids, each data storage nucleic acid comprising one of N different bit-mer sequences,
wherein each bit-mer sequence represents:
(a) information carried by a bit in a primary bit string n bits in length and the position p of the bit within the primary bit string, and
(b) information carried by A adjacent bits in the primary bit string; and
wherein N equals $B^{(A+1)} \cdot n$ where the primary bit string is a base-B bit string, and where each of $B^{(A+1)} \cdot n$ bit-mer sequences represents a base-B digit at a particular position within the primary bit string along with the one or more base-B digits at the positions occupied by the A adjacent bits.

20. The collection of data storage nucleic acids of claim 19, the each data storage nucleic acid further comprising one of x secondary positional indices, each secondary positional index comprising one or more secondary positional index nucleic acid sequences,
wherein the data storage nucleic acids that represent bits from the same primary bit string all comprise the same secondary positional index, and
wherein each secondary positional index represents the position of one of x primary bit strings relative to other primary bit strings within a secondary bit string x times n bits in length.

21. The collection of data storage nucleic acids of claim 20, the each data storage nucleic acid further comprising one of y tertiary positional indices, each tertiary positional index comprising one or more tertiary positional index nucleic acid sequences,
wherein the data storage nucleic acids that represent bits from the same secondary bit string all comprise the same tertiary positional index, and
wherein each tertiary positional index represents the position of one of y secondary bit strings relative to other secondary bit strings within a tertiary bit string x times y times n bits in length.

22. The collection of data storage nucleic acids of claim 19, the each data storage nucleic acid further comprising a document identification sequence and a document-specific primer binding sequence,
wherein the data storage nucleic acids that represent bits from the same document all comprise the same document identification sequence and document-specific primer binding sequence.

23. The collection of data storage nucleic acids of claim 22, the each data storage nucleic acid further comprising a page recognition sequence,
wherein the data storage nucleic acids that represent bits from the same page within a document all comprise the same page recognition sequence, and
wherein the page recognition sequence, together with the document identification sequence and document-specific primer binding sequence, forms a primer binding site allowing data storage nucleic acids sharing a single page recognition sequence to be selectively amplified from the collection together.

24. The collection of data storage nucleic acids of claim 22, the each data storage nucleic acid further comprising a folder identification sequence and a folder-specific primer binding sequence,
wherein the data storage nucleic acids that represent bits from one or more documents in the same folder all comprise the same folder identification sequence and folder-specific primer binding sequence.

25. The collection of data storage nucleic acids of claim 19, wherein B is 256 such that the primary bit string is a base-256 bit string.

26. A method for storing data in a collection of data storage nucleic acids, the method comprising:
(a) converting the data into a base-B bit string;
(b) sub-dividing the base-B bit string into y secondary bit strings, and sub-dividing each secondary bit string into x primary bit strings n bits in length;
(c) for each of x primary bit strings:
(i) from a library of $B^{A+1} \cdot n$ primary data storage nucleic acids, each comprising a single bit-mer sequence, each of $B^{(A+1)} \cdot n$ bit-mer sequences representing (1) a particular base-B digit at a specific position p of the primary bit string, in addition to (2) a base-B digit at each of A positions adjacent to position p, selecting the primary data storage nucleic acid with the appropriate bit-mer sequence for each position p of the primary bit string;
wherein all primary data storage nucleic acids comprise the same 5' and 3' 1° primer binding sequences flanking the bit-mer sequence therein;
(ii) pooling the selected data storage nucleic acids to form one of x pools of primary data storage nucleic acids storing the data of one of x primary bit strings;
(iii) using a 1° primer pair that binds to the 5' and 3' 1° primer binding sequences to add to each primary data storage nucleic acid the same 5' and 3' secondary positional index sequences and, optionally, the same 5' and 3' 2° primer binding sequences to produce a pool of secondary data storage nucleic acids, wherein each of x pools of secondary data storage nucleic acids comprise different 5' and 3' secondary positional index sequences; and (d) pooling the x pools of secondary data storage nucleic acids corresponding to the x primary bit strings within each of y secondary bit strings into a single pool, to form y pools of secondary data storage nucleic acids, each storing the data of one of y secondary bit strings.

27. The method of claim 26, wherein the base-B bit string is instead sub-divided into z tertiary bit strings, each tertiary bit string sub-divided into y secondary bit strings, and each secondary bit string sub-divided into x primary bit strings n bits in length, the method further comprising:

(e) for each of y pools of secondary data storage nucleic acids, using a 2° primer pair that binds to the 5' and 3' 2° primer binding sequences to add to each secondary data storage nucleic acid the same 5' and 3' tertiary positional index sequences;

optionally, the same 5' and 3' tertiary recognition sequences; and, optionally, the same 5' and 3' document identification sequences and the same 5' and 3' document-specific primer binding sequences to produce tertiary data storage nucleic acids;

wherein each of y pools of tertiary data storage nucleic acids comprise different 5' and 3' tertiary positional index sequences; and wherein tertiary data storage nucleic acids representing bits from the same document all comprise the same 5' and 3' document identification sequences and the same 5' and 3' document-specific primer binding sequences; and (f) pooling they pools of tertiary data storage nucleic acids corresponding to the y secondary bit strings within each of z tertiary bit strings into a single pool, to form z pools of tertiary data storage nucleic acids, each storing the data of one of z tertiary bit strings.

28. The method of claim 27, further comprising:

(g) using one or more 3° primers that bind to the 5' and 3' document-specific primer binding sequences to add to one or more of z pools of tertiary data storage nucleic acids the same 5' and 3' folder identification sequences and the same folder-specific primer binding sequences, wherein tertiary data storage nucleic acids representing bits from one or more documents within the same folder all comprise the same 5' and 3' folder identification sequences and the same 5' and 3' folder-specific primer binding sequences.

29. The method of claim 26, wherein B is 256 such that the primary bit string is a base-256 bit string and each bit-mer sequence represents (1) a byte of information at a specific position p of the primary bit string, in addition to (2) a byte of information at each of A positions adjacent to position p.

* * * * *